(12) United States Patent
Frost et al.

(10) Patent No.: US 7,872,010 B2
(45) Date of Patent: Jan. 18, 2011

(54) SUBSTITUTED DIAZABICYCLOALKANE DERIVATIVES HAVING AFFINITY FOR NICOTINIC ACETYLCHOLINE RECEPTORS

(75) Inventors: Jennifer M. Frost, Grayslake, IL (US); Jianguo Ji, Libertyville, IL (US); Tao Li, Grayslake, IL (US); Diana L. Nersesian, Gurnee, IL (US); Karin R. Tietje, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 88 days.

(21) Appl. No.: 12/132,009

(22) Filed: Jun. 3, 2008

(65) Prior Publication Data

US 2008/0275048 A1 Nov. 6, 2008

Related U.S. Application Data

(62) Division of application No. 10/942,035, filed on Sep. 16, 2004, now Pat. No. 7,399,765.

(60) Provisional application No. 60/504,353, filed on Sep. 19, 2003.

(51) Int. Cl.
| | |
|---|---|
| C07D 401/00 | (2006.01) |
| C07D 401/14 | (2006.01) |
| C07D 239/34 | (2006.01) |
| C07D 487/14 | (2006.01) |
| A61K 31/4462 | (2006.01) |
| A61K 31/506 | (2006.01) |
| A61K 31/501 | (2006.01) |
| A61K 31/4704 | (2006.01) |

(52) U.S. Cl. .................. 514/252.03; 514/328; 514/274; 514/314; 544/316; 544/238; 546/276.7; 546/256; 546/167

(58) Field of Classification Search ................. 546/256, 546/276.4, 276.7, 167; 514/338, 328, 274, 514/252.03, 314; 544/316, 238
See application file for complete search history.

(56) References Cited

U.S. PATENT DOCUMENTS

| | | | |
|---|---|---|---|
| 2002/0013309 A1 | 1/2002 | Miller et al. | |
| 2002/0019388 A1 | 2/2002 | Schrimpf et al. | |
| 2003/0104324 A1* | 6/2003 | Uehira et al. ............... | 430/557 |
| 2003/0225268 A1 | 12/2003 | Bunnelle et al. | |
| 2004/0092559 A1* | 5/2004 | Hamann et al. ............. | 514/362 |
| 2005/0187360 A1* | 8/2005 | Blackmon et al. ........ | 526/124.3 |
| 2006/0211656 A1* | 9/2006 | Albert et al. .................. | 514/80 |
| 2009/0054397 A1* | 2/2009 | Ohi et al. ............... | 514/210.21 |
| 2009/0247471 A1* | 10/2009 | Quibell ......................... | 514/19 |

FOREIGN PATENT DOCUMENTS

| | | |
|---|---|---|
| WO | 00/34284 | 6/2000 |
| WO | 00/44755 | 8/2000 |
| WO | 00/71534 | 11/2000 |
| WO | 01/44243 | 6/2001 |
| WO | 01/81347 | 11/2001 |
| WO | 01/90109 | 11/2001 |
| WO | 02/02564 | 1/2002 |
| WO | 02/04446 | 1/2002 |
| WO | 02/44183 | 6/2002 |
| WO | 02/069901 | 9/2002 |
| WO | 02/096911 | 12/2002 |
| WO | 03/044020 | 5/2003 |
| WO | 03/094831 | 11/2003 |
| WO | 2004009589 | 1/2004 |

OTHER PUBLICATIONS

Adler et al, "Schizophrenia, sensory gating, and nicotinic receptors," Schizophrenia Bulletin 24(2):189-202 (1998).
Banker et al., "Modern Pharmaceutics" Third Edition. Marcel Dekker, New York. 1996, p. 596.
Cordero-Erausquin et al., "Tonic nicotinic modulation of serotoninergic transmission in the spinal cord," PNAS 98(5):2803-2807 (2001).
Friedman et al., "A double blind placebo controlled trial of donepezil adjunctive treatment to risperidone for the cognitive impairment of schizophrenia," Biol. Psychiatry 51:349-357 (2002).
Heeschen et al., "Nicotine stimulates angiogenesis and promotes tumor growth and athersclerosis," Nature Medicine 7(7):833-839 (2001).
Heeshcen et al., "A novel angiogenic pathway mediated by non-neuronal nicotinic acetylcholine receptors," Journal of Clinical Investigation 110(4):527-536 (2002).
Jonnala et al., "Relationship between the increased cell surface α7 nicotinic receptor expression and neuroprotection induced by several nicotinic receptor agonists," Journal of Neuroscience Research 66:565-572 (2001).
Kihara et al., "α7 nicotinic receptor transduces signals to phosphatidylinositol 3-kinase to block A β-amyloid-induced neurotoxicity," Journal of Biological Chemistry 276(17):13541-13546 (2001).
Leonard et al., "Smoking and schizophrenia: abnormal nicotinic receptor expression," European Journal of Pharmacology 393:237-242 (2000).
Levin, "Nicotinic receptor subtypes and cognitive function," J. Neurobiol. 53:633-640 (2002).
Liu et al., "β-Amyloid peptide blocks the response of α7-containing nicotinic receptors on hippocampal neurons," PNAS 98(8):4734-4739 (2001).
Pirrung et al., "Photochmically removable silyl protecting groups," J. Am. Chem. Soc. 123:3638-3643 (2001).

(Continued)

*Primary Examiner*—James O Wilson
*Assistant Examiner*—Cecilia M Jaisle
(74) *Attorney, Agent, or Firm*—Antonia M. Holland

(57) ABSTRACT

Provided herein are compositions of a class of substituted diazabicycloalkane derivative compounds, which are useful as modulators of nicotinic acetylcholine receptors. The compounds are useful in treating conditions and disorders prevented by, or ameliorated by, nicotinic acetylcholine receptors.

20 Claims, No Drawings

OTHER PUBLICATIONS

Rowley et al., "Current and novel approaches to the drug treatment of schizophrenia," Journal of Medicinal Chemistry 44(4):477-501 (2001).

Shimohama et al., "Nicotinic α7 receptors protect against glutamate neurotoxicity and neuronal ischemic damage," Brain Research 779:359-363 (1998).

Son et al., "Evidence suggesting that the Mouse sperm acrosome reaction initiated by the zona pellucida involves an α7 nicotinic acetylcholine receptor," Biology of Reproduction 68:1348-1351 (2003).

Stevens et al., "Selective $\alpha_7$-nicotinic agonists normalize inhibition of auditory response in DBA mice," Psychopharmacology 136:320-327 (1998).

Torii et al., "A versatile cycloaddition for the generation of pyrrolidine derivatives via C-N-C 1,3-dipoles," Chemistry Letters 747-748 (1996).

Wang et al., "Nicotinic acetylcholine receptor α7 subunit is an essential regulator of inflammation," Nature 421:384-388 (2003).

Wolff Me, "Burger's Medicinal Chemistry and Drug Discovery" Fifth Edition. John Wiley & Sons, 1995, pp. 975-977.

* cited by examiner

SUBSTITUTED DIAZABICYCLOALKANE DERIVATIVES HAVING AFFINITY FOR NICOTINIC ACETYLCHOLINE RECEPTORS

This application is a divisional application of U.S. non-Provisional application Ser. No. 10/942,035, filed Sep. 16, 2004, which claims priority to U.S. Provisional Application Ser. No. 60/504,353, filed Sep. 19, 2003, which are hereby incorporated by reference herein.

BACKGROUND OF THE INVENTION

1. Technical Field

The invention relates to diazabicycloalkane derivatives, compositions comprising such compounds, and methods of treating conditions and disorders using such compounds and compositions.

2. Description of Related Technology

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, α2-α10 and β2-β4, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the α4β2 subtype), while another major population of receptors is comprised of the homomeric $(\alpha 7)_5$ (the α7 subtype).

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The α7 nAChRs have been shown to play a significant role in enhancing cognitive function, including aspects of learning, memory and attention (Levin, E. D., J. Neurobiol. 53: 633-640, 2002). For example, α7 nAChRs have been linked to conditions and disorders related to attention deficit disorder, attention deficit hyperactivity disorder (ADHD), Alzheimer's disease (AD), mild cognitive impairment, senile dementia, dementia associated with Lewy bodies, dementia associated with Down's syndrome, AIDS dementia, Pick's Disease, as well as cognitive deficits associated with schizophrenia, among other systemic activities.

The activity at the α7 nAChRs can be modified or regulated by the administration of α7 nAChR ligands. The ligands can exhibit antagonist, agonist, partial agonist, or inverse agonist properties. Thus, α7 ligands have potential in treatment of various cognitive disorders.

Although various classes of compounds demonstrating α7 nAChR-modulating activity exist, it would be beneficial to provide additional compounds demonstrating activity at the α7 nAChRs that can be incorporated into pharmaceutical compositions useful for therapeutic methods. Specifically, it would be beneficial to provide compounds that interact selectively with α7-containing neuronal nAChRs compared to other subtypes.

SUMMARY OF THE INVENTION

The invention is directed to diazabicycloalkane derivative compounds as well as compositions comprising such compounds, and method of using the same. Compounds of the invention have the formula:

or a pharmaceutically acceptable salt, ester, amide, or prodrug thereof, wherein:

Z is a diazabicyclic amine of the formula:

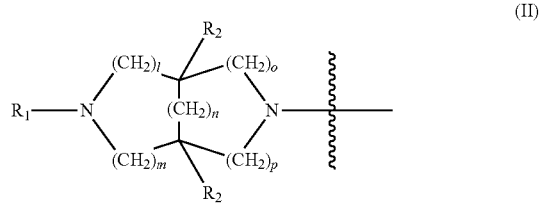

$Ar_1$ is a 5- or 6-membered aromatic ring of the formula (a) or (b):

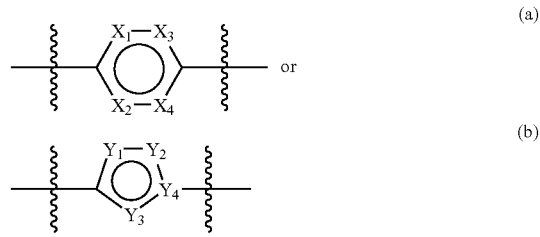

$Ar_2$ is selected from the group consisting of an unsubstituted or substituted 5- or 6-membered heteroaryl ring; unsubstituted or substituted bicyclic heteroaryl ring; 3,4-(methylenedioxy)phenyl; carbazolyl; tetrahydrocarbazolyl; naphthyl; and phenyl; wherein the carbazolyl; tetrahydrocarbazolyl; naphthyl; and phenyl is substituted with 0, 1, 2, or 3 substituents selected from the group consisting of alkenyl, alkoxy, alkoxyalkoxy, alkoxyalkyl, alkoxycarbonyl, alkoxysulfonyl, alkyl, alkylcarbonyl, arylcarbonyl, alkylcarbonyloxy, alkylsulfonyl, alkylthio, alkynyl, carboxy, cyano, formyl, haloalkoxy, haloalkyl, halogen, hydroxy, hydroxyalkyl, mercapto, nitro, —$NR_AR_B$, ($NR_AR_B$)alkyl, ($NR_AR_B$)carbonyl, ($NR_AR_B$)sulfonyl, and phenyl; provided that when $Y_1$ is O or S, $Y_2$ is N, $Y_3$ is —$CR_3$ and $R_3$ is hydrogen, and $Y_4$ is C, then $Ar_2$ is not 5-tetrazolyl;

$X_1$, $X_2$, $X_3$, and $X_4$ are each independently selected from the group consisting of N and —$CR_3$, provided that $R_3$ is not hydrogen at least in one occurrence when $X_1$, $X_2$, $X_3$, and $X_4$ are all —$CR_3$;

$Y_1$, $Y_2$, and $Y_3$ are each independently selected from the group consisting of N, O, S, and —$CR_3$;

$Y_4$ is selected from the group consisting of C and N, provided that when $Y_4$ is C at least one of $Y_1$, $Y_2$, and $Y_3$, is other than —$CR_3$;

l, m, n, o, and p are each independently selected from the group consisting of 0, 1, or 2, provided that the sum total of l, m, n, o, and p is 3, 4, or 5, and further provided that the sum of l and o is at least 1 and the sum of m and p is at least 1;

$R_1$ is selected from the group consisting of hydrogen, alkenyl, alkyl alkoxycarbonyl, arylalkyl, and heteroarylalkyl;

$R_2$ at each occurrence is independently selected from the group consisting of hydrogen, alkoxycarbonyl, and alkyl;

$R_3$ at each occurrence is independently selected from the group consisting of hydrogen and alkyl;

$R_A$ and $R_B$ are each independently selected from the group consisting of hydrogen, alkyl, alkylcarbonyl, alkylsulfonyl, arylcarbonyl, formyl and ($NR_CR_D$)sulfonyl; and $R_C$ and $R_D$ are each independently selected from the group consisting of hydrogen and alkyl.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α7 nAChR activity.

Yet another aspect of the invention relates to a method of selectively modulating to nAChR activity, for example α7 nAChR activity. The method is useful for treating and/or preventing conditions and disorders related to α7 nAChR activity modulation in mammals. More particularly, the method is useful for conditions and disorders related to attention deficit disorder, attention deficit hyperactivity disorder (ADHD), Alzheimer's disease (AD), mild cognitive impairment, senile dementia, AIDS dementia, Parkinson's disease, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation, more particularly circulation around a vascular occlusion, among other systemic activities.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group.

The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, arylcarbonyl, alkylcarbonyloxy, alkylthio, alkynyl, carboxy, cyano, haloalkoxy, haloalkyl, halogen, hydroxy, hydroxyalkyl, mercapto, and nitro.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "carbonyl" as used herein, means a —C(O)— group.

The term "carboxy" as used herein, means a —CO$_2$H group.

The term "cyano" as used herein, means a —CN group.

The term "formyl" as used herein, means a —C(O)H group.

The term "halo" or "halogen" means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" means an aromatic five- or six-membered ring containing 1, 2, 3, or 4 heteroatoms independently selected from nitrogen, oxygen, or sulfur. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazinyl, and triazolyl.

The heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)carbonyl, and (NR$_A$R$_B$)sulfonyl.

The term "bicyclic heteroaryl" refers to fused aromatic nine- and ten-membered bicyclic rings containing 1, 2, 3, or 4 heteroatoms independently selected from nitrogen, oxygen, or sulfur. The bicyclic heteroaryl groups are connected to the parent molecular moiety through a carbon or nitrogen atom. Representative examples of bicyclic heteroaryl rings include, but are not limited to, indolyl, benzothiazolyl, benzofuranyl, isoquinolinyl, and quinolinyl. Bicyclic heteroaryl groups of the invention are substituted with 0, 1, 2, or 3 substituents independently selected from alkenyl, alkoxy, alkoxyalkoxy, alkoxyalkyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)carbonyl, and (NR$_A$R$_B$)sulfonyl.

The term "heteroarylalkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "—NR$_A$R$_B$" as used herein, means two groups, R$_A$ and R$_B$, which are appended to the parent molecular moiety through a nitrogen atom. R$_A$ and R$_B$ are each independently hydrogen, alkyl, alkylcarbonyl, alkylsulfonyl, arylcarbonyl, formyl or (NR$_C$R$_D$)sulfonyl. Representative examples of —NR$_A$R$_B$ include, but are not limited to, amino, methylamino, acetylamino, and acetylmethylamino.

The term "(NR$_A$R$_B$)alkyl" as used herein, means a —NR$_A$R$_B$ group, as defined herein, appended to the parent molecular moiety through an alkyl group, as defined herein. Representative examples of (NR$_A$R$_B$)alkyl include, but are not limited to, (amino)methyl, (dimethylamino)methyl, and (ethylamino)methyl.

The term "(NR$_A$R$_B$)alkoxy" as used herein, means a —NR$_A$R$_B$ group, as defined herein, appended to the parent molecular moiety through an alkoxy group, as defined herein. Representative examples of (NR$_A$R$_B$)alkoxy include, but are not limited to, (amino)methoxy, (dimethylamino)methoxy, and (diethylamino)ethoxy.

The term "(NR$_A$R$_B$)carbonyl" as used herein, means a —NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "(NR$_A$R$_B$)sulfonyl" as used herein, means a —NR$_A$R$_B$ group, as defined herein, appended to the parent molecular moiety through a sulfonyl group, as defined herein. Representative examples of (NR$_A$R$_B$)sulfonyl include, but are not limited to, aminosulfonyl, (methylamino)sulfonyl, (dimethylamino)sulfonyl, and (ethylmethylamino)sulfonyl.

The term "—NR$_C$R$_D$" as used herein, means two groups, R$_C$ and R$_D$, which are appended to the parent molecular moiety through a nitrogen atom. R$_C$ and R$_D$ are each independently hydrogen or alkyl. Representative examples of —NR$_C$R$_D$ include, but are not limited to, amino, methylamino and dimethylamino.

The term "(NR$_C$R$_D$)sulfonyl" as used herein, means a —NR$_C$R$_D$ group, as defined herein, appended to the parent molecular moiety through a sulfonyl group, as defined herein. Representative examples of (NR$_C$R$_D$)sulfonyl include, but are not limited to, aminosulfonyl, (methylamino)sulfonyl, (dimethylamino)sulfonyl, and (ethylmethylamino)sulfonyl.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric $(α7)_5$ receptors and α7* receptors, which denote a nAChR containing at least one α7 subunit.

Compounds of the Invention

Compounds of the invention can have the formula (I) as described above. More particularly, compounds of formula (I):

   (I)

are those wherein Z is a moiety of the formula (II):

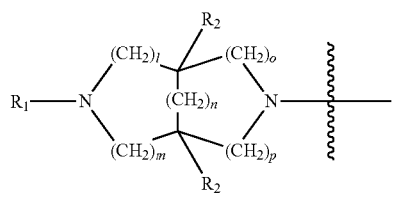   (II)

wherein $R_1$, $R_2$, $Ar_1$, $Ar_2$, l, m, n, o, and p are as previously defined. The variables l, m, n, o, and p denote numbers that are each independently selected from 0, 1, or 2, provided that the sum total of l, m, n, o, and p is 3, 4, or 5, such that the group represented by Z is a 7-, 8-, or 9-membered diazabicycloalkane, respectively. Preferably, Z is a 7- or 8-membered ring. In one particular embodiment, n is zero, such that Z is a fused bicyclic ring.

Z can have substituents represented by $R_1$ and $R_2$. Examples of moieties suitable for Z can include, but are not limited to:

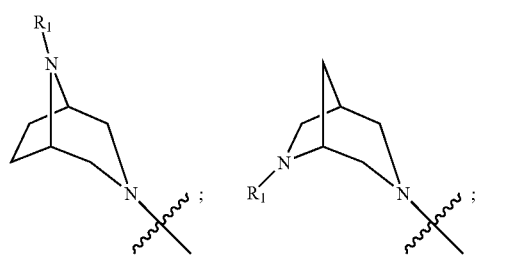

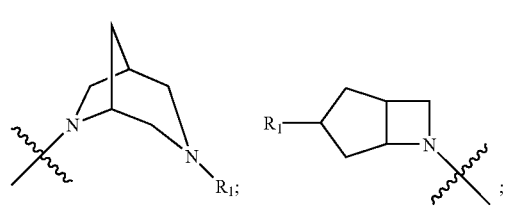

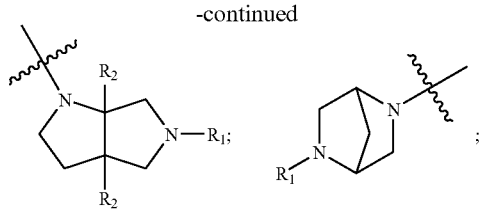

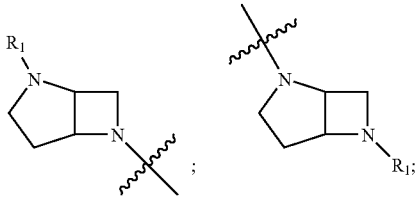

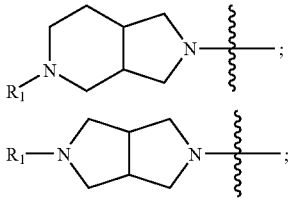

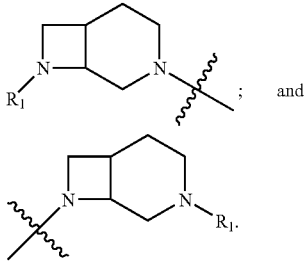

The substituent represented by $R_1$ can be selected from hydrogen, alkoxycarbonyl, alkyl, arylalkyl, and heteroarylalkyl, particularly methyl, benzyl and pyridin-3-ylmethyl. $R_2$ can be selected from hydrogen, alkenyl, alkyl, and alkoxycarbonyl, particularly methyl.

The $Ar_1$ moiety can be selected independently of the moiety selected for Z. Suitable moieties for $Ar_1$ are those represented by a 5- or 6-membered aromatic ring of the formula:

(a)

(b)

In such moieties, $X_1$, $X_2$, $X_3$, and $X_4$ are each independently selected from the group consisting of N and —$CR_3$, provided that $R_3$ is not hydrogen at least in one occurrence when $X_1$, $X_2$, $X_3$, and $X_4$ all are —$CR_3$, such that a phenyl group contains at least one substituent. The moiety represented by formula (a) is attached to the diazabicyclic amine and the $Ar_2$ moiety by 1,4-substitution or para-attachment. Preferably, the moiety represented by formula (a) contains at least one heteroatom, particularly when $Ar_2$ is a phenyl group.

Formula (b) represents a five-membered ring wherein $Y_1$, $Y_2$, and $Y_3$ are each independently selected from the group consisting of N, O, S, and —$CR_3$.

$Y_4$ is selected from C or N. When $Y_4$ is C at least one of the substituents represented by $Y_1$, $Y_2$, and $Y_3$, is other than —$CR_3$, such that the moiety represented by formula (b) contains at least one heteroatom. The moiety generally is attached to the diazabicyclic amine and the $Ar_2$ moiety by 1,3-substitution.

Examples of specific rings suitable for $Ar_1$ include, but are not limited to, isoxazolyl, oxadiazolyl, oxazolyl, pyrazolyl, pyridazinyl, pyridyl, pyrimidinyl, thiadiazolyl, isothiazolyl, thiazolyl, thienyl, and phenyl, wherein the pyridazinyl, pyridyl, and phenyl, are substituted with 0 or 1 substitutent selected from the group consisting of alkoxy, alkyl, cyano, and hydroxy. More particularly, the rings represented by $Ar_1$ are, for example,

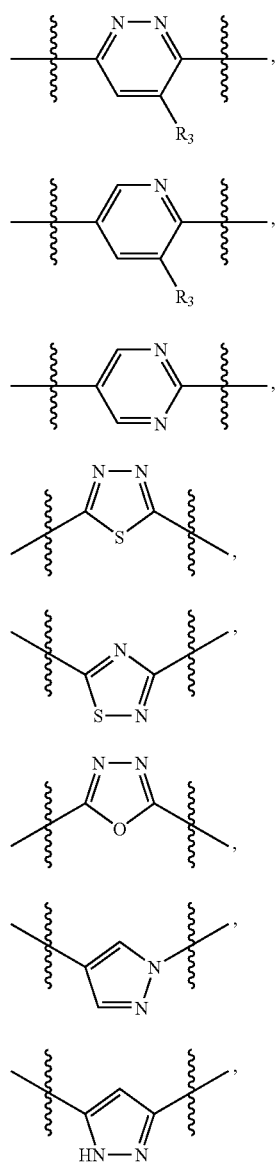

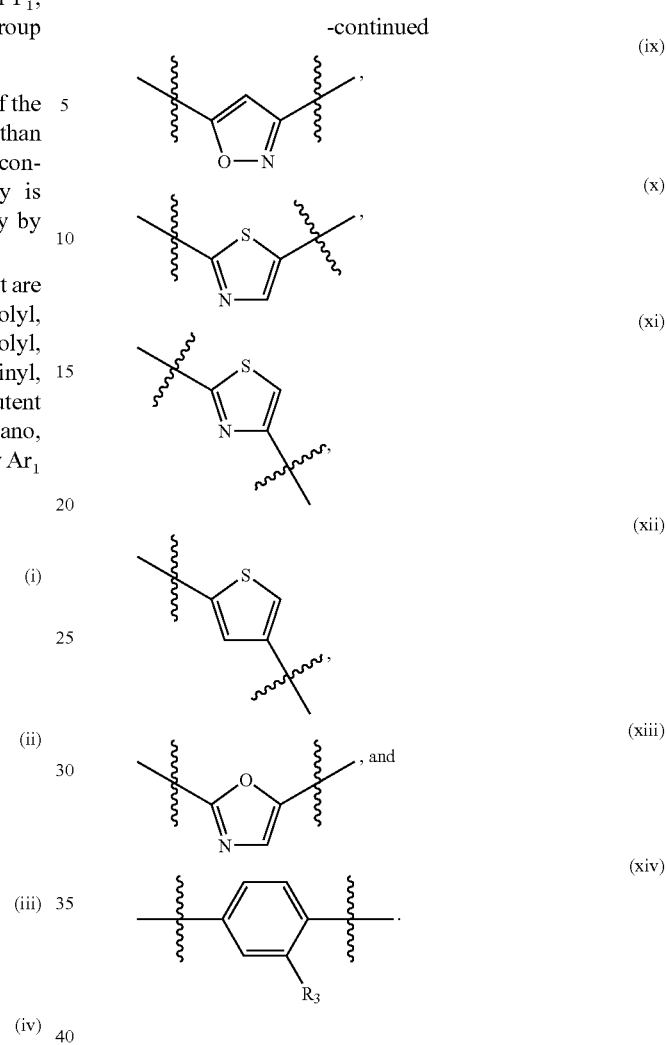

The preferred ring for $Ar_1$ is pyridazinyl, exemplified by (i), wherein $R_3$ is hydrogen, alkoxy, alkyl, cyano, or hydroxy, wherein hydrogen or methyl are preferred. Another preferred ring for $Ar_1$ is pyridyl, exemplified by (ii), wherein $R_3$ is hydrogen, alkoxy, alkyl, cyano, or hydroxy, wherein hydrogen or cyano are preferred. Another preferred ring for $Ar_1$ is pyrimidinyl, exemplified by (iii). Another preferred ring for $Ar_1$ is thiadiazolyl, exemplified by (iv) and (v). Another preferred ring for $Ar_1$ is oxadiazolyl, exemplified by (vi). Another preferred ring for $Ar_1$ is pyrazolyl, exemplified by (vii) and (viii). Another preferred ring for $Ar_1$ is isoxazolyl, exemplified by (ix). Another preferred ring for $Ar_1$ is thiazolyl, exemplified by (x) and (xi). Another preferred ring for $Ar_1$ is thienyl, exemplified by (xii). Another preferred ring for $Ar_1$ is oxazolyl, exemplified by (xiii). Another preferred ring for $Ar_1$ is phenyl, exemplified by (xiv), wherein $R_3$ is hydrogen, alkoxy, alkyl, cyano, or hydroxy. It is to be understood that either end of the rings (i), (ii), (iii), (v), (vii), (ix), (x), (xi), (xii), and (xiii) can be attached to Z.

$Ar_2$ can be independently selected regardless of the moiety selected for Z or $Ar_1$. When $Ar_2$ is phenyl or substituted phenyl, $Ar_1$ preferably contains at least one heteroatom. Moieties suitable for $Ar_2$ can be an unsubstituted or substituted 5- or 6-membered heteroaryl ring; an unsubstituted or substituted bicyclic heteroaryl ring; 3,4-(methylenedioxy)phenyl; carbazolyl; tetrahydrocarbazolyl; naphthyl; or phenyl. The carbazolyl, tetrahydrocarbazolyl, naphthyl, and phenyl moieties can be substituted with 0, 1, 2, or 3 substituents preferably in the meta- or para-position.

Examples of heteroaryl or bicyclic heteroaryl rings are, for example, furyl, imidazolyl, isoxazolyl, isothiazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazinyl, triazolyl, indolyl, benzothiazolyl, benzofuranyl, isoquinolinyl, and quinolinyl. Suitable substituents for the heteroaryl and bicyclic heteroaryl ring include, but are not limited to, alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halogen, hydroxy, hydroxyalkyl, mercapto, nitro, —NR$_A$R$_B$, wherein R$_A$ and R$_B$ are each independently selected from hydrogen, alkyl, alkylcarbonyl, or formyl, (NR$_A$R$_B$)carbonyl, and (NR$_A$R$_B$)sulfonyl. More particularly, Ar$_2$ are preferably selected from benzofuranyl; benzothienyl; furyl; imidazolyl; 3-methylindazolyl; 3-indolyl; 5-indolyl; 1-methyl-3-indolyl; 1-methyl-5-indolyl; 3-methyl-5-indolyl; 3-[(dimethylamino)methyl]indolyl; 1-[(4-methylphenyl)sulfonyl]indolyl; 3,5-dimethyl isoxazolyl; naphthyl; pyrazolyl; 3,5-dimethylpyrazolyl; 1-methylpyrazolyl; 6-oxopyridazinyl; pyridyl; 6-aminopyridyl; 2-cyanopyridyl; pyrimidinyl; 2-methoxypyrimidinyl; 2-pyrrolyl; 3-pyrrolyl; quinolinyl; or thienyl.

Phenyl and substituted phenyl groups, for example benzodioxolyl and 3,4-(methylenedioxy)phenyl, also are suitable for Ar$_2$. Additional suitable substituents for the phenyl ring can include, but are not limited to, alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halogen, hydroxy, hydroxyalkyl, mercapto, nitro, —NR$_A$R$_B$, (NR$_A$R$_B$)alkyl, (NR$_A$R$_B$)carbonyl, (NR$_A$R$_B$)sulfonyl, and phenyl. R$_A$ and R$_B$ are each independently hydrogen, alkyl, alkylcarbonyl, alkylsulfonyl, arylcarbonyl, formyl or (NR$_C$R$_D$)sulfonyl. R$_C$ and R$_D$ are each independently hydrogen or alkyl. For example, Ar$_2$ can be phenyl substituted with 0, 1, or 2 substituents, such as alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl. More specific examples of moieties suitable for Ar$_2$ include, but are not limited to:

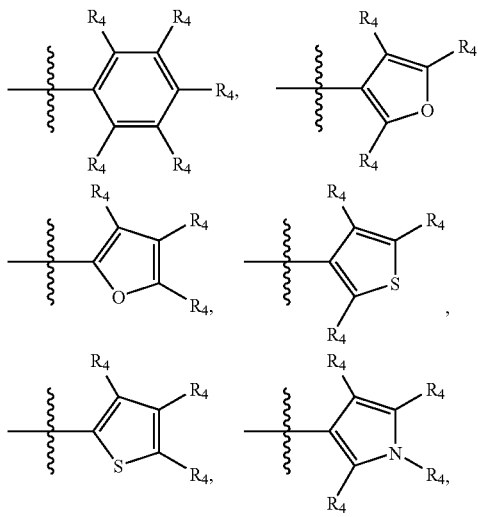

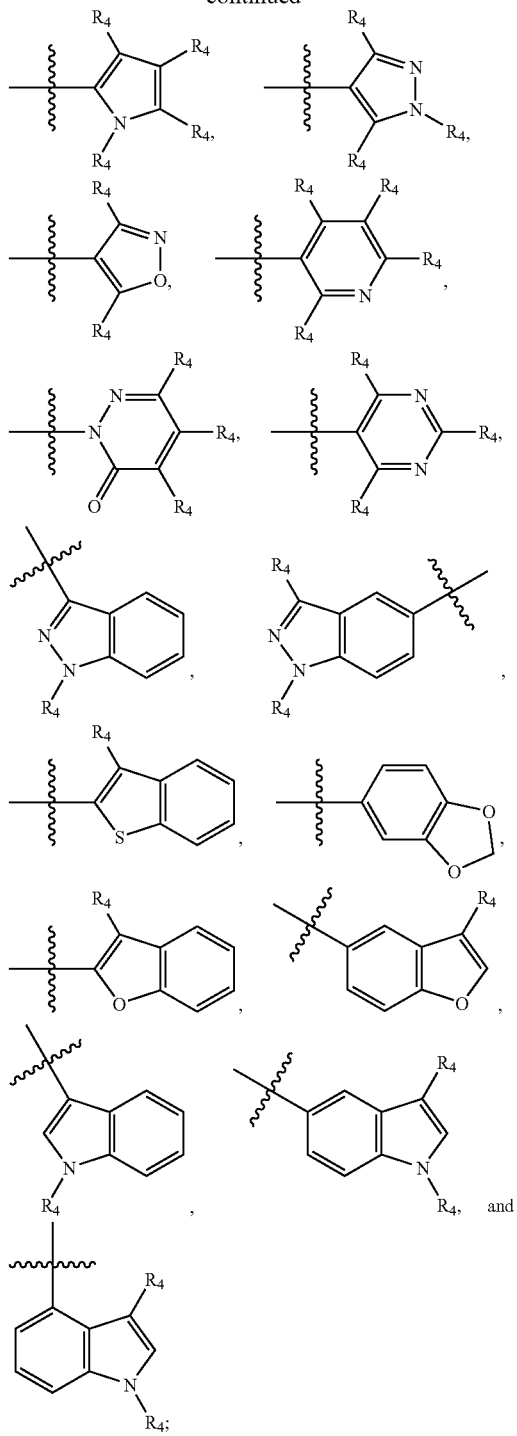

wherein R$_4$ at each occurrence is independently selected and represents a substituent selected from the group consisting of hydrogen, alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl. Preferably, the substituent represented by R$_4$ is selected from the group consisting of hydrogen, alkoxy, alkoxycarbonyl, alkyl, alkylcarbonyl, —NR$_A$R$_B$, and haloalkyl. Preferred moieties for Ar$_2$, particularly when Ar$_1$ is heteroaryl, are phenyl, para-acetylaminophenyl, meta-aminophenyl, para-aminophenyl, para(2-(diethylamino)ethoxy)phenyl, meta(2-(diethylamino)ethoxy)phenyl, para-(dimethylamino)phenyl, para-bromophenyl, meta-cyanophenyl, para-cyanophenyl, meta-hydroxyphenyl, para-hydroxyphenyl, para-iodophenyl, meta-methylphenyl, para-methylphenyl, 3,5-dimethylphenyl, meta-methoxyphenyl, para-methoxyphenyl, meta-trifluoromethoxyphenyl, meta-nitrophenyl, para-nitrophenyl, meta-trifluoromethylphenyl, and the like. When ring of formula (b) is defined by $Y_1$ is O or S, $Y_2$ is N, $Y_3$ is —$CR_3$ and $R_3$ is hydrogen, and $Y_4$ is C, then $Ar_2$ is not 5-tetrazolyl.

One example of a particular embodiment of the compounds for the invention is wherein Z is a seven-membered fused bicyclic ring, for example

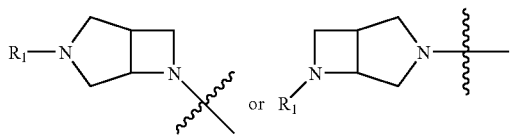

$Ar_1$ is selected from the group consisting of isoxazolyl, oxadiazolyl, oxazolyl, pyrazolyl, pyridazinyl, 4-methylpyridazinyl, 5-methylpyridazinyl, pyridyl, 5-cyanopyridyl, pyrimidinyl, thiadiazolyl, thiazolyl, thienyl, and phenyl substituted with 0 or 1 substituent selected from the group consisting alkoxy, alkyl, cyano, and hydroxy; $Ar_2$ is selected from the group consisting of benzofuranyl, benzothienyl, carbazolyl, tetrahydrocarbazolyl, furyl; imidazolyl, 3-methylindazolyl, 3-indolyl, 5-indolyl, 1-methyl-3-indolyl, 1-methyl-5-indolyl, 3-methyl-5-indolyl, 3-[(dimethylamino)methyl]indolyl, 1-[(4-methylphenyl)sulfonyl]indolyl, 3,5-dimethylisoxazolyl, naphthyl, pyrazolyl, 3,5-dimethylpyrazolyl, 1-methylpyrazolyl, 6-oxopyridazinyl, pyridyl, 6-aminopyridyl, 2-cyanopyridyl, pyrimidinyl, 2-methoxypyrimidinyl, 2-pyrrolyl, 3-pyrrolyl, quinolinyl, thienyl, 3,4-(methylenedioxy)phenyl, and phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —$NR_AR_B$, ($NR_AR_B$)alkyl, ($NR_AR_B$)alkoxy, and phenyl.

Another example of a particular embodiment of the compounds for the invention is wherein Z is a seven-membered fused bicyclic ring, for example

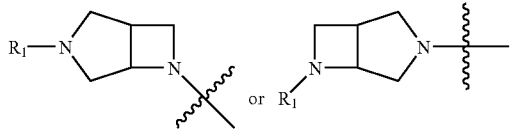

$Ar_1$ is pyridazinyl or pyridyl, and $Ar_2$ is as described, either generally or particularly, and more particularly $Ar_2$ is selected from the group consisting of 3-indolyl, 5-indolyl, 1-methyl-3-indolyl, 1-methyl-5-indolyl, 3-methyl-5-indolyl, 3,4-(methylenedioxy)phenyl, and phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —$NR_AR_B$, ($NR_AR_B$)alkyl, ($NR_AR_B$)alkoxy, and phenyl.

One example of a particular embodiment of the compounds for the invention is wherein Z is an eight-membered bridged bicyclic ring, for example

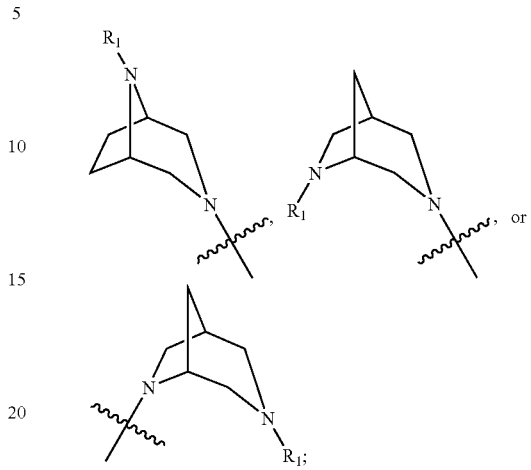

$Ar_1$ is selected from the group consisting of isoxazolyl, oxadiazolyl, oxazolyl, pyrazolyl, pyridazinyl, 4-methylpyridazinyl, 5-methylpyridazinyl, pyridyl, 5-cyanopyridyl, pyrimidinyl, thiadiazolyl, thiazolyl, thienyl, and phenyl substituted with 0 or 1 substituent selected from the group consisting alkoxy, alkyl, cyano, and hydroxy; $Ar_2$ is selected from the group consisting of benzofuranyl, benzothienyl, carbazolyl, tetrahydrocarbazolyl, furyl; imidazolyl, 3-methylindazolyl, 3-indolyl, 5-indolyl, 1-methyl-3-indolyl, 1-methyl-5-indolyl, 3-methyl-5-indolyl, 3-[(dimethylamino)methyl]indolyl, 1-[(4-methylphenyl)sulfonyl]indolyl, 3,5-dimethylisoxazolyl, naphthyl, pyrazolyl, 3,5-dimethylpyrazolyl, 1-methylpyrazolyl, 6-oxopyridazinyl, pyridyl, 6-aminopyridyl, 2-cyanopyridyl, pyrimidinyl, 2-methoxypyrimidinyl, 2-pyrrolyl, 3-pyrrolyl, quinolinyl, thienyl, 3,4-(methylenedioxy)phenyl, and phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —$NR_AR_B$, ($NR_AR_B$)alkyl, ($NR_AR_B$)alkoxy, and phenyl.

Another example of a particular embodiment of the compounds for the invention is wherein Z is an eight-membered bridged bicyclic ring, for example

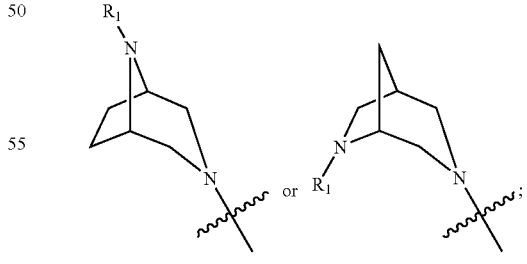

$Ar_1$ is pyridazinyl, and $Ar_2$ is as described, either generally or particularly, and more particularly $Ar_2$ is phenyl substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —$NR_AR_B$, ($NR_AR_B$)alkyl, ($NR_AR_B$)alkoxy, and phenyl.

One example of a particular embodiment of the compounds for the invention is wherein Z is a eight-membered fused bicyclic ring, for example

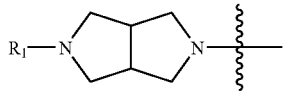

Ar₁ is selected from the group consisting of isoxazolyl, oxadiazolyl, oxazolyl, pyrazolyl, pyridazinyl, 4-methylpyridazinyl, 5-methylpyridazinyl, pyridyl, 5-cyanopyridyl, pyrimidinyl, thiadiazolyl, thiazolyl, thienyl, and phenyl substituted with 0 or 1 substituent selected from the group consisting alkoxy, alkyl, cyano, and hydroxy; Ar₂ is selected from the group consisting of benzofuranyl, benzothienyl, carbazolyl, tetrahydrocarbazolyl, furyl; imidazolyl, 3-methylindazolyl, 3-indolyl, 5-indolyl, 1-methyl-3-indolyl, 1-methyl-5-indolyl, 3-methyl-5-indolyl, 3-[(dimethylamino)methyl]indolyl, 1-[(4-methylphenyl)sulfonyl]indolyl, 3,5-dimethylisoxazolyl, naphthyl, pyrazolyl, 3,5-dimethylpyrazolyl, 1-methylpyrazolyl, 6-oxopyridazinyl, pyridyl, 6-aminopyridyl, 2-cyanopyridyl, pyrimidinyl, 2-methoxypyrimidinyl, 2-pyrrolyl, 3-pyrrolyl, quinolinyl, thienyl, 3,4-(methylenedioxy)phenyl, and phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl.

Yet another example of a particular embodiment of the compounds for the invention is wherein Z is an eight-membered fused bicyclic ring, for example,

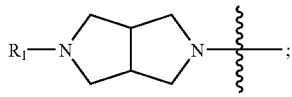

Ar₁ is pyridazinyl; and Ar₂ is as described, or more particularly, phenyl substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl.

Still yet another example of a particular embodiment of the compounds for the invention is wherein Z is an eight-membered fused bicyclic ring, for example,

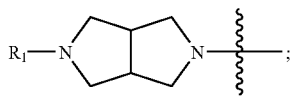

Ar₁ is pyridyl; and Ar₂ is as described, or more particularly, furyl, benzothienyl, or phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl. Particularly in this embodiment, Ar₂ preferably is heteroaryl or bicyclic heteroaryl when Ar₁ is pyridyl, provided that Ar₂ is not 1-pyrrolyl or 1-indolyl.

Yet another example of a particular embodiment of the compounds for the invention is wherein Z is an eight-membered fused bicyclic ring, for example,

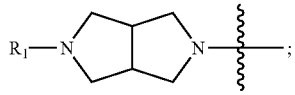

Ar₁ is either isoxazolyl, oxadiazolyl, pyrazolyl, pyrimidinyl, thiadiazolyl, or thiazolyl; and Ar₂ is as described, or more particularly, furyl or phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl.

One example of a particular embodiment of the compounds for the invention is wherein Z is a eight-membered fused bicyclic ring, for example

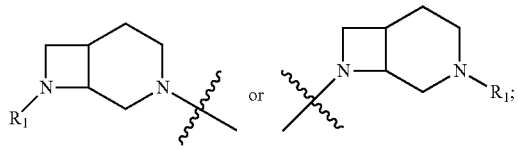

Ar₁ is selected from the group consisting of isoxazolyl, oxadiazolyl, oxazolyl, pyrazolyl, pyridazinyl, 4-methylpyridazinyl, 5-methylpyridazinyl, pyridyl, 5-cyanopyridyl, pyrimidinyl, thiadiazolyl, thiazolyl, thienyl, and phenyl substituted with 0 or 1 substituent selected from the group consisting alkoxy, alkyl, cyano, and hydroxy; Ar₂ is selected from the group consisting of benzofuranyl, benzothienyl, carbazolyl, tetrahydrocarbazolyl, furyl; imidazolyl, 3-methylindazolyl, 3-indolyl, 5-indolyl, 1-methyl-3-indolyl, 1-methyl-5-indolyl, 3-methyl-5-indolyl, 3-[(dimethylamino)methyl]indolyl, 1-[(4-methylphenyl)sulfonyl]indolyl, 3,5-dimethylisoxazolyl, naphthyl, pyrazolyl, 3,5-dimethylpyrazolyl, 1-methylpyrazolyl, 6-oxopyridazinyl, pyridyl, 6-aminopyridyl, 2-cyanopyridyl, pyrimidinyl, 2-methoxypyrimidinyl, 2-pyrrolyl, 3-pyrrolyl, quinolinyl, thienyl, 3,4-(methylenedioxy)phenyl, and phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl.

Another example of a particular embodiment of the compounds for the invention is an eight-membered fused bicyclic ring, for example wherein Z is

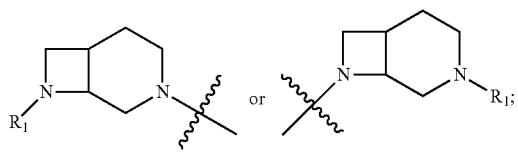

Ar₁ is pyridazinyl, pyrimidinyl, or thiazolyl; and Ar₂ is as described, or more particularly, selected from the group consisting of 3,4-(methylenedioxy)phenyl and phenyl wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl.

Another example of a particular embodiment of the compounds for the invention is an eight-membered fused bicyclic ring, for example wherein Z is

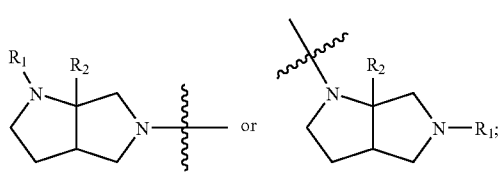

Ar$_1$ is selected from the group consisting of isoxazolyl, oxadiazolyl, oxazolyl, pyrazolyl, pyridazinyl, 4-methylpyridazinyl, 5-methylpyridazinyl, pyridyl, 5-cyanopyridyl, pyrimidinyl, thiadiazolyl, thiazolyl, thienyl, and phenyl substituted with 0 or 1 substituent selected from the group consisting alkoxy, alkyl, cyano, and hydroxy; Ar$_2$ is selected from the group consisting of benzofuranyl, benzothienyl, carbazolyl, tetrahydrocarbazolyl, furyl; imidazolyl, 3-methylindazolyl, 3-indolyl, 5-indolyl, 1-methyl-3-indolyl, 1-methyl-5-indolyl, 3-methyl-5-indolyl, 3-[(dimethylamino)methyl]indolyl, 1-[(4-methylphenyl)sulfonyl]indolyl, 3,5-dimethylisoxazolyl, naphthyl, pyrazolyl, 3,5-dimethylpyrazolyl, 1-methylpyrazolyl, 6-oxopyridazinyl, pyridyl, 6-aminopyridyl, 2-cyanopyridyl, pyrimidinyl, 2-methoxypyrimidinyl, 2-pyrrolyl, 3-pyrrolyl, quinolinyl, thienyl, 3,4-(methylenedioxy) phenyl, and phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl.

Another example of a particular embodiment of the compounds for the invention is a seven-membered bridged bicyclic ring, for example wherein Z is

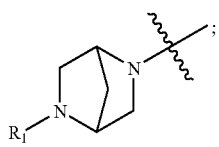

Ar$_1$ is selected from the group consisting of isoxazolyl, oxadiazolyl, oxazolyl, pyrazolyl, pyridazinyl, 4-methylpyridazinyl, 5-methylpyridazinyl, pyridyl, 5-cyanopyridyl, pyrimidinyl, thiadiazolyl, thiazolyl, thienyl, and phenyl substituted with 0 or 1 substituent selected from the group consisting alkoxy, alkyl, cyano, and hydroxy; Ar$_2$ is selected from the group consisting of benzofuranyl, benzothienyl, carbazolyl, tetrahydrocarbazolyl, furyl; imidazolyl, 3-methylindazolyl, 3-indolyl, 5-indolyl, 1-methyl-3-indolyl, 1-methyl-5-indolyl, 3-methyl-5-indolyl, 3-[(dimethylamino)methyl]indolyl, 1-[(4-methylphenyl)sulfonyl]indolyl, 3,5-dimethylisoxazolyl, naphthyl, pyrazolyl, 3,5-dimethylpyrazolyl, 1-methylpyrazolyl, 6-oxopyridazinyl, pyridyl, 6-aminopyridyl, 2-cyanopyridyl, pyrimidinyl, 2-methoxypyrimidinyl, 2-pyrrolyl, 3-pyrrolyl, quinolinyl, thienyl, 3,4-(methylenedioxy) phenyl, and phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl.

Another example of a particular embodiment of the compounds for the invention is a nine-membered fused bicyclic ring, for example wherein Z is

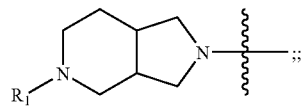

Ar$_1$ is selected from the group consisting of isoxazolyl, oxadiazolyl, oxazolyl, pyrazolyl, pyridazinyl, 4-methylpyridazinyl, 5-methylpyridazinyl, pyridyl, 5-cyanopyridyl, pyrimidinyl, thiadiazolyl, thiazolyl, thienyl, and phenyl substituted with 0 or 1 substituent selected from the group consisting alkoxy, alkyl, cyano, and hydroxy; Ar$_2$ is selected from the group consisting of benzofuranyl, benzothienyl, carbazolyl, tetrahydrocarbazolyl, furyl; imidazolyl, 3-methylindazolyl, 3-indolyl, 5-indolyl, 1-methyl-3-indolyl, 1-methyl-5-indolyl, 3-methyl-5-indolyl, 3-[(dimethylamino)methyl]indolyl, 1-[(4-methylphenyl)sulfonyl]indolyl, 3,5-dimethylisoxazolyl, naphthyl, pyrazolyl, 3,5-dimethylpyrazolyl, 1-methylpyrazolyl, 6-oxopyridazinyl, pyridyl, 6-aminopyridyl, 2-cyanopyridyl, pyrimidinyl, 2-methoxypyrimidinyl, 2-pyrrolyl, 3-pyrrolyl, quinolinyl, thienyl, 3,4-(methylenedioxy) phenyl, and phenyl, wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl.

Specific embodiments contemplated include, but are not limited to, compounds of formula (I), as defined, wherein:
3-(6-phenyl-pyridazin-3-yl)-3,8-diaza-bicyclo[3.2.1]octane;
8-methyl-3-(6-phenyl-pyridazin-3-yl)-3,8-diaza-bicyclo [3.2.1]octane;
6-methyl-3-(6-phenyl-pyridazin-3-yl)-3,6-diaza-bicyclo [3.2.1]octane;
3-(6-phenyl-pyridazin-3-yl)-3,8-diaza-bicyclo[4.2.0]octane;
8-methyl-3-(6-phenyl-pyridazin-3-yl)-3,8-diaza-bicyclo [4.2.0]octane;
2-(6-phenyl-pyridazin-3-yl)-octahydro-pyrrolo[3,4-c]pyrrole;
2-methyl-5-(6-phenyl-pyridazin-3-yl)-octahydro-pyrrolo[3, 4-c]pyrrole;
2-(6-m-tolyl-pyridazin-3-yl)-octahydro-pyrrolo[3,4-c]pyrrole;
2-methyl-5-(6-m-tolyl-pyridazin-3-yl)-octahydro-pyrrolo[3, 4-c]pyrrole;
2-[6-(4-methoxy-phenyl)-pyridazin-3-yl]-octahydro-pyrrolo[3,4-c]pyrrole;
2-(6-biphenyl-3-yl-pyridin-3-yl)-octahydro-pyrrolo[3,4-c] pyrrole;
2-(6-biphenyl-3-yl-pyridin-3-yl)-5-methyl-octahydro-pyrrolo[3,4-c]pyrrole;
2-[6-(3-trifluoromethyl-phenyl)-pyridin-3-yl]-octahydropyrrolo[3,4-c]pyrrole;
2-methyl-5-[6-(3-trifluoromethyl-phenyl)-pyridin-3-yl]-octahydro-pyrrolo[3,4-c]pyrrole;
3-[5-(hexahydro-pyrrolo[3,4-c]pyrrol-2-yl)-pyridin-2-yl]-phenylamine;
5-(6-furan-3-yl-pyridin-3-yl)-hexahydro-pyrrolo[3,4-c]pyrrole;
2-(6-furan-3-yl-pyridin-3-yl)-5-methyl-octahydro-pyrrolo [3,4-c]pyrrole;

2-(6-benzo[b]thiophen-2-yl-pyridin-3-yl)-octahydro-pyrrolo[3,4-c]pyrrole;
2-(6-benzo[b]thiophen-2-yl-pyridin-3-yl)-5-methyl-octahydro-pyrrolo[3,4-c]pyrrole;
2-(5-phenyl-pyridin-2-yl)-octahydro-pyrrolo[3,4-c]pyrrole;
2-methyl-5-(5-phenyl-pyridin-2-yl)-octahydro-pyrrolo[3,4-c]pyrrole;
2-(2-phenyl-pyrimidin-5-yl)-octahydro-pyrrolo[3,4-c]pyrrole;
2-methyl-5-(2-phenyl-pyrimidin-5-yl)-octahydro-pyrrolo[3,4-c]pyrrole;
diethyl-(2-{3-[6-(hexahydro-pyrrolo[3,4-c]pyrrol-2-yl)-pyridazin-3-yl]-phenoxy}-ethyl)-amine;
diethyl-(2-{3-[6-(5-methyl-hexahydro-pyrrolo[3,4-c]pyrrol-2-yl)-pyridazin-3-yl]-phenoxy}-ethyl)-amine;
2-(5-phenyl-[1,3,4]thiadiazol-2-yl)-octahydro-pyrrolo[3,4-c]pyrrole;
2-(3-phenyl-[1,2,4]thiadiazol-5-yl)-octahydro-pyrrolo[3,4-c]pyrrole;
2-methyl-5-(3-phenyl-[1,2,4]thiadiazol-5-yl)-octahydro-pyrrolo[3,4-c]pyrrole;
2-(1-phenyl-1h-pyrazol-4-yl)-octahydro-pyrrolo[3,4-c]pyrrole;
2-(2-methoxy-biphenyl-4-yl)-octahydro-pyrrolo[3,4-c]pyrrole;
2-(2-methoxy-biphenyl-4-yl)-5-methyl-octahydro-pyrrolo[3,4-c]pyrrole;
2-methyl-5-(3-phenyl-isoxazol-5-yl)-octahydro-pyrrolo[3,4-c]pyrrole;
(1S,5S) 3-(6-phenyl-pyridazin-3-yl)-3,6-diaza-bicyclo[3.2.0]heptane;
(1S,5S)-6-methyl-3-(6-phenyl-pyridazin-3-yl)-3,6-diaza-bicyclo[3.2.0]heptane;
(1R,5S)-6-(6-phenyl-pyridazin-3-yl)-3,6-diaza-bicyclo[3.2.0]heptane;
(1R,5S)-3-methyl-6-(6-phenyl-pyridazin-3-yl)-3,6-diaza-bicyclo[3.2.0]heptane;
(1R,5R) 3-(6-phenyl-pyridazin-3-yl)-3,6-diaza-bicyclo[3.2.0]heptane;
(1R,5R)-6-methyl-3-(6-phenyl-pyridazin-3-yl)-3,6-diaza-bicyclo[3.2.0]heptane;
(1R,5R)-3-(6-benzo[1,3]dioxol-5-yl-pyridazin-3-yl)-3,6-diaza-bicyclo[3.2.0]heptane;
(1R,5R)-3-(6-benzo[1,3]dioxol-5-yl-pyridazin-3-yl)-6-methyl-3,6-diaza-bicyclo[3.2.0]heptane;
(1R,5R)-1-{4-[5-(3,6-diaza-bicyclo[3.2.0]hept-3-yl)-pyridin-2-yl]-phenyl}-ethanone;
(1R,5R)-1-{4-[5-(6-methyl-3,6-diaza-bicyclo[3.2.0]hept-3-yl)-pyridin-2-yl]-phenyl}ethanone;
6a-methyl-5-(6-m-tolyl-pyridin-3-yl)-octahydro-pyrrolo[3,4-b]pyrrole;
2-(5-phenyl-thiazol-2-yl)-octahydro-pyrrolo[3,4-c]pyrrole;
2-methyl-5-(5-phenyl-thiazol-2-yl)-octahydro-pyrrolo[3,4-c]pyrrole;
3-(6-Phenyl-pyridazin-3-yl)-3,8-diaza-bicyclo[4.2.0]octane;
8-(6-Phenyl-pyridazin-3-yl)-3,8-diaza-bicyclo[4.2.0]octane;
3-Methyl-8-(6-phenyl-pyridazin-3-yl)-3,8-diaza-bicyclo[3.2.1]octane;
6a-Methyl-5-(6-phenyl-pyridazin-3-yl)-octahydro-pyrrolo[3,4-b]pyrrole;
2-(6-Phenyl-pyridazin-3-yl)-hexahydro-pyrrolo[3,4-c]pyrrole-3a-carboxylic acid ethyl ester;
2,5-Bis-(6-phenyl-pyridazin-3-yl)-hexahydro-pyrrolo[3,4-c]pyrrole-3a-carboxylic acid ethyl ester;
(1R,5R)-6-(6-Phenyl-pyridazin-3-yl)-2,6-diaza-bicyclo[3.2.0]heptane;
(1R,5R)-2-(6-Phenyl-pyridazin-3-yl)-2,6-diaza-bicyclo[3.2.0]heptane;
Ethyl 2-Methyl-5-(6-phenyl-pyridazin-3-yl)-hexahydro-pyrrolo[3,4-c]pyrrole-3a-carboxylate;
5-Methyl-2-(6-phenyl-pyridazin-3-yl)-octahydro-pyrrolo[3,4-c]pyridine;
1-Benzyl-6a-methyl-5-(6-phenyl-pyridazin-3-yl)-octahydro-pyrrolo[3,4-b]pyrrole;
3-Methyl-6-(6-phenyl-pyridazin-3-yl)-3,6-diaza-bicyclo[3.2.1]octane;
8-(6-Phenyl-pyridazin-3-yl)-3,8-diaza-bicyclo[4.2.0]octane;
3-Methyl-8-(6-phenyl-pyridazin-3-yl)-3,8-diaza-bicyclo[4.2.0]octane;
3-Methyl-8-(6-phenyl-pyridazin-3-yl)-3,8-diaza-bicyclo[4.2.0]octane;
3-Methyl-8-(6-phenyl-pyridazin-3-yl)-3,8-diaza-bicyclo[3.2.1]octane;
1,6a-Dimethyl-5-(6-phenyl-pyridazin-3-yl)-octahydro-pyrrolo[3,4-b]pyrrole;
2-[6-(4-Bromo-phenyl)-pyridazin-3-yl]-5-methyl-octahydro-pyrrolo[3,4-c]pyrrole;
(1S,5S)-3-[6-(4-Bromo-phenyl)-pyridazin-3-yl]-3,6-diaza-bicyclo[3.2.0]heptane;
(1S,5S)-3-[6-(4-Bromo-phenyl)-pyridazin-3-yl]-6-methyl-3,6-diaza-bicyclo[3.2.0]heptane;
3-[6-(Hexahydro-pyrrolo[3,4-c]pyrrol-2-yl)-pyridazin-3-yl]-1H-indole;
3-[6-(5-Methyl-hexahydro-pyrrolo[3,4-c]pyrrol-2-yl)-pyridazin-3-yl]-1H-indole;
(1R,5R)-3-[6-(3,6-Diaza-bicyclo[3.2.0]hept-3-yl)-pyridazin-3-yl]-1H-indole;
(1S,5S)-3-[6-(3,6-Diaza-bicyclo[3.2.0]hept-3-yl)-pyridazin-3-yl]-1H-indole;
(1R,5R)-3-[6-(6-Methyl-3,6-diaza-bicyclo[3.2.0]hept-3-yl)-pyridazin-3-yl]-1H-indole;
2-[6-(4-Nitro-phenyl)-pyridazin-3-yl]-octahydro-pyrrolo[3,4-c]pyrrole;
2-[6-(2-Nitro-phenyl)-pyridazin-3-yl]-octahydro-pyrrolo[3,4-c]pyrrole;
2-[6-(3-Nitro-phenyl)-pyridazin-3-yl]-octahydro-pyrrolo[3,4-c]pyrrole;
2-Methyl-5-[6-(4-nitro-phenyl)-pyridazin-3-yl]-octahydro-pyrrolo[3,4-c]pyrrole;
2-Methyl-5-[6-(3-nitro-phenyl)-pyridazin-3-yl]-octahydro-pyrrolo[3,4-c]pyrrole;
2-(6-Imidazol-1-yl-pyridazin-3-yl)-5-methyl-octahydro-pyrrolo[3,4-c]pyrrole;
2-(6-Imidazol-1-yl-pyridazin-3-yl)-octahydro-pyrrolo[3,4-c]pyrrole;
(1R,5S)-6-[6-(4-Iodo-phenyl)-pyridazin-3-yl]-3,6-diaza-bicyclo[3.2.0]heptane;
(1S,5S)-3-[6-(4-Iodo-phenyl)-pyridazin-3-yl]-3,6-diaza-bicyclo[3.2.0]heptane;
(1S,5S)-3-[6-(4-Iodo-phenyl)-pyridazin-3-yl]-6-methyl-3,6-diaza-bicyclo[3.2.0]heptane;
2-(5-Methyl-6-phenyl-pyridazin-3-yl)-octahydro-pyrrolo[3,4-c]pyrrole;
2-Methyl-5-(5-methyl-6-phenyl-pyridazin-3-yl)-octahydro-pyrrolo[3,4-c]pyrrole;
2-(4-Methyl-6-phenyl-pyridazin-3-yl)-octahydro-pyrrolo[3,4-c]pyrrole;
2-Methyl-5-(4-methyl-6-phenyl-pyridazin-3-yl)-octahydro-pyrrolo[3,4-c]pyrrole;
2-(6-o-Tolyl-pyridazin-3-yl)-octahydro-pyrrolo[3,4-c]pyrrole;
2-(6-p-Tolyl-pyridazin-3-yl)-octahydro-pyrrolo[3,4-c]pyrrole;

2-[6-(3,5-Dimethyl-phenyl)-pyridazin-3-yl]-octahydro-pyrrolo[3,4-c]pyrrole;
2-(6-Furan-3-yl-pyridazin-3-yl)-octahydro-pyrrolo[3,4-c]pyrrole;
2-(6-Thiophen-3-yl-pyridazin-3-yl)-octahydro-pyrrolo[3,4-c]pyrrole;
2-Methyl-5-(6-thiophen-3-yl-pyridazin-3-yl)-octahydro-pyrrolo[3,4-c]pyrrole;
5-[6-(Hexahydro-pyrrolo[3,4-c]pyrrol-2-yl)-pyridazin-3-yl]-1H-indole;
5-[6-(Hexahydro-pyrrolo[3,4-c]pyrrol-2-yl)-pyridazin-3-yl]-1-methyl-1H-indole;
2-Methyl-5-(6-o-tolyl-pyridazin-3-yl)-octahydro-pyrrolo[3,4-c]pyrrole;
2-Methyl-5-(6-p-tolyl-pyridazin-3-yl)-octahydro-pyrrolo[3,4-c]pyrrole;
2-[6-(3,5-Dimethyl-phenyl)-pyridazin-3-yl]-5-methyl-octahydro-pyrrolo[3,4-c]pyrrole;
2-(6-Furan-3-yl-pyridazin-3-yl)-5-methyl-octahydro-pyrrolo[3,4-c]pyrrole;
3-Methyl-8-(6-phenyl-pyridazin-3-yl)-3,8-diaza-bicyclo[4.2.0]octane;
5-[6-(5-Methyl-hexahydro-pyrrolo[3,4-c]pyrrol-2-yl)-pyridazin-3-yl]-1H-indole;
3-Methyl-5-[6-(5-methyl-hexahydro-pyrrolo[3,4-c]pyrrol-2-yl)-pyridazin-3-yl]-1H-indole;
2-Methyl-5-[6-(5-methyl-hexahydro-pyrrolo[3,4-c]pyrrol-2-yl)-pyridazin-3-yl]-phenylamine;
4-[6-(5-Methyl-hexahydro-pyrrolo[3,4-c]pyrrol-2-yl)-pyridazin-3-yl]-phenylamine;
4-[6-(5-Methyl-hexahydro-pyrrolo[3,4-c]pyrrol-2-yl)-pyridazin-3-yl]-1H-indole;
2-(6-Benzofuran-2-yl-pyridazin-3-yl)-5-methyl-octahydro-pyrrolo[3,4-c]pyrrole;
5-[6-(5-Methyl-hexahydro-pyrrolo[3,4-c]pyrrol-2-yl)-pyridazin-3-yl]-pyridin-2-ylamine;
2-Methyl-5-[6-(1H-pyrrol-3-yl)-pyridazin-3-yl]-octahydro-pyrrolo[3,4-c]pyrrole;
2-Methyl-5-(6-thiophen-2-yl-pyridazin-3-yl)-octahydro-pyrrolo[3,4-c]pyrrole;
2-Methyl-5-[6-(1H-pyrazol-4-yl)-pyridazin-3-yl]-octahydro-pyrrolo[3,4-c]pyrrole;
3-[6-(5-Methyl-hexahydro-pyrrolo[3,4-c]pyrrol-2-yl)-pyridazin-3-yl]-9H-carbazole;
2-(6-Furan-2-yl-pyridazin-3-yl)-5-methyl-octahydro-pyrrolo[3,4-c]pyrrole;
2-Methyl-5-(5-pyrimidin-5-yl-pyridin-2-yl)-octahydro-pyrrolo[3,4-c]pyrrole;
2-Methyl-5-[5-(1H-pyrazol-4-yl)-pyridin-2-yl]-octahydro-pyrrolo[3,4-c]pyrrole;
3-[6-(5-Methyl-hexahydro-pyrrolo[3,4-c]pyrrol-2-yl)-pyridin-3-yl]-benzonitrile;
2-[5-(2-Methoxy-pyrimidin-5-yl)-pyridin-2-yl]-5-methyl-octahydro-pyrrolo[3,4-c]pyrrole;
2-[5-(3,5-Dimethyl-1H-pyrazol-4-yl)-pyridin-2-yl]-5-methyl-octahydro-pyrrolo[3,4-c]pyrrole;
2-Methyl-5-[5-(1-methyl-1H-pyrazol-4-yl)-pyridin-2-yl]-octahydro-pyrrolo[3,4-c]pyrrole;
2-[5-(3,5-Dimethyl-isoxazol-4-yl)-pyridin-2-yl]-5-methyl-octahydro-pyrrolo[3,4-c]pyrrole;
6-(5-Methyl-hexahydro-pyrrolo[3,4-c]pyrrol-2-yl)-[3,3']bipyridinyl;
6-(5-Methyl-hexahydro-pyrrolo[3,4-c]pyrrol-2-yl)-[3,4']bipyridinyl;
4-[6-(5-Methyl-hexahydro-pyrrolo[3,4-c]pyrrol-2-yl)-pyridin-3-yl]-benzonitrile;
6'-(5-Methyl-hexahydro-pyrrolo[3,4-c]pyrrol-2-yl)-[3,3']bipyridinyl-6-ylamine;
2-Methyl-5-[5-(1H-pyrrol-3-yl)-pyridin-2-yl]-octahydro-pyrrolo[3,4-c]pyrrole;
2-Methyl-5-[5-(1H-pyrrol-2-yl)-pyridin-2-yl]-octahydro-pyrrolo[3,4-c]pyrrole;
6'-(5-Methyl-hexahydro-pyrrolo[3,4-c]pyrrol-2-yl)-[3,3']bipyridinyl-2-carbonitrile;
2-(5-Furan-3-yl-pyridin-2-yl)-5-methyl-octahydro-pyrrolo[3,4-c]pyrrole;
2-Methyl-5-(5-thiophen-2-yl-pyridin-2-yl)-octahydro-pyrrolo[3,4-c]pyrrole;
2-Methyl-5-(5-thiophen-3-yl-pyridin-2-yl)-octahydro-pyrrolo[3,4-c]pyrrole;
2-(5-Benzofuran-5-yl-pyridin-2-yl)-5-methyl-octahydro-pyrrolo[3,4-c]pyrrole;
2-(5-Furan-2-yl-pyridin-2-yl)-5-methyl-octahydro-pyrrolo[3,4-c]pyrrole;
3-[6-(5-Methyl-hexahydro-pyrrolo[3,4-c]pyrrol-2-yl)-pyridin-3-yl]-9H-carbazole;
5-[6-(5-Methyl-hexahydro-pyrrolo[3,4-c]pyrrol-2-yl)-pyridin-3-yl]-1H-indole;
4-[6-(5-Methyl-hexahydro-pyrrolo[3,4-c]pyrrol-2-yl)-pyridin-3-yl]-1H-indole;
2-[6-(5-Methyl-hexahydro-pyrrolo[3,4-c]pyrrol-2-yl)-pyridin-3-yl]-2H-pyridazin-3-one;
2-(6-Phenyl-pyridin-3-yl)-octahydro-pyrrolo[3,4-c]pyrrole;
2-(6-o-Tolyl-pyridin-3-yl)-octahydro-pyrrolo[3,4-c]pyrrole;
2-(6-m-Tolyl-pyridin-3-yl)-octahydro-pyrrolo[3,4-c]pyrrole;
2-[6-(3-Methoxy-phenyl)-pyridin-3-yl]-octahydro-pyrrolo[3,4-c]pyrrole
2-[6-(3-Trifluoromethoxy-phenyl)-pyridin-3-yl]-octahydro-pyrrolo[3,4-c]pyrrole;
2-(6-Thiophen-3-yl-pyridin-3-yl)-octahydro-pyrrolo[3,4-c]pyrrole;
8-[5-(Hexahydro-pyrrolo[3,4-c]pyrrol-2-yl)-pyridin-2-yl]-quinoline;
2-(6-Naphthalen-2-yl-pyridin-3-yl)-octahydro-pyrrolo[3,4-c]pyrrole;
2-(6-Benzofuran-2-yl-pyridin-3-yl)-octahydro-pyrrolo[3,4-c]pyrrole;
2-Methyl-5-(6-o-tolyl-pyridin-3-yl)-octahydro-pyrrolo[3,4-c]pyrrole;
2-Methyl-5-(6-m-tolyl-pyridin-3-yl)-octahydro-pyrrolo[3,4-c]pyrrole;
2-Methyl-5-(6-phenyl-pyridin-3-yl)-octahydro-pyrrolo[3,4-c]pyrrole;
2-[6-(3-Methoxy-phenyl)-pyridin-3-yl]-5-methyl-octahydro-pyrrolo[3,4-c]pyrrole;
2-Methyl-5-[6-(3-trifluoromethoxy-phenyl)-pyridin-3-yl]-octahydro-pyrrolo[3,4-c]pyrrole;
2-Methyl-5-[6-(3-nitro-phenyl)-pyridin-3-yl]-octahydro-pyrrolo[3,4-c]pyrrole;
2-Methyl-5-(6-thiophen-3-yl-pyridin-3-yl)-octahydro-pyrrolo[3,4-c]pyrrole;
8-[5-(5-Methyl-hexahydro-pyrrolo[3,4-c]pyrrol-2-yl)-pyridin-2-yl]-quinoline;
2-Methyl-5-(6-naphthalen-2-yl-pyridin-3-yl)-octahydro-pyrrolo[3,4-c]pyrrole;
5-[5-(5-Methyl-hexahydro-pyrrolo[3,4-c]pyrrol-2-yl)-pyridin-2-yl]-1H-indole;
4-[5-(5-Methyl-hexahydro-pyrrolo[3,4-c]pyrrol-2-yl)-pyridin-2-yl]-1H-indole;
5-[5-(5-Methyl-hexahydro-pyrrolo[3,4-c]pyrrol-2-yl)-pyridin-2-yl]-quinoline;

(1R,5R)-3-(6-p-Tolyl-pyridazin-3-yl)-3,6-diaza-bicyclo[3.2.0]heptane;
(1R,5R)-3-(6-o-Tolyl-pyridazin-3-yl)-3,6-diaza-bicyclo[3.2.0]heptane;
(1R,5R)-3-(6-m-Tolyl-pyridazin-3-yl)-3,6-diaza-bicyclo[3.2.0]heptane;
(1R,5R)-6-Methyl-3-(6-p-tolyl-pyridazin-3-yl)-3,6-diaza-bicyclo[3.2.0]heptane;
(1R,5R)-6-Methyl-3-(6-o-tolyl-pyridazin-3-yl)-3,6-diaza-bicyclo[3.2.0]heptane;
(1S,5S)-5-[6-(3,6-Diaza-bicyclo[3.2.0]hept-3-yl)-pyridazin-3-yl]-1H-indole;
(1S,5S)-5-[6-(6-Methyl-3,6-diaza-bicyclo[3.2.0]hept-3-yl)-pyridazin-3-yl]-1H-indole;
(1S,5S)-4-[6-(6-Methyl-3,6-diaza-bicyclo[3.2.0]hept-3-yl)-pyridazin-3-yl]-1H-indole;
(1S,5S)-3-(6-Benzofuran-5-yl-pyridazin-3-yl)-6-methyl-3,6-diaza-bicyclo[3.2.0]heptane;
(1S,5S)-4-[6-(3,6-Diaza-bicyclo[3.2.0]hept-3-yl)-pyridazin-3-yl]-phenylamine;
(1R,5S)-3-[6-(3-Methyl-3,6-diaza-bicyclo[3.2.0]hept-6-yl)-pyridazin-3-yl]-thiophene;
(1R,5S)-5-[6-(3-Methyl-3,6-diaza-bicyclo[3.2.0]hept-6-yl)-pyridazin-3-yl]-1H-indole
(1R,5S)-4-[6-(3-Methyl-3,6-diaza-bicyclo[3.2.0]hept-6-yl)-pyridazin-3-yl]-1H-indole
3-Methyl-5-[6-(5-methyl-hexahydro-pyrrolo[3,4-c]pyrrol-2-yl)-pyridazin-3-yl]-1H-indazole;
(1S,5S)-5-[6-(3,6-Diaza-bicyclo[3.2.0]hept-3-yl)-pyridin-3-yl]-3-methyl-1H-indazole;
(1R,5R)-{4-[5-(3,6-Diaza-bicyclo[3.2.0]hept-3-yl)-pyridin-2-yl]-phenyl}-dimethyl-amine;
(1R,5R)-6-Methyl-3-(6-m-tolyl-pyridin-3-yl)-3,6-diaza-bicyclo[3.2.0]heptane;
(1R,5R)-6-Methyl-3-(6-p-tolyl-pyridin-3-yl)-3,6-diaza-bicyclo[3.2.0]heptane;
(1R,5R)-3-[5-(6-Methyl-3,6-diaza-bicyclo[3.2.0]hept-3-yl)-pyridin-2-yl]-benzonitrile;
(1R,5R)-3-[6-(4-Ethyl-phenyl)-pyridin-3-yl]-6-methyl-3,6-diaza-bicyclo[3.2.0]heptane;
(1R,5R)-Dimethyl-{4-[5-(6-methyl-3,6-diaza-bicyclo[3.2.0]hept-3-yl)-pyridin-2-yl]-phenyl}-amine;
(1R,5R)-3-[6-(3-Methoxy-phenyl)-pyridin-3-yl]-6-methyl-3,6-diaza-bicyclo[3.2.0]heptane;
(1R,5R)-3-(6-Benzo[1,3]dioxol-5-yl-pyridin-3-yl)-6-methyl-3,6-diaza-bicyclo[3.2.0]heptane;
(1R,5R)-3-[6-(4-Methoxy-phenyl)-pyridin-3-yl]-6-methyl-3,6-diaza-bicyclo[3.2.0]heptane;
(1R,5R)-3-[6-(3,4-Dimethoxy-phenyl)-pyridin-3-yl]-6-methyl-3,6-diaza-bicyclo[3.2.0]heptane;
(1R,5R)-6-Methyl-3-(6-phenyl-pyridin-3-yl)-3,6-diaza-bicyclo[3.2.0]heptane;
(1R,5R)-5-(6-Methyl-3,6-diaza-bicyclo[3.2.0]hept-3-yl)-[2,3']bipyridinyl;
(1R,5R)-5-[5-(6-Methyl-3,6-diaza-bicyclo[3.2.0]hept-3-yl)-pyridin-2-yl]-1H-indole;
(1S,5S)-5-[5-(6-Methyl-3,6-diaza-bicyclo[3.2.0]hept-3-yl)-pyridin-2-yl]-1H-indole;
(1R,5S)-6-(6-Phenyl-pyridin-3-yl)-3,6-diaza-bicyclo[3.2.0]heptane;
(1R,5S)-6-(6-m-Tolyl-pyridin-3-yl)-3,6-diaza-bicyclo[3.2.0]heptane;
(1R,5S)-3-Methyl-6-(6-phenyl-pyridin-3-yl)-3,6-diaza-bicyclo[3.2.0]heptane;
(1R,5S)-5-[5-(3-Methyl-3,6-diaza-bicyclo[3.2.0]hept-6-yl)-pyridin-2-yl]-1H-indole;
(1S,5S)-5-[6-(3,6-Diaza-bicyclo[3.2.0]hept-3-yl)-pyridin-3-yl]-1H-indole;
(1S,5S)-3-(5-Phenyl-pyridin-2-yl)-3,6-diaza-bicyclo[3.2.0]heptane;
(1S,5S)-6-Methyl-3-(5-phenyl-pyridin-2-yl)-3,6-diaza-bicyclo[3.2.0]heptane;
(1S,5S)-5-[6-(6-Methyl-3,6-diaza-bicyclo[3.2.0]hept-3-yl)-pyridin-3-yl]-H-indole;
2-(4-Phenyl-thiophen-2-yl)-octahydro-pyrrolo[3,4-c]pyrrole;
2-Methyl-5-(5-phenyl-[1,3,4]thiadiazol-2-yl)-octahydro-pyrrolo[3,4-c]pyrrole;
2-(2-Phenyl-thiazol-5-yl)-octahydro-pyrrolo[3,4-c]pyrrole;
2-Methyl-5-(2-phenyl-thiazol-5-yl)-octahydro-pyrrolo[3,4-c]pyrrole;
2-(4-Phenyl-thiazol-2-yl)-octahydro-pyrrolo[3,4-c]pyrrole;
2-Benzyl-5-(6-phenyl pyridazin-3-yl)-octahydropyrrolo[3,4-c]pyrrole;
2-(6-Phenyl pyridazin-3-yl)-5-(pyridin-4-ylmethyl)-octahydropyrrolo[3,4-c]pyrrole;
2-(6-Phenyl pyridazin-3-yl)-5-(pyridin-2-ylmethyl)-octahydropyrrolo[3,4-c]pyrrole;
2-(6-Chloropyridin-3-ylmethyl)-5-(6-phenylpyridazin-3-yl)-octahydropyrrolo[3,4-c]pyrrole;
2-(6-Phenyl pyridazin-3-yl)-5-(2-pyridin-3-ylethyl)-octahydropyrrolo[3,4-c]pyrrole;
2-(6-Phenyl pyridazin-3-yl)-5-(pyridin-3-ylmethyl)-octahydropyrrolo[3,4-c]pyrrole;
2-Allyl-5-(6-phenyl-pyridazin-3-yl)-octahydro-pyrrolo[3,4-c]pyrrole;
2-But-2-enyl-5-(6-phenyl-pyridazin-3-yl)-octahydro-pyrrolo[3,4-c]pyrrole;
2-Ethyl-5-(6-phenyl-pyridazin-3-yl)-octahydro-pyrrolo[3,4-c]pyrrole;
2-(6-Phenyl-pyridazin-3-yl)-5-propyl-octahydro-pyrrolo[3,4-c]pyrrole;
2-Isopropyl-5-(6-phenyl-pyridazin-3-yl)-octahydro-pyrrolo[3,4-c]pyrrole;
(3aR,6aR)-5-(5-Phenyl-[1,3,4]oxadiazol-2-yl)-octahydro-pyrrolo[3,4-b]pyrrole;
2-(5-Phenyl-[1,3,4]oxadiazol-2-yl)-octahydro-pyrrolo[3,4-c]pyrrole;
2-[5-(4-Methoxy-phenyl)-[1,3,4]oxadiazol-2-yl]-octahydro-pyrrolo[3,4-c]pyrrole;
2-[5-(4-Methoxy-phenyl)-[1,3,4]oxadiazol-2-yl]-5-methyl-octahydro-pyrrolo[3,4-c]pyrrole;
2-[5-(4-Chloro-phenyl)-[1,3,4]oxadiazol-2-yl]-octahydro-pyrrolo[3,4-c]pyrrole;
6-Methyl-3-(5-phenyl-[1,3,4]oxadiazol-2-yl)-3,6-diaza-bicyclo[3.2.1]octane;
4-(Hexahydro-pyrrolo[3,4-c]pyrrol-2-yl)-biphenyl-2-ol;
4-(5-Methyl-hexahydro-pyrrolo[3,4-c]pyrrol-2-yl)-biphenyl-2-ol;
Diethyl-(2-{3-[6-(hexahydro-pyrrolo[3,4-c]pyrrol-2-yl)-pyridazin-3-yl]-phenoxy}-ethyl)-amine;
4-[6-(Hexahydro-pyrrolo[3,4-c]pyrrol-2-yl)-pyridazin-3-yl]-phenol;
Diethyl-(2-{4-[6-(hexahydro-pyrrolo[3,4-c]pyrrol-2-yl)-pyridazin-3-yl]-phenoxy}-ethyl)-amine;
(2-{4-[6-(Hexahydro-pyrrolo[3,4-c]pyrrol-2-yl)-pyridazin-3-yl]-phenoxy}-ethyl)-dimethyl-amine;
3-[6-(5-Methyl-hexahydro-pyrrolo[3,4-c]pyrrol-2-yl)-pyridazin-3-yl]-phenol;
4-[6-(5-Methyl-hexahydro-pyrrolo[3,4-c]pyrrol-2-yl)-pyridazin-3-yl]-phenol;
Diethyl-(2-{4-[6-(5-methyl-hexahydro-pyrrolo[3,4-c]pyrrol-2-yl)-pyridazin-3-yl]-phenoxy}-ethyl)-amine;

N-{4-[6-(5-Methyl-hexahydro-pyrrolo[3,4-c]pyrrol-2-yl)-pyridazin-3-yl]-phenyl}-methanesulfonamide;
N-{4-[6-(Hexahydro-pyrrolo[3,4-c]pyrrol-2-yl)-pyridazin-3-yl]-phenyl}-benzamide;
N-{4-[6-(Hexahydro-pyrrolo[3,4-c]pyrrol-2-yl)-pyridazin-3-yl]-phenyl}-methanesulfonamide;
N-{4-[6-(Hexahydro-pyrrolo[3,4-c]pyrrol-2-yl)-pyridazin-3-yl]-phenyl}-dimethylaminosulfonamide;
N-{4-[6-(Hexahydro-pyrrolo[3,4-c]pyrrol-2-yl)-pyridazin-3-yl]-phenyl}-acetamide;
N-{4-[6-(5-Methyl-hexahydro-pyrrolo[3,4-c]pyrrol-2-yl)-pyridazin-3-yl]-phenyl}-acetamide;
2-[5-(Hexahydro-pyrrolo[3,4-c]pyrrol-2-yl)-pyrimidin-2-yl]-phenol;
2-[5-(5-Methyl-hexahydro-pyrrolo[3,4-c]pyrrol-2-yl)-pyrimidin-2-yl]-phenol;
2-(4-Pyridin-3-yl-phenyl)-octahydro-pyrrolo[3,4-c]pyrrole;
2-Methyl-5-(4-pyridin-3-yl-phenyl)-octahydro-pyrrolo[3,4-c]pyrrole;
2-Biphenyl-4-yl-octahydro-pyrrolo[3,4-c]pyrrole;
2-Biphenyl-4-yl-5-methyl-octahydro-pyrrolo[3,4-c]pyrrole;
1-Methyl-5-[6-(5-methyl-hexahydro-pyrrolo[3,4-c]pyrrol-2-yl)-pyridazin-3-yl]-1H-indole;
Dimethyl-{5-[6-(5-methyl-hexahydro-pyrrolo[3,4-c]pyrrol-2-yl)-pyridazin-3-yl]-1H-indol-3-ylmethyl}-amine;
(1S,5S)-6-[6-(6-Methyl-3,6-diaza-bicyclo[3.2.0]hept-3-yl)-pyridazin-3-yl]-2,3,4,9-tetrahydro-1H-carbazole;
(1R,5S)-5-(3,6-Diaza-bicyclo[3.2.0]hept-6-yl)-2-thiophen-2-yl-nicotinonitrile;
(1R,5S)-5-(3-Methyl-3,6-diaza-bicyclo[3.2.0]hept-6-yl)-2-thiophen-2-yl-nicotinonitrile;
(1S,5S)-3-(4-Pyridin-3-yl-phenyl)-3,6-diaza-bicyclo[3.2.0]heptane;
(1S,5S)-6-Methyl-3-(4-pyridin-3-yl-phenyl)-3,6-diaza-bicyclo[3.2.0]heptane; and
(1S,5S)-5-[4-(3,6-Diaza-bicyclo[3.2.0]hept-3-yl)-phenyl]-3-methyl-1H-indazole;

or pharmaceutically acceptable salts, esters, amides, and prodrugs thereof.

Compound names are assigned by using AUTONOM naming software, which is provided by MDL Information Systems GmbH (formerly known as Beilstein Informationssysteme) of Frankfurt, Germany, and is part of the CHEMDRAW® ULTRA v. 6.0.2 software suite.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

As used in the descriptions of the schemes and the examples, certain abbreviations are intended to have the following meanings: Ac for acetyl; Bu for n-butyl; BINAP for 2,2'-bis(diphenylphosphino)-1,1'-binaphthyl; DBU for 1,8-diazabicyclo[5.4.0]undec-7-ene; DMSO for dimethylsulfoxide; EtOAc for ethyl acetate; EtOH for ethanol; Et$_3$N for triethylamine; Et$_2$O for diethyl ether; HPLC for high pressure liquid chromatography; i-Pr for isopropyl; MeOH for methanol; NBS for N-bromosuccinimide; OAc for acetate; Ph for phenyl; t-Bu for tert-butyl; and THF for tetrahydrofuran.

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (BOC), benzyloxycarbonyl (CBZ), benzyl (Bn), acetyl, and trifluoroacetyl. More particularly, the BOC protecting group may be removed by treatment with an acid such as trifluoroacetic acid or hydrochloric acid. The CBZ and Bn protecting groups may be removed by catalytic hydrogenation. The acetyl and trifluoroacetyl protecting groups may be removed by a hydroxide ion.

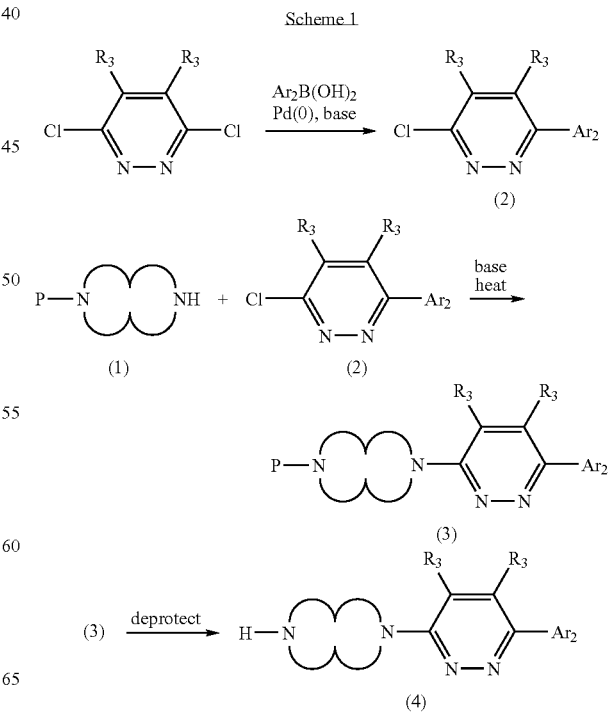

Scheme 1

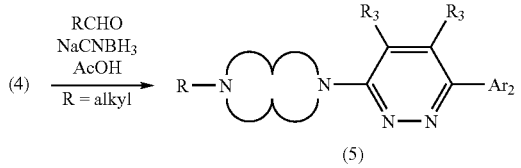

Pyridazines of general formula (4) and (5), wherein $Ar_2$ and $R_3$ are as defined in formula (I), can be prepared as described in Scheme 1. 3,6-Dichloropyridazines can be treated with a boronic acid, palladium (0), and a base to provide monochloropyridazines of general formula (2). Monochloropyridazines of general formula (2) can be treated with diazabicycles of the present invention and a base to provide pyridazines of general formula (3), wherein P is a nitrogen protecting group. Pyridazines of general formula (3) can be deprotected to provide pyridazines of general formula (4). Pyridazines of general formula (4) can be alkylated using reductive amination methods well-known to those of skill in the art to provide pyridazines of general formula (5) wherein R is alkyl.

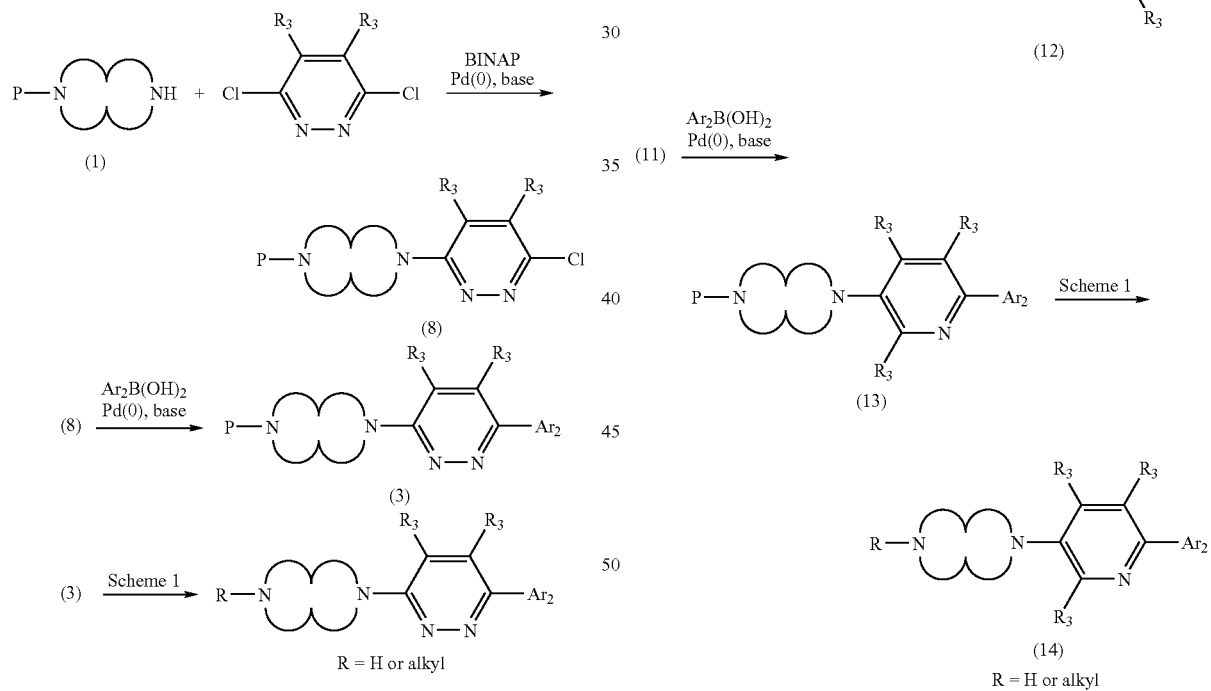

An alternative procedure for preparing pyridazines of general formula (4) and (5), wherein $Ar_2$ and $R_3$ are as defined in formula (I), is exemplified in Scheme 2. 3,6-Dichloropyridazines can be treated with diazabicycles of the present invention, palladium (0), BINAP, and a base to provide pyridazines of general formula (8), wherein P is a nitrogen protecting group. Pyridazines of general formula (8) can be treated with a boronic acid, palladium (0), and a base to provide pyridazines of general formula (3). Pyridazines of general formula (3) can be processed as described in Scheme 1 to provide pyridazines of general formula (4) and (5).

-continued

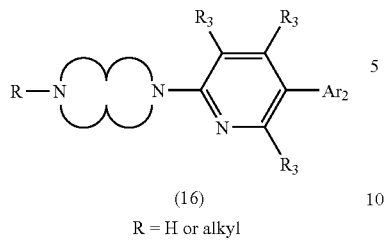

(16)

R = H or alkyl

Pyridines of general formula (14) and (16), wherein $Ar_2$ and $R_3$ are as defined in formula (I), can be prepared as described in Scheme 3. 2,5-Dihalopyridines can be treated with palladium (0), BINAP, a base, and diazabicycles of the present invention wherein P is a nitrogen protecting group to provide 5-diazabicyclo-2-halopyridines of general formula (11) and 2-diazabicyclo-5-halopyridines of general formula (12). 5-Diazabicyclo-2-halopyridines of general formula (11) and 2-diazabicyclo-5-halopyridines of general formula (12) can be processed as described in Scheme 1 to provide pyridines of general formula (14) and (16).

Scheme 4

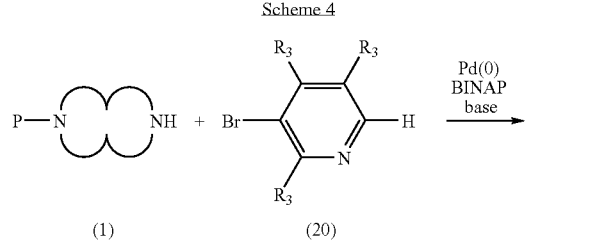

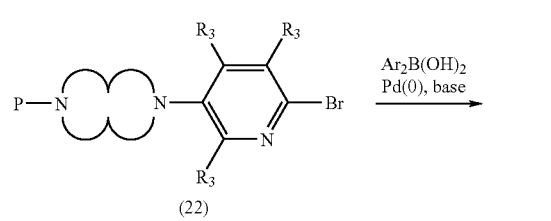

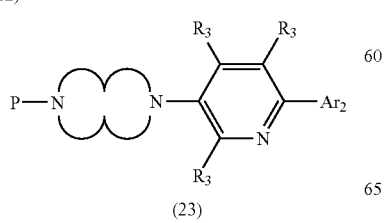

-continued

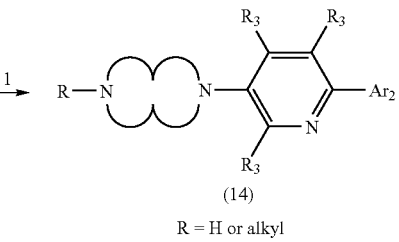

(14)

R = H or alkyl

An alternative procedure for preparing pyridines of general formula (14), wherein $Ar_2$ and $R_3$ are as defined in formula (I), is exemplified in Scheme 4. Diazabicycles of the present invention, wherein P is a nitrogen protecting group, can be treated with 5-bromopyridine, BINAP, palladium (0), and a base to provide pyridines of general formula (21). Pyridines of general formula (21) can be treated with N-bromosuccinimide to provide bromides of general formula (22). Bromides of general formula (22) can be treated with a boronic acid, palladium (0), and a base to provide biarylcompounds of general formula (23). Biarylcompounds of general formula (23) can be processed as described in Scheme 1 to provide pyridines of general formula (14).

Scheme 5

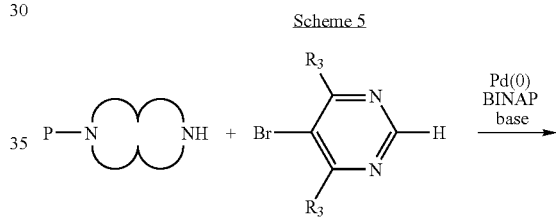

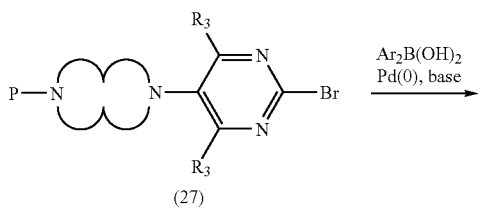

-continued

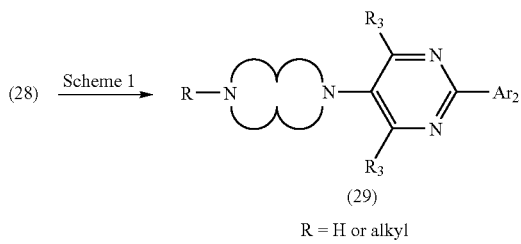

R = H or alkyl

Pyrimidines of general formula (29), wherein $Ar_2$ and $R_3$ are as defined in formula (1), can be prepared as described in Scheme 5. Diazabicycles of the present invention, wherein P is a nitrogen protecting group, can be treated with 5-bromopyrimidines of general formula (25), BINAP, palladium (0), and a base to provide pyrimidines of general formula (26). Pyrimidines of general formula (26) can be treated with N-bromosuccinimide to provide bromides of general formula (27). Bromides of general formula (27) can be treated with a boronic acid, palladium (0), and a base to provide biarylcompounds of general formula (28). Biarylcompounds of general formula (28) can be processed as described in Scheme 1 to provide pyrimidines of general formula (29).

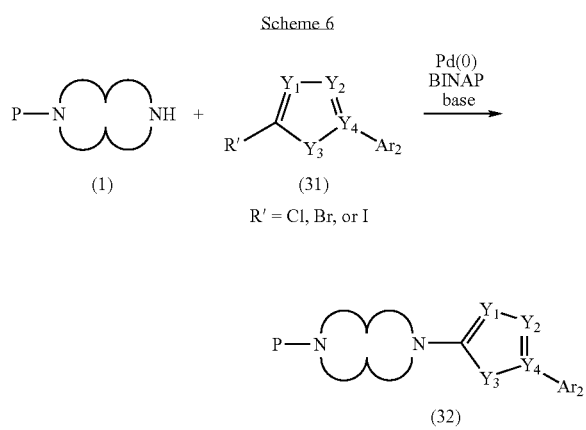

Compounds of general formula (33), wherein $Ar_2$, $Y_1$, $Y_2$, $Y_3$, and $Y_4$ are as defined in formula (I) can be prepared as described in Scheme 6. Diazabicyclic compounds of general formula (1), can be treated with 5-membered aromatic heteroaryls of general formula (31), purchased commercially or prepared using methodology well-known to those in the art, preferably in the presence of palladium (0), BINAP, and a base to provide compounds of general formula (32). Compounds of general formula (32) can be processed as described in Scheme 1 to provide compounds of general formula (33).

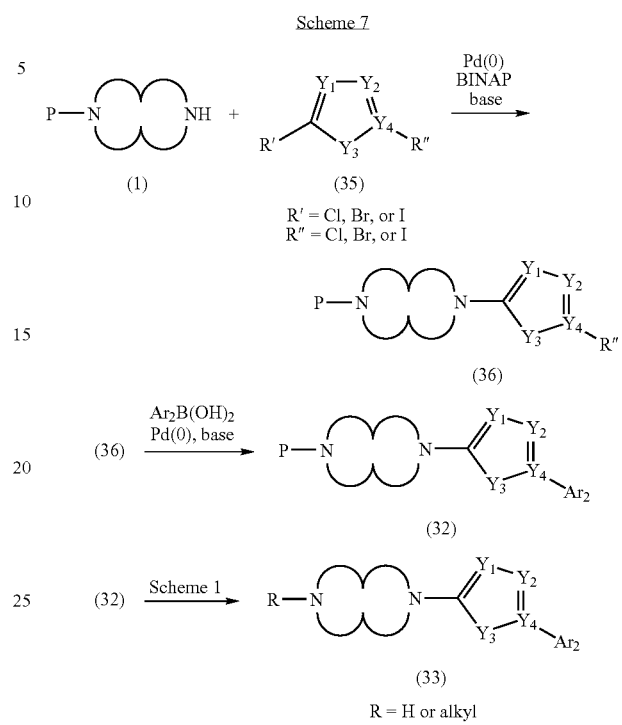

An alternate method of preparing compounds of general formula (33), wherein $Ar_2$, $Y_1$, $Y_2$, $Y_3$, and $Y_4$ are as defined in formula (I), is described in Scheme 7. Diazabicyclic compounds of general formula (1) can be treated with dihalo-5-membered aromatic heteroaryls of general formula (35), purchased commercially or prepared using methodology well-known to those in the art, in the presence of palladium (0), BINAP, and a base to provide monohalo compounds of general formula (36). Monohalo compounds of general formula (36) can be treated with boronic acids, palladium (0), and a base to provide compounds of general formula (32). Compounds of general formula (32) can be processed as described in Scheme 1 to provide compounds of general formula (33).

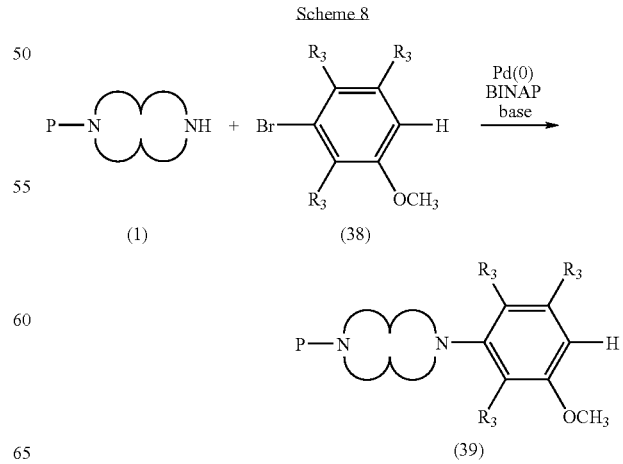

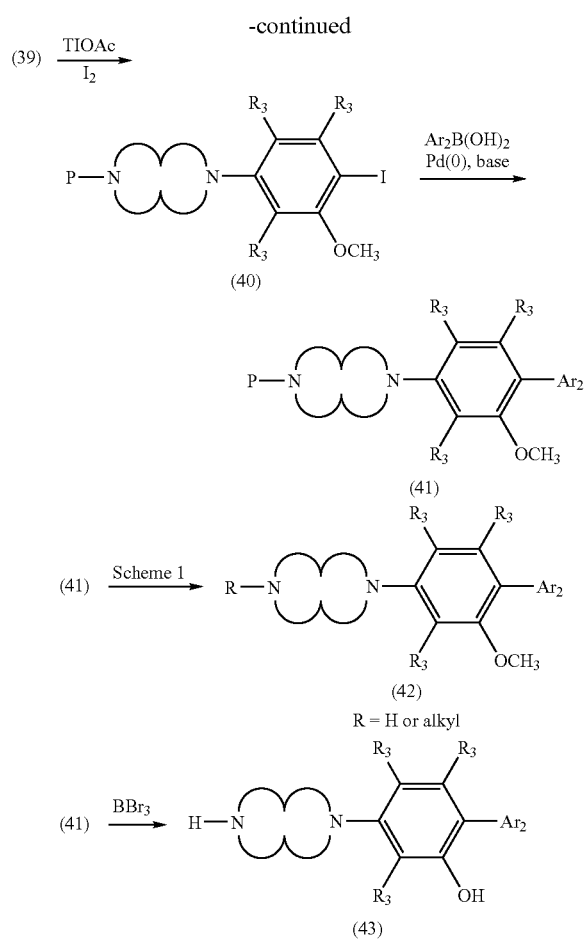

Compounds of general formula (42) and (43), wherein Ar$_2$ and R$_3$ are as defined in formula (I), can be prepared as described in Scheme 8. Diazabicycles of the present invention, wherein P is a nitrogen protecting group, can be treated with bromides of general formula (38), BINAP, palladium (0), and a base to provide compounds of general formula (39). Compounds of general formula (39) can be treated with iodine and thallium acetate to provide iodo compounds of general formula (40). Iodo compounds of general formula (40) can be treated with a boronic acid, palladium (0), and a base to provide biarylcompounds of general formula (41). Biarylcompounds of general formula (41) can be processed as described in Scheme 1 to provide compounds of general formula (42) and (43).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Methods of the Invention

Compounds and compositions of the invention are useful for modulating the effects of nAChRs, and more particularly α7 nAChRs. In particular, the compounds and compositions of the invention can be used for treating and preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

The compounds of the invention, including but not limited to those specified in the examples, possess an affinity for nAChRs, and more particularly α7 nAChRs. As α7 nAChRs ligands, the compounds of the invention can be useful for the treatment and prevention of a number of α7 nAChR-mediated diseases or conditions.

For example, α7 nAChRs have been shown to play a significant role in enhancing cognitive function, including aspects of learning, memory and attention (Levin, E. D., J. Neurobiol. 53: 633-640, 2002). As such, α7 ligands are suitable for the treatment of cognitive disorders including, for example, attention deficit disorder, attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Parkinson's disease is characterized by muscular rigidity, tremor, and bradykinesia. Epidemiologic studies have long demonstrated that cigarette-smoking subjects have lower risk of parkinsonism than nonsmokers (Baron, J. A. Neurology 36: 1490-1496, 1986). Moreover, direct administration of nicotine has been shown to improve tremor in Parkinson's patients. At least part of the beneficial effect of nicotine is thought to involve neuroprotection, a feature that is now understood to be mediated by α7 neuronal nAChRs (Jonnala, R. R., Buccausco, J. J. J. Neurosci. Res. 66: 565-571, 2001).

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833-839, 2001). Improved angiogenesis has been shown to involve activation of the α7 nAChR (Heeschen, C. et al, J. Clin. Invest. 110: 527-536, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M. and Changeux, J.-P. PNAS 98:2803-2807, 2001). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384-388, 2003). Therefore, selective α7 ligands demonstrate potential for treating conditions involving inflammation and pain.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 68: 1348-1353 2003). Consequently, selective α7 agents demonstrate utility for treating fertility disorders.

Compounds of the invention are particularly useful for treating and preventing a condition or disorder affecting cognition, neurodegeneration, and schizophrenia. Cognitive impairment associated with schizophrenia often limits the ability of patients to normally function, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 mg/kg body weight to about 1 g/kg body weight. More preferable doses can be in the range of from about 0.10 mg/kg body weight to about 100 mg/kg body weight. If desired, the effective daily dose can be divided into multiple doses for purposes of administration. Consequently, single dose compositions may contain such amounts or submultiples thereof to make up the daily dose.

The compounds and processes of the invention will be better understood by reference to the following examples and reference examples, which are intended as an illustration of and not a limitation upon the scope of the invention.

EXAMPLES

Examples 1-25, entitled "Diamine Cores", describe diamine moieties that can be are used as referenced in the Examples to prepare compounds identified in Examples 31-110, 114-128, 131-188, 191-197, 204-213, 225-240, and 243-320. General procedures for coupling the 3-chloro-6-phenylpyridazine, deprotecting the resulting compound, methylating the amine nitrogen, and preparing a salt of the compound obtained thereof, as described in the Examples, are described in Example 31, and additional methods are further described in later Examples.

Diamine Cores

Example 1

3,8-Diaza-bicyclo[3.2.1]octane-8-carboxylic acid tert-butyl ester

Example 1A

5-Oxo-pyrrolidine-2-carboxylic acid methyl ester

To a solution of DL-pyroglutamic acid (50 g, 0.387 mol) in 157 mL $CH_3OH$ (3.87 mol) and 100 mL toluene was added concentrated $H_2SO_4$ (2.5 mL). This mixture was warmed to reflux and allowed to stir for 16 h. Since starting material remained, another 4 mL concentrated $H_2SO_4$ was added and the mixture stirred at reflux for an additional 24 h then was cooled to ambient temperature and 20% aqueous NaOH was added to bring the solution to pH ~6. The mixture was concentrated under reduced pressure and the residue was dissolved in $CH_2Cl_2$, filtered through Celite® diatomaceous earth, concentrated and purified via Kugelrohr distillation. The resulting material was carried on directly to the next reaction.

Example 1B

1-Benzyl-5-oxo-pyrrolidine-2-carboxylic acid methyl ester

To a slurry of NaH (22 g of 60% NaH in mineral oil, 0.55 mol) in 400 mL benzene was added the product of Example 1A (0.387 mol) in 100 mL benzene dropwise via addition funnel. The mixture stirred for 30 minutes after the addition was complete, then was warmed to reflux and allowed to stir for 1.5 h. The reaction was cooled to 45° C. and stirred for 16 h. A portion of benzyl bromide (45 mL, 0.38 mol) was added, the mixture was warmed to reflux and an additional amount of benzyl bromide was added (45 mL, 0.38 mol). This solution stirred for 24 h at reflux, then was cooled to ambient temperature, filtered through Celite® diatomaceous earth and the residue was washed with $CH_2Cl_2$. The combined filtrates were concentrated under reduced pressure and excess benzyl bromide was removed via distillation. The distillation residue was purified via column chromatography ($SiO_2$, 75% hexanes-EtOAc) to give 46.6 g of the title compound (0.2 mol, 52% yield). MS (DCI/$NH_3$) m/z 234 (M+H)$^+$.

Example 1C

1-Benzyl-5-ethoxy-2-methoxycarbonyl-3,4-dihydro-2H-pyrrolium tetrafluoroborate

The product of Example 1B (46.6 g, 0.2 mol) in 200 mL $CH_2Cl_2$ was added via addition funnel to a solution of Meerwein's reagent ($Et_3O^+BF_4^-$) (Aldrich, 200 mL of 1 M solution in $CH_2Cl_2$, 0.2 mol) at ambient temperature. The reaction mixture stirred for 18 h then was concentrated and the residue was determined to be a 1.8:1 mixture of starting material to product. This mixture was carried on to the next step without further purification.

Example 1D

1-Benzyl-5-nitromethylene-pyrrolidine-2-carboxylic acid methyl ester

To the mixture obtained in Example 1C (0.2 mol) in 130 mL $CH_2Cl_2$ at ambient temperature was added $Et_3N$ (33.5 mL, 0.24 mol) followed by $CH_3NO_2$ (13 mL, 0.24 mol). The mixture stirred at ambient temperature for 8 h then was diluted with $CH_2Cl_2$, the layers were separated and the organic layer was washed with 20 mL 5% $H_2SO_4$ and 20 mL brine. The organic layer was dried over anhydrous $Na_2SO_4$, concentrated and purified via column chromatography ($SiO_2$, 50% hexanes-EtOAc) to give 10.2 g of the title compound (36.9 mmol). MS ($DCl/NH_3$) m/z 277 $(M+H)^+$.

Example 1E

8-Benzyl-3,8-diaza-bicyclo[3.2.1]octan-2-one

The product of Example 1D (10.2 g, 36.9 mmol) and 5% Pt/C (2 g) in 200 mL $CH_3OH$ was shaken under a 30 psi atmosphere of $H_2$ at ambient temperature for 24 h. The mixture was then filtered through Celite® diatomaceous earth, and concentrated to give 2.88 g (13.3 mmol, 36%) of the title. MS ($DCl/NH_3$) m/z 217 $(M+H)^+$.

Example 1F

8-Benzyl-3,8-diaza-bicyclo[3.2.1]octane

The product of Example 1E (2.88 g, 13.3 mmol) in 40 mL THF was added via cannula to a mixture of $LiAlH_4$ (1.52 g, 39.9 mmol) in 40 mL THF at 0° C. After the addition was complete, the reaction mixture was allowed to warm to ambient temperature and stir for 2 h. The mixture was warmed to reflux and stirred for 1 h. The reaction was cooled to 0° C. then 1.5 mL $H_2O$, 1.5 mL 15% NaOH and 4.5 mL $H_2O$ were added sequentially to quench the reaction. The material was filtered, the residue was washed with EtOAc, and the filtrate was concentrated under reduced pressure and carried on directly to the next reaction. MS ($DCl/NH_3$) m/z 203 $(M+H)^+$.

Example 1G 1-(8-Benzyl-3,8-diaza-bicyclo[3.2.1]oct-3-yl)-2,2,2-trifluoro-ethanone To the product of Example 1F (2.0 g, 9.8 mmol) in 50 mL $CH_2Cl_2$ was added $Et_3N$ (7.0 mL, 50 mmol). The mixture was cooled to 0° C. and trifluoroacetic anhydride (3.53 mL, 25 mmol) was added. The ice-bath was removed after the addition was complete and the reaction stirred for 16 h at ambient temperature. The mixture was concentrated under reduced pressure and purified by column chromatography ($SiO_2$, 50% hexanes-EtOAc) to give 2.5 g of the title compound (8.4 mmol, 86% yield). MS ($DCl/NH_3$) m/z 299 $(M+H)^+$.

Example 1H 3-(2,2,2-Trifluoro-acetyl)-3,8-diaza-bicyclo[3.2.1]octane-8-carboxylic acid tert-butyl ester To the product of Example 1G (2.5 g, 8.4 mmol) in 20 mL EtOAc, was added di-tert-butyl dicarbonate (2.0 g, 9.22 mmol) and Pd/C (10 wt %, 0.25 g). This mixture was placed under 1 atm. of $H_2$ via balloon and was allowed to stir for 48 h. The reaction mixture was filtered, concentrated under reduced pressure and purified via column chromatography ($SiO_2$, 50% hexanes-EtOAc) to give 2 g of the title compound (6.5 mmol, 77% yield). MS ($DCl/NH_3$) m/z 253 $(M+H)^+$.

Example 1I 3,8-Diaza-bicyclo[3.2.1]octane-8-carboxylic acid tert-butyl ester To the product of Example 1H (2.0 g, 6.5 mmol) in 57 mL $CH_3OH$ and 11 mL $H_2O$ was added 2.8 g $K_2CO_3$ (20.3 mmol). The mixture stirred for 16 h at ambient temperature then was filtered, concentrated under reduced pressure and purified via column chromatography ($SiO_2$, 50% hexanes-EtOAc) to give 1.2 g of the title compound (5.65 mmol, 87% yield). MS ($DCl/NH_3$) m/z 213 $(M+H)^+$.

Example 2

3,6-Diaza-bicyclo[3.2.1]octane-6-carboxylic acid tert-butyl ester

Example 2A tert-Butyl 2-Azabicyclo[2.2.1]hept-5-en-2-carboxylate

Aqueous formalin (37%, 114 mL, 1.41 mol) was added to a well-stirred solution of $NH_4Cl$ (85.0 g, 1.59 mol) in water (250 mL). Freshly distilled cyclopentadiene (170 g, 2.58 mol) was added all at once, and the mixture was stirred vigorously at ambient temperature for 17 h. The lower, aqueous phase was separated, and was treated with di-t-butyl dicarbonate (172 g, 0.78 mol). Aqueous 1M NaOH (100 mL) was added to adjust the pH to ~8, and the mixture was stirred for 7 h at ambient temperature with addition of solid NaOH (40 g total) to maintain pH ~8. The mixture was extracted with hexanes (2×200 mL), and the combined organic phase was washed with brine (50 mL), dried over $MgSO_4$, and concentrated under vacuum. The residue was distilled under vacuum to provide the title compound (bp 80-92° C./10 Torr) as a pale yellow liquid that crystallized on cooling (123 g, 0.63 mol, 45% yield). $^1$H NMR ($CDCl_3$, 300 MHz) δ 1.44 (s, 9H), 1.57 (m, 2H), 2.63 (m, 1H), 3.16 (br s, 1H), 3.31 (dd, J=9, 3 Hz, 1H), 4.55-4.73 (br m, 1H), 6.25-6.41 (br m, 2H). MS ($DCl/NH_3$) m/z 196 $(M+H)^+$.

Example 2B 2,4-Diformyl-pyrrolidine-1-carboxylic acid tert-butyl ester

Through a solution of Example 2A (0.57 g, 2.9 mmol) in 1.5 mL acetic acid and 25 mL $CH_2Cl_2$ at −78° C. was bubbled O$_3$ until the solution turned blue. O$_2$ was then flushed through the system for 10 min after which dimethylsulfide (0.54 mL, 7.30 mmol) was added. The mixture was slowly warmed to 20° C. and allowed to stir for 18 h. The solution was concentrated and the crude product was carried on directly to the next reaction. MS (DCl/NH$_3$) m/z 228 (M+H)$^+$.

Example 2C

3-Benzyl-3,6-diaza-bicyclo[3.2.1]octane-6-carboxylic acid tert-butyl ester

To a solution of the crude product of Example 2B (2.92 mmol) in CH$_3$OH at 0° C. was added benzylamine (0.35 mL, 3.21 mmol) and NaCNBH$_3$ (1.83 g, 29.2 mmol). The ice-bath was removed and the mixture stirred at 20° C. for 24 h. The solution was cooled to 0° C. and 10 mL EtOAc and 10 mL H$_2$O were added followed by 5 mL of saturated, aqueous NaHCO$_3$. The layers were separated and the aqueous layer was extracted with 10 mL EtOAc. The combined organic layers were washed with 5 mL H$_2$O followed by 5 mL brine, then were dried over anhydrous Na$_2$SO$_4$. The mixture was filtered and the filtrate was concentrated and purified via flash column chromatography to give 0.68 g (2.25 mmol, 77% two-step yield) of the title compound. $^1$H NMR (CH$_3$OH-d$_4$, 300 MHz) δ 1.37 and 1.51 (s, rotamers, 9H), 1.46 (m, 1H), 1.57 (dd, J=11.2, 7.46 Hz, 1H), 1.88 (m, 1H), 1.97 (m, 1H), 2.32 (m, 2H), 2.82 (m, 1H), 3.02 (m, 1H), 3.52 (m, 3H), 3.91 (m, 1H), 7.20 (m, 1H), 7.27 (m, 4H); MS (DCl/NH$_3$) m/z 303 (M+H)$^+$.

Example 2D 3,6-Diaza-bicyclo[3.2.1]octane-6-carboxylic acid tert-butyl ester

To the product of Example 2C (0.553 g, 1.83 mmol) in 50 mL CH$_3$OH was added 111 mg Pd(OH)$_2$/C (20 wt %). The mixture was put under 60 psi of H$_2$, warmed to 50° C. and allowed to stir for 36 h. The solution was then cooled to 20° C., filtered through Celite® diatomaceous earth, and concentrated to give the desired product. $^1$H NMR (CH$_3$OH-d$_4$, 300 MHz) δ 1.46 and 1.48 (s, rotamers, 9H), 1.78 (dd, J=11.2, 5.43 Hz, 1H), 1.91 (m, 1H), 2.28 (m, 1H), 2.61 (d, J=12.9 Hz, 1H), 2.82 (m, 3H), 3.41 (m, 2H), 3.93 (m, 1H); MS (DCl/NH$_3$) m/z 213 (M+H)$^+$.

Example 3

3,8-Diaza-bicyclo[4.2.0]octane-8-carboxylic acid tert-butyl ester

Example 3A

3-Oxo-piperidine-1,4-dicarboxylic acid 1-tert-butyl ester 4-ethyl ester

A mixture of commercially available ethyl-N-benzyl-3-oxo-4-piperidinecarboxylate hydrochloride (Aldrich, 75.4 g, 0.25 mol), di-t-butyl dicarbonate (58.5 g, 0.27 mol), Et$_3$N (36 mL, 0.26 mol), and Pd(OH)$_2$/C (7.5 g, 50% in H$_2$O) in 660 mL EtOH was put under 60 psi of H$_2$ and was shaken for 25 min. The mixture was then filtered and the filtrate was concentrated under reduced pressure to provide the title compound which was used in the next step without further purification. MS (DCl/NH$_3$) m/z 272 (M+H)$^+$.

Example 3B 5-((1R)-1-Phenyl-ethylamino)-3,6-dihydro-2H-pyridine-1,4-dicarboxylic acid 1-tert-butyl ester 4-ethyl ester A mixture of the product of Example 3A (72 g, 0.265 mol) and D-(+)-α-methylbenzylamine (Aldrich, 35.9 mL, 0.279 mol) in 750 mL of toluene was combined in a 1 L, round-bottom flask equipped with a Dean-Stark trap. The mixture was refluxed for 36 h with water being removed via the Dean-Stark trap. After cooling to ambient temperature, the solution was concentrated and redissolved in EtOAc. Filtration through silica gel and Celite® diatomaceous earth gave the crude title compound which was carried on directly to the next reaction. MS (DCl/NH$_3$) m/z 375 (M+H)$^+$.

Example 3C 3-((1R)-1-Phenyl-ethylamino)-piperidine-1,4-dicarboxylic acid 1-tert-butyl ester 4-ethyl ester To a mixture of the product of Example 3B (0.265 mol), NaBH(OAc)$_3$ (280.8 g, 1.33 mol), and 200 g of 4 Å powdered molecular sieves in 900 mL toluene in a 3-neck round bottom flask equipped with an internal thermometer, mechanical stirrer and addition funnel at 0° C. was added acetic acid (303 mL, 5.3 mol) dropwise via the addition funnel. After the addition was complete, the mixture was allowed to warm to ambient temperature and stir for 16 h. The reaction was filtered and concentrated under reduced pressure to remove as much of the acetic acid as possible. The residue was dissolved in 750 mL EtOAc and 500 mL saturated aqueous NaHCO$_3$ solution was added slowly to neutralize the residual acid. The layers were separated and the aqueous layer was extracted with 2×100 mL EtOAc. The combined organics were dried over Na$_2$SO$_4$ and concentrated under reduced pressure to give the title compound which was carried on to the next reaction without further purification. MS (DCl/NH$_3$) m/z 377 (M+H)$^+$.

Example 3D

4-Hydroxymethyl-3-((1R)-1-phenyl-ethylamino)-piperidine-1-carboxylic acid tert-butyl ester To a slurry of LiAlH$_4$ (0.292 mol) in 1 L tetrahydrofuran at 0° C. was added the product of Example 3C (0.265 mol) dropwise via addition funnel. The ice-bath was removed after the addition was complete and the mixture stirred at ambient temperature for 1 h. The reaction was quenched by the slow addition of approximately 100 g Na$_2$SO$_4$.10H$_2$O (excess). The mixture stirred for 16 h then was filtered, concentrated under reduced pressure and purified via column chromatography (SiO$_2$, 33% hexanes-EtOAc) to give 76.5 g of the mixture of isomers (0.23 mol, 86%). MS (DCl/NH$_3$) m/z 335 (M+H)$^+$.

Example 3E 8-((1R)-1-Phenyl-ethyl)-3,8-diaza-bicyclo[4.2.0]
octane-3-carboxylic acid tert-butyl ester To the mixture of isomers from Example 3D (76.5 g, 0.23 mol) in 1.1 L of tetrahydrofuran at 0° C. was added $Et_3N$ (95.8 mL, 0.687 mol) followed by methanesulfonyl chloride (23 mL, 0.30 mol). The ice-bath was removed after the additions were complete and the reaction was allowed to warm to ambient temperature and stirred for 1 h. $Cs_2CO_3$ (excess) was added and the mixture was warmed to 60° C. and stirred for 16 h. The reaction was cooled to ambient temperature, filtered, and the filtrate was washed with 2×100 mL $H_2O$. The layers were separated and the aqueous layer was extracted with 2×100 mL EtOAc. The combined organics were dried over $Na_2SO_4$ and concentrated under reduced pressure. The material was purified and the isomers separated via column chromatography ($SiO_2$, 50% hexanes-EtOAc) to give 30.65 g of the major isomer ((1S,6R)-3,8-diaza-bicyclo[4.2.0]octane-3-carboxylic acid tert-butyl ester (97 mmol, 42%) and 16.5 g of the minor isomer ((1R,6S)-3,8-diaza-bicyclo[4.2.0]-octane-3-carboxylic acid tert-butyl ester (52 mmol, 23%). MS (DCl/$NH_3$) m/z 317 $(M+H)^+$.

Example 3F (1R,6S)-8-((1R)-1-Phenyl-ethyl)-3,8-diaza-bicyclo
[4.2.0]octane

To the minor isomer product of Example 3E (9.3 g, 29.4 mmol) in 40 mL $CH_2Cl_2$ at 0° C. was added 20 mL trifluoroacetic acid. The ice bath was removed after the addition and the mixture stirred at ambient temperature for 3 h then was concentrated under reduced pressure and the residue was purified via column chromatography ($SiO_2$, 1% $NH_4OH$:9% $CH_3OH$:90% $CH_2Cl_2$) to give the title compound. MS (DCl/$NH_3$) m/z 217 $(M+H)^+$.

Example 3G 2,2,2-Trifluoro-1-[(1R,6S)-8-(1-phenyl-ethyl)-3,8-
diaza-bicyclo[4.2.0]oct-3-yl]-ethanone To the product of Example 3F (29.4 mmol) in 210 mL tetrahydrofuran (THF) at −30° C. was added triethylamine (5.15 mL, 36.8 mmol) followed by trifluoroacetic anhydride (TFAA, 4.36 mL, 30.9 mmol). The mixture was warmed to −10° C. and stirred for 30 min. The reaction was quenched with 50 mL saturated, aqueous $NaHCO_3$ then was diluted with 100 mL $H_2O$ and 100 mL EtOAc. The layers were separated and the aqueous layer was extracted 2×50 mL EtOAc. The combined organic layers were dried over $Na_2SO_4$, filtered through silica gel and Celite® diatomaceous earth with EtOAc and the filtrate was concentrated under reduced pressure to give 8.8 g of the title compound (28.2 mmol, 96% two-step yield). MS (DCl/$NH_3$) m/z 313 $(M+H)^+$.

Example 3H (1R,6S)-3-(2,2,2-Trifluoro-acetyl)-3,8-diaza-bicyclo
[4.2.0]octane-8-carboxylic acid tert-butyl ester A mixture of the product of Example 3G (8.8 g, 28.2 mmol), di-t-butyl dicarbonate (6.15 g, 28.2 mmol), and 2.21 g of 20% $Pd(OH)_2/C$ in 100 mL $CH_3OH$ was shaken under 60 psi of $H_2$ for 5 h at 50° C. then for 9.5 h at ambient temperature. The reaction was filtered and concentrated under reduced pressure. $^1$H-NMR indicated the presence of a bis-di-t-butyl dicarbamide-3,8-diaza-bicyclo[4.2.0]octane side product which carried on to the next step along with the crude product. MS (DCl/$NH_3$) m/z 326 $(M+NH_4)^+$.

Example 3I (1R,6S)-3,8-Diaza-bicyclo[4.2.0]octane-8-carboxylic
acid tert-butyl ester To the crude product of Example 3H (~28.2 mmol) in 140 mL $CH_3OH$ and 30 mL $H_2O$ was added 4.7 g $K_2CO_3$ (33.8 mmol). The mixture stirred at ambient temperature for 16 h then was diluted with a 100 mL of a solution of 1% $NH_4OH$: 9% $CH_3OH$:90% $CH_2Cl_2$ and filtered through Celite® diatomaceous earth and silica gel. The filtrate was concentrated under reduced pressure and purified via column chromatography ($SiO_2$, 1% $NH_4OH$:9% $CH_3OH$:90% $CH_2Cl_2$) to give 3.3 g of the title compound (15.6 mmol, 55% yield). MS (DCl/$NH_3$) m/z 213 $(M+H)^+$.

Example 4

(1S,6R)-3,8-Diaza-bicyclo[4.2.0]octane-8-carboxylic
acid tert-butyl ester

The major isomer from Example 3E was processed according to the procedures of Examples 3F, 3G, 3H, and 3I to provide the title compound: MS (DCl/$NH_3$) m/z 213 $(M+H)^+$

Example 5 t-Butyl 3,6-diazabicyclo[3.2.1]octane-3-carboxylate

Example 5A 1-(3-Benzyl-3,6-diazabicyclo[3.2.1]oct-6-yl)-2,2,2-
trifluoro-ethanone To the product of Example 2C (0.68 g, 2.25 mmol) in 7 mL $CH_2Cl_2$ at 0° C. was added 3.5 mL trifluoroacetic anhydride. The ice-bath was removed and the mixture stirred at 20° C. fr 2 h. The solution was then concentrated and the residue was dissolved in THF (15 mL). Triethylamine (0.41 mL, 2.92 mmol, 1.3 eq) was added, followed by trifluoroacetic anhydride (0.38 mL, 2.70 mmol, 1.2 eq). The mixture was stirred for 15 min at 0° C. then was allowed to warm to 20° C. at which temperature it stirred for 18 h. The solution was concentrated and purified via flash column chromatography to give quantitative yield of the desired trifluoroacetamide (0.67 g, 2.25 mmol, 100% two-step yield). $^1$H NMR ($CH_3OH$-$d_4$, 300 MHz) δ1.97 (m, 1H), 2.06 (m, 1H), 2.12 (m, 1H), 2.84 (m, 1H), 3.41 (m, 2H), 3.61 (m, 2H), 3.82 (m, 1H), 4.32 (m, 2H), 4.64 (m, 1H), 7.48 (m, 5H); MS (DCl/$NH_3$) m/z 299 $(M+H)^+$.

Example 5B t-Butyl 3,6-Diazabicyclo[3.2.1]octane-6-carboxylate

To the product of Example 5A (0.67 g, 2.25 mmol) and $Boc_2O$ (0.55 g, 2.51 mmol, 1.1 eq) in 50 mL $CH_3OH$ was added 135 mg $Pd(OH)_2/C$ (20 wt %). The mixture was put under 60 psi of $H_2$ and allowed to stir for 18 h. The solution was then filtered through Celite®, and concentrated. The residue was dissolved in CH₃OH (10 mL) and H₂O (2 mL) and treated with K₂CO₃ (0.5 g, 3.62 mmol, 1.6 eq). The mixture stirred for 20 h and then concentrated. The residue was taken up in a mixture of 90% CH$_2$Cl$_2$, 9% CH$_3$OH and 1% NH$_4$OH and filtered through diatomaceous earth and silica gel. The filtrate was concentrated to provide 0.47 g of the title compound (2.21 mmol, 98% yield). $^1$H NMR (CH$_3$OH-d$_4$, 300 MHz) δ 1.42 (m, 1H), 1.46 (s, 9H), 1.89 (m, 2H), 2.58 (m, 1H), 3.00 (m, 2H), 3.12 (m, 2H), 3.78 (m, 1H), 3.84 (dd, J=12.88, 3.39 Hz, 1H), 3.92 (br d, J=13.9 Hz, 1H); MS (DCI/NH$_3$) m/z 213 (M+H)$^+$.

Example 6

Hexahydro-pyrrolo[3,4-c]pyrrole-2-carboxylic acid tert-butyl ester

Example 6A

5-Benzyl-tetrahydro-pyrrolo[3,4-c]pyrrole-1,3-dione

To the maleimide (80.4 g, 0.83 mol) in 1.5 L of CH$_2$Cl$_2$ in a 3-neck, 3-L round bottom flask equipped with an addition funnel, internal thermometer, and N$_2$ inlet at 0° C. was added trifluoroacetic acid (TFA) (6.4 mL, 83 mmol). Benzyl(methoxymethyl)trimethylsilylmethylamine (261 g, 1.1 mol) in 500 mL CH$_2$Cl$_2$ was added dropwise via addition funnel over 3 hours with the reaction temperature being maintained below 5° C. After the addition was complete, the mixture was allowed to warm slowly to ambient temperature and then was stirred for 16 h. The mixture was concentrated and the residue was dissolved in 500 mL CH$_2$Cl$_2$ and was washed with 2×50 mL saturated NaHCO$_3$. The layers were separated and the aqueous layer was extracted 2×25 mL CH$_2$Cl$_2$. The combined organics were washed with 25 mL brine, dried over saturated, aqueous Na$_2$SO$_3$, and concentrated under reduced pressure to give the title compound which was carried on to the next step without further purification. MS (DCI/NH$_3$) m/z 231 (M+H)$^+$.

Example 6B

5-Benzyl-hexahydro-pyrrolo[3,4-c]pyrrole-2-carboxylic acid tert-butyl ester

To a slurry of LiAlH$_4$ (25 g, 0.63 mol) in 1 L THF at 0° C. in a 3-L round bottom flask equipped with an addition funnel and an N$_2$ inlet, was added 48 g (0.19 mmol) of the crude product of Example 6A (0.21 mol) in 500 mL THF dropwise via the addition funnel over 3 h. After the addition was complete, the ice-bath was removed and the mixture stirred at ambient temperature for 30 min before being warmed to reflux and stirred for 4 h. The reaction was cooled to 0° C. and quenched by the slow addition of Na$_2$SO$_4$.10H$_2$O (excess). This mixture stirred for 16 h at ambient temperature then was filtered and the residue was washed with EtOAc. The combined filtrates were concentrated and the residue was dissolved in 500 mL THF. Di-t-butyl dicarbonate (46 g, 0.21 mol) and 100 mL saturated, aqueous NaHCO$_3$ were added and the mixture stirred for 16 h at ambient temperature. The reaction was quenched with 50 mL H$_2$O and 250 mL EtOAc was added. The layers were separated, the aqueous layer was extracted 3×50 mL EtOAc, and the combined organic layers were dried over Na$_2$SO$_4$ and concentrated under reduced pressure. Purification via column chromatography (SiO$_2$, 50% hexanes-EtOAc) gave 33.4 g of the title compound (0.11 mol, 53% yield). MS (DCI/NH$_3$) m/z 303 (M+H)$^+$.

Example 6C

Hexahydro-pyrrolo[3,4-c]pyrrole-2-carboxylic acid tert-butyl ester

To the product of Example 6B (107.8 g, 0.356 mol) in 250 mL CH$_3$OH was added 10.8 g of 20% Pd(OH)$_2$/C, wet. This mixture was hydrogenated for 2.5 h under 60 psi of H$_2$ at 50° C. The mixture was filtered and concentrated to give 74 g of the title compound (0.35 mmol, 98% yield). MS (DCI/NH$_3$) m/z 213 (M+H)$^+$.

Example 7

Benzyl (1S,5S)-3,6-diazabicyclo[3.2.0]heptane-3-carboxylate

Example 7A (2,2-Dimethoxy-ethyl)-carbamic acid benzyl ester

Benzyl chloroformate (Aldrich, 231.3 g, 1.3 mol) was added gradually to a mixture of aminoacetaldehyde dimethyl acetal (Aldrich, 152.0 g, 1.3 mol) in toluene (750 mL) and aqueous NaOH (72.8 g, 1.82 mol; in 375 mL of water) at 10-20° C. After the addition was complete, the mixture was stirred at ambient temperature for 4 h. The layers were separated and the organic layer was washed with brine (2×100 mL) and concentrated under reduced pressure to provide the title compound as an oil (281.5 g, 90% yield). $^1$H NMR (CDCl$_4$, 300 MHz) δ 3.33 (t, J=6.0 Hz, 2H), 3.39 (s, 6H), 4.37 (t, J=6.0 Hz, 1H), 5.11 (s, 2H), 7.30 (m, 5H); MS (DCI/NH$_3$) m/z 257 (M+NH$_4$)$^+$, 240 (M+H)$^+$.

Example 7B

Allyl-(2,2-dimethoxy-ethyl)-carbamic acid benzyl ester

The product of Example 7A (281.0 g, 1.18 mol) in dry toluene (1.0 L) was treated with powdered KOH (291.2 g, 5.20 mol) and triethylbenzylammonium chloride (Aldrich, 4.4 g, 0.02 mol). A solution of allyl bromide (Aldrich, 188.7 g, 1.56 mol) in toluene (300 mL) was then added dropwise over 1 hour at 20-30° C. The mixture was stirred for ~18 h at ambient temperature and then water (300 mL) was added over 20 minutes at 20-30° C. The layers were separated and the aqueous phase was extracted with toluene (2×300 mL). The organic phases were combined, washed with brine (2×100 mL), dried (K$_2$CO$_3$), filtered and the filtrate concentrated under reduced pressure to provide the title compound as an oil (315.6 g, 1.13 mol, 96%, yield). $^1$H NMR (MeOH-d$_4$, 300 MHz) δ 3.32 (s, 3H) 3.37 (m, 5H), 3.97 (d, J=5.4 Hz, 2H), 4.50-4.40 (m, 1H), 5.15 (m, 4H), 5.75 (m, 1H), 7.23 (m, 5H); MS (DCI/NH$_3$) m/z 297 (M+NH$_4$)$^+$, 280 (M+H)$^+$.

Example 7C

Allyl-(2-oxo-ethyl)-carbamic acid benzyl ester

The product of Example 7B (314.0 g, 1.125 mol) was treated with formic acid (88%, 350 mL) at room temperature and allowed to stir for 15 hours. Most of the formic acid was removed by concentration under reduced pressure at 40-50° C. The residue was extracted with ethyl acetate (3×500 mL). The extracts were combined and washed with brine until the wash had a pH=6-7. The organic phase was concentrated under reduced pressure to provide the title compound as a slightly yellow oil (260.0 g, 1.12 mmol 99% yield). $^1$H NMR (CDCl$_3$, 300 MHz) δ 3.20 (m, 1H), 3.97 (m, 2H), 4.10 (m, 1H), 5.10 (m, 4H), 5.75 (m, 1H), 7.45 (m, 5H), 9.50 (d, J=6.4 Hz, 1H); MS (DCl/NH$_3$) m/z 234 (M+H)$^+$.

Example 7D

Allyl-(2-hydroxyimino-ethyl)-carbamic acid benzyl ester

The product of Example 7C (260 g, 1.12 mol) in acetonitrile (1.5 L) was treated with sodium acetate trihydrate (170.6 g, 4.41 mol, in 0.75 L distilled water) and NH$_2$OH.hydrochloride (98.0 g, 4.41 mol) under N$_2$. The mixture was stirred at ambient temperature over 20 hours. The volatiles were removed under reduced pressure and the residue was extracted with ethyl acetate (2×750 mL). The combined organic phases were washed with brine until the wash had a pH=7. The organic phase was concentrated under reduced pressure to provide the title compound as an oil (271 g, 1.09 mol, 98% yield). $^1$H NMR (MeOH-d$_4$, 300 MHz) δ 3.94 (m, 2H), 3.98 (d, J=5.5 Hz, 1H), 4.17 (d, J=4.4 Hz, 1H), 5.30 (m, 4H), 5.60 (m, 1H), 7.40 (m, 5H); MS (DCl/NH$_3$) m/z 266 (M+NH$_4$)$^+$, 249 (M+H)$^+$.

Example 7E benzyl (cis)-3-amino-4-(hydroxymethyl)-1-pyrrolidinecarboxylate

A solution of the product of Example 7D (240 g, 0.97 mol) in xylene (1.0 L) was heated at reflux under N$_2$ for 10 hours. The resulting brown solution was cooled to 10-15° C. and acetic acid (1.0 L) was added under N$_2$. Zinc powder (100 g, 1.54 mol) was added gradually, and the gray mixture was stirred at ambient temperature for 3 hours. The mixture was filtered and water (1.0 L) was added to the filtrate. The filtrate was stirred for 10 minutes and the brown organic layer was separated. The aqueous phase was washed well with xylenes (4×400 mL) and then concentrated under reduced pressure to a volume of approximately 200 mL. This residue was adjusted to pH 9-10 by cautious addition of saturated, aqueous Na$_2$CO$_3$. The precipitated white solid was removed by filtration and the filtrate was extracted with CHCl$_3$ (3×600 mL). The combined organic phases were washed with saturated, aqueous Na$_2$CO$_3$ solution (2×50 mL) and dried over anhydrous Na$_2$CO$_3$. The mixture was filtered through a short column of diatomaceous earth and the filtrate was concentrated under reduced pressure to provide the title compound as a slightly yellow oil (145 g, 0.58 mol, 60% yield). $^1$H NMR (MeOH-d$_4$, 300 MHz) δ 2.40 (m, 1H), 3.30 (m, 2H), 3.80-3.50 (m, 5H), 5.10 (s, 2H), 7.35 (m, 5H); MS (DCl/NH$_3$) m/z 251 (M+H)$^+$.

Example 7F

Benzyl (cis)-2,2-dimethylhexahydropyrrolo[3,4-d][1,3]oxazine-6(4H)-carboxylate (R)-Mandelate The product of Example 7E (140 g, 0.56 mol) in dry acetone (150 mL) was treated with 2-methoxypropene (55 mL, 0.57 mol) at ambient temperature for ~18 h. The reaction mixture was concentrated under reduced pressure and the residue was dissolved in dry acetone (750 mL). (R)-Mandelic acid (85 g, 0.56 mol) was added and the brown solution was stirred at ambient temperature for 48 hours. The precipitate was isolated by filtration and dried under reduced pressure to a mixture of the title compound as a white solid (57.0 g, 0.13 mol, yield, 23%) and the hydrolyzed compound benzyl (cis)-3-amino-4-(hydroxymethyl)-1-pyrrolidinecarboxylate (R)-mandelate. $^1$H NMR for title compound (MeOH-D$_4$, 300 MHz) δ 1.20-1.40 (m, 3H), 2.09 (s, 3H), 3.30 (m, 1H), 3.48-3.75 (m, 6H), 4.20 (m, 1H), 5.10 (m, 3H), 7.25-7.52 (m, 10H); MS (DCl/NH$_3$) m/z 291 (M+H)$^+$ (for the title compound) 251 (M+H)$^+$ (for the hydrolyzed product).

Example 7G

Benzyl (3S,4S)-3-[(tert-butoxycarbonyl)amino]-4-(hydroxymethyl)-1-pyrrolidinecarboxylate The product of Example 7F (56 g, 127 mmol) in ethanol (50 mL) was treated with 5% aqueous H$_2$SO$_4$ (100 mL) at ambient temperature and allowed to stir for 16 hours. The mixture was adjusted to pH ~10 with 20% aqueous NaOH (50 mL) and then the mixture was treated with di-t-butyl dicarbonate (41.5 g, 190 mmol) in ethanol (50 mL) at 10-20° C. After stirring at ambient temperature for 4 hours, the ethanol was removed under reduced pressure and the residue was extracted with ethyl acetate (3×500 mL). The combined organic phases were washed with brine (2×100 mL) and concentrated under reduced pressure to provide the title compound (43.7 g, 0.125 mol, 98% yield). $^1$H NMR (MeOH-d$_4$, 300 MHz) δ 1.46 (s, 9H), 2.50 (m, 1H), 3.25 (m, 1H), 3.40 (m, 1H), 3.50-3.75 (m, 4H), 4.20 (m, 1H), 5.10 (s, 2H), 7.35 (m, 5H); MS (DCl/NH$_3$) m/z 368 (M+NH$_4$)$^+$, 351 (M+H)$^+$. The enantiopurity of the title compound was determined to be ≥99% ee by HPLC (HPLC conditions: Chiracel AD column; ethanol/hexanes=20/80, flow rate, 1.0 mL/min; uv 220 nm; retention time for the title compound as the more mobile isomer: 10.8 minutes; Retention time for less mobile isomer: 13.9 minutes; reference: JP 2000 026408).

Example 7H

Benzyl (3S,4S)-3-[(tert-butoxycarbonyl)amino]-4-{[(methylsulfonyl)oxy]methyl}-1-pyrrolidinecarboxylate The product of Example 7G (43.7 g, 125 mmol) and triethylamine (25.2 g, 250 mmol) in CH$_2$Cl$_2$ (600 mL) were treated with methanesulfonyl chloride (12.6 mL, 163 mmol) over 30 minutes at −10° C. The solution was allowed to warm to ambient temperature over 1 hour and was monitored by HPLC. When the reaction was completed, it was quenched with water (100 mL). The layers were separated and the aqueous phase was extracted with CH$_2$Cl$_2$ (2×400 mL). The combined organic phases were washed with brine (2×100 mL), dried over Na$_2$SO$_4$, filtered and the filtrate concentrated under reduced pressure to provide the title compound as a brown oil (52.0 g, 0.12 mol, 97% yield). $^1$H NMR (CDCl$_3$, 300 MHz) δ 1.46 (s, 9H), 2.80 (m, 1H), 3.08 (s, 3H), 3.40 (m, 2H), 3.70 (m, 2H), 4.10 (m, 1H), 4.40 (m, 2H), 4.75 (m, 1H), 5.16 (s, 2H), 7.30 m, 5H); MS (DCl/NH$_3$) m/z 446 (M+NH$_4$)$^+$, 429 (M+H)$^+$. HPLC conditions: HPLC conditions: Zorbax-XDB-C8 column 4.6×250 mm with solvents H$_2$O (0.2 v. % HClO$_4$)/MeCN (from v.80:20 to 10:90 within 15 min.) at 1.0 mL/Min., UV detection @220 nm. 20/80, flow rate, 1.0 mL/min; uv 220 nm; $t_R$=13.1 minutes.

Example 7I

Benzyl (3S,4S)-3-(amino)-4-{[(methylsulfonyl)oxy]methyl}-1-pyrrolidinecarboxylate trifluoroacetate The product of Example 7H (43.7 g, 125 mmol) in $CH_2Cl_2$ (150 mL) was treated with trifluoroacetic acid (50 mL) at ambient temperature and allowed to stir for 1 h. The reaction was monitored with HPLC. After the reaction went to completion, the mixture was concentrated under reduced pressure to give the title compound in quantitative yield. $^1$H NMR ($CDCl_3$, 300 MHz) δ 2.80 (m, 1H), 3.15 (s, 3H), 3.40 (m, 1H), 3.70 (m, 3H), 4.10 (m, 1H), 4.05 (m, 1H), 4.44 (m, 2H), 5.16 (s, 2H), 7.30-7.50 (m, 5H); MS ($DCl/NH_3$) m/z 329 $(M+H-CF_3CO_2H)^+$. HPLC conditions: Zorbax-XDB-C8 column 4.6×250 mm with solvents $H_2O$ (0.2 v. % $HClO_4$)/$CH_3CN$ (from v.80:20 to 10:90 within 15 min.) at 1.0 mL/Min., UV detection @220 nm. 20/80, flow rate, 1.0 mL/min; uv 220 nm; $t_R$=8.2 minutes.

Example 7J

Benzyl (1S,5S)-3,6-diazabicyclo[3.2.0]heptane-3-carboxylate

The product of Example 7I (125 mmol) was dissolved in ethanol (250 mL) and adjusted to pH ~12 with 25% aqueous NaOH. The mixture was warmed to 60° C. for 1.5 h and monitored via HPLC. After the reaction went to completion, it was allowed to cool down to ambient temperature and used for the next step with the exception of ~1 mL which was used for characterization. The ~1 mL sample was concentrated under reduced pressure to remove most of the ethanol. The residue was extracted with $CHCl_3$ (2×5 mL). The extracts were combined, washed with brine (3×2 mL) and then passed through a short column of diatomaceous earth. The filtrate was concentrated under reduced pressure to provide the title compound as a yellow oil. $^1$H NMR (MeOH-$d_4$, 300 MHz) δ 3.30-3.16 (m, 3H), 3.36 (m, 1H), 3.82 (m, 3H), 4.55 (m, 1H), 5.20 (s, 2H), 7.36 (m, 5H); MS ($DCl/NH_3$) m/z 250 $(M+NH_4)^+$, 233 $(M+H)^+$. HPLC conditions: Zorbax-XDB-C8 column 4.6×250 mm with solvents $H_2O$ (0.2 v. % $HClO_4$)/MeCN (from v.80:20 to 10:90 within 15 min.) at 1.0 mL/Min., UV detection @220 nm. 20/80, flow rate, 1.0 mL/min; uv 220 nm; $t_R$=7.2 min.

Example 8 tert-Butyl (1R,5S)-3,6-diazabicyclo[3.2.0]heptane-6-carboxylate

Example 8A

3-Benzyl, 6-tert-butyl-(1R,5S)-3,6-diazabicyclo[3.2.0]heptane-3,6-dicarboxylate

To the solution of Example 7J (~125 mmol) was slowly added di-t-butyl dicarbonate (40.9 g, 188 mmol) ethanol (50 mL) solution over 30 min at ambient temperature. The mixture was stirred at ambient temperature for an additional 0.5-1 h with monitoring by HPLC. After the reaction went to completion, it was concentrated under reduced pressure to remove most of the ethanol. The residue was extracted with EtOAc (3×500 mL). The extracts were combined, washed with brine (3×50 mL) and stirred with $KHSO_4$ (5%, 100 mL) for 10 min. to remove unreacted di-t-butyl dicarbonate. The layers were separated and the organic layer was washed with brine (3×50 mL) and passed through a short column of diatomaceous earth. The filtrate was concentrated under reduced pressure to provide the title compound as a yellow oil (40.2 g, 97% three-step yield). $^1$H NMR (MeOH-$d_4$, 300 MHz) δ 1.4 (s, 9H), 3.10 (m, 2H), 3.30 (m, 1H), 3.45 (m, 1H), 3.90 (d, J=12.2 Hz, 1H), 4.06 (m, 2H), 4.66 (dd, J=6.4, 2.0 Hz, 1H), 5.16 (s, 2H), 7.36 (m, 5H); MS ($DCl/NH_3$) m/z 333 $(M+H)^+$. HPLC conditions: Zorbax-XDB-C8 column 4.6×250 mm with solvents $H_2O$ (0.2 v. % $HClO_4$)/MeCN (from v.80:20 to 10:90 within 15 min.) at 1.0 mL/Min., UV detection @220 nm. 20/80, flow rate, 1.0 mL/min; uv 220 nm; $t_R$=13.6 minutes.

Example 8B tert-Butyl (1R,5S)-3,6-diazabicyclo[3.2.0]heptane-6-carboxylate

The product of Example 8A (40.0 g, 0.120 mol) was dissolved in methanol (400 mL) and treated with Pd/C (10 wt %, 4.0 g) under $H_2$ at ambient temperature for 10 h. The reaction was monitored with HPLC. After the reaction was complete, the catalyst was removed by filtration through a short column of diatomaceous earth. The filtrate was concentrated under reduced pressure to provide the title compound as a colorless oil (22.8 g, 11.5 mmol, 96% yield). $^1$H NMR (MeOH-$d_4$, 300 MHz) δ 1.43 (s, 9H), 2.47 (dd, J=12.6, 3.8 Hz, 1H), 2.62 (dd, J=12.2, 5.7 Hz, 1H), 2.96 (m, 1H), 3.05 (d, J=12.2 Hz, 1H), 3.22 (d, J=12.5 Hz, 1H), 3.45 (m, 1H), 3.95 (m, 1H), 4.63 (dd, J=6.1, 3.7 Hz, 1H); MS ($DCl/NH_3$) m/z 199 $(M+H)^+$. HPLC conditions: Zorbax-XDB-C8 column 4.6×250 mm with solvents $H_2O$ (0.2 v. % $HClO_4$)/MeCN (from v.80:20 to 10:90 within 15 min.) at 1.0 mL/Min., UV detection @ 220 nm. 20/80, flow rate, 1.0 mL/min; uv 220 nm; $t_R$=8.6 minutes.

Example 9

Benzyl (1R,5R)-3,6-diazabicyclo[3.2.0]heptane-3-carboxylate

The product of Example 7E was processed according to the procedure of Example 7F, substituting (S)-mandelic acid for the (R)-mandelic acid therein. The resulting material was processed according to the procedures of Examples 7G, 7H, 7I, and 7J to provide the title compound: $^1$H NMR (MeOH-$d_4$, 300 MHz) δ 3.30-3.16 (m, 3H), 3.36 (m, 1H), 3.82 (m, 3H), 4.55 (m, 1H), 5.20 (s, 2H), 7.36 (m, 5H); MS ($DCl/NH_3$) m/z 250 $(M+NH_4)^+$, 233 $(M+H)^+$.

Example 10 tert-Butyl (1S,5R)-3,6-diazabicyclo[3.2.0]heptane-6-carboxylate

The product of Example 9 was treated with di-t-butyl dicarbonate, then Pd/C under a hydrogen atmosphere according to the procedures of Example 8A and 8B, to provide the title compound. $^1$H NMR (MeOH-$d_4$, 300 MHz) 1.43 (s, 9H), 2.47 (dd, J=12.6, 3.8 Hz, 1H), 2.62 (dd, J=12.2, 5.7 Hz, 1H), 2.96

(m, 1H), 3.05 (d, J=12.2 Hz, 1H), 3.22 (d, J=12.5 Hz, 1H), 3.45 (m, 1H), 3.95 (m, 1H), 4.63 (dd, J=6.1, 3.7 Hz, 1H); MS (DCl/NH$_3$) m/z 199 (M+H)$^+$.

Example 11

Benzyl 2,6-diazabicyclo[3.2.1]octane-6-carboxylate

Example 11A

Benzyl 3-oxo-2,6-diazabicyclo[3.2.1]octane-6-carboxylate

Benzyl 5-oxo-2-azabicyclo[2.2.1]heptane-2-carboxylate (2.46 g, 10.0 mmol), prepared according to the procedures described by (Carroll, F. I.; et. al., J. Med. Chem. (1992) 35, 2184), in 50 mL of 95% aqueous ethanol at ambient temperature was treated with sodium acetate (2.47 g, 30.1 mmol) and hydroxylamine hydrochloride (3.48 g, 50.1 mmol). After 45 minutes, the mixture was concentrated under reduced pressure and the residue was diluted with saturated aqueous NaHCO$_3$ and extracted with EtOAc. The organic extract was dried (MgSO$_4$) and concentrated to afford 2.50 grams (96%) of a mixture of the desired oximes as a white solid. A portion of this material (1.57 g, 6.03 mmol) was stirred in a 5:1 solution of CH$_2$Cl$_2$/trimethylsilylpolyphosphate for 12 hours at ambient temperature. The solution was diluted with H$_2$O and extracted twice with EtOAc. The combined organic extracts were dried (MgSO$_4$) and concentrated under reduced pressure. The residue was purified by chromatography (silica gel; 95:5 CH$_2$Cl$_2$/MeOH) to provide 1.08 grams (68%) of the title compound as a white solid. MS (DCl/NH$_3$) m/z 261 (M+H)$^+$, 278 (M+NH$_4$)$^+$.

Example 11B benzyl 2,6-diazabicyclo[3.2.1]octane-6-carboxylate

The product from example 11A (800 mg, 3.07 mmol) in THF (12 mL) at 0° C. was treated dropwise with a 2.0 M solution of borane-methyl sulfide complex in THF (3.4 mL, 6.8 mmol). The solution was stirred for 14 hours at ambient temperature, then recooled to 0° C. and quenched by the careful addition of MeOH and concentrated under reduced pressure. The residue was dissolved in toluene (12 mL) and treated with n-propylamine (1.7 mL). The mixture was stirred for 3 hours at 60° C., allowed to cool to ambient temperature, and concentrated under reduced pressure. The residue was diluted with saturated aqueous NaHCO$_3$ and extracted with CH$_2$Cl$_2$ (4×). The organic extracts were combined, dried (K$_2$CO$_3$), and concentrated. The residue was purified by chromatography (silica gel; 90:10:1 CH$_2$Cl$_2$/MeOH/NH$_4$OH) to provide 453 mg (60%) of the title compound as a colorless oil. MS (DCl/NH$_3$) m/z 247 (M+H)$^+$.

Example 12 tert-butyl 2,6-diazabicyclo[3.2.1]octane-2-carboxylate

The product from Example 11B (140 mg, 0.568 mmol) in CH$_2$Cl$_2$ at ambient temperature was treated with triethylamine followed by di-tert-butyl dicarbonate. The solution was stirred for 2 hours, diluted with saturated aqueous K$_2$CO$_3$, and extracted with CH$_2$Cl$_2$ (2×). The organic extracts were combined, dried (Na$_2$SO$_4$), and concentrated under reduced pressure to provide 190 mg a colorless oil. A suspension of the oil and 10% Pd/C (20 mg) in MeOH (10 mL) were stirred under one atmosphere of hydrogen (balloon) for 6 hours. The catalyst was removed by filtration through a plug of Celite (CH$_2$Cl$_2$ wash). The filtrate was concentrated to provide (106 mg, 91%) the title compound as a colorless oil. MS (DCl/NH$_3$) m/z 213 (M+H)$^+$, 230 M+NH$_4$)$^+$.

Example 13

9-Methyl-3,9-diazabicyclo[4.2.1]nonane

The title compound was prepared as described in U.S. Pat. No. 2,999,091.

Example 14 tert-butyl (3aR,6aR)-hexahydropyrrolo[3,4-b]pyrrole-1(2H)-carboxylate

Example 14A ethyl {[(1R)-1-phenylethyl]-amino}acetate

Ethyl bromoacetate (4.14 g; 24.8 mmol) was treated with (R) α-methylbenzylamine (3 g, 24.8 mmol) and ethyldiisopropylamine (3.2 g; 24.8 mmol) in toluene (100 mL). After heating at reflux for 18 hours, the mixture was cooled to room temperature and concentrated under reduced pressure. The residue was purified by flash chromatography (SiO$_2$, 20% ethyl acetate/pentane) to provide the title compound (3.2 g, 63% yield). MS (DCl/NH$_3$) m/z 208 (M+H)$^+$.

Example 14B

{[(1R)-1-phenylethyl]amino}acetic acid

The product from Example 14A (4.5 g; 15.6 mmol) in water (100 mL) was heated to reflux for 18 hours. The mixture was cooled to 30° C. and concentrated under reduced pressure to provide the title compounds as a white solid (2.7 g; 80% yield). MS (DCl/NH$_3$) m/z 180 (M+H)$^+$.

Example 14C ethyl cis-1-[(1R)-1-phenylethyl]hexahydropyrrolo[3,4-b]pyrrole-5(1H)-carboxylate The product from Example 14B (27.5 g, 154 mmol) and ethyl allyl(2-oxoethyl)carbamate (26.3 g, 154 mmol), prepared as described in (U.S. Pat. No. 5,071,999), in toluene (500 mL) were heated at reflux for 17 hours. The solvent was evaporated under reduced pressure to provide the crude product (45 g) as a nearly 1:1 mixture of diastereomers. These were separated by flash chromatography on silica gel, eluting with 30% ethyl acetate in pentane.

The more mobile diastereomer was obtained as a thick syrup (R$_f$=0.42, pentane:ethyl acetate (3:7) 17 g, 38% yield). The stereocenters were determined to be (R,R) using X-Ray diffraction as described in Example 14E. MS (DCl/NH$_3$) m/z 289 (M+H)$^+$.

The less mobile diastereomer was obtained as a thick syrup (R$_f$=0.21, pentane:ethyl acetate (3:7) 17.8 g, 40% yield). The

Example 14D (3aR,6aR)-1-[(1R)-1-phenylethyl]octahydropyrrolo[3,4-b]pyrrole

The more mobile diastereomer from Example 14C (17 g, 59.0 mmol) in hydrochloric acid (12N, 200 mL) was heated in an oil bath at 120° C. for 20 hours. The mixture was cooled to 20° C. and concentrated under reduced pressure to remove excess HCl. The residue was taken in 10% $Na_2CO_3$ (100 mL) and extracted with $CH_2Cl_2$ (3×200 mL). The organic layers were combined, washed with brine, dried ($Na_2CO_3$), and concentrated. The residue was purified by chromatography ($SiO_2$, eluted with $CH_2Cl_2$:MeOH:$NH_4OH$; 90:10:1) to afford the title compound as a brownish oil (11.4 g, 89% yield). MS (DCl/$NH_3$) m/z 217 (M+H)$^+$.

Example 14E (3aR,6aR)-5-[(4-nitrophenyl)sulfonyl]-1-[(1R)-1-phenylethyl]octahydropyrrolo[3,4-b]pyrrole The product from Example 14D was processed as described in Example 15B to provide the title compound. The stereocenters were determined to be (R,R) using X-ray diffraction as described in Example 15B.

Example 14F (3aR,6aR)-1-[(1R)-1-phenylethyl]-5-(trifluoroacetyl)octahydropyrrolo[3,4-b]pyrrole The product from Example 14D (11.3 g, 52 mmol) and triethylamine (6.8 g, 68 mmol) in anhydrous THF (200 mL) at 0-5° C. was treated with trifluoroacetic anhydride (25.2 g, 63 mmol) dropwise. The reaction mixture was allowed to warm to room temperature overnight. The THF was removed under reduced pressure and replaced with $CH_2Cl_2$ (200 mL). The methylene chloride was washed with brine, dried ($MgSO_4$), and concentrated. The residue was purified using chromatography ($SiO_2$, eluting with 5-15% ethyl acetate/hexanes) to provide the title compound as a light yellow oil (13.7 g, 84% yield). MS (DCl/$NH_3$) m/z 313 (M+H)$^+$.

Example 14G tert-butyl (3aR,6aR)-5-(trifluoroacetyl)hexahydropyrrolo[3,4-b]pyrrole-1(2H)-carboxylate The product from Example 14F (11.2 g; 35.8 mmol) and di-tert-butyl dicarbonate (8.58 g, 39.4 mmol) in methanol (400 mL) was treated with 10% Pd/C (0.6 g). The mixture was shaken under an atmosphere of hydrogen (4 atm) at 25° C. for 18 hours. After filtration, the solution was concentrated under reduced pressure and the residue was purified by chromatography ($SiO_2$, 2:1 ethyl acetate:hexanes) to provide the title compound as a crystalline solid (9.88 g, 89% yield). MS (DCl/$NH_3$) m/z 326 (M+$NH_4$)$^+$.

Example 14H tert-butyl (3aR,6aR)-hexahydropyrrolo[3,4-b]pyrrole-1(2H)-carboxylate The product from Example 14G (9.88 g, 32 mmol) in methanol (200 mL) and water (40 mL) was treated with solid potassium carbonate (4.86 g; 35 mmol). After stirring at 20° C. for 18 hours, the solvent was removed under reduced pressure. The residue was azeotroped with ethyl acetate (50 mL) twice and finally with toluene (100 mL). The dry powder was stirred with 20% MeOH/$CH_2Cl_2$ (100 mL), filtered, and the filtercake was rinsed with 20% MeOH/$CH_2Cl_2$ (100 mL). The filtrate was concentrated to provide the title compound as a white solid. MS (DCl/$NH_3$) m/z 213 (M+H)$^+$.

Example 15

(tert-butyl (3aS,6aS)-hexahydropyrrolo[3,4-b]pyrrole-1(2H)-carboxylate

Example 15A (3aS,6aS)-1-[(1R)-1-phenylethyl]octahydropyrrolo[3,4-b]pyrrole

The less mobile diastereomer from Example 14C was processed as described in Example 14D to provide the title compound as a brownish oil (11.3 g, 76% yield). MS (DCl/$NH_3$) m/z 217 (M+H)$^+$.

Example 15B (3aS,6aS)-5-[(4-nitrophenyl)sulfonyl]-1-[(1R)-1-phenylethyl]octahydropyrrolo[3,4-b]pyrrole The product from Example 15A (148 mg, 0.68 mmol) and triethyl amine (0.15 mL, 1.08 mmol) in dichloromethane (5 mL) at 0° C. was treated with 4-nitrobenzenesulfonyl chloride (166 mg, 0.75 mmol) in dichloromethane (2 mL) over 1 minute. The reaction mixture was allowed to warm to room temperature. After 1 hour, the mixture was diluted with dichloromethane (20 mL) and washed with 5% $NaHCO_3$ (10 mL), brine (10 mL), dried ($MgSO_4$) and concentrated under reduced pressure to provide the title compound as a light yellow solid (270 mg, 98%). Single crystals suitable for x-ray diffraction were grown by slow evaporation from ethyl acetate solution. Crystal data: MW=401.48, $C_{20}H_{23}N_3O_4S$, crystal dimensions 0.60×0.10×0.10 mm, orthorhombic, $P2_12_12_1$ (#19), a=5.4031(5), b=16.168(2), c=22.687(2) Å, V=1981.8(3) Å$^3$, Z=4, $D_{calc}$=1.345 g/cm$^{-3}$. Crystallographic data were collected using Mo K □ radiation (□=0.71069 Å). Refinement of the structure using full matrix least squares refinement of 253 parameters on 2005 reflections with I>3.00□(I) gave R=0.117, $R_w$=0.123.

Example 15C (3aS,6aS)-1-[(1R)-1-phenylethyl]-5-(trifluoroacetyl)octahydropyrrolo[3,4-b]pyrrole The product from Example 15A (11.3 g, 52 mmol) was processed as described in Example 14F to provide the title compound (11.2 g, 69% yield). MS (DCl/$NH_3$) m/z 313 (M+H)$^+$.

Example 15D tert-butyl (3aS,6aS)-5-(trifluoroacetyl)hexahydropyrrolo[3,4-b]pyrrole-1(2H)-carboxylate The product from example 15C was processed as described in Example 14G to provide the title compound (97% yield). MS (DCI/NH$_3$) m/z 326 (M+NH$_4$)$^+$.

Example 15E tert-butyl (3aS,6aS)-hexahydropyrrolo[3,4-b]pyrrole-1(2H)-carboxylate The product from Example 15D was processed as described in the Example 14H to provide the title compound.

Example 16 tert-butyl (3aR,6aR)-hexahydropyrrolo[3,4-b]pyrrole-5-carboxylate

The product of Example 14D was treated with di-t-butyl dicarbonate, then hydrogenated over palladium according to U.S. Pat. No. 5,071,999 (Example 3) to provide the title compound.

Example 17 tert-butyl (3aS,6aS)-hexahydropyrrolo[3,4-b]pyrrole-5-carboxylate

The product of Example 15A was processed as described in Example 16 to provide the title compound.

Example 18

(1R,6S)-3,8-Diaza-bicyclo[4.2.0]octane-3-carboxylic acid tert-butyl ester

To the minor isomer product of Example 3E (2.4 g, 7.5 mmol) in 30 mL CH$_3$OH was added 0.58 g of 20% Pd(OH)$_2$/C (wet). This mixture was shaken under 60 psi of H$_2$ for 16.5 h at 50° C. The mixture was filtered, concentrated to proved the title compound, suitable for use without further purification. MS (DCI/NH$_3$) m/z 213 (M+H)$^+$.

Example 19

(1S,6R)-3,8-Diaza-bicyclo[4.2.0]octane-3-carboxylic acid tert-butyl ester

The major product from Example 3E was processed according to the procedure of Example 18 to provide the title compound: MS (DCI/NH$_3$) m/z 213 (M+H)$^+$.

Example 20

6a-Methyl-octahydro-pyrrolo[3,4-b]pyrrole

Example 20A

N-Allyl-N-(2-hydroxypropyl)-carbamic acid benzyl ester

The product of Example 7C (13.2 g, 56.6 mmol) in THF (100 mL) was treated with MeMgBr (3M in THF, 24.5 mL, 73.5 mmol) at −78° C. over 2 hours. The mixture was then warmed to ambient temperature. The reaction was quenched with saturated, aqueous NH$_4$Cl solution (50 mL) at 0° C., the layers were separated and the aqueous layer was extracted with EtOAc (3×200 mL). The organic layers were combined and concentrated under reduced pressure. The residues were purified by column chromatography (SiO$_2$, 40% hexanes-ethyl acetate) to give the title compound (6.48 g, 26 mmol, 46% yield). $^1$H NMR (CDCl$_3$, 300 MHz) δ 1.16 (d, J=6.4 Hz, 3H), 3.14-3.41 (m, 2H), 3.83-4.09 (m, 3H), 5.02-5.22 (m, 4H), 5.69-5.90 (m, 1H), 7.20-7.40 (m, 5H); MS (DCI/NH$_3$) m/z 250 (M+H)$^+$, 267 (M+NH$_4$)$^+$.

Example 20B

N-Allyl-N-(2-oxo-propyl)-carbamic acid benzyl ester

Dimethylsulfoxide (DMSO, 4.7 g, 60.1 mmol) was added slowly into a solution of oxalyl chloride (3.82 g, 30.1 mmol) in CH$_2$Cl$_2$ (150 ml) at −78° C. After the addition was complete, the mixture was stirred for 15 minutes. The product of Example 20A (6.25 g, 25.1 mmol) in CH$_2$Cl$_2$ (20 mL) was added to the above mixture at −78° C. After the mixture was stirred for 30 minutes, triethylamine (12.6 g, 125 mmol) was added. The reaction mixture was then warmed slowly to ambient temperature. After the reaction was complete, it was quenched with water (10 mL). The layers were separated and the aqueous layer was extracted with EtOAc (3×200 mL). The extracts were combined and concentrated under reduced pressure. The residue was purified by column chromatography (SiO$_2$, 40% hexanes-ethyl acetate) to give the title compound (4.3 g, 17.4 mmol, 70% yield). $^1$H NMR (CDCl$_3$, 300 MHz) δ 2.05 (s, 1.4 H), 2.14 (s, 1.6H), 3.91-4.08 (m, 4H), 5.06-5.21 (m, 4H), 5.68-5.86 (m, 1H), 7.25-7.40 (m, 5H); MS (DCI/NH$_3$) m/z 248 (M+H)$^+$, 265 (M+NH$_4$)$^+$.

Example 20C

1-Benzyl-6a-methyl-hexahydro-pyrrolo[3,4-b]pyrrole-5-carboxylic acid benzyl ester The product of Example 20B (3.0 g, 12.1 mmol) was treated with benzylaminoacetic acid (Aldrich, 2.0 g, 12.1 mmol) in toluene (50 mL) at 110° C. over 2 days. The toluene was removed under reduced pressure and the residue was purified by column chromatography (SiO$_2$, 40% hexanes-ethyl acetate) to give the title compound (2.8 g, 8.0 mmol, 66% yield). $^1$H NMR (MeOH-d$_4$, 300 MHz) δ 1.23 (s, 3H), 1.49-1.64 (m, 1H), 1.93-2.10 (m, 1H), 2.36-2.51 (m, 1H), 2.56-2.67 (m, 1H), 2.73-2.87 (m, 1H), 3.10 (d, J=11.5 Hz, 1H), 3.32-3.41 (m, 1H), 3.52 (d, J=13.2 Hz, 1H), 3.58-3.78 (m, 3H), 5.03-5.22 (m, 2H), 7.14-7.42 (m, 10H); MS (DCI/NH$_3$) m/z 351 (M+H)$^+$.

Example 20D

1-Benzyl-6a-methyl-octahydro-pyrrolo[3,4-b]pyrrole

The product of Example 20C (1.7 g, 4.85 mmol) was treated with Pd/C (10 wt %, 300 mg) i-PrOH (50 mL) at ambient temperature under 1 atm of H$_2$ for 18 h. After the reaction went completion, the catalyst was filtered off and the filtrate was concentrated under reduced pressure to give the title compound (0.7 g, 3.2 mmol, 66% yield). $^1$H NMR (MeOH-d$_4$, 300 MHz) δ 1.23 (s, 3H), 1.32-1.46 (m, 1H), 1.94-2.07 (m, 1H), 2.23-2.39 (m, 2H), 2.46-2.56 (m, 1H), 2.66-2.75 (m, 2H), 2.95-3.04 (m, 2H), 3.62 (d, J=12.9 Hz, 1H), 3.73 (d, J=12.9 Hz, 1H), 7.13-7.37 (m, 5H); MS (DCl/NH$_3$) m/z 217 (M+H)$^+$.

Example 20E

1-Benzyl-6a-methyl-hexahydro-pyrrolo[3,4-b]pyrrole-5-carboxylic acid tert-butyl ester The product of Example 20D (700 mg, 3.24 mmol) was treated with di-tert-butyl dicarbonate (706 mg, 3.24 mmol) and Et$_3$N (2 mL) in CH$_2$Cl$_2$ (10 mL) for 16 hours. The mixture was then concentrated under reduced pressure and purified by column chromatography (SiO$_2$, 40% hexanes-ethyl acetate) to give the title compound (1.02 g, 3.24 mmol, 100% yield). $^1$H NMR (MeOH-d$_4$, 300 MHz) δ 1.22 (s, 3H), 1.47 (s, 9H), 1.49-1.62 (m, 1H), 1.94-2.11 (m, 1H), 2.34-2.46 (m, 1H), 2.57-2.68 (m, 1H), 2.73-2.87 (m, 1H), 3.02 (d, J=11.5 Hz, 1H), 3.21-3.27 (m, 1H), 3.50-3.74 (m, 4H), 7.15-7.32 (m, 5H); MS (DCl/NH$_3$) m/z 317 (M+H)$^+$.

Example 20F

6a-Methyl-hexahydro-pyrrolo[3,4-b]pyrrole-1,5-dicarboxylic acid 1-benzyl ester 5-tert-butyl ester The product of Example 20E (1.02 g, 3.24 mmol) was treated with Pd/C (10 wt %, 100 mg) in MeOH (50 mL) under 1 atm. H$_2$ at 50° C. for 16 hours. The reaction mixture was cooled to ambient temperature. The catalyst was filtered off and the filtrate was concentrated under reduced pressure. The residue was treated with CbzCl (0.5 mL, 3.5 mmol) and Et$_3$N (3 mL) in CH$_2$Cl$_2$ (20 mL) at 0° C. for 2 h. After the reaction was complete, it was quenched with water (5 mL) and extracted with CH$_2$Cl$_2$ (3×20 mL). The extracts were combined and concentrated under reduced pressure. The residue was purified by column chromatography (SiO$_2$, 40% hexanes-ethyl acetate) to give the title compound (0.87 g, 2.42 mmol, 75% yield). $^1$H NMR (MeOH-d$_4$, 300 MHz) δ 1.36-1.50 (m, 13H), 1.67-1.80 (m, 1H), 1.98-2.14 (m, 1H), 2.53-2.68 (m, 1H), 3.14-3.32 (m, 2H), 3.49-3.68 (m, 3H), 5.09 (s, 2H), 7.22-7.42 (m, 5H).

Example 20G

6a-Methyl-hexahydro-pyrrolo[3,4-b]pyrrole-1-carboxylic acid benzyl ester

The product of Example 20F (0.8 g, 2.22 mmol) was treated with TFA (5 mL) in CH$_2$Cl$_2$ (10 mL) at ambient temperature for 1 h. The mixture was then concentrated under reduced pressure and the residue was purified by column chromatography (SiO$_2$, 90:9:1 CH$_2$Cl$_2$:MeOH:NH$_4$OH) to give the title compound (0.32 g, 1.23 mmol, 55% yield). $^1$H NMR (MeOH-d$_4$, 300 MHz) δ 1.42, 1.47 (s, 3H, rotamers), 1.63-1.75 (m, 1H), 1.98-2.13 (m, 1H), 2.37-2.52 (m, 1H), 2.62-2.76 (m, 2H), 3.00-3.12 (m, 1H), 3.26, 3.47 (d, J=12.6 Hz, 1H, rotamers), 3.53-3.62 (m, 2H), 5.08, 5.13 (s, 2H, rotamers), 7.25-7.42 (m, 5H); MS (DCl/NH$_3$) m/z 261 (M+H)$^+$.

Example 21

Hexahydro-pyrrolo[3,4-c]pyrrole-3a-carboxylic acid ethyl ester

Example 21A

2,5-Dibenzyl-hexahydro-pyrrolo[3,4-c]pyrrole-3a-carboxylic acid ethyl ester To the ethyl propynoate (Aldrich, 3.96 g, 40 mmol) in THF (200 mL) in a 3-neck, 3-L round bottom flask equipped with an addition funnel, internal thermometer, and N$_2$ inlet at 0° C. was added trifluoroacetic acid (TFA) (Aldrich, 0.3 mL, 4 mmol). Benzyl(methoxymethyl)trimethylsilylmethylamine (Aldrich, 23.7 g, 100 mmol) in 50 mL THF was added dropwise via addition funnel over 30 minutes with the reaction temperature being maintained below 5° C. After the addition was complete, the mixture was allowed to warm slowly to ambient temperature and then was stirred for 10 h. The mixture was concentrated and the residue was dissolved in 500 mL EtOAc. It was washed with 2×50 mL saturated NaHCO$_3$ and 25 mL brine, dried over Na$_2$SO$_4$, and concentrated under reduced pressure. The residue was purified by column chromatography (SiO$_2$, 50% hexanes-EtOAc) to give 14.5 g of the title compound (36.6 mmol, 91% yield). MS (DCl/NH$_3$) m/z 365 (M+H)$^+$.

Example 21B

Hexahydro-pyrrolo[3,4-c]pyrrole-3a-carboxylic acid ethyl ester

To the product of Example 21A (1.0 g, 2.75 mmol) in EtOH (10 mL) was added Pd(OH)$_2$/C (Aldrich, 20% wet, 0.20 g). This mixture was hydrogenated for 2.5 h under H$_2$ at 50° C. The mixture was filtered and concentrated to give the title compound (0.50 g, 2.71 mmol, 99% yield). $^1$H NMR (CDCl$_3$, 300 MHz) 1.26 (t, J=7.1 Hz, 3 H), 2.67 (dd, J=11.5, 4.4 Hz, 2 H), 2.79 (d, J=11.9 Hz, 2 H), 2.87-3.03 (m, 1 H), 3.10 (dd, J=11.5, 7.8 Hz, 2 H), 4.17 (q, J=7.1 Hz, 2 H); MS (DCl/NH$_3$) m/z 185 (M+H)$^+$.

Example 22

Cis-3-methyl-3,8-diazabicyclo[4.3.0]nonane

Example 22A

2-Benzyl-hexahydro-cyclopenta[c]pyrrol-4-one

A 3-neck, 1-L round bottom flask equipped with an addition funnel, internal thermometer, and N$_2$ inlet at RT was charged with cyclopentenone (16.48 g, 0.20 mol) in 0.5 L of CH$_2$Cl$_2$. Benzyl(methoxymethyl)trimethylsilylmethylamine (5.0 grams, 21 mmol) and trifluoroacetic acid (TFA) (1.07 mL, 13.9 mmol) were added. To this mixture was added additional benzyl(methoxymethyl)-trimethylsilylmethylamine (40 g, 0.168 mol) dropwise via addition funnel over 1 hour with the reaction temperature being maintained below 25° C. (water bath). After the addition was complete, the mixture was stirred for 4 h. The mixture was washed with 1×100 mL 10% Na$_2$CO$_3$. The layers were separated and the organic layer was washed with 1×100 mL 23% NaCl. The organic extract was concentrated under reduced pressure to give an oil. The oil was redissolved in methyl-t-butyl ether (250 mL) and extracted into 1M H$_3$PO$_4$ (200 mL). The aqueous layer was basified with 50% NaOH to pH 12. The product was extracted with methyl-t-butyl ether (250 mL). The layers were separated and the organic layer was washed with 23% NaCl. The layers were separated. The organic layer was charged with acetonitrile (50 mL) and silica gel (10 gms). The mixture was stirred 5 minutes and filtered through a silica gel pad (10 grams). The filtrate was concentrated to give the title compound (35.0 grams, 81.4% of theory), which was carried on to the next step without further purification. MS (ESI/APCI) m/z 216 (M+H)+.

Example 22B

2-Benzyl-hexahydro-cyclopenta[c]pyrrol-4-one oxime

To the ketone from Example 22A (32.4 grams, 150 mmol) in a 1-L round bottom flask equipped with an condenser and an $N_2$ inlet was added EtOH (absolute, 375 mL). To this solution was added a solution comprised of hydroxylamine hydrochloride (13.08 g, 190 mmol) and NaOAc in water (40 mL). The reaction mixture was heated at 65° C. for 1 h until TLC showed the reaction was complete (5:1 MTBE/$CH_3CN$ w/0.1% $Et_3N$; PMA char; $R_f$ SM 0.75, $R_f$ 0.3 and 0.4 for oxime isomers). The reaction mixture was concentrated in vacuo to dryness. The residue was extracted with MTBE (200 mL) and water (200 mL). The biphasic mixture was treated with 50% NaOH solution until the pH of the solution was >12. The MTBE layer was washed with 23% NaCl solution (1×50 mL). The layers were separated and the organic layer was concentrated in vacuo to afford 34 g of crude material. The residue was dissolved in MTBE (25 mL) and pentane (40 mL) and seeded with ~10 mg of authentic seeds. The mixture was stirred and swirled occasionally for 20 minutes and filtered. The cake was washed with 2:1 pentanes-MTBE (3×25 mL). The solid was dried in a vacuum oven to a constant weight of 11.4 grams (33%). The solid was primarily one geometrical isomer of the oxime. MS (ESI) m/z 231 (M+H)+.

Example 22C

2-Benzyl-octahydro-pyrrolo[3,4-c]pyridin-4-one

A 500 mL, 3-neck, round bottom flask was charged with the syn-oxime from Example 22B (12.0 g, 51.9 mmol) and polyphosphoric acid (120 g). The flask was purged with $N_2$/vacuum 3 times. The thick mixture was heated for 1.25 h at 100° C. The mixture was cooled to rt and poured onto ice (240 g). The mixture was adjusted to pH=12 with 25% NaOH and extracted with EtOAc (150 mL). The layers were separated and the aqueous layer was washed with 1×100 mL EtOAc. The organic layers were combined and washed with 1×50 mL of 23% aq. NaCl. The residue was concentrated in vacuo to afford 11 g of an oil. The oil was dissolved in MTBE (40 mL) and treated with ~10 mg of seed crystals, followed by pentane (15 mL). The resulting slurry was stirred for 30 minutes, filtered and washed with 2:1 MTBE-pentanes. The solid was dried to a constant weight of 6.4 grams. MS (CI) m/z 231 (M+H)+.

Example 22D

2-Benzyl-octahydro-pyrrolo[3,4-c]pyridine

To a solution of the lactam from Example 22C (0.46 g) in THF (5 mL) was added 1M LiAlH$_4$ (4.0 mL). The mixture was heated at 50° C. for 2 h, cooled to 15° C., and quenched by cautious addition of water (0.15 mL), followed by 15% NaOH (0.15 mL), then water (0.456 mL). The mixture was stirred for 5 minutes and filtered and washed with THF (3×5 mL). The filtrate was concentrated in vacuo to afford 442 mg of the title compound as a clear oil (quantitative yield). MS (CI) m/z 217 (M+H)+; $^1$H NMR: δ 1.8-1.5 (m, 3H), 2.33-2.10 (m, 2H), 2.8-2.4 (m, 8H), 3.75 (s, 2H), 7.25 ppm (m, 5H).

Example 23

3,8-Diaza-bicyclo[3.2.1]octane-3-carboxylic acid tert-butyl ester

Example 23A

8-Benzyl-3,8-diaza-bicyclo[3.2.1]octane-3-carboxylic acid tert-butyl ester

Di-tert-butyl dicarbonate (0.79 g, 3.6 mmol) was added to a mixture of the product of Example 1F (0.70 g, 3.5 mmol) in tetrahydrofuran (30 mL) and saturated, aqueous NaHCO$_3$ (5 mL). This mixture was stirred at ambient temperature for 18 h then diluted with H$_2$O (10 mL) and EtOAc (15 mL). The layers were separated and the aqueous layer was extracted with EtOAc (3×5 mL). The combined extract was dried over anhydrous Na$_2$SO$_4$, concentrated and purified by column chromatography (SiO$_2$, 50% hexanes in EtOAc) to provide the title compound (0.62 g, 59% yield). MS (DCl/NH$_3$) m/z 303 (M+H)+.

Example 23B 3,8-Diaza-bicyclo[3.2.1]octane-3-carboxylic acid tert-butyl ester

A solution of the product of Example 23A (0.62 g. 0.12 mmol) in EtOH (10 mL) was stirred with Pd/C (Aldrich, 60 mg, 10 wt %) under 1 atmosphere of H$_2$ (balloon) for 18 h. The mixture was filtered, concentrated and purified by column chromatography (SiO$_2$, 1% NH$_4$OH:9% CH$_3$OH:90% CH$_2$Cl$_2$) to provide the title compound (0.44 g, 100% yield). MS (DCl/NH$_3$) m/z 213 (M+H)+.

Example 24

6-Benzyl-2,6-diaza-bicyclo[3.2.0]heptane

Example 24A (2S,3S)-3-Hydroxy-pyrrolidine-1,2-dicarboxylic acid 1-tert-butyl ester 3-Hydroxy-pyrrolidine-2-carboxylic acid (Aldrich, 1.31 g, 10 mmol) was treated with di-tert-butyl dicarbanate (Aldrich, 2.18 g, 10 mmol) and NaOH (5%, 20 mL, 25 mmol) at room temperature for 2 hours. The mixture was acidified with 5% HCl solution at 0-10° C. to bring to pH=4. The mixture was extracted with EtOAc (3×50 mL). The extracts were combined and washed with brine (2×10 mL). The organic solution was concentrated under vacuum to give the title compound as white solid (2.0 g, 8.6 mmol, 86% yield). $^1$H NMR (300 MHz, CH$_3$OH-d$_4$) δ 1.40-1.49 (m, 9 H), 1.82-1.93 (m, 1 H), 1.97-

2.12 (m, 1 H), 3.46-3.60 (m, 2 H), 4.07-4.18 (m, 1 H), 4.38 (dd, J=4.2, 1.9 Hz, 1 H); MS (DCl/NH$_3$) m/z 232 (M+H)$^+$.

Example 24B (2R,3S)-3-Hydroxy-2-hydroxymethyl-pyrrolidine-1-carboxylic acid tert-butyl ester The product of Example 24A (2.0 g, 8.6 mmol) was treated with BH$_3$ (Aldrich, 1M, in THF, 17 mL, 17 mmol) in THF (50 mL) at 65° C. for 1 h. The mixture was cooled and quenched with methanol (5 mL) at 0-10° C., then concentrated under reduced pressure. The residue was treated with saturated NaHCO$_3$ solution (15 mL) and stirred for additional 1 h. The slightly yellow mixture was extracted with EtOAc (3×50 mL). The extracts were combined, washed with brine (2×10 mL), and then concentrated under vacuum to give 1.8 gram title compound as white solid (8.25 mmol, 96% yield). $^1$H NMR (300 MHz, CH$_3$OH-d$_4$) δ 1.47 (s, 9 H), 1.76-1.88 (m, 1 H), 2.03-2.19 (m, 1 H), 3.33-3.58 (m, 3 H), 3.59-3.71 (m, 2 H), 4.30 (dd, J=15.8, 3.6 Hz, 1 H); MS (DCl/NH$_3$) m/z 218 (M+H)$^+$.

Example 24C (2R,3S)-3-Methanesulfonyloxy-2-methanesulfonyloxymethyl-pyrrolidine-1-carboxylic acid tert-butyl ester The product of Example 24B (1.8 g, 8.25 mmol) was treated with methanesulfonyl chloride (Aldrich, 2.37 g, 20.7 mmol) and triethylamine (3.3 g, 33.1 mmol) in methylene chloride (50 mL) at 0° C. for 4 h. The mixture was concentrated and the residue was diluted with ethyl acetate (100 mL), washed with saturated NaHCO$_3$ (3×10 mL) and brine (2×10 mL). The organic solution was concentrated and the residue was purified by column chromatography (SiO$_2$, hexanes:EtOAc=40:60, v.) to provide the title compound (3.0 g, 8.0 mol, 97% yield). $^1$H NMR (300 MHz, CH$_3$OH-d$_4$) δ 1.45-1.54 (s, 9 H), 2.14-2.28 (m, 1 H), 2.28-2.46 (m, 1 H), 3.08-3.19 (m, 6 H), 3.51 (dd, J=9.8, 5.8 Hz, 2 H), 4.19 (s, 1 H), 4.25-4.46 (m, 2 H), 5.24 (s, 1 H); MS (DCl/NH$_3$) m/z 374 (M+H)$^+$.

Example 24D (2R,5R)-6-Benzyl-2,6-diaza-bicyclo[3.2.0]heptane-2-carboxylic acid tert-butyl ester The product of Example 24C (3.0 g, 8 mmol) was treated with benzyl amine (Aldrich, 2.67 g, 25 mmol) in toluene (50 mL) at 110° C. for 16 h. Toluene was removed under vacuum, and the residue was diluted with methylene chloride (50 mL), then washed with 1N NaOH solution (2×5 mL). The organic solution was concentrated and the residue was purified by column chromatography (SiO$_2$, hexanes/EtOAc=20/80, v.) to provide the title compound (1.8 g, 6.25 mol, 78% yield). $^1$H NMR (300 MHz, CH$_3$OH-d$_4$) δ 1.44 (d, J=11.2 Hz, 9 H), 1.52-1.65 (m, J=8.3, 3.6 Hz, 2 H), 3.15-3.21 (m, 2 H), 3.59-3.76 (m, 4 H), 3.99 (t, J=5.4 Hz, 1 H), 4.16-4.28 (m, J=6.1 Hz, 1 H), 7.18-7.35 (m, 5 H); MS (DCl/NH$_3$) m/z 289 (M+H)$^+$.

Example 24E (2R,5R)-2,6-Diaza-bicyclo[3.2.0]heptane-2-carboxylic acid tert-butyl ester The product of Example 24D (0.8 g, 2.78 mmol) in MeOH (50 mL) was stirred with Pd/C (Aldrich, 5%, 120 mg) under 1 atmosphere of hydrogen at 50° C. for 2 h. The catalyst was filtered off and the filtrate was concentrated to give 0.46 g of the title compound (2.3 mmol, 84% yield). $^1$H NMR (300 MHz, CH$_3$OH-d$_4$) δ 1.45 (d, J=10.2 Hz, 9 H), 1.73-1.93 (m, 2 H), 3.07 (dd, J=9.5, 2.4 Hz, 1 H), 3.65-3.90 (m, 3 H), 4.42 (s, 1 H), 4.59 (t, J=5.6 Hz, 1 H); MS (DCl/NH$_3$) m/z 199 (M+H)$^+$.

Example 24F (2R,5R)-6-Benzyl-2,6-diaza-bicyclo[3.2.0]heptane

The product of Example 24D (1.0 g, 3.47 mmol) was treated with trifluoroacetic acid (5 mL) in methylene chloride (20 mL) at ambient temperature for 2 h. It was then concentrated, and the residue was purified by column chromatography (SiO$_2$, CH$_2$Cl$_2$/MeOH/NH$_4$OH=90/10/1, v.) to give 0.43 g of the title compound (2.29 mol, 66% yield). $^1$H NMR (300 MHz, CH$_3$OH-d$_4$) δ 1.68-1.88 (m, 1 H), 1.91-2.06 (m, 1 H), 3.53-3.80 (m, 4 H), 3.96 (s, 2 H), 4.34-4.46 (m, J=6.4 Hz, 2 H), 7.26-7.43 (m, 5 H); MS (DCl/NH$_3$) m/z 189 (M+H)$^+$.

Example 24G (2R,5R)-2,6-Diaza-bicyclo[3.2.0]heptane-2,6-dicarboxylic acid 6-benzyl ester 2-tert-butyl ester The product of example 24E (6.83 g, 34.5 mmol) and triethylamine (7 g, 69.0 mmol) in 50 ml methylene chloride was cooled to 0° C. then treated with CBzCl (6.45 g, 38 mmol), the mixture was stirred at 0° C. for 3 hours then concentrated under vacuum, after diluted with 50 ml Ethyl Acetate and washed with water (30 ml×3), the organic solution was concentrated and the residue was purified by column chromatography (SiO$_2$, hexanes/EtOAc=40/60, v.) to provide the title compound (6.25 g, 18.8 mol, 55% yield). $^1$H NMR (300 MHz, CD$_3$OD) δ 1.37-1.53 (m, 9 H) 1.75-1.94 (m, 1 H) 2.17 (s, 1 H) 3.42-3.61 (m, 2 H) 3.77-3.91 (m, 1 H) 4.03-4.23 (m, 1 H) 4.40 (s, 1 H) 4.89-4.98 (m, 1 H) 5.02-5.19 (m, 2 H) 7.17-7.45 ppm (m, 5 H); MS (DCl/NH$_3$) m/z 333 (M+H)$^+$ 350 (M+NH$_4$)$^+$.

Example 24H (2R,5R)-2,6-Diaza-bicyclo[3.2.0]heptane-6-carboxylic acid benzyl ester The product of Example 24G (1.2 g, 3.61 mmol) was treated with trifluoroacetic acid (5 mL) in methylene chloride (20 mL) at ambient temperature for 2 h. It was then concentrated, and the residue was purified by column chromatography (SiO$_2$, CH$_2$Cl$_2$/MeOH/NH$_4$OH=90/10/1, v.) to give 0.6 g of the title compound (2.59 mol, 72% yield). $^1$H NMR (300 MHz, CD$_3$OD) δ 1.85-2.02 (m, 1 H) 2.31-2.46 (m, 1 H) 3.54-3.77 (m, 2 H) 3.78-3.92 (m, 1 H) 4.25-4.37 (m, 1 H)

4.41-4.49 (m, 1 H) 5.00 (t, J=4.9 Hz, 1 H) 5.11 (s, 2 H) 7.27-7.42 ppm (m, 5 H); MS (DCl/NH$_3$) m/z 233 (M+H)$^+$.

Example 25

(1R,4R)-2-(6-chloro-3-pyridinyl)-2,5-diazabicyclo[2.2.1]heptane 4-methylbenzenesulfonate

Example 25A tert-butyl (1R,4R)-5-benzyl-2,5-diazabicyclo[2.2.1]heptane-2-carboxylate (1R,4R)-2-(benzyl)-2,5-diazabicylo[2.2.1]heptane dihydrobromide (12.4 g, 35.5 mmol), prepared as described in (J. Med. Chem., (1990) 33,1344) and K$_2$CO$_3$ (16.2 g, 117 mmol) in 100 mL of DMF were treated with di-tert-butyl dicarbonate (8.1 g, 37 mmol) at ambient temperature. After stirring for 16 hours, the mixture was filtered and the filtrate diluted with water (500 mL). The mixture was extracted with Et$_2$O (3×300 mL). The extracts were combined, washed with 50% brine (10×20 mL), dried over MgSO$_4$, and the solvent removed under reduced pressure to provide the title compound (9.7 g, 94%). $^1$H NMR (DMSO-d$_6$, 300 MHz) 61.62 (m, 1H), 1.79 (d, J=9.2 Hz, 1H), 2.51 (m, 1H), 2.75 (m, 1H) 3.07 (t, J=10.2 Hz, 1H), 3.32-3.41 (m, 2H), 3.67 (s, 1H), 4.16 (d, 9.8 Hz, 1H), 7.19-7.33 ppm (m, 5H); MS (DCl/NH$_3$) m/z 199 (M+H)$^+$, 216 (M+NH$_4$)$^+$.

Example 25B tert-butyl (1R,4R)-2,5-diazabicyclo[2.2.1]heptane-2-carboxylate

The product from Example 25A (2 g, 6.9 mmol) in 50 mL of EtOH was treated with 10% Pd/C (150 mg) under an H$_2$ atmosphere (1 atm) for 16 hours. The mixture was filtered and the solvent was evaporated under reduced pressure to yield 1.28 g (93.4%) of the title compound. $^1$H NMR (DMSO-d$_6$, MHz) δ 1.39 (s, 9H), 1.54 (d, J=5.6 Hz, 1H), 1.58 (t, J=9.5 Hz, H), 2.70-2.81 (M, 2H), 3.50 (dd, J=1.02, 10.50. 1H), 3.17 (m, 1H), 3.50 (s, 1H), 4.17 ppm (d, J=10.17 Hz, H); MS (DCl/NH$_3$) m/z 199 (M+H)$^+$, 216 (M+NH$_4$)$^+$.

Examples 31-89

General Procedures for Coupling with 3-Chloro-6-phenylpyridazines

Method (A): The bicyclic secondary amine (5 mmol) was combined with 3-chloro-6-phenylpyridazine (Aldrich, 7.5 mmol) in toluene (50 mL). Cesium carbonate (5.5 mmol), 1,3-bis(2,6-di-1-propylphenyl)imidazolium chloride (Strem, 0.3 mmol), tris(dibenzylideneacetone)dipalladium (0) (Pd$_2$(dba)$_3$, Strem, 0.2 mmol) were added, and the mixture was evacuated, then purged with N$_2$ (three times). The mixture was warmed under N$_2$ to 85° C. for 12-72 h. The reaction was cooled to room temperature, filtered and concentrated under reduced pressure. The residue was purified by column chromatography to provide respective aminopyridazine.

Method B: The bicyclic secondary amine (4.1 mmol), 3-chloro-6-phenylpyridazine (Aldrich, 4.92 mmol) and triethylamine (1.7 mL, 12.3 mmol) were combined in dry toluene (30 mL) in a sealed tube and warmed to 110° C. for 1-5 days. The mixture was cooled to room temperature, diluted with CH$_2$Cl$_2$ (10 mL) and H$_2$O (10 mL) and the layers were separated. The aqueous layer was extracted with CH$_2$Cl$_2$ (2×5 mL). The combined extract was dried (Na$_2$SO$_4$), concentrated under reduced pressure, and the residue was purified by column chromatography to provide the respective aminopyridazine.

Method C: The bicyclic secondary amine (95 mmol), 3-chloro-6-phenylpyridazine (Aldrich, 95 mmol) and N,N-diisopropyl)ethylamine (50 mL) were combined with dimethylsulfoxide (50 mL) and the mixture was warmed to 105° C. for 24-60 h. The mixture was cooled to room temperature, diluted with water (300 mL) and extracted with CH$_2$Cl$_2$ (2×150 mL). The combined extract was concentrated under vacuum, and the residue purified by column chromatography to provide the aminopyridazine.

Method D: The bicyclic secondary amine (1.4 mmol), 3-chloro-6-arylpyridazine (1.4 mmol) and N,N-(diisopropyl)ethylamine (0.3 mL, 1.7 mmol) were combined with 1,2-dichlorobenzene (1.5 mL). The mixture was heated in a sealed tube to 140° C. at 330 watts for 60 min in an Emry™ Creator microwave. The mixture was cooled to room temperature and loaded directly onto a silica column. The product was purified by column chromatography to provide the aminopyridazine.

General Procedures for Deprotection

Method FB: The Boc-protected amine (1 mmol) was dissolved in CH$_2$Cl$_2$ (2 mL) and cooled in ice as trifluoroacetic acid (1 mL) was added over 5 min. The resulting solution was allowed to warm to room temperature over 1 h, then concentrated under vacuum. The residue was purified by column chromatography (eluting with MeOH—H$_2$Cl$_2$—NH$_4$OH (10:90:1)) to provide the free base.

Method PD: A solution of the N-benzyl or Cbz-protected amine (1 mmol) in ethanol (10 mL) was stirred with Pd/C (100 mg, 10 wt %) under hydrogen (1-4 atm) at ambient temperature for 2-4 h. The mixture was purged with nitrogen, filtered through diatomaceous earth, and concentrated to give the free amine.

General Procedures for N-Methylation

Method EC: The Boc-protected or free amine (1 mmol) was combined with 36% aqueous formalin (1-2 mmol) and 88% formic acid (1-5 mL) was added. The mixture was warmed to 100° C. for 1-2 h, then cooled to room temperature and concentrated under vacuum. The residue was purified by column chromatography chromatography (eluting with MeOH—CH$_2$Cl$_2$—NH$_4$OH (10:90:1)) to provide the N-methylated free base, which was converted to a salt by one of procedures S1-S5.

Method RA: The free amine (1 mmol) and NaBH(OAc)$_3$ (1 mmol) in 36% aqueous formalin (10-20 mL) was stirred at ambient temperature for 5-20 h. The mixture was quenched with saturated, aqueous NaHCO$_3$ (25 mL), extracted with CH$_2$Cl$_2$ (3×25 mL), dried (Na$_2$SO$_4$) and concentrated under reduced pressure. The residue was purified by column chromatography (eluting with MeOH—CH$_2$Cl$_2$—NH$_4$OH (10:90:1)) to provide the N-methylated free base, which was converted to a salt by one of procedures S1-S5.

Method MEPD: The free amine (1 mmol) and paraformaldehyde (1.1 mmol) in ethanol (10 mL) was stirred with Pd/C (100 mg, 10 wt %) under hydrogen (1-4 atm) at ambient temperature for 2-4 h. The mixture was purged with nitrogen, filtered through diatomaceous earth, and concentrated to give the free amine. The residue was purified by column chromatography (eluting with MeOH—CH$_2$Cl$_2$—NH$_4$OH (10:90:1)) to provide the N-methylated free base, which was converted to a salt by one of procedures S1-S5, below.

General Methods for Salt Formation

Methods S1-S5: The base was combined with 1-2 equivalents of one of the following acids in the solvent indicated, and the resulting precipitate was isolated by filtration and dried to provide the named salt:

Method S1: 4-methylbenzenesulfonic acid (EtOH-EtOAc)
Method S2: fumaric acid (10% MeOH-ether)
Method S3: HCl (EtOH-EtOAc)
Method S4: Trifluoroacetic acid (10% MeOH-ether)
Method S5: L-tartaric acid (MeOH-EtOAc)

| Example | Starting Material | Conditions | Resulting Compound |
|---|---|---|---|
| 31 | Example 1I | 1) A<br>2) FB<br>3) S1 | 3-(6-Phenyl-pyridazin-3-yl)-3,8-diaza-bicyclo[3.2.1]octane bis-p-toluenesulfonate<br>$^1$H NMR (MeOH-d$_4$, 300 MHz) δ 2.15 (m, 4H), 2.35 (s, 6H), 3.53 (m, 1H), 3.58 (m, 1H), 4.32 (m, 3H), 4.37 (m, 1H), 7.22 (m, 4H), 7.64 (m, 3H), 7.68 (m, 4H), 7.93 (m, 2H), 7.97 (d, J = 9.8 Hz, 1H), 8.36 (d, J = 9.3 Hz, 1H); MS (DCI/NH$_3$) m/z 267; Anal. C$_{16}$H$_{18}$N$_4$•2C$_7$H$_8$O$_3$S: C, H, N |
| 32 | Example 3I | 1) A<br>2) FB<br>3) S4 | 3-(6-Phenyl-pyridazin-3-yl)-3,8-diaza-bicyclo[4.2.0]octane bis(trifluoroacetate)<br>$^1$H NMR (CH$_3$OH-d$_4$, 300 MHz) δ 2.10 (dq, J = 15.3, 4.1 Hz, 1H), 2.31 (m, 1H), 3.27 (m, 1H), 3.72 (ddd, J = 12.2, 5.4, 3.7 Hz, 1H), 3.83 (dd, J = 15.3, 3.4 Hz, 1H), 4.05 (m, 2H), 4.22 (dd, J = 11.2, 9.2 Hz, 1H), 4.61 (dd, J = 15.3, 3.1 Hz, 1H), 4.90 (m, 1H), 7.54 (m, 3H), 7.63 (d, J = 9.8 Hz, 1H), 7.95 (m, 2H), 8.16 (d, J = 9.8 Hz, 1H); MS (DCI/NH$_3$) m/z 267 (M + H)$^+$; Anal. calculated for C$_{16}$H$_{18}$N$_4$•2CF$_3$CO$_2$H: C, 48.59; H, 4.08; N, 11.33. Found: C, 48.69; H, 4.34; N, 11.04. |
| 33 | Example 3I | 1) B<br>2) FB<br>3) S4 | 3-(6-Phenyl-pyridazin-3-yl)-3,8-diaza-bicyclo[4.2.0]octane bis-trifluoroacetate<br>$^1$H NMR (300 MHz, CD$_3$OD) δ 2.10 (m, 1H), 2.31 (m, 1H), 3.24 (m, 1H), 3.73 (dt, J = 12.6, 5.7, 4.1 Hz, 1H), 3.83 (dd, J = 15.3, 3.4 Hz, 1H), 4.05 (m, 2H), 4.23 (dd, J = 11.2, 9.2 Hz, 1H), 4.61 (dd, J = 15.3, 3.1 Hz, 1H), 4.91 (dt, J = 9.3, 3.2, 3.1 Hz, 1H), 7.55 (m, 3H), 7.64 (d, J = 9.8 Hz, 1H), 7.95 (m, 2H), 8.19 ppm (d, J = 9.5 Hz, 1H); MS (DCI/NH$_3$) m/z 267 (M + H)$^+$; Anal. calculated for C$_{16}$H$_{18}$N$_4$•2CF$_3$CO$_2$H: C, 48.59; H, 4.08; N, 11.33. Found: C, 48.15; H, 4.16; N, 11.07. |
| 34 | Example 18 | 1) B<br>2) FB<br>3) S1 | 8-(6-Phenyl-pyridazin-3-yl)-3,8-diaza-bicyclo[4.2.0]octane p-toluenesulfonate<br>$^1$H NMR (300 MHz, CD$_3$OD) δ 2.09 (m, 1H), 2.34 (s, 3H), 2.39 (m, 2H), 2.99 (m, 1H), 3.22 (m, 1H), 3.41 (dd, J = 14.4, 3.2 Hz, 1H), 3.59 (m, 1H), 3.92 (m, 2H), 4.19 (t, J = 7.6 Hz, 1H), 4.78 (m, 1H), 7.21 (m, 3H), 7.51 (m, 3H), 7.68 (m, 2H), 7.92 (m, 2H), 8.04 ppm (d, J = 9.5 Hz, 1H); MS (DCI/NH$_3$) m/z 267 (M + H)$^+$; Anal. calculated for C$_{16}$H$_{18}$N$_4$•1.35C$_7$H$_8$O$_3$S: C, 61.28; H, 5.82; N, 11.23. Found: C, 61.08; H, 5.88; N, 11.37. |
| 35 | Example 23B | 1) B<br>2) FB<br>3) S1 | 3-Methyl-8-(6-phenyl-pyridazin-3-yl)-3,8-diaza-bicyclo[3.2.1]octane bis p-toluenesulfonate<br>$^1$H NMR (300 MHz, CD3OD) δ 2.20 (m, 2H), 2.36 (s, 6H), 2.40 (m, 2H), 2.91 (s, 3H), 3.27 (m, 1H), 3.43 (m, 1H), 3.43 (m, 1H), 3.64 (br d, J = 11.9 Hz, 1H), 5.02 (m, 2H), 7.22 (m, 4H), 7.62 (m, 3H), 7.69 (m, 4H), 7.94 (m, 2H), 8.03 (d, J = 9.8 Hz, 1H), 8.43 ppm (d, J = 9.8 Hz, 1H); MS (DCI/NH3) m/z 281 (M + H)+; Anal. calculated for C17H20N4•2.3C7H8O3S•0.6H2O: C, 57.85; H, 5.81; N, 8.15. Found: C, 57.58; H, 5.83; N, 8.46. |
| 36 | Example 6C | 1) C<br>2) FB<br>3) S4 | 2-(6-Phenyl-pyridazin-3-yl)-octahydro-pyrrolo[3,4-c]pyrrole trifluoroacetate<br>$^1$H NMR (CH$_3$OH-d$_4$, 300 MHz) δ 3.36 (m, 4H), 3.65 (m, 2H), 3.75 (dd, J = 11.5, 3.1 Hz, 2H), 3.89 (m, 2H), 7.46 (d, J = 9.5 Hz, 1H), 7.53 (m, 3H), 7.96 (m, 2H), 8.17 (d, J = 9.8 Hz, 1H); MS (DCI/NH$_3$) m/z 267 (M + H)$^+$; Anal. calculated for C$_{16}$H$_{18}$N$_4$•1.7CF$_3$CO$_2$H: C, 50.63; H, 4.31; N, 12.17. Found: C, 50.50; H, 4.14; N, 12.14. |
| 37 | Example 20D | 1) A<br>2) PD<br>3) S2 | 6a-Methyl-5-(6-phenyl-pyridazin-3-yl)-octahydro-pyrrolo[3,4-b]pyrrole fumarate<br>$^1$H NMR (CH$_3$OH-d$_4$, 300 MHz) δ ppm 1.66 (s, 3H), 2.02-2.15 (m, 1H), 2.40-2.54 (m, 1H), 2.88-2.98 (m, 1H), 3.42-3.49 (m, 2H), 3.59-3.70 (m, 2H), 3.82 (dd, J = 10.9, 8.1 Hz, 1H), 4.20 (d, J = 12.5 Hz, 1H), 6.68 (s, 2H), 7.15 (d, J = 9.5 Hz, 1H), 7.39-7.53 (m, 3H), 7.90-7.97 (m, 3H); MS (DCI/NH$_3$) m/z 281 (M + H)$^+$. Anal. C$_{17}$H$_{20}$N$_4$•C$_4$H$_4$O$_4$: C, H, N. |
| 38 | Example 7J | 1) A<br>2) FB<br>3) S2 | (1S,5S)-6-(6-Phenyl-pyridazin-3-yl)-3,6-diaza-bicyclo[3.2.0]heptane fumarate<br>$^1$H NMR (MeOH-d$_4$, 300 MHz) δ 3.25 (dd, J = 13.2, 4.0 Hz, 1H), 2.38 (dd, J = 12.2, 7.0 Hz, 1H), 3.50 (m, 1H), 3.74 (d, J = 12.3 Hz, 1H), 3.87 (d, J = 12.9 Hz, 1H), 3.90 (dd, J = 8.6, 3.4 Hz, 1H), 4.29 (t, J = 8.3 Hz, 1H), 5.21 (dd, J = 6.4, 3.6 Hz, 1H), 6.67 (s, 2H), 6.99 (d, J = 9.5 Hz, 1H), 7.38-7.52 (m, 3H), 7.90-7.99 (m, 3H); MS (DCI/NH$_3$) m/z 253 (M + H)$^+$; Anal. calculated for C$_{15}$H$_{16}$N$_4$•C$_4$H$_4$O$_4$•0.3H$_2$O: C, 61.05; H, 5.55; N, 14.99. Found: C, 61.27; H, 5.55; N, 14.63. |
| 39 | Example 8B | 1) A<br>2) FB | (1R,5S)-3-(6-Phenyl-pyridazin-3-yl)-3,6-diaza-bicyclo[3.2.0]heptane bis-p-toluenesulfonate |

-continued

| Example | Starting Material | Conditions | Resulting Compound |
|---|---|---|---|
| | | 3) S1 | $^1$H NMR (MeOH-d$_4$, 300 MHz) δ 2.24 (s, 6H), 3.70 (m, 2H), 3.81 (dd, J = 13.9, 5.7 Hz, 1H), 3.88 (dd, J = 13.2, 4.0 Hz, 1H), 4.32 (m, 2H), 4.60 (d, J = 13.9 Hz, 1H), 5.22 (m, 1H), 7.19 (d, J = 7.8 Hz, 4H), 7.62 (m, 3H), 7.67 (d, J = 8.2 Hz, 4H), 7.90-8.02 (J = m, 3H), 8.40 (d, J = 9.5 Hz, 1H).; MS (DCI/NH$_3$) m/z 253 (M + H)$^+$. Anal. Calculated for C$_{15}$H$_{16}$N$_4$•2.00C$_7$H$_8$SO$_3$: C, 58.37; H, 5.41; N, 9.39. Found: C, 58.27; H, 5.29; N, 9.21. |
| 40 | Example 10 | 1) A<br>2) FB<br>3) S1 | (1S,5R3-(6-Phenyl-pyridazin-3-yl)-3,6-diaza-bicyclo[3.2.0]heptane bis-p-toluenesulfonate<br>$^1$H NMR (MeOH-d$_4$, 300 MHz) δ 2.23 (s, 3H), 3.34 (m, 1H), 3.70 (m, 1H), 3.81 (dd, J = 13.9, 3.8 Hz, 1H), 3.86 (m, 1H), 4.32 (m, 2H), 4.58 (d, J = 13.6 Hz, 1H), 5.22 (m, 1H), 7.20 (d, J = 8.1 Hz, 2H), 7.62 (m, 3H), 7.67 (d, J = 8.5 Hz, 2H), 7.80 (m, 3H), 8.42 (d, J = 9.9 Hz, 1H); MS (DCI/NH$_3$) m/z 253 (M + H)$^+$. Anal. Calculated for C$_{15}$H$_{16}$N$_4$•2.00C$_7$H$_8$SO$_3$•1.00H$_2$O: C, 56.66; H, 5.57; N, 9.11. Found: C, 56.59; H, 5.25; N, 8.80. |
| 41 | Example 25B | 1) B<br>2) FB<br>3) S1 | 2-(6-Phenyl-pyridazin-3-yl)-2,5-diaza-bicyclo[2.2.1]heptane p-toluenesulfonate<br>$^1$H NMR (300 MHz, D$_2$O) d ppm 2.11-2.26 (m, 1H) 2.40 (s, 3H) 2.30-2.33 (m, 1H) 3.52 (s, 2H) 3.65-3.80 (m, 1H) 3.80-3.99 (m, 1H) 4.60-4.75 (m, 2H) 7.24 (d, J = 9 Hz, 1H) 7.37 (d, J = 8 Hz, 2H) 7.53-7.64 (m, 3H) 7.69 (d, J = 8 Hz, 2H) 7.82-8.00 (m, 3H); MS (DCI/NH$_3$) m/z 257 (M + H)$^+$. Anal. Calculated for C15H16N4•1.1C$_7$H$_8$SO$_3$ Ca, 61.53, H 5.66, N12.68. Found C, 61.53, H, 5.50, N, 12.82 |
| 42 | Example 21B | 1) A<br>2) S3 | 2-(6-Phenyl-pyridazin-3-yl)-hexahydro-pyrrolo[3,4-c]pyrrole-3a-carboxylic acid ethyl ester trihydrochloride<br>$^1$H NMR (MeOH-d$_4$, 300 MHz) δ 1.34 (t, J = 7.1 Hz, 3H), 3.46-3.72 (m, 4H), 3.78 (dd, J = 11.7, 7.0 Hz, 1H), 3.93 (dd, J = 11.7, 4.6 Hz, 1H), 4.02-4.20 (m, 2H), 4.24-4.45 (m, 3H), 7.40-7.75 (m, 3H), 7.43-7.74 (m, 3H), 7.86 (d, J = 9.8 Hz, 1H), 7.91-8.14 (m, 2H), 8.47 (d, J = 9.8 Hz, 1H), 8.46 (d, 1H); MS (DCI/NH$_3$) m/z 339 (M + H)$^+$. Anal. Calculated for C$_{19}$H$_{22}$N$_4$O$_2$•3.00HCl•1.00H$_2$O: C, 48.99; H, 5.84; N, 12.03. Found: C, 49.12; H, 5.45; N, 12.43. |
| 43 | Example 21B | 1) A<br>2) S3 | 2,5-Bis-(6-phenyl-pyridazin-3-yl)-hexahydro-pyrrolo[3,4-c]pyrrole-3a-carboxylic acid ethyl ester bishydrochloride<br>$^1$H NMR (MeOH-d$_4$, 300 MHz) δ 1.33 (t, J = 7.1 Hz, 3H), 3.67-3.84 (m, 1H), 3.86-4.03 (m, 2H), 4.10 (q, J = 7.1 Hz, 5H), 4.33 (q, J = 7.1 Hz, 2H), 4.44 (d, J = 11.9 Hz, 1H), 7.45-7.71 (m, 6H), 7.86 (d, J = 9.8 Hz, 2H), 7.90-8.12 (m, 4H), 8.47 (d, J = 9.8 Hz, 2H); MS (DCI/NH3) m/z 493 (M + H)+. Anal. Calculated for C29H28N6O2•2.45HCl•1.6C4H8O2: C, 58.82; H, 6.03; N, 11.63. Found: C, 59.12; H, 5.65; N, 11.35. |
| 44 | Example 24E | 1) A<br>2) FB<br>3) S2 | (1R,5R)-6-(6-Phenyl-pyridazin-3-yl)-2,6-diaza-bicyclo[3.2.0]heptane Bisfumarate<br>$^1$H NMR (300 MHz, CH$_3$OH-d$_4$) δ 1.98-2.14 (m, 1H), 2.55 (dd, J = 14.2, 5.4 Hz, 1H), 3.69-3.84 (m, 2H), 4.11 (dd, J = 10.3, 2.9 Hz, 1H), 4.47 (dd, J = 10.5, 7.1 Hz, 1H), 4.60-4.67 (m, 1H), 5.22 (t, J = 5.1 Hz, 1H), 6.75 (s, 4H), 7.05 (d, J = 9.2 Hz, 1H), 7.42-7.54 (m, 3H), 7.90-7.97 (m, 3H); MS (DCI/NH$_3$) m/z 253 (M + H)$^+$; Anal. C$_{15}$H$_{16}$N$_4$•2C$_4$H$_4$O$_4$•1.2C$_2$F$_3$HO$_2$: C, H, N. |
| 45 | Example 24F | 1) A<br>2) PD<br>3) S2 | (1R,5R)-2-(6-Phenyl-pyridazin-3-yl)-2,6-diaza-bicyclo[3.2.0]heptane fumarate<br>$^1$H NMR (300 MHz, CH$_3$OH-d$_4$) δ 2.38-2.58 (m, 2H), 3.64 (dd, J = 11.4, 3.2 Hz, 1H), 3.81-3.94 (m, 1H), 4.15-4.26 (m, 1H), 4.39 (dd, J = 11.4, 5.9 Hz, 1H), 5.05 (dt, J = 5.9, 3.1 Hz, 1H), 5.22 (t, J = 6.1 Hz, 1H), 6.68 (s, 2H), 7.25 (d, J = 9.5 Hz, 1H), 7.40-7.53 (m, 3H), 7.89-8.01 (m, 3H); MS (DCI/NH$_3$) m/z 253 (M + H)$^+$; Anal. C$_{15}$H$_{16}$N$_4$•1.2C$_4$H$_4$O$_4$: C, H, N. |
| 46 | Example 25B | 1) B<br>2) FB<br>3) MEPD<br>4) S1 | 2-Methyl-5-(6-phenyl-pyridazin-3-yl)-2,5-diaza-bicyclo[2.2.1]heptane p-toluenesulfonate<br>$^1$H NMR MeOH-d$_4$, (300 MHz) d ppm 2.34 (s, 3H) 2.36-2.42 (m, 1H) 2.39-2.61 (m, 1H) 3.02 (s, 3H) 3.86 (s, 4H) 4.50 (s, 1H) 5.12 (s, 1H) 7.20 (dd, J = 9, 4 Hz, 3H) 7.34-7.60 (m, 3H) 7.68 (d, J = 8 Hz, 2H) 7.85-8.04 (m, 3H), MS (DCI/NH$_3$) m/z 267 (M + H)$^+$; Anal. Calculated for C$_{16}$H$_{18}$N$_4$•1.1C$_7$H$_8$SO$_3$ C, 62.73,, 5.51, N.12.35. Found C, 62.81, H, 5.90, N, 12.46. |
| 47 | Example 21B | 1) A<br>2) RA<br>3) S3 | Ethyl 2-Methyl-5-(6-phenyl-pyridazin-3-yl)-hexahydro-pyrrolo[3,4-c]pyrrole-3a-carboxylate dihydrochloride<br>$^1$H NMR (MeOH-d$_4$, 300 MHz) δ 1.34 (t, J = 7.1 Hz, 3H), 3.05 (s, 3H), 3.22-3.45 (m, 4H), 3.96-4.25 (m, 5H), 4.33 (q, J = 7.1 Hz, 2H) 7.52-7.67 (m, 3H) 7.84 (d, J = 9.8 Hz, 1H) 7.91-8.07 (m, 2H) 8.45 (d, J = 9.8 Hz, 1H); MS (DCI/NH$_3$) m/z 353 (M + H)$^+$; Anal. calculated for C$_{20}$H$_{24}$N$_4$O$_2$•2.00HCl•1.7H$_2$O•0.20C$_4$H$_9$O$_2$: C, 57.73; H, 6.42; N, 13.46. Found: C, 58.86; H, 5.21; N, 12.25. |
| 48 | Example 22 | 1) RA<br>2) PD<br>3) D<br>4) S4 | 5-Methyl-2-(6-phenyl-pyridazin-3-yl)-octahydro-pyrrolo[3,4-c]pyridine trifluoroacetate<br>$^1$H NMR (MeOH-d$_4$, 300 MHz) δ 1.87-2.26 (m, 2H) 2.67-2.78 (m, J = 4.7 Hz, 1H) 2.80-2.88 (m, J = 5.4 Hz, 1H) 2.90 (s, 3H) 3.22-3.29 (m, J = 5.1 Hz, 2H) 3.37-3.49 (m, J = 12.4, 4.6 Hz, 2H) 3.55-3.65 (m, 2H) |

| Example | Starting Material | Conditions | Resulting Compound |
|---|---|---|---|
| | | | 3.74 (dd, J = 10.5, 7.8 Hz, 2H) 7.06 (d, J = 9.5 Hz, 1H) 7.37-7.53 (m, 3H) 7.89 (d, J = 9.8 Hz, 1H) 7.89-7.96 (m, 2H); MS (DCI/NH$_3$) m/z 295; Anal. C$_{18}$H$_{22}$N$_4$•C$_2$HF$_3$O$_2$: C, H, N |
| 49 | Example 25B | 1) B<br>2) FB<br>3) S1 | 2-Benzyl-5-(6-phenyl-pyridazin-3-yl)-2,5-diaza-bicyclo[2.2.1]heptane p-toluenesulfonate<br>1H NMR (300 MHz, DEUTERIUM OXIDE) d ppm 2.40 (s, 3H) 2.41-2.59 (m, 1H) 3.60 (s, 2H) 3.88 (s, 1H) 4.15 (q, J = 7 Hz, 1H) 4.37-4.83 (m, 5H) 7.22 (d, J = 9 Hz, 1H) 7.37 (d, J = 8 Hz, 2H) 7.47-7.65 (m, 8H) 7.69 (d, J = 8 Hz, 2H) 7.81-7.99 (m, 3H)); MS (DCI/NH$_3$) m/z 343 (M + H)$^+$; Anal. calculated for C$_{22}$H$_{22}$ N$_4$O$_2$•C$_7$H$_8$O$_3$S: C, 67.68; H, 5.86; N, 10.89. Found: C, 67.43; H, 5.73; N, 10.72. |
| 50 | Example 20D | 1) A<br>2) S2 | 1-Benzyl-6a-methyl-5-(6-phenyl-pyridazin-3-yl)-octahydro-pyrrolo[3,4-b]pyrrole difumarate<br>$^1$H NMR (MeOH-d$_4$, 300 MHz) δ ppm 1.42-1.52 (m, 3H), 1.64-1.77 (m, 1H), 1.99-2.22 (m, 2H), 2.58-2.79 (m, 2H), 2.81-2.92 (m, 1H), 3.49-3.57 (m, 1H), 3.64-3.96 (m, 4H), 7.04 (d, J = 9.5 Hz, 1H), 7.14-7.52 (m, 9H), 7.84 (d, J = 9.8 Hz, 1H), 7.89-7.97 (m, 1H); MS (DCI/NH$_3$) m/z 371 (M + H)$^+$; Anal. C$_{24}$H$_{26}$N$_4$•2C$_4$H$_4$O$_4$•0.2H$_2$O: C, H, N |
| 51 | Example 6C | 1) C<br>2) FB<br>3) EC<br>4) S3 | 2-Methyl-5-(6-phenyl-pyridazin-3-yl)-octahydro-pyrrolo[3,4-c]pyrrole dihydrochloride<br>$^1$H NMR (CH$_3$OH-d$_4$, 300 MHz) δ 2.96 and 3.03 (rotamer s, 3H), 3.16 (m, 1H), 3.47 (m, 2H), 3.60 (m, 1H), 3.77 (m, 1H), 3.93 (m, 3H), 4.01 (m, 2H), 7.58 (m, 3H), 7.79 and 7.81 (rotamer d, J = 9.4 Hz, 1H), 7.95 (m, 2H), 8.41 and 8.42 (rotamer d, J = 9.4 Hz, 1H); MS (DCI/NH$_3$) m/z 281 (M + H)$^+$; Anal. calculated for C$_{17}$H$_{20}$N$_4$•2HCl•1.5H$_2$O: C, 53.69; H, 6.63; N, 14.73. Found: C, 53.59; H, 6.72; N, 14.96. |
| 52 | Example 2D | 1) B<br>2) FB<br>3) EC<br>4) S1 | 6-Methyl-3-(6-phenyl-pyridazin-3-yl)-3,6-diaza-bicyclo[3.2.1]octane p-toluenesulfonate<br>$^1$H NMR (MeOH-d$_4$, 300 MHz) δ 2.15 (m, 1H), 2.34 (s, 3H), 2.48 (m, 1H), 2.95 (s, 3H), 3.22 (m, 3H), 3.31 (m, 1H), 3.80 (m, 1H), 4.12 (m, 2H), 4.60 (m, 1H), 7.21 (m, 2H), 7.39 (d, J = 9.5 Hz, 1H), 7.50 (m, 3H), 7.69 (m, 2H), 7.94 (m, 2H), 7.95 (d, J = 9.5 Hz, 1H). MS (DCI/NH$_3$) m/z 281 (M + H)$^+$; Anal. C$_{17}$H$_{20}$N$_4$•C$_7$H$_8$O$_3$S: C, H, N. |
| 53 | Example 5B | 1) B<br>2) EC<br>3) S1 | 3-Methyl-6-(6-phenyl-pyridazin-3-yl)-3,6-diaza-bicyclo[3.2.1]octane p-toluenesulfonate<br>$^1$H NMR (300 MHz, CD$_3$OD) δ ppm 2.16 (m, 2H), 2.34 (s, 3H), 2.88 (s, 3H), 2.94 (m, 1H), 3.24 (m, 2H), 3.41 (m, 1H), 3.64 (m, 2H), 3.78 (m, 2H), 7.21 (m, 3H), 7.49 (m, 3H), 7.67 (m, 2H), 7.92 (m, 2H), 7.98 (m, 1H); MS (DCI/NH$_3$) m/z 281 (M + H)$^+$; Anal. calculated for C$_{17}$H$_{20}$N$_4$•C$_7$H$_8$O$_3$S: C, 63.69; H, 6.24; N, 12.38. Found: C, 64.10; H, 5.96; N, 11.81. |
| 54 | Example 4 | 1) B<br>2) FB<br>3) EC<br>4) S1 | 8-(6-Phenyl-pyridazin-3-yl)-3,8-diaza-bicyclo[4.2.0]octane p-toluenesulfonate<br>$^1$H NMR (300 MHz, CD$_3$OD) δ 2.10 (m, 1H), 2.35 (m, 1H), 2.36 (s, 3H), 2.93 (m, 1H), 3.20 (m, 2H), 3.39 (dd, J = 14.2, 3.1 Hz, 1H), 3.56 (m, 1H), 3.88 (dd, J = 7.8, 2.7 Hz, 1H), 3.93 (dd, J = 14.6, 2.0 Hz, 1H), 4.14 (t, J = 7.5 Hz, 1H), 4.73 (dt, J = 5.2, 2.5 Hz, 1H), 7.10 (d, J = 9.2 Hz, 1H), 7.22 (d, J = 8.1 Hz, 2H), 7.49 (m, 3H), 7.70 (d, J = 8.1 Hz, 2H), 7.92 (m, 2H), 7.97 ppm (d, J = 9.2 Hz, 1H); MS (DCI/NH$_3$) m/z 267 (M + H)$^+$; Anal. calculated for C$_{16}$H$_{18}$N$_4$•C$_7$H$_8$O$_3$S•0.25H$_2$O: C, 62.35; H, 6.03; N, 12.65. Found: C, 62.19; H, 6.00; N, 12.30. |
| 55 | Example 3I | 1) B<br>2) EC<br>3) S1 | 8-Methyl-3-(6-phenyl-pyridazin-3-yl)-3,8-diaza-bicyclo[4.2.0]octane p-toluenesulfonate<br>$^1$H NMR (CH$_3$OH-d$_4$, 300 MHz) δ 2.15 (dq, J = 14.9, 4.8 Hz, 1H), 2.29 (s, 6H), 2.35 (m, 1H), 3.02 (m, 3H), 3.26 (m, 1H), 3.72 (dt, J = 12.9, 4.8 Hz, 1H), 3.84 (dd, J = 15.3, 3.1 Hz, 1H), 4.14 (m, 2H), 4.32 (dd, J = 11.2, 4.8 Hz, 1H), 4.59 (dd, J = 15.6, 2.4 Hz, 1H), 4.79 (dt, J = 9.5, 2.7 Hz, 1H), 7.16 (m, 4H), 7.61 (m, 3H), 7.63 (m, 4H), 7.92 (m, 2H), 7.93 (d, J = 9.8 Hz, 1H), 8.28 (d, J = 10.0 Hz, 1H); MS (DCI/NH$_3$) m/z 281 (M + H)$^+$; Anal. calculated for C$_{17}$H$_{20}$N$_4$•2C$_7$H$_8$O$_3$S•H$_2$O: C, 57.93; H, 5.96; N, 8.72. Found: C, 57.84; H, 5.75; N, 8.62. |
| 56 | Example 19 | 1) B<br>2) FB<br>3) S5 | 3-Methyl-8-(6-phenyl-pyridazin-3-yl)-3,8-diaza-bicyclo[4.2.0]octane L-tartrate $^1$H NMR (300 MHz, CD$_3$OD) δ 2.22 (m, 1H), 2.49 (m, 1H), 2.81 (m, 1H), 2.89 (s, 3H), 3.02 (ddd, J = 12.0, 3.9 Hz, 1H), 3.26 (m, 1H), 3.54 (m, 1H), 3.75 (dd, J = 7.3, 1.9 Hz, 1H), 4.07 (m, 2H), 4.39 (s, 2H), 4.69 (m, 1H), 7.07 (d, J = 9.2 Hz, 1H), 7.48 (m, 3H), 7.92 (m, 2H), 7.94 ppm (d, J = 9.2 Hz, 1H); MS (DCI/NH$_3$) m/z 281 (M + H)$^+$; Anal. calculated for C$_{17}$H$_{20}$N$_4$•C$_4$H$_6$O$_6$: C, 58.59; H, 6.09; N, 13.02. Found: 58.24; H, 5.97; N, 12.74. |
| 57 | Example 18 | 1)<br>2)<br>3) | 3-Methyl-8-(6-phenyl-pyridazin-3-yl)-3,8-diaza-bicyclo[4.2.0]octane L-tartrate $^1$H NMR (300 MHz, CD$_3$OD) δ 2.22 (m, 1H), 2.50 (m, 1H), 2.80 (m, 1H), 2.88 (s, 3H), 3.00 (m, 1H), 3.24 (dd, J = 13.9, 3.4 Hz, 1H), 3.55 (m, 1H), 3.75 (dd, J = 7.3, 1.9 Hz, 1H), 4.07 (m, 2H), 4.39 (s, 2H), 4.68 (m, 1H), 7.07 (d, J = 9.5 Hz, 1H), |

-continued

| Example | Starting Material | Conditions | Resulting Compound |
|---|---|---|---|
| | | | 7.49 (m, 3H), 7.92 (m, 2H), 7.94 ppm (d, J = 9.2 Hz, 1H); MS (DCI/NH$_3$) m/z 281 (M + H)$^+$; Anal. calculated for C$_{17}$H$_{20}$N$_4$•1.2C$_4$H$_6$O$_6$•1 H$_2$O: C, 54.32; H, 6.15; N, 11.71. Found: C, 54.94; H, 6.54; N, 11.37. |
| 58 | Example 23B | 1)<br>2)<br>3) | 3-Methyl-8-(6-phenyl-pyridazin-3-yl)-3,8-diaza-bicyclo[3.2.1]octane bis p-toluenesulfonate<br>$^1$H NMR (300 MHz, CD$_3$OD) δ 2.20 (m, 2H), 2.36 (s, 6H), 2.40 (m, 2H), 2.91 (s, 3H), 3.27 (m, 1H), 3.43 (m, 1H), 3.43 (m, 1H), 3.64 (br d, J = 11.9 Hz, 1H), 5.02 (m, 2H), 7.22 (m, 4H), 7.62 (m, 3H), 7.69 (m, 4H), 7.94 (m, 2H), 8.03 (d, J = 9.8 Hz, 1H), 8.43 ppm (d, J = 9.8 Hz, 1H); MS (DCI/NH$_3$) m/z 281 (M + H)$^+$; Anal. calculated for C$_{17}$H$_{20}$N$_4$•2.3C$_7$H$_8$O$_3$S•6H$_2$O: C, 57.85; H, 5.81; N, 8.15. Found: C, 57.58; H, 5.83; N, 8.46. |
| 59 | Example 8 | 1) A<br>2) FB<br>3) RA<br>4) S2 | (1S,5S)-6-Methyl-3-(6-phenyl-pyridazin-3-yl)-3,6-diaza-bicyclo[3.2.0]heptane fumarate<br>$^1$H NMR (MeOH-d$_4$, 300 MHz) δ 2.88 (s, 3H), 3.37-3.60 (m, 3H), 3.89 (dd, J = 11.2, 4.7 Hz, 1H), 4.00-4.15 (m, 2H), 4.48 (d, J = 13.6 Hz, 1H), 4.90 (m, 1H), 6.69 (s, 2.4H), 7.32 (d, J = 9.5 Hz, 1H), 7.39-7.53 (m, 3H), 7.90-8.02 (m, 3H).; MS (DCI/NH$_3$) m/z 267 (M + H)$^+$; Anal. C$_{16}$H$_{18}$N$_4$•1.2C$_4$H$_4$O$_4$•0.5H$_2$O: C, H, N. |
| 60 | Example 10 | 1) A<br>2) FB<br>3) RA<br>4) S1 | (1R,5S)-6-Methyl-3-(6-phenyl-pyridazin-3-yl)-3,6-diaza-bicyclo[3.2.0]heptane bis-p-toluenesulfonate<br>$^1$H NMR (MeOH-d$_4$, 300 MHz) δ 2.31 (s, 3H) 2.94-3.11 (m, 3H), 3.45-3.77 (m, 2H), 4.06-4.36 (m, 2H), 4.60 (d, J = 13.6 Hz, 1H), 4.94-5.13 (m, 1H), 7.18 (d, J = 8.1 Hz, 2H), 7.44-7.54 (m, 3H), 7.60 (d, J = 9.5 Hz, 1H), 7.66 (d, J = 8.1 Hz, 1H), 8.15 (d, J = 9.5 Hz, 1H); MS (DCI/NH$_3$) m/z 267 (M + H)$^+$; Anal. Calculated for C$_{16}$H$_{18}$N$_4$•1.34C$_7$H$_8$SO$_3$•0.5H$_2$O: C, 60.23; H, 5.92; N, 11.07. Found: C, 60.32; H, 5.72; N, 10.67. |
| 61 | Example 7 | 1) A<br>2) FB<br>3) RA<br>4) S2 | (1R,5S)-3-Methyl-6-(6-phenyl-pyridazin-3-yl)-3,6-diaza-bicyclo[3.2.0]heptane fumarate<br>$^1$H NMR (MeOH-d$_4$, 300 MHz) δ 3.00 (s, 3H), 3.12 (dd, J = 12.2, 3.7 Hz, 1H), 3.20 (dd, J = 12.2, 7.5 Hz, 1H), 3.50 (m, 1H), 3.89 (d, J = 12.2 Hz, 1H), 3.93 (dd, J = 8.4, 3.4 Hz, 1H), 4.01 (d, J = 12.2 Hz, 1H), 4.29 (t, J = 8.2 Hz, 1H), 5.21 (dd, J = 7.1, 3.7 Hz, 1H), 6.69 (s, 3H), 7.01 (d, J = 9.2 Hz, 1H), 7.38-7.52 (m, 3H), 7.90-7.99 (m, 3H).; MS (DCI/NH$_3$) m/z 267 (M + H)$^+$; Anal. calculated for C$_{16}$H$_{18}$N$_4$•1.5C$_4$H$_4$O$_4$•0.5H$_2$O: C, 58.79; H, 5.61; N, 12.47. Found: C, 58.86; H, 5.21; N, 12.25. |
| 62 | Example 1I | 1) A<br>2) EC<br>3) S1 | 8-Methyl-3-(6-phenyl-pyridazin-3-yl)-3,8-diaza-bicyclo[3.2.1]octane p-toluenesulfonate<br>$^1$H NMR (MeOH-d$_4$, 300 MHz) δ 2.13 (m, 2H), 2.34 (m, 2H), 2.35 (s, 3H), 2.93 (br s, 3H), 3.23 (m, 1H), 3.42 (m, 1H), 4.15 (m, 2H), 4.41 (m, 2H), 7.22 (m, 2H), 7.40 (d, J = 9.5 Hz, 1H), 7.49 (m, 3H), 7.69 (m, 2H), 7.93 (m, 2H), 7.97 (d, J = 9.5 Hz, 1H); MS (DCI/NH$_3$) m/z 281 (M + H)$^+$; Anal. Calculated for C$_{17}$H$_{20}$N$_4$•C$_7$H$_8$O$_3$S•0.7H$_2$O: C, 61.97; H, 6.37; N, 12.04. Found: C, 62.34; H, 6.17; N, 11.68. |
| 63 | Example 24E | 1) A<br>2) FB<br>3) RA<br>4) S2 | (2R,5R)-2-Methyl-6-(6-phenyl-pyridazin-3-yl)-2,6-diaza-bicyclo[3.2.0]heptane Fumarate<br>$^1$H NMR (300 MHz, CD$_3$OD) δ 2.01-2.18 (m, 1H) 2.33 (dd, J = 13.7, 5.3 Hz, 1H) 2.73 (s, 3H) 3.33-3.48 (m, 2H) 4.11-4.19 (m, 1H) 4.21-4.28 (m, 1H) 4.30-4.38 (m, 1H) 5.14 (t, J = 5.1 Hz, 1H) 6.70-6.75 (m, 3H) 6.99 (d, J = 9.5 Hz, 1H) 7.38-7.52 (m, 3H) 7.86-7.95 ppm (m, 3H); MS (DCI/NH$_3$) m/z 267 (M + H)$^+$. |
| 64 | Example 24H | 1) A<br>2) PD<br>3) RA<br>4) S2 | (2R,5R)-6-Methyl-2-(6-phenyl-pyridazin-3-yl)-2,6-diaza-bicyclo[3.2.0]heptane fumarate<br>$^1$H NMR (300 MHz, CD$_3$OD) δ ppm 2.27-2.43 (m, 1H) 2.44-2.56 (m, J = 6.8 Hz, 1H) 2.85 (s, 3H) 3.74-3.90 (m, 2H) 4.00 (dd, J = 10.7, 6.3 Hz, 1H) 4.08-4.18 (m, 1H) 4.75-4.82 (m, 1H) 4.91-4.99 (m, 1H) 6.70 (s, 2H) 7.20 (d, J = 9.5 Hz, 1H) 7.38-7.55 (m, 3H) 7.87-8.02 (m, 3H); MS (DCI/NH$_3$) m/z 267 (M + H)$^+$. |
| 65 | Example 20G | 1) A<br>2) PD<br>3) RA<br>4) S2 | 1,6a-Dimethyl-5-(6-phenyl-pyridazin-3-yl)-octahydro-pyrrolo[3,4-b]pyrrole fumarate<br>$^1$H NMR (MeOH-d$_4$, 300 MHz) δ ppm 1.59 (s, 3H), 1.90-2.02 (m, 1H), 2.41-2.56 (m, 1H), 2.86 (s, 3H), 2.91-3.02 (m, 1H), 3.34-3.56 (m, 3H), 3.65-3.72 (m, 1H), 3.77-3.86 (m, 1H), 4.22 (d, J = 12.9 Hz, 1H), 6.71 (s, 3H), 7.18 (d, J = 9.5 Hz, 1H), 7.40-7.53 (m, 3H), 7.90-7.96 (m, 3H); MS (DCI/NH$_3$) m/z 295 (M + H)$^+$; Anal. C$_{18}$H$_{22}$N$_4$•C$_4$H$_4$O$_4$: C, H, N. |

Example 66

3-(4-Bromophenyl)-3-chloropyridazine

Example 66A

6-(4-Bromo-phenyl)-4,5-dihydro-2H-pyridazin-3-one

A solution of 4-(4-bromo-phenyl)-4-oxo-butyric acid (Aldrich, 25.0 g, 97.3 mmol) in EtOH (100 mL) was treated with aqueous hydrazine (Aldrich, 55%, 9.1 mL, 100 mmol) at 80° C. for 2 h. The mixture was cooled to room temperature and the precipitate was collected by filtration and dried under vacuum to provide the title compound (24 g, 97% yield). $^1$H NMR (300 MHz, CDCl$_3$) δ 2.35-2.76 (m, 2 H), 2.80-3.11 (m, 2 H), 7.45-7.77 (m, 4 H), 8.55 (s, 1 H); MS (DCI/NH$_3$) m/z 253 (M+H)$^+$, 255 (M+H)$^+$.

Example 66B

6-(4-Bromo-phenyl)-2H-pyridazin-3-one

The product of example 66A (24.0 g, 94.5 mmol) was dissolved in HOAc (200 mL) and treated with bromine (Aldrich, 18.81 g, 104.5 mmol) in acetic acid (20 mL) at ambient temperature. The brown mixture was then warmed to 100° C. for 1 h, cooled down to ambient temperature and diluted with of water (200 mL) while stirring. The white precipitate was isolated by filtration and dried under vacuum overnight to provide the title compound (25.0 g, 100%). $^1$H NMR (300 MHz, CDCl$_3$) δ 7.07 (d, J=10.2 Hz, 1 H), 7.55-7.69 (m, 4 H), 7.72 (d, J=9.8 Hz, 1 H); MS (DCI/NH$_3$) m/z 251 (M+H)$^+$, 253 (M+H)$^+$.

Example 66C

3-(4-Bromo-phenyl)-6-chloro-pyridazine

The product of example 66B (25.0 g, 99 mmol) was stirred with POCl$_3$ (200 mL) at 100° C. for 16 h. Most of the POCl$_3$ was removed by distillation, and the residue was quenched by pouring onto crushed ice with vigorous stirring. The mixture was stirred for an additional 1 h. The white sold was filtered off, washed with water and dried under vacuum to provide the title compound (26.2 g, 97 mmol, yield, 98%). $^1$H NMR (300 MHz, MeOH-D$_4$) δ 7.64-7.78 (m, 2 H), 7.86 (d, J=8.8 Hz, 1 H), 7.93-8.08 (m, 2 H), 8.19 (d, J=9.2 Hz, 1 H); MS (DCI/NH$_3$) m/z 269 (M+H)$^+$, 271 (M+H)$^+$. 273 (M+H)$^+$.

Examples 67-69

The product of Example 66C was coupled to the listed amine according to the indicated method. Further processing as noted in the table below provided the title compounds.

| Example | Starting Material | Conditions | Resulting Compound |
|---|---|---|---|
| 67 | Example 6C | 1) A<br>2) FB<br>3) RA<br>4) S3 | 2-[6-(4-Bromo-phenyl)-pyridazin-3-yl]-5-methyl-octahydro-pyrrolo[3,4-c]pyrrole bis hydrochloride<br>$^1$H NMR (D$_2$O, 300 MHz) δ 2.90 (s, 3H), 3.05 (m, 1H) 3.29-4.09 (m, 9H), 7.60 (d, J = 10.2 Hz, 1H), 7.67 (d, J = 8.5 Hz, 2H) 7.74 (d, J = 8.5 Hz, 2H), 8.17 (d, J = 9.8 Hz, 1H); MS (DCI/NH$_3$) m/z 359 (M + H)$^+$, 361 (M + H)$^+$; Anal. Calculated for C$_{17}$H$_{19}$BrN$_4$•2.00HCl•2.00H$_2$O: C, 43.61; H, 5.38; N, 11.97. Found: C, 43.52; H, 5.12; N, 11.70. |
| 68 | Example 7J | 1) A<br>2) FB<br>3) S1 | (1S,5S)-3-[6-(4-Bromo-phenyl)-pyridazin-3-yl]-3,6-diaza-bicyclo[3.2.0]heptane bis(p-toluenesulfonate)<br>$^1$H NMR (MeOH-D$_4$, 300 MHz) δ 2.33 (s, 6H), 3.68-3.89 (m, 4H), 4.28-4.36 (m, 2H), 4.60 (d, J = 13.9 Hz, 1H), 5.24 (t, J = 6.3 Hz, 1H), 7.19 (d, J = 8.1 Hz, 4H) 7.65 (d, J = 8.1 Hz, 4H), 7.78 (d, J = 6.6 Hz, 2H), 7.82-8.08 (m, 3H), 8.38 (d, J = 9.8 Hz, 1H); MS (DCI/NH$_3$) m/z 331 (M + H)$^+$, 333 (M + H)$^+$; Anal. Calculated for C$_{15}$H$_{15}$BrN$_4$•2.10C$_7$H$_8$SO$_3$•0.50H$_2$O: C, 50.83; H, 4.71; N, 7.98. Found: C, 50.84; H, 4.64; N, 7.66. |
| 69 | Example 7J | 1) A<br>2) FB<br>3) RA<br>4) S1 | (1S,5S)-3-[6-(4-Bromo-phenyl)-pyridazin-3-yl]-6-methyl-3,6-diaza-bicyclo[3.2.0]heptane p-toluenesulfonate<br>$^1$H NMR (MeOH-D$_4$, 300 MHz) δ 2.32 (s, 3H), 2.90 (S, 3H), 3.43-3.81 (m, 3H), 4.09-4.31 (m, 3H), 4.60 (d, J = 13.9 Hz, 1H), 5.03 (dd, J = 7.1, 5.1 Hz, 1H), 7.19 (d, J = 7.8 Hz, 2H), 7.57 (d, J = 9.8 Hz, 1H), 7.61-7.78 (m, 4H), 7.90 (d, J = 8.8 Hz, 2H), 8.14 (d, J = 9.5 Hz, 1H); MS (DCI/NH$_3$) m/z 345 (M + H)$^+$, 347 (M + H)$^+$; Anal. Calculated for C$_{16}$H$_{17}$BrN$_4$•1.40C$_7$H$_8$SO$_3$•0.50H$_2$O: C, 52.05; H, 4.94; N, 9.41. Found: C, 52.31; H, 4.89; N, 9.09. |

Examples 70-74

The listed diamine was coupled with 3-(6-chloropyridazin-3-yl)-1H-indole in place of 3-chloro-6-phenylpyridazine, and further processed according to the listed methods, to provide the title compounds.

| Example | Starting Material | Conditions | Resulting Compound |
|---|---|---|---|
| 70 | Example 6C | 1) C<br>2) FB<br>3) S2 | 3-[6-(Hexahydro-pyrrolo[3,4-c]pyrrol-2-yl)-pyridazin-3-yl]-1H-indole Bis(trifluoroacetate)<br>$^1$H NMR (CH$_3$OH-d$_4$, 300 MHz) δ ppm 3.32-3.49 (m, 4H), 3.68 (dd, |

-continued

| Example | Starting Material | Conditions | Resulting Compound |
|---|---|---|---|
| | | | J = 11.5, 7.1 Hz, 2H), 3.77 (dd, J = 11.5, 3.1 Hz, 2H), 3.92-4.02 (m, 2H), 7.19-7.31 (m, 2H), 7.48-7.52 (m, 1H), 7.65 (d, J = 9.8 Hz, 1H), 8.10 (s, 1H), 8.27 (d, J = 7.5 Hz, 1H), 8.37 (d, J = 9.8 Hz, 1H); MS (DCI/NH$_3$) m/z 306 (M + H)$^+$; Anal. C$_{18}$H$_{19}$N$_5$•2.15C$_2$F$_3$HO$_2$: C, H, N. |
| 71 | Example 121B | 1) C<br>2) FB<br>3) S2 | 3-[6-(5-Methyl-hexahydro-pyrrolo[3,4-c]pyrrol-2-yl)-pyridazin-3-yl]-1H-indole Trifluoroacetate<br>$^1$H NMR (CH$_3$OH-d$_4$, 300 MHz) δ ppm 2.99 (s, 3H), 3.36-3.98 (m, 10H), 7.17-7.32 (m, 2H), 7.50 (d, J = 7.5 Hz, 1H), 7.65 (d, J = 9.8 Hz, 1H), 8.09 (s, 1H), 8.26 (d, J = 7.1 Hz, 1H), 8.35 (d, J = 9.8 Hz, 1H); MS (DCI/NH$_3$) m/z 320 (M + H)$^+$; Anal. C$_{19}$H$_{21}$N$_5$•2.1C$_2$F$_3$HO$_2$: C, H, N. |
| 72 | Example 10 | 1) C<br>2) FB<br>3) S4 | (1R,5R)-3-[6-(3,6-Diaza-bicyclo[3.2.0]hept-3-yl)-pyridazin-3-yl]-1H-indole Bis(trifluoroacetate)<br>$^1$H NMR (CH$_3$OH-d$_4$, 300 MHz) δ ppm 3.52-3.61 (m, 1H), 3.68 (dd, J = 13.7, 5.6 Hz, 2H), 3.81 (dd, J = 11.4, 5.3 Hz, 1H), 4.25 (d, J = 11.5 Hz, 1H), 4.33 (dd, J = 11.2, 8.5 Hz, 1H), 4.51 (d, J = 13.6 Hz, 1H), 5.18 (d, J = 6.1 Hz, 1H), 7.22-7.34 (m, 2H), 7.49-7.56 (m, 1H), 7.81 (d, J = 9.8 Hz, 1H), 8.12 (s, 1H), 8.17-8.24 (m, 1H), 8.40 (d, J = 9.8 Hz, 1H); MS (DCI/NH$_3$) m/z 292 (M + H)$^+$; Anal. C$_{17}$H$_{17}$N$_5$•2.1CF$_3$CO$_2$H: C, H, N. |
| 73 | Example 8 | 1) C<br>2) FB<br>3) S4 | (1S,5S)-3-[6-(3,6-Diaza-bicyclo[3.2.0]hept-3-yl)-pyridazin-3-yl]-1H-indole trifluoroacetate<br>$^1$H NMR (CH$_3$OH-d$_4$, 300 MHz) δ ppm 3.46 (dd, J = 11.5, 6.4 Hz, 1H), 3.52-3.69 (m, 2H), 3.80 (dd, J = 11.4, 5.3 Hz, 1H), 4.21 (d, J = 11.2 Hz, 1H), 4.32 (dd, J = 11.0, 8.6 Hz, 1H), 4.49 (d, J = 13.6 Hz, 1H), 5.10-5.18 (m, 1H), 7.16-7.31 (m, 2H), 7.49 (d, J = 7.1 Hz, 1H), 7.61 (d, J = 9.8 Hz, 1H), 8.01 (s, 1H), 8.18-8.29 (m, 2H); MS (DCI/NH$_3$) m/z 292 (M + H)$^+$; Anal. C$_{17}$H$_{17}$N$_5$•1.6C$_2$F$_3$HO$_2$: C, H, N. |
| 74 | Example 10 | 1) C<br>2) FB<br>3) RA<br>4) S4 | (1R,5R)-3-[6-(6-Methyl-3,6-diaza-bicyclo[3.2.0]hept-3-yl)-pyridazin-3-yl]-1H-indole fumarate<br>$^1$H NMR (CH$_3$OH-d$_4$, 300 MHz) δ ppm 2.95 (s, 3H), 3.31-3.38 (m, 1H), 3.43 (dd, J = 13.6, 4.7 Hz, 1H), 3.51-3.62 (m, 1H), 3.93-4.04 (m, 1H), 4.13 (d, J = 11.2 Hz, 1H), 4.17-4.27 (m, 1H), 4.51 (d, J = 13.6 Hz, 1H), 4.92-5.00 (m, 1H), 6.72 (s, 4H), 7.11-7.24 (m, 2H), 7.33 (d, J = 9.5 Hz, 1H), 7.45 (d, J = 7.8 Hz, 1H), 7.85 (s, 1H), 7.97 (d, J = 9.5 Hz, 1H), 8.31 (d, J = 7.5 Hz, 1H); MS (DCI/NH$_3$) m/z 306 (M + H)$^+$; Anal. C$_{18}$H$_{19}$N$_5$•2.9C$_4$H$_4$O$_4$: C, H, N. |

Examples 75-85

The product of Example 6C was coupled with the chloropyridazines described in Examples 82A-E and processed according to the conditions listed in the table to provide the title compounds.

Example 82A

3-Chloro-6-(nitrophenyl)-pyridazine

To an ice-cold solution of 3-chloro-6-phenylpyridazine (Aldrich, 1.4 g, 7.5 mmol) in conc. sulfuric acid (30 mL) was added 90% nitric acid (0.6 mL, 15 mmol). After 15 min. the mixture was poured over ice (200 mL) and neutralized with 25% aq. NaOH. The resulting precipitate was collected by filtration and dried under vacuum. The crude product (1.84 g) was a 1:1:0.5 mixture of ortho:meta:para isomers.

Example 82B

3-Chloro-6-(2-nitrophenyl)-pyridazine

The crude product from Example 82A was dissolved in warm methanol (80 mL) and allowed to crystallize for 18 h. The supernatant liquid was concentrated and the major component was isolated by column chromatography (SiO$_2$, 0.5% methanol-CH$_2$Cl$_2$) to give 560 mg of the pure ortho isomer (2.4 mmol, 32% yield). MS (ESI) m/z 236 (M+H)$^+$.

Example 82C

3-Chloro-6-(4-nitrophenyl)-pyridazine

The precipitate (500 mg) from Example 82B was dissolved in warm ethanol (100 mL) and allowed to crystallize for 18 h. The solid was collected by filtration and washed with cold ethanol and dried to give 75 mg of the pure para isomer (0.32 mmol, 4% yield). MS (ESI) m/z 236 (M+H)$^+$.

Example 82D

3-Chloro-6-(3-nitrophenyl)-pyridazine

The supernate from Example 82C (300 mg) was concentrated to a solid (300 mg), which was dissolved in warm methanol (50 mL). A cloudy solution was obtained. The mixture was filtered and the supernate was concentrated. The resulting solid was dissolved in methanol, filtered and allowed to crystallize for 18 h. The solid was collected by filtration and dried to give 106 mg of the pure meta isomer (0.45 mmol, 6% yield). MS (ESI) m/z 236 (M+H)$^+$.

Example 82E

3-Chloro-6-imidazol-1-yl-pyridazine

A solution of 3,6-dichloropyridazine (Aldrich, 300 mg, 2.0 mmol), imidazole (Aldrich, 163 mg, 2.4 mmol), and diisopropylethylamine (620 mg, 4.8 mmol) in 1.5 mL 1,2-dichlorobenzene was heated in a sealed tube to 120° C. at 330 watts for 45 min in an Emry™ Creator microwave. The crude reaction mixture was purified by column chromatography (SiO$_2$, 1% methanol-CH$_2$Cl$_2$) to give 135 mg of the title compound (0.75 mmol, 38% yield) as the major product. MS (DCl/NH$_3$) m/z 181 (M+H)$^+$.

glacial acetic acid (600 mL). The mixture was stirred for 10 h, then concentrated under reduced pressure and the residue was diluted with ethyl acetate (100 mL), and washed with brine (3×50 mL). The organic layer was concentrated, and the residue was crystallized from ethyl ether to provide the title compound as a yellow solid (150 g, 462 mmol, 91% yield). $^1$H NMR (300 MHz, CDCl$_3$) δ 4.39 (s, 2H), 7.69 (d, J=8.5 Hz,

| Example | Starting Material | Conditions | Resulting Compound |
|---|---|---|---|
| 75 | Example 82C | 1) D<br>2) FB | 2-[6-(4-Nitro-phenyl)-pyridazin-3-yl]-octahydro-pyrrolo[3,4-c]pyrrole<br>$^1$H NMR (MeOD-d$_4$, 300 MHz) δ 2.86 (dd, J = 11.5, 3.7 Hz, 2H) 3.02-3.14 (m, J = 7.1, 3.4 Hz, 2H) 3.21 (dd, J = 11.4, 7.6 Hz, 2H) 3.55 (dd, J = 11.4, 3.2 Hz, 2H) 3.75-3.86 (m, 2H) 7.09 (d, J = 9.8 Hz, 1H) 7.98 (d, J = 9.5 Hz, 1H) 8.17-8.25 (m, 2H) 8.29-8.39 (m, 2H); MS (DCl/NH$_3$) m/z 312 (M + H)$^+$; Anal. C$_{16}$H$_{17}$N$_5$O$_2$•0.7H$_2$O: C, H, N. |
| 76 | Example 82B | 1) D<br>2) FB<br>3) S2 | 2-[6-(2-Nitro-phenyl)-pyridazin-3-yl]-octahydro-pyrrolo[3,4-c]pyrrole fumarate<br>$^1$H NMR (MeOD-d$_4$, 300 MHz) δ 3.24-3.37 (m, 4H) 3.57-3.65 (m, 2H) 3.65-3.72 (m, 2H) 3.74-3.83 (m, 2H) 6.67 (s, 2H) 7.12 (d, J = 9.5 Hz, 1H) 7.62 (d, J = 9.2 Hz, 1H) 7.64-7.70 (m, 2H) 7.78 (td, J = 7.5, 1.0 Hz, 1H) 7.97-8.02 (m, 1H); MS (DCl/NH$_3$) m/z 312 (M + H)$^+$. |
| 77 | Example 82D | 1) D<br>2) FB | 2-[6-(3-Nitro-phenyl)-pyridazin-3-yl]-octahydro-pyrrolo[3,4-c]pyrrole<br>$^1$H NMR (DMSO-d$_6$, 300 MHz) δ 2.81 (dd, J = 6.6, 4.9 Hz, 3H) 2.86-2.96 (m, 1H) 3.04-3.20 (m, 1H) 3.23-3.36 (m, 2H) 3.47-3.58 (m, 2H) 3.59-3.66 (m, 2H) 3.66-3.82 (m, 2H) 3.83 (s, 3H) 7.05-7.16 (m, 2H) 7.75-7.86 (m, 2H); MS (DCl/NH$_3$) m/z 312 (M + H)$^+$. |
| 78 | Example 82C | 1) D<br>2) FB<br>3) RA | 2-Methyl-5-[6-(4-nitro-phenyl)-pyridazin-3-yl]-octahydro-pyrrolo[3,4-c]pyrrole<br>$^1$H NMR (MeOD-d$_4$, 300 MHz) δ 2.36 (s, 3H) 2.57 (dd, J = 9.8, 3.7 Hz, 2H) 2.82 (dd, J = 9.8, 7.5 Hz, 2H) 3.06-3.17 (m, 2H) 3.58 (dd, J = 10.9, 3.1 Hz, 2H) 3.77 (dd, J = 11.0, 7.7 Hz, 2H) 7.10 (d, J = 9.5 Hz, 1H) 7.98 (d, J = 9.5 Hz, 1H) 8.17-8.27 (m, 2H) 8.30-8.39 (m, 2H); MS (DCl/NH$_3$) m/z 326 (M + H)$^+$; Anal. C$_{17}$H$_{19}$N$_5$O$_2$•0.3H$_2$O: C, H, N. |
| 79 | Example 82D | 1) D<br>2) FB<br>3) RA | 2-Methyl-5-[6-(3-nitro-phenyl)-pyridazin-3-yl]-octahydro-pyrrolo[3,4-c]pyrrole<br>$^1$H NMR (DMSO-d$_6$, 300 MHz) δ 3.11-3.22 (m, 4H) 3.38-3.49 (m, 2H) 3.51-3.59 (m, 2H) 3.64-3.74 (m, 2H) 7.44-7.75 (m, 2H) 7.79-8.00 (m, 2H) 8.97 (s, 2H); MS (DCl/NH$_3$) m/z 326 (M + H)$^+$. |
| 80 | Example 82E | 1) C<br>2) FB<br>3) RA<br>4) S3 | 2-(6-Imidazol-1-yl-pyridazin-3-yl)-5-methyl-octahydro-pyrrolo[3,4-c]pyrrole hydrochloride<br>$^1$H NMR (MeOD-d$_4$, 300 MHz) δ 2.97 (s, 3H) 3.35-3.51 (m, 4H) 3.63-3.75 (m, 4H) 3.75-3.86 (m, 2H) 7.28 (s, 1H) 7.30 (d, J = 9.8 Hz, 1H) 7.87 (d, J = 9.8 Hz, 1H) 7.90 (s, 1H) 8.61 (s, 1H); MS (DCl/NH$_3$) m/z 271 (M + H)$^+$; Anal. C$_{14}$H$_{18}$N$_6$•1.5HCl: C, H, N. |
| 81 | Example 82E | 1) C<br>2) FB<br>3) S3 | 2-(6-Imidazol-1-yl-pyridazin-3-yl)-octahydro-pyrrolo[3,4-c]pyrrole bis hydrochloride<br>$^1$H NMR (MeOD-d$_4$, 300 MHz) δ 3.33-3.42 (m, 4H) 3.61-3.70 (m, 2H) 3.72-3.77 (m, 2H) 3.83-3.90 (m, 2H) 7.35 (d, J = 9.8 Hz, 1H) 7.77-7.82 (m, 1H) 8.01 (d, J = 9.8 Hz, 1H) 8.29-8.32 (m, 1H) 9.68 (t, J = 1.5 Hz, 1H); MS (DCl/NH$_3$) m/z 257 (M + H)$^+$; Anal. C$_{13}$H$_{16}$N$_6$•2.2HCl: C, H, N. |

Examples 83-85

The title compounds were prepared by coupling the listed diamine with 3-(4-iodophenyl)-6-chloropyridazine (described in Example 83F) and processing according to the specified methods to provide the title salt.

Example 83

Example 83A

2-Bromo-1-(4-iodo-phenyl)-ethanone

A solution of bromine (79.3 g, 508 mmol) in glacial acetic acid (50 mL) was added at room temperature to a solution of 1-(4-Iodo-phenyl)-ethanone (Aldrich, 125 g, 508 mmol) in 2H), 7.87 ppm (d, J=8.5 Hz, 2H); MS (DCl/NH$_3$) m/z 246 (M−Br)$^+$ 264 (M−Br+NH$_4$)$^+$.

Example 83B

2-[2-(4-Iodo-phenyl)-2-oxo-ethyl]-malonic acid diethyl ester

Diethyl malonate (8 g, 50 mmol) was treated with sodium hydride (1.2 g, 50 mmol) in dry THF (120 mL) under nitrogen at 0° C. for 30 minutes. A solution of the product from Example 83A (15.8 g, 48.6 mmol) in THF (30 mL) was added, and the mixture stirred for 30 minutes. The reaction mixture was diluted with ethyl acetate (200 mL) and washed with brine (3×20 mL). The organic layer was concentrated to give the title compound as oil (15 g, 36 mmol, 74% yield): $^1$H NMR (300 MHz, CDCl$_3$) δ 1.25-1.32 (m, J=7.1, 7.1 Hz, 7H), 3.57 (d, J=7.1 Hz, 2H), 4.16-4.29 (m, 4H), 7.69 (d, J=8.5 Hz, 2H), 7.84 ppm (d, J=8.8 Hz, 2H); MS (DCl/NH$_3$) m/z 405 (M+H)$^+$, 422 (M+NH$_4$)$^+$.

Example 83C

2-[2-(4-Iodo-phenyl)-2-oxo-ethyl]-malonic acid

The product of Example 83B (1 g, 2.5 mmol) was treated with NaOH solution (1 N, 7.5 ml, 7.5 mmol) in ethanol (5 mL) at 60° C. for 1.5 hours, and then filtered through a pad of diatomaceous earth. The filtrate was concentrated under vacuum and the residue was diluted with water (20 mL) and acidified with HCl (6 N) to bring to pH=1. The resulting precipitate was collected by filtration and dried to provide the title compound as white solid (730 mg, 2.1 mmol, 84% yield): $^1$H NMR (300 MHz, MeOH-D$_4$) δ 3.58 (d, J=7.1 Hz, 2H), 3.93 (t, J=7.0 Hz, 1H), 7.75 (d, J=8.5 Hz, 2H), 7.91 ppm (d, J=8.8 Hz, 2H); MS (DCl/NH$_3$) m/z 366 (M+NH$_4$)$^+$.

Example 83D 6-(4-Iodo-phenyl)-4,5-dihydro-2H-pyridazin-3-one

The product of Example 83C (25 g, 71.8 mmol) was treated with hydrazine hydrate (55% aq., 16 mL, ~275 mmol) in ethanol (300 mL) at 78° C. for 60 hours. The mixture was then concentrated under reduced pressure, and the residue was stirred with water (250 mL) for 1 h. The solid was filtered and dried under vacuum to provide the title compound (20.5 g, 68.3 mmol, 95.1% yield): $^1$H NMR (300 MHz, CDCl$_3$) δ 2.62 (t, J=8.3 Hz, 2H), 2.96 (t, J=8.3 Hz, 2H), 7.45 (d, J=8.5 Hz, 2H), 7.75 (d, J=8.8 Hz, 2H), 8.51 ppm (s, 1H); MS (DCl/NH$_3$) m/z 301 (M+H)$^+$ 318 (M+NH$_4$)$^+$.

Example 83E 6-(4-Iodo-phenyl)-2H-pyridazin-3-one

The product of Example 83D (20.5 g, 68.3 mmol) in glacial acetic acid (200 mL) was treated with a solution of bromine (12 g, 75 mmol) in glacial acetic acid (50 mL) at 100° C. for 1 h. The mixture was then cooled to room temperature and stirred for an additional 16 h. Most of the acetic acid solvent was removed under vacuum, and the residue was stirred with water (250 mL) for 1 h. The solid was filtered and dried under vacuum to provide the title compound (20 g, 66.7 mmol, 98% yield): $^1$H NMR (300 MHz, MeOH-D$_4$) δ 7.06 (d, J=9.8 Hz, 1H), 7.65 (d, J=8.8 Hz, 2H), 7.84 (d, J=8.8 Hz, 2H), 8.01 ppm (d, J=9.8 Hz, 1H); MS (DCl/NH$_3$) m/z 299 (M+H)$^+$.

Example 83F

3-Chloro-6-(4-iodo-phenyl)-pyridazine

The product of Example 83E (20 g, 66.7 mmol) was treated with POCl$_3$ (200 mL) at 100° for 16 hours. Most of the POCl$_3$ was removed by distillation, and the residue was poured into ice (500 g) slowly while stirring. The precipitated solid was filtered and dried under vacuum to provide the title compound (19.2 g, 60.7 mmol, 91% yield): $^1$H NMR (300 MHz, CHLOROFORM-D) δ ppm 7.57 (d, J=8.8 Hz, 1H), 7.76-7.83 (m, 3H), 7.85-7.91 ppm (m, 2H); MS (DCl/NH$_3$) m/z 317 (M+H)$^+$.

| Example | Starting Material | Conditions | Resulting Compound |
|---|---|---|---|
| 83 | Example 7 | 1) C<br>2) TFA<br>3) S4 | (1R,5S)-6-[6-(4-Iodo-phenyl)-pyridazin-3-yl]-3,6-diaza-bicyclo[3.2.0]heptane Trifluoroacetate<br>$^1$H NMR (CH$_3$OH-d$_4$, 300 MHz) δ ppm 3.23-3.31 (m, 1H), 3.39 (dd, J = 12.4, 7.3 Hz, 1H), 3.47-3.60 (m, 1H), 3.76 (d, J = 12.2 Hz, 1H), 3.82-3.93 (m, 2H), 4.32 (t, J = 8.3 Hz, 1H), 5.24 (dd, J = 6.4, 3.7 Hz, 1H), 7.04 (d, J = 9.5 Hz, 1H), 7.69-7.76 (m, J = 8.8 Hz, 2H), 7.86 (d, J = 8.5 Hz, 2H), 7.95 (d, J = 9.2 Hz, 1H); MS (DCl/NH$_3$) m/z 379 (M + H)$^+$; Anal. C$_{15}$H$_{15}$IN$_4$•1.15C$_2$F$_3$HO$_2$: C, H, N. |
| 84 | Example 8 | 1) C<br>2) FB<br>3) S4 | (1S,5S)-3-[6-(4-Iodo-phenyl)-pyridazin-3-yl]-3,6-diaza-bicyclo[3.2.0]heptane Trifluoroacetate<br>$^1$H NMR (CH$_3$OH-d$_4$, 300 MHz) δ ppm 3.42 (dd, J = 11.4, 6.3 Hz, 1H), 3.50-3.67 (m, 2H), 3.78 (dd, J = 11.4, 5.3 Hz, 1H), 4.20 (d, J = 11.5 Hz, 1H), 4.30 (dd, J = 11.2, 8.5 Hz, 1H), 4.51 (d, J = 13.6 Hz, 1H), 5.12 (dd, J = 6.8, 5.8 Hz, 1H), 7.45 (d, J = 9.5 Hz, 1H), 7.76 (d, J = 8.8 Hz, 2H), 7.89 (d, J = 8.8 Hz, 2H), 8.08 (d, J = 9.5 Hz, 1H); MS (DCl/NH$_3$) m/z 379 (M + H)$^+$; Anal. C$_{15}$H$_{15}$IN$_4$•1.85C$_2$F$_3$HO$_2$: C, H, N. |
| 85 | Example 8 | 1) C<br>2) EC<br>3) S4 | (1S,5S)-3-[6-(4-Iodo-phenyl)-pyridazin-3-yl]-6-methyl-3,6-diaza-bicyclo[3.2.0]heptane Trifluoroacetate<br>$^1$H NMR (CH$_3$OH-d$_4$, 300 MHz) δ ppm 3.02 (s, 3H), 3.34-3.44 (m, 1H), 3.49 (dd, J = 13.7, 4.9 Hz, 1H), 3.54-3.66 (m, 1H), 4.04-4.22 (m, 3H), 4.55 (d, J = 13.9 Hz, 1H), 4.92-5.01 (m, 1H), 7.35 (d, J = 9.5 Hz, 1H), 7.76 (d, J = 8.5 Hz, 2H), 7.88 (d, J = 8.8 Hz, 2H), 8.01 (d, J = 9.5 Hz, 1H); MS (DCl/NH$_3$) m/z 393 (M + H)$^+$; Anal. C$_{16}$H$_{17}$IN$_4$•1.3C$_2$F$_3$HO$_2$: C, H, N. |

Example 86

Examples 86A and 86B

The product of Example 6C (0.60 g, 2.8 mmol), 3,6-dichloro-4-methylpyridazine (Aldrich, 0.60 g, 3.7 mmol), $Cs_2CO_3$ (1.4 g, 4.2 mmol), 1,3-bis(2,6-di-1-propylphenyl)imidazolium chloride (Strem, 0.12 g, 0.28 mmol), tris(dibenzylideneacetone)dipalladium (0) ($Pd_2(dba)_3$, Strem, 0.10 g, 0.11 mmol) were combined and the mixture was evacuated, then purged with $N_2$ (three times). This reaction mixture was warmed to 85° C., stirred for 18 h then cooled to ambient temperature and filtered. Purification via column chromatography ($SiO_2$, 50% hexanes in EtOAc) yielded 0.40 g of the major regioisomer (5-(6-Chloro-5-methyl-pyridazin-3-yl)-hexahydro-pyrrolo[3,4-c]pyrrole-2-carboxylic acid tert-butyl ester, Example 86A, 1.2 mmol, 42% yield) and 0.27 g of the mino regioisomer (5-(6-Chloro-4-methyl-pyridazin-3-yl)-hexahydro-pyrrolo[3,4-c]pyrrole-2-carboxylic acid tert-butyl ester, Example 86B, 0.80 mmol, 28% yield). Major and minor regioisomer: MS (DCl/$NH_3$) m/z 339 (M+H)$^+$.

Examples 86-89

A chloropyridazinyl diamine (Example 86A or 86B) (0.40 g, 1.2 mmol), phenylboronic acid (0.29 g, 2.4 mmol), aqueous $Na_2CO_3$ (2 M, 2 mL), tris(dibenzylideneacetone)dipalladium (0) ($Pd_2(dba)_3$, Strem, 43 mg, 0.047 mmol) and 1,3-bis(2,6-di-1-propylphenyl)imidazolium chloride (Strem, 50 mg, 0.12 mmol) were combined and evacuated, then purged with $N_2$ (three times). The mixture was stirred at 85° C. for 20 h then was cooled to ambient temperature, filtered, concentrated under reduced pressure and purified via column chromatography ($SiO_2$, 50% hexanes in EtOAc) to provide the phenyl-substituted pyridazine. This product was processed through the deprotection, methylation (if applicable) and salt formation steps according to the conditions in the table below to provide the title compounds.

| Example | Starting Material | Conditions | Resulting Compound |
|---|---|---|---|
| 86 | Example 86A | 1) FB<br>2) S1 | 2-(5-Methyl-6-phenyl-pyridazin-3-yl)-octahydro-pyrrolo[3,4-c]pyrrole bis-p-toluenesulfonate<br>$^1$H NMR (300 MHz, $CD_3OD$) δ ppm 2.35 (s, 6H), 2.39 (d, J = 1.4 Hz, 3H), 3.43 (m, 4H), 3.65 (m, 2H), 3.77 (dd, J = 11.7, 2.9 Hz, 2H), 3.95 (m, 2H), 7.22 (d, J = 8.1 Hz, 4H), 7.57 (m, 6H), 7.67 (m, 4H); MS (DCl/$NH_3$) m/z 281 (M + H)$^+$; Anal. calculated for $C_{17}H_{20}N_4 \cdot 2C_7H_8O_3S$: C, 59.59; H, 5.81; N, 8.97. Found: C, 59.35; H, 5.74; N, 8.81. |
| 87 | Example 86A | 1) FB<br>2) RA<br>3) S1 | 2-Methyl-5-(5-methyl-6-phenyl-pyridazin-3-yl)-octahydro-pyrrolo[3,4-c]pyrrole bis-p-toluenesulfonate $^1$H NMR (300 MHz, $CD_3OD$) δ ppm 2.35 (s, 6H), 2.39 (s, 3H), 2.99 (s, 3H), 3.16 (m, 2H), 3.48 (m, 2H), 3.89 (m, 6H), 7.22 (d, J = 8.1 Hz, 4H), 7.58 (m, 6H), 7.68 (m, 4H); MS (DCl/$NH_3$) m/z 295 (M + H)$^+$; Anal. calculated for $C_{18}H_{22}N_4 \cdot 2.25C_7H_8O_3S \cdot H_2O$: C, 57.92; H, 6.05; N, 8.01. Found: C, 57.55; H, 5.96; N, 8.31. |
| 88 | Example 86B | 1) FB<br>2) S5 | 2-(4-Methyl-6-phenyl-pyridazin-3-yl)-octahydro-pyrrolo[3,4-c]pyrrole bis-L-tartrate<br>$^1$H NMR (300 MHz, $CD_3OD$) δ ppm 2.50 (d, J = 0.7 Hz, 3H), 3.31 (m, 4H), 3.60 (m, 4H), 3.71 (m, 2H), 4.45 (s, 4H), 7.48 (m, 3H), 7.80 (d, J = 0.7 Hz, 1H), 7.95 (m, 2H); MS (DCl/$NH_3$) m/z 281 (M + H)$^+$; Anal. calculated for $C_{17}H_{20}N_4 \cdot 2C_4H_6O_6$: C, 51.72; H, 5.56; N, 9.65. Found: C, 51.89; H, 5.47; N, 10.22. |
| 89 | Example 86B | 1) FB<br>2) RA<br>3) S2 | 2-Methyl-5-(4-methyl-6-phenyl-pyridazin-3-yl)-octahydro-pyrrolo[3,4-c]pyrrole fumarate<br>). $^1$H NMR (300 MHz, $CD_3OD$) δ ppm 2.50 (d, J = 0.7 Hz, 3H), 2.91 (s, 3H), 3.25 (m, 4H), 3.48 (m, 2H), 3.64 (m, 2H), 3.71 (d, J = 11.2 Hz, 2H), 6.68 (s, 2H), 7.48 (m, 3H), 7.81 (d, J = 1.0 Hz, 1H), 7.95 (m, 2H); MS (DCl/$NH_3$) m/z 295 (M + H)$^+$; Anal. calculated for $C_{18}H_{22}N_4 \cdot C_4H_4O_4 \cdot H_2O$: C, 64.09; H, 6.41; N, 13.59. Found: C, 63.78; H, 6.32; N, 13.27. |

Examples 90-110

Example 90

5-(6-Chloro-pyridazin-3-yl)-hexahydro-pyrrolo[3,4-c]pyrrole-2-carboxylic acid tert-butyl ester The product of Example 6c (1.5 g, 7.1 mmol) was dissolved in 1,4-dioxane (35 mL). 3,6-Dichloropyridazine (Aldrich, 1.37 g, 9.2 mmol), tris(dibenzylideneacetone)dipalladium (0) ($Pd_2(dba)_3$, Strem, 0.28 g, 0.31 mmol), 1,3-bis(2,6-di-1-propylphenyl)imidazolium chloride (Strem, 0.38 g, 0.90 mmol), and $Cs_2CO_3$ (6.97 g, 21.2 mmol) were added and the mixture was stirred at 85° C. for 18 h, then cooled to room temperature, filtered, and concentrated under vacuum. The residue was triturated with 80% EtOAc-hexanes (50 mL) and the resulting solid was filtered and dried under vacuum to give 0.81 g of the title compound (2.5 mmol, 35% yield). MS (DCl/$NH_3$) m/z 325 (M+H)$^+$.

Examples 91-110

The General Procedures for preparing compounds described in Examples 91-110 are described below.

General Procedure for Suzuki Coupling

Method G: The aryl chloride from Example 90 (5 mmol) and the listed arylboronic acid (6 mmol) were dissolved in 1,4-dioxane (50 mL). Cesium carbonate (14 mmol), tris (dibenzylideneacetone)dipalladium (0) (Pd$_2$(dba)$_3$, Strem, 0.3 mmol) and 1,3-bis(2,6-di-1-propylphenyl)imidazolium chloride (Strem, 0.8 mmol) were added, and the mixture was stirred at 85° C. and for 20 h. The reaction was then cooled to room temperature and concentrated under vacuum. The residue was purified by column chromatography to provide the arylated pyridazine. Deprotection and/or N-methylation, followed by salt formation according to the procedures previously described in Example 31, provided the title compounds.

Method H: The aryl chloride from Example 90 (1.5 mmol) and the listed arylboronic acid (3 mmol) were stirred in toluene (25 mL). Aqueous Na$_2$CO$_3$ (2M, 2.5 mL), tris(dibenzylideneacetone)dipalladium (0) (Pd$_2$(dba)$_3$, Strem, 0.06 mmol) and 1,3-bis(2,6-di-1-propylphenyl)imidazolium chloride (Strem, 0.15 mmol) were added, and the mixture was stirred at 85° C. for 16 h. The mixture was then cooled to ambient temperature, filtered through diatomaceous earth and concentrated under reduced pressure. The residue was purified by column chromatography to provide the arylated pyridazine. Deprotection and/or N-methylation, followed by sal formation according to the procedures previously described in Example 31, provided the title compounds.

Method I: The aryl chloride from Example 90 (0.6 mmol) and the listed arylboronic acid (0.66 mmol) were combined in dioxane (15 mL). Cesium carbonate (0.72 mmol), tris(dibenzylideneacetone)dipalladium (0) (Pd$_2$(dba)$_3$, Strem, 9 μmol) and Bu$_3$P (Strem, 70 μL of 10 wt % in hexanes, 24 μmol) were added, and the mixture was warmed to 95° C. for 18 h. The reaction mixture was cooled to room temperature, filtered through diatomaceous earth and concentrated under reduced pressure. The crude material was purified by column chromatography to provide the arylated pyridazine. Deprotection and/or N-methylation, followed by salt formation according to the procedures previously described in Example 31, provided the title compounds.

Method MW: The aryl halide from Example 90 (0.5 mmol) and the arylboronic acid or arylboronic ester (1.5 mmol) were dissolved in dioxane-ethanol (1:1, 2 mL). Dichlorobis(triphenylphosphine)-palladium(II) (Aldrich, 0.05 mmol) and 2-(dicyclohexylphosphino)biphenyl (Strem, 0.0125 mmol) were added followed by 1 N Na$_2$CO$_{3\ (aq)}$ (1 mL) and the suspension was stirred for 5 minutes. The reaction mixture was heated in a sealed tube to 150° C. at 330 Watts for 10 min. in an Emry™ Creator microwave. The reaction was then cooled to room temperature and concentrated under vacuum. The residue was purified by HPLC (Xterra C$_{18}$ 30, X 100 mm). The salt was prepared according to the procedures previously described in Example 31, to provide the title compounds.

| Example | Boronic Acid | Conditions | Resulting Compound |
|---|---|---|---|
| 91 | o-tolyl boronic acid | 1) H<br>2) FB<br>3) S4 | 2-(6-o-Tolyl-pyridazin-3-yl)-octahydro-pyrrolo[3,4-c]pyrrole bis-trifluoroacetate<br>$^1$H NMR (300 MHz, CD$_3$OD) δ 2.36 (s, 3H), 3.25 (m, 2H), 3.39 (m, 2H), 3.66 (m, 2H), 3.75 (dd, J = 11.7, 3.2 Hz, 2H), 3.90 (m, 2H), 7.39 (m, 4H), 7.52 (d, J = 9.5 Hz, 1H), 7.89 ppm (d, J = 9.5 Hz, 1H); MS (DCI/NH$_3$) m/z 281 (M + H)$^+$; Anal. calculated for C$_{17}$H$_{20}$N$_4$•2CF$_3$CO$_2$H: C, 49.61; H, 4.36; N, 11.02. Found: C, 50.09; H, 4.47; N, 11.24. |
| 92 | m-tolyl boronic acid | 1) G<br>2) FB<br>3) S4 | 2-(6-(3-methylphenyl)pyridazin-3-yl)-octahydro-pyrrolo[3,4-c]pyrrole Bis(trifluoroacetate)<br>$^1$H NMR (CH$_3$OH-d$_4$, 300 MHz) δ 2.44 (m, 3H), 3.30 (m, 1H), 3.40 (m, 3H), 3.66 (m, 2H), 3.76 (m, 2H), 3.91 (m, 2H), 7.36 (m, 1H), 7.43 (m, 1H), 7.54 (d, J = 9.8 Hz, 1H), 7.70 (m, 1H), 7.79 (m, 1H), 8.22 (d, J = 9.8 Hz, 1H); MS (DCI/NH$_3$) m/z 281 (M + H)$^+$; Anal. C$_{17}$H$_{20}$N$_4$•2CF$_3$CO$_2$H: C, H, N. |
| 93 | p-tolyl boronic acid | 1) G<br>2) FB<br>3) S4 | 2-(6-p-Tolyl-pyridazin-3-yl)-octahydro-pyrrolo[3,4-c]pyrrole trifluoroacetate<br>$^1$H NMR (300 MHz, CD$_3$OD) δ 2.42 (s, 3H), 3.40 (m, 4H), 3.66 (m, 2H), 3.75 (dd, J = 11.9, 3.4 Hz, 2H), 3.91 (m, 2H), 7.36 (m, 2H), 7.54 (d, J = 9.8 Hz, 1H), 7.85 (m, 2H), 8.22 ppm (d, J = 9.8 Hz, 1H); MS (DCI/NH$_3$) m/z 281 (M + H)$^+$; Anal. calculated for C$_{17}$H$_{20}$N$_4$•1.9CF$_3$CO$_2$H: C, 50.27; H, 4.44; N, 11.27. Found: C, 50.23; H, 4.52; N, 11.57. |
| 94 | 3,5-dimethylphenylboronic acid | 1) G<br>2) FB<br>3) S4 | 2-[6-(3,5-Dimethyl-phenyl)-pyridazin-3-yl]-octahydro-pyrrolo[3,4-c]pyrrole trifluoroacetate<br>$^1$H NMR (300 MHz, CD$_3$OD) δ ppm 2.40 (s, 6H), 3.38 (m, 4H), 3.66 (m, 2H), 3.75 (dd, J = 11.7, 3.2 Hz, 2H), 3.92 (m, 2H), 7.20 (s, 1H), 7.56 (d, J = 9.5 Hz, 1H), 7.56 (s, 2H), 8.23 (d, J = 9.5 Hz, 1H); MS (DCI/NH$_3$) m/z 295 (M + H)$^+$; Anal. calculated for C$_{18}$H$_{22}$N$_4$•2CF$_3$CO$_2$H: C, 50.58; H, 4.63; N, 10.72. Found: C, 50.66; H, 4.56; N, 10.66. |
| 95 | p-methoxyphenyl boronic acid | 1) H<br>2) FB<br>3) S3 | 2-[6-(4-Methoxy-phenyl)-pyridazin-3-yl]-octahydro-pyrrolo[3,4-c]pyrrole hydrochloride<br>$^1$H NMR (CH$_3$OH-d$_4$, 300 MHz) δ 3.35 (m, 2H), 3.43 (m, 2H), 3.66 (m, 2H), 3.77 (m, 2H), 3.88 (s, 3H), 3.97 (m, 2H), 7.11 (m, 2H), 7.72 (d, J = 9.8 Hz, 1H), 7.93 (m, 2H), 8.37 (d, J = 9.8 Hz, 1H); MS (DCI/NH$_3$) m/z 297 (M + H)$^+$; Anal. calculated for C$_{17}$H$_{20}$N$_4$•3HCl: C, 50.32; H, 5.71; N, 13.81. Found: C, 50.42; H, 6.11; N, 13.71. |
| 96 | Furan-3-yl boronic acid | 1) H<br>2) FB<br>3) S4 | 2-(6-Furan-3-yl-pyridazin-3-yl)-octahydro-pyrrolo[3,4-c]pyrrole bis-trifluoroacetate<br>$^1$H NMR (300 MHz, CD$_3$OD) δ ppm 3.39 (m, 4H), 3.65 (m, 2H), 3.74 (dd, J = 11.7, 3.2 Hz, 2H), 3.92 (m, 2H), 7.00 (dd, |

-continued

| Example | Boronic Acid | Conditions | Resulting Compound |
|---|---|---|---|
| | | | J = 1.7, 0.7 Hz, 1H), 7.56 (d, J = 9.8 Hz, 1H), 7.69 (t, J = 1.7 Hz, 1H), 8.10 (d, J = 9.5 Hz, 1H), 8.29 (m, 1H); MS (DCI/NH$_3$) m/z 257 (M + H)$^+$; Anal. calculated for C$_{14}$H$_{16}$N$_4$O•2CF$_3$CO$_2$H: C, 44.64; H, 3.75; N, 11.57. Found: C, 44.49; H, 3.70; N, 11.42. |
| 97 | Thiophen-3-yl boronic acid | 1)H 2)FB 3)S1 | 2-(6-Thiophen-3-yl-pyridazin-3-yl)-octahydro-pyrrolo[3,4-c]pyrrole p-toluenesulfonate <br> $^1$H NMR (300 MHz, CD$_3$OD) δ ppm 2.33 (s, 3H), 3.32 (m, 4H), 3.64 (m, 2H), 3.71 (m, 2H), 3.82 (m, 2H), 7.21 (m, 2H), 7.27 (d, J = 9.5 Hz, 1H), 7.56 (dd, J = 5.1, 3.1 Hz, 1H), 7.68 (m, 3H), 8.00 (m, 2H); MS (DCI/NH$_3$) m/z 273 (M + H)$^+$; Anal. calculated for C$_{14}$H$_{16}$N$_4$S•C$_7$H$_8$O$_3$S•0.5H$_2$O: C, 54.53; H, 5.42; N, 10.38. Found: C, 54.58; H, 5.25; N, 10.58. |
| 98 | Thiophen-3-yl boronic acid | 1)H 2)FB 3)RA 4)S1 | 2-Methyl-5-(6-thiophen-3-yl-pyridazin-3-yl)-octahydro-pyrrolo[3,4-c]pyrrole p-toluenesulfonate <br> $^1$H NMR (300 MHz, CD$_3$OD) δ ppm 2.36 (s, 3H), 2.94 (s, 3H), 3.26 (m, 2H), 3.38 (m, 2H), 3.64 (m, 4H), 3.77 (m, 2H), 7.14 (d, J = 9.5 Hz, 1H), 7.22 (m, 2H), 7.53 (dd, J = 5.1, 3.1 Hz, 1H), 7.70 (m, 3H), 7.88 (d, J = 9.5 Hz, 1H), 7.93 (dd, J = 2.9, 1.2 Hz, 1H); MS (DCI/NH$_3$) m/z 287 (M + H)$^+$; Anal. calculated for C$_{15}$H$_{18}$N$_4$S•C$_7$H$_8$O$_3$S: C, 57.62; H, 5.71; N, 12.22. Found: C, 57.49; H, 5.71; N, 12.07. |
| 99 | 5-indolyl boronic acid | 1) I 2) FB 3) S1 | 5-[6-(Hexahydro-pyrrolo[3,4-c]pyrrol-2-yl)-pyridazin-3-yl]-1H-indole Bis(p-toluenesulfonate) <br> $^1$H NMR (CH$_3$OH-d$_4$, 300 MHz) δ ppm 2.31 (s, 7.5H), 3.23-3.50 (m, 4H), 3.58-3.72 (m, 2H), 3.78 (dd, J = 11.7, 2.2 Hz, 2H), 3.95 (dd, J = 11.2, 6.8 Hz, 2H), 6.63 (d, J = 3.1 Hz, 1H), 7.19 (d, J = 7.8 Hz, 5H), 7.39 (d, J = 3.1 Hz, 1H), 7.59 (d, J = 8.8 Hz, 1H), 7.64-7.77 (m, 7H), 8.19 (s, 1H), 8.41 (d, J = 9.8 Hz, 1H); MS (DCI/NH$_3$) m/z 306 (M + H)$^+$; Anal. C$_{18}$H$_{19}$N$_5$•2.3C$_7$H$_8$O$_3$S: C, H, N. |
| 100 | N-=methylindol-5-yl boronic acid | 1) I 2) FB 3) S2 | 5-[6-(Hexahydro-pyrrolo[3,4-c]pyrrol-2-yl)-pyridazin-3-yl]-1-methyl-1H-indole Fumarate <br> $^1$H NMR (CH$_3$OH-d$_4$, 300 MHz) δ ppm 3.19-3.39 (m, 4H), 3.56-3.79 (m, 6H), 3.84 (s, 3H), 6.52 (dd, J = 3.1, 0.7 Hz, 1H), 6.67 (s, 3H), 7.12 (d, J = 9.5 Hz, 1H), 7.21 (d, J = 3.1 Hz, 1H), 7.48 (d, J = 8.8 Hz, 1H), 7.78 (dd, J = 8.5, 1.7 Hz, 1H), 7.92 (d, J = 9.5 Hz, 1H), 8.09 (d, J = 1.4 Hz, 1H); MS (DCI/NH$_3$) m/z 320 (M + H)$^+$; Anal. C$_{19}$H$_{21}$N$_5$•1.3C$_4$H$_4$O$_4$•NH$_4$O: C, H, N. |
| 102 | o-tolyl boronic acid | 1) H 2) FB 3) RA 4) S5 | 2-Methyl-5-(6-o-tolyl-pyridazin-3-yl)-octahydro-pyrrolo[3,4-c]pyrrole bis-L-tartrate <br> $^1$H NMR (300 MHz, CD$_3$OD) δ ppm 2.31 (s, 3H), 2.94 (s, 3H), 3.26 (m, 2H), 3.40 (m, 2H), 3.67 (m, 4H), 3.80 (m, 2H), 4.45 (s, 4H), 7.17 (d, J = 9.5 Hz, 1H), 7.32 (m, 4H), 7.56 (d, J = 9.5 Hz, 1H); MS (DCI/NH$_3$) m/z 295 (M + H)$^+$; Anal. calculated for C$_{18}$H$_{22}$N$_4$•2 C$_4$H$_6$O$_6$: C, 52.52; H, 5.76; N, 9.42. Found: C, 52.29; H, 5.82; N, 9.42. |
| 103 | m-tolyl boronic acid | 1) G 2) FB 3) RA 4) S3 | 2-Methyl-5-(6-(3-methylphenyl)pyridazin-3-yl)-octahydro-pyrrolo[3,4-c]pyrrole dihydrochloride <br> $^1$H NMR (CH$_3$OH-d$_4$, 300 MHz) δ 2.45 (s, 3H), 2.96 and 3.02 (rotamer s, 3H), 3.20 (m, 1H), 3.48 (m, 2H), 3.61 (m, 1H), 3.79 (m, 1H), 3.98 (m, 5H), 7.44 (m, 2H), 7.81 (m, 3H), 8.41 and 8.44 (rotamer d, J = 9.8 Hz, 1H); MS (DCI/NH$_3$) m/z 295 (M + H)$^+$; Anal. C$_{18}$H$_{22}$N$_4$•2.5HCl•0.5H$_2$O: C, H, N. |
| 104 | p-tolyl boronic acid | 1) G 2) S3 | 2-Methyl-5-(6-p-tolyl-pyridazin-3-yl)-octahydro-pyrrolo[3,4-c]pyrrole di-hydrochloride <br> $^1$H NMR (300 MHz, CD$_3$OD) δ ppm 2.43 (s, 3H), 2.97 (s, 3H), 3.17 (m, 2H), 3.54 (m, 2H), 3.93 (m, 6H), 7.40 (d, J = 7.8 Hz, 2H), 7.76 (m, 1H), 7.88 (m, 2H), 8.38 (d, J = 9.5 Hz, 1H); MS (DCI/NH$_3$) m/z 295 (M + H)$^+$; Anal. calculated for C$_{18}$H$_{22}$N$_4$•2HCl•1.7H$_2$O: C, 54.33; H, 6.94; N, 14.08. Found: C, 54.79; H, 7.01; N, 13.65. |
| 105 | 3,5-dimethylphenyl boronic acid | 1) G 2) FB 3) RA 4) S3 | 2-[6-(3,5-Dimethyl-phenyl)-pyridazin-3-yl]-5-methyl-octahydro-pyrrolo[3,4-c]pyrrole di-hydrochloride <br> $^1$H NMR (300 MHz, CD$_3$OD) δ ppm 2.41 (s, 6H), 2.97 (s, 3H), 3.17 (m, 1H), 3.52 (m, 3H), 3.91 (m, 6H), 7.25 (s, 1H), 7.58 (s, 2H), 7.78 (t, J = 9.2 Hz, 1H), 8.39 (m, 1H); MS (DCI/NH$_3$) m/z 309 (M + H)$^+$; Anal. calculated for C$_{19}$H$_{24}$N$_4$•2HCl•1.7H$_2$O: C, 55.39; H, 7.19; N, 13.60. Found: C, 55.21; H, 7.37; N, 13.51. |
| 106 | Furan-3-yl boronic acid | 1)H 2)FB 3)RA 4)S1 | 2-(6-Furan-3-yl-pyridazin-3-yl)-5-methyl-octahydro-pyrrolo[3,4-c]pyrrole bis-p-toluenesulfonate <br> $^1$H NMR (300 MHz, CD$_3$OD) δ ppm 2.32 (s, 6H), 2.99 (s, 3H), 3.19 (m, 1H), 3.49 (m, 3H), 3.91 (m, 6H), 6.97 (m, 1H), 7.19 (d, J = 8.1 Hz, 4H), 7.65 (m, 5H), 7.72 (m, 1H), 8.12 (dd, J = 27.8, 9.8 Hz, 1H), 8.32 (d, J = 5.8 Hz, 1H); MS (DCI/NH$_3$) |

-continued

| Example | Boronic Acid | Conditions | Resulting Compound |
|---|---|---|---|
| 107 | 1-(4-methylbenzene-sulfonyl)indol-5-boronic acid | 1) I<br>2) FB<br>3) S1 | m/z 271 (M + H)+; Anal. calculated for $C_{15}H_{18}N_4O \cdot 2C_7H_8O_3S$: C, 56.66; H, 5.57; N, 9.11. Found: C, 56.61; H, 5.56; N, 8.81.<br>5-[6-(Hexahydro-pyrrolo[3,4-c]pyrrol-2-yl)-pyridazin-3-yl]-1-(toluene-4-sulfonyl)-1H-indole<br>$^1$H NMR (300 MHz, $CD_3OD$) δ 2.27 (s, 6H), 2.35 (s, 3H), 3.37-3.51 (m, 4H), 3.57-3.72 (m, 2H), 3.80 (dd, J = 11.9, 2.0 Hz, 2H), 3.99 (dd, J = 11.2, 6.8 Hz, 2H), 6.86 (d, J = 3.7 Hz, 1H), 7.17 (d, J = 8.1 Hz, 4H), 7.34 (d, J = 8.8 Hz, 2H), 7.65 (d, J = 8.1 Hz, 4H), 7.71 (d, J = 9.8 Hz, 1H), 7.79 (d, J = 3.7 Hz, 1H), 7.86 (d, J = 8.5 Hz, 2H), 7.92 (dd, J = 8.8, 1.7 Hz, 1H), 8.11-8.20 (m, 2H), 8.34 ppm (d, J = 9.8 Hz, 1H); MS (DCI/NH3) m/z 460 (M + H)+; Anal. calculated for $C_{25}H_{25}N_5O_2S \cdot 2.3C_7H_8O_3S$: C, 57.69; H, 5.11; N, 8.18. Found: C, 57.34; H, 4.82; N 8.41. |
| 108 | p-methoxyphenyl boronic acid | 1)H<br>2)FB<br>3)RA<br>4)S1 | 3-Methyl-8-(6-phenyl-pyridazin-3-yl)-3,8-diaza-bicyclo[4.2.0]octane L-tartrate<br>$^1$H NMR (300 MHz, $CD_3OD$) δ ppm 2.22 (m, 1H), 2.50 (m, 1H), 2.80 (m, 1H), 2.88 (s, 3H), 3.00 (m, 1H), 3.24 (dd, J = 13.9, 3.4 Hz, 1H), 3.55 (m, 1H), 3.75 (dd, J = 7.3, 1.9 Hz, 1H), 4.07 (m, 2H), 4.39 (s, 2H), 4.68 (m, 1H), 7.07 (d, J = 9.5 Hz, 1H), 7.49 (m, 3H), 7.92 (m, 2H), 7.94 (d, J = 9.2 Hz, 1H); MS (DCI/NH$_3$) m/z 281 (M + H)+; Anal. calculated for $C_{17}H_{20}N_4 \cdot 1.2C_4H_6O_6 \cdot 1$ $H_2O$: C, 54.32; H, 6.15; N, 11.71. Found: C, 54.94; H, 6.54; N, 11.37. |

Example 114-128

Example 114A 2-(6-Chloro-pyridazin-3-yl)-octahydro-pyrrolo[3,4-c]pyrrole

The product from Example 90 (1.5 g, 4.6 mmol) was deprotected using Method FB to give 1.02 g of the title compound (4.6 mmol, 100% yield). $^1$H NMR (300 MHz, $CD_3OD$) δ 2.78 (dd, J=11, 4 Hz, 2H) 2.97-3.06 (m, 2H) 3.09-3.18 (m, 2H) 3.42 (dd, J=11, 4 Hz, 2H) 3.63-3.75 (m, 2H) 7.02 (d, J=9 Hz, 1H) 7.40 ppm (d, J=9 Hz, 1H). MS m/z 225 (M+H)+.

Example 114B 2-(6-Chloro-pyridazin-3-yl)-5-methyl-octahydro-pyrrolo[3,4-c]pyrrole The product from Example 114A (1.0 g, 4.5 mmol) was N-methylated using method EC to give 1.0 g of the title compound (4.4 mmol, 96% yield). H NMR (300 MHz, $CD_3OD$) δ 2.34 (s, 3H) 2.52 (dd, J=10, 4 Hz, 2H) 2.73-2.84 (m, 2H) 3.01-3.14 (m, 2H) 3.47 (dd, J=11, 3 Hz, 2H) 3.57-3.73 (m, 2H) 7.03 (d, J=9 Hz, 1H) 7.40 ppm (d, J=9 Hz, 1H). MS (DCl/NH$_3$) m/z 239 (M+H)+.

Examples 115-127

The aryl halide from Example 114B (0.5 mmol) and the arylboronic acid or arylboronic ester (1.5 mmol) were processed according to the procedure of method MW, and the product carried further through the listed procedures to provide the title compounds.

| Example | Boronic Acid | Conditions | Resulting Compound |
|---|---|---|---|
| 115 | 5-indolyl boronic acid (Frontier) | 1. I<br>2. S2 | 5-[6-(5-Methyl-hexahydro-pyrrolo[3,4-c]pyrrol-2-yl)-pyridazin-3-yl]-1H-indole fumarate<br>$^1$H NMR (CH$_3$OH-d$_4$, 300 MHz) δ ppm 2.87 (s, 3H), 3.18-3.43 (m, 4H), 3.51-3.70 (m, 4H), 3.72-3.81 (m, 2H), 6.54 (d, J = 3.4 Hz, 1H), 6.69 (s, 2H), 7.17 (d, J = 9.5 Hz, 1H), 7.29 (d, J = 3.4 Hz, 1H), 7.48 (d, J = 8.5 Hz, 1H), 7.72 (dd, J = 8.5, 1.7 Hz, 1H), 7.94 (d, J = 9.5 Hz, 1H), 8.10 (d, J = 1.7 Hz, 1H); MS (DCI/NH$_3$) m/z 320 (M + H)+; Anal. $C_{19}H_{21}N_5 \cdot 1.2C_4H_4O_4 \cdot H_2O$: C, H, N. |
| 116 | 3-Methyl-5-(4,4,5,5-tetramethyl-[1,3,2]dioxaborolan-2-yl)-1H-indole | 1. I<br>2. S2 | 3-Methyl-5-[6-(5-methyl-hexahydro-pyrrolo[3,4-c]pyrrol-2-yl)-pyridazin-3-yl]-1H-indole fumarate<br>$^1$H NMR (CH$_3$OH-d$_4$, 300 MHz) δ ppm 2.36 (s, 3H), 2.88 (s, 3H), 3.21-3.38 (m, 4H), 3.54-3.68 (m, 4H), 3.74-3.81 (m, 2H), 6.69 (s, 2H), 7.05 (d, J = 1.0 Hz, 1H), 7.17 (d, J = 9.5 Hz, 1H), |

-continued

| Example | Boronic Acid | Conditions | Resulting Compound |
|---|---|---|---|
| | | | 7.42 (dd, J = 8.5, 0.7 Hz, 1H), 7.70 (dd, J = 8.5, 1.7 Hz, 1H), 7.96 (d, J = 9.5 Hz, 1H), 8.05 (dd, J = 1.7, 0.7 Hz, 1H); MS (DCI/NH$_3$) m/z 334 (M + H)$^+$; Anal. C$_{19}$H$_{21}$N$_5$•1.2C$_4$H$_4$O$_4$•0.3H$_2$O: C, H, N. |
| 117 | 3-amino-4-methylphenyl boronic acid (Lancaster) | 1. H 2. S2 | 2-Methyl-5-[6-(5-methyl-hexahydro-pyrrolo[3,4-c]pyrrol-2-yl)-pyridazin-3-yl]-phenylamine hemifumarate<br>$^1$H NMR (CH$_3$OH-d$_4$, 300 MHz) δ ppm 2.20 (s, 3H), 2.71 (s, 3H), 3.02 (dd, J = 10.5, 4.1 Hz, 2H), 3.18-3.41 (m, 4H), 3.59-3.74 (m, 4H), 6.66 (s, 1H), 7.05-7.19 (m, 3H), 7.30 (d, J = 1.4 Hz, 1H), 7.79 (d, J = 9.5 Hz, 1H); MS (DCI/NH$_3$) m/z 310 (M + H)$^+$; Anal. C$_{18}$H$_{23}$N$_5$•0.6C$_4$H$_4$O$_4$•0.9H$_2$O: C, H, N. |
| 118 | 4-aminophenyl boronic acid (Asymchem) | 1. H 2. S2 | 4-[6-(5-Methyl-hexahydro-pyrrolo[3,4-c]pyrrol-2-yl)-pyridazin-3-yl]-phenylamine Fumarate<br>$^1$H NMR (CH$_3$OH-d$_4$, 300 MHz) δ ppm 2.90 (s, 3H), 3.22-3.40 (m, 4H), 3.55-3.67 (m, 4H), 3.71-3.79 (m, 2H), 6.69 (s, 2H), 6.75-6.82 (m, 2H), 7.12 (d, J = 9.5 Hz, 1H), 7.64-7.72 (m, 2H), 7.80 (d, J = 9.5 Hz, 1H); MS (DCI/NH$_3$) m/z 296 (M + H)$^+$; Anal. C$_{17}$H$_{21}$N$_5$•1.3C$_4$H$_4$O$_4$•0.5H$_2$O: C, H, N. |
| 119 | 4-indolyl boronic acd (Apollo) | 1. I 2. S2 | 4-[6-(5-Methyl-hexahydro-pyrrolo[3,4-c]pyrrol-2-yl)-pyridazin-3-yl]-1H-indole Trifluoroacetate<br>$^1$H NMR (CH$_3$OH-d$_4$, 300 MHz) δ ppm 2.99 (s, 3H), 3.21-4.00 (m, 10H), 6.88 (d, J = 2.4 Hz, 1H), 7.27-7.35 (m, 1H), 7.42-7.52 (m, 2H), 7.63 (d, J = 8.1 Hz, 1H), 7.69 (d, J = 9.5 Hz, 1H), 8.38 (d, J = 9.8 Hz, 1H); MS (DCI/NH$_3$) m/z 320 (M + H)$^+$; Anal. C$_{19}$H$_{21}$N$_5$•2.15C$_2$F$_3$HO$_2$: C, H, N. |
| 120 | 2-Benzofuran boronic acid (Aldrich) | 3. I 4. S2 | 2-(6-Benzofuran-2-yl-pyridazin-3-yl)-5-methyl-octahydro-pyrrolo[3,4-c]pyrrole Trifluoroacetate<br>$^1$H NMR (CH$_3$OH-d$_4$, 300 MHz) δ ppm 2.98 (s, 3H), 3.33-4.08 (m, 10H), 7.26-7.43 (m, 3H), 7.52 (s, 1H), 7.59 (d, J = 8.1 Hz, 1H), 7.70 (d, J = 7.5 Hz, 1H), 8.12 (d, J = 9.5 Hz, 1H); MS (DCI/NH$_3$) m/z 321 (M + H)$^+$; Anal. C$_{19}$H$_{20}$N$_4$O•2.1C$_2$F$_3$HO$_2$: C, H, N. |
| 122 | 2-amino-5-pyridinyl boronic acid | 1)MW 2)S3 | 5-[6-(5-Methyl-hexahydro-pyrrolo[3,4-c]pyrrol-2-yl)-pyridazin-3-yl]-pyridin-2-ylamine<br>$^1$H NMR (300 MHz, CD$_3$OD) δ ppm 2.35 (s, 3H) 2.52 (dd, J = 10, 4 Hz, 2H) 2.78-2.89 (m, 2H) 3.02-3.16 (m, 2H) 3.47-3.58 (m, 2H) 3.62-3.75 (m, 2H) 6.67 (d, J = 8 Hz, 1H) 7.05 (d, J = 10 Hz, 1H) 7.76 (d, J = 9 Hz, 1H) 8.05 (dd, J = 9, 3 Hz, 1H) 8.45 (s, 1H); MS (DCI/NH$_3$) m/z 297 (M + H)$^+$; Anal; C$_{16}$H$_{20}$N$_6$•3.6HCl•1.38H$_2$O |
| 123 | Pyrrole-3-boronic acid | 1)MW 2)DeSi 3)S3 | 2-Methyl-5-[6-(1H-pyrrol-3-yl)-pyridazin-3-yl]-octahydro-pyrrolo[3,4-c]pyrrole<br>$^1$H NMR (300 MHz, CD$_3$OD) δ ppm 2.34 (s, 3H) 2.48 (dd, J = 10, 4 Hz, 2H) 2.80-2.91 (m, 2H) 3.00-3.13 (m, 2H) 3.46-3.56 (m, 2H) 3.56-3.70 (m, 2H) 6.59-6.66 (m, 1H) 6.75-6.83 (m, 1H) 7.00 (d, J = 9 Hz, 1H) 7.28-7.37 (m, 1H) 7.62 (d, J = 9 Hz, 1H); MS (DCI/NH$_3$) m/z 270 (M + H)$^+$. |
| 124 | Thiphen-2-yl boronic acid | 1)MW 2)S3 | 2-Methyl-5-(6-thiophen-2-yl-pyridazin-3-yl)-octahydro-pyrrolo[3,4-c]pyrrole<br>$^1$H NMR (300 MHz, CD$_3$OD) δ ppm 2.35 (s, 3H) 2.53 (dd, J = 10, 4 Hz, 2H) 2.75-2.90 (m, 2H) 3.01-3.15 (m, 2H) 3.48-3.58 (m, 2H) 3.63-3.75 (m, 2H) 7.04 (d, J = 9 Hz, 1H) 7.11 (d, J = 9 Hz, 1H) 7.43 (d, J = 6 Hz, 1H) 7.54 (d, J = 5 Hz, 1H) 7.81 (d, J = 9 Hz, 1H); MS (DCI/NH$_3$) m/z 287 (M + H)$^+$; Anal; C$_{15}$H$_{18}$N$_4$S•3.5HCl•0.19H$_2$O |
| 125 | Pyrazol-4-yl boronic acid | 1)MW 2)S3 | 2-Methyl-5-[6-(1H-pyrazol-4-yl)-pyridazin-3-yl]-octahydro-pyrrolo[3,4-c]pyrrole<br>$^1$H NMR (300 MHz, CD$_3$OD) δ ppm 2.35 (s, 3H) 2.52 (dd, J = 10, 4 Hz, 2H) 2.79-2.90 (m, 2H) 3.02-3.15 (m, 2H) 3.49-3.58 (m, 2H) 3.62-3.72 (m, 2H) 7.04 (d, J = 9 Hz, 1H) 7.69 (d, J = 9 Hz, 1H) 8.11 (bs, 2H); MS (DCI/NH$_3$) m/z 271 (M + H)$^+$; Anal; C$_{14}$H$_{18}$N$_6$•4.08HCl•0.46C$_4$H$_8$O$_2$ |
| 126 | 3-carbazole boronic acid | 1)MW 2)S3 | 3-[6-(5-Methyl-hexahydro-pyrrolo[3,4-c]pyrrol-2-yl)-pyridazin-3-yl]-9H-carbazole<br>$^1$H NMR (300 MHz, CD$_3$OD) δ ppm 2.37 (s, 3H) 2.55 (dd, J = 11, 3 Hz, 2H) 2.82-2.94 (m, 2H) 3.05-3.17 (m, 2H) 3.54-3.63 (m, 2H) 3.66-3.79 (m, 2H) 7.12 (d, J = 9 Hz, 1H) 7.17-7.23 (m, 1H) 7.34-7.50 (m, 2H) 7.54 (d, J = 8 Hz, 1H) 7.93-8.04 (m, 2H) 8.13 (d, J = 8 Hz, 1H) 8.61 (s, 1H); ); MS (DCI/NH$_3$) m/z 370 (M + H)$^+$; Anal; C$_{23}$H$_{23}$N$_5$•4.62HCl•0.87CH$_3$OH |

-continued

| Example | Boronic Acid | Conditions | Resulting Compound |
|---|---|---|---|
| 127 | Furyl-2-boronic acid | 1)MW 2)S3 | 2-(6-Furan-2-yl-pyridazin-3-yl)-5-methyl-octahydro-pyrrolo[3,4-c]pyrrole<br>$^1$H NMR (300 MHz, CD$_3$OD) δ ppm 2.34 (s, 3H) 2.52 (dd, J = 10, 4 Hz, 2H) 2.75-2.90 (m, 2H) 3.03-3.16 (m, 2H) 3.50-3.60 (m, 2H) 3.64-3.78 (m, 2H) 6.54-6.62 (m, J = 13 Hz, 1H) 6.98-7.02 (m, 1H) 7.05 (d, J = 9 Hz, 1H) 7.64 (s, 1H) 7.75 (d, J = 9 Hz, 1H); MS (DCI/NH$_3$) m/z 271 (M + H)$^+$; Anal; C$_{15}$H$_{18}$N$_4$O•3.05HCl•0.98CH$_3$OH |

Example 128

Example 128A

5-(5-Bromo-pyridin-2-yl)-hexahydro-pyrrolo[3,4-c]pyrrole-2-carboxylic acid tert-butyl ester To a solution of hexahydro-pyrrolo[3,4-c]pyrrole-2-carboxylic acid tert-butyl ester (7.0317 g, 33.2 mmol) in 180 mL toluene was added 2,5-dibromopyridine (22.03 g, 92.9 mmol), tris(dibenzylidenacetone)dipalladium (0) (Pd$_2$(dba)$_3$, Strem, 0.6087 g, 0.664 mmol), 2,2'-bis(diphenyphosphino)-1,1'binaphthyl (BINAP, Aldrich, 1.0506 g, 1.68 mmol), and NaOtBu (Aldrich, 4.778 g, 49.7 mmol. The reaction mixture was heated to 90° C. under dry N$_2$ for 6 hours. The reaction mixture was cooled to room temperature and was filtered through diatomaceous earth and the residue was washed with 250 mL ethyl acetate. The combined organic extracts were concentrated under reduced pressure. The residue was purified via column chromatography (SiO$_2$, gradient 5% to 60% EtOAc-hexanes) to give 7.71 g (20.6 mmol, 62% yield). H NMR (300 MHz) δ 1.45 (s, 9H) 2.94-3.14 (m, 2H) 3.17-3.38 (m, 4H) 3.51-3.76 (m, 4H) 6.46 (d, J=9 Hz, 1H) 7.59 (dd, J=9, 3 Hz, 1H) 8.05 ppm (s, 1H)

Example 128B

2-(5-Bromo-pyridin-2-yl)-octahydro-pyrrolo[3,4-c]pyrrole

The product from Example 128A (7.6 g, 21 mmol) was deprotected using Method FB to give 5.5 g of the title compound (21 mmol, 100% yield). H NMR (300 MHz, CD$_3$OD) δ 2.75 (dd, J=11, 4 Hz, 2H) 2.90-3.02 (m, 2H) 3.07-3.17 (m, 2H) 3.34-3.38 (m, 2H) 3.51-3.63 (m, 2H) 6.49 (d, J=9 Hz, 1H) 7.59 (dd, J=9, 3 Hz, 1H) 8.05 ppm (s, 1H). MS (DCI/NH$_3$) m/z 270 (M+H)$^+$.

Example 128C

2-(5-Bromo-pyridin-2-yl)-5-methyl-octahydro-pyrrolo[3,4-c]pyrrole

The product from Example 128B (5.5 g, 20 mmol) was N-methylated using method EC to give 4.7 g of the title compound (1.7 mmol, 82% yield). H NMR (300 MHz, CD$_3$OD) δ 2.29-2.36 (m, 3H) 2.45 (dd, J=10, 4 Hz, 2H) 2.73-2.90 (m, 2H) 2.97 (s, 2H) 3.34-3.43 (m, 2H) 3.48-3.58 (m, 2H) 6.51 (d, J=9 Hz, 1H) 7.59 (dd, J=9, 3 Hz, 1H) 8.06 ppm (s, 1H). MS (DCI/NH$_3$) m/z 283 (M+H)$^+$.

Examples 131-132

The product of Example 128A was coupled with the indicated boronic acid, and further processed according to the indicated procedures, to provide the title compound.

| Example | Boronic Acid | Conditions | Resulting Compound |
|---|---|---|---|
| 131 | phenyl boronic acid | 1) H<br>2) FB<br>3) S4 | 2-(5-Phenyl-pyridin-2-yl)-octahydro-pyrrolo[3,4-c]pyrrole trifluoroacetate<br>$^1$H NMR (CH$_3$OH-d$_4$, 300 MHz) δ 3.33 (br d, J = 4.4 Hz, 1H), 3.37 (m, 1H), 3.44 (m, 1H), 3.70 (m, 4H), 3.92 (m, 2H), 7.08 (d, J = 9.5 Hz, 1H), 7.52 (m, 3H), 7.65 (m, 2H), 8.18 (br d, J = 2.4 Hz, 1H), 8.25 (dd, J = 9.5, 2.4 Hz, 1H); MS (DCI/NH$_3$) m/z 266 (M + H)$^+$; Anal. calculated for C$_{20}$H$_{21}$N$_3$S•2.1CF$_3$CO$_2$H: C, 50.44; H, 4.21; N, 8.32. Found: C, 50.57; H, 4.38; N, 8.32. |
| 132 | phenyl boronic acid | 1) H<br>2) RA<br>3) FB<br>4) S4 | 2-(5-Phenyl-pyridin-2-yl)-octahydro-pyrrolo[3,4-c]pyrrole trifluoroacetate<br>The product of Example 20A (0.20 g, 0.55 mmol) in 5 mL CH$_2$Cl$_2$ was treated with 5 mL TFA as described in Example 11D to give 0.233 g of the title compound (0.46 mmol, 84% yield). $^1$H NMR (CH$_3$OH-d$_4$, 300 MHz) δ 3.33 (br d, J = 4.4 Hz, 1H), 3.37 (m, 1H), 3.44 (m, 1H), 3.70 (m, 4H), 3.92 (m, 2H), 7.08 (d, J = 9.5 Hz, 1H), 7.52 (m, 3H), 7.65 (m, 2H), 8.18 (br d, J = 2.4 Hz, 1H), 8.25 (dd, J = 9.5, 2.4 Hz, 1H); MS (DCI/NH$_3$) m/z 266 (M + H)$^+$; Anal. calculated for C$_{20}$H$_{21}$N$_3$S•2.1CF$_3$CO$_2$H: C, 50.44; H, 4.21; N, 8.32. Found: C, 50.57; H, 4.38; N, 8.32. |

Examples 133-155

The product of Example 128C was coupled with the indicated boronic acid, and further processed according to the indicated procedures, to provide the title compound.

| Example | Reactants | Conditions | Resulting Compound |
|---|---|---|---|
| 133 | 5-pyrimidine boronic acid | 1) MW 2) S4 | 2-Methyl-5-(5-pyrimidin-5-yl-pyridin-2-yl)-octahydro-pyrrolo[3,4-c]pyrrole<br>$^1$H NMR (300 MHz, CD$_3$OD) δ ppm 2.44 (s, 3H) 2.57-2.70 (m, 2H) 2.91-3.03 (m, 2H) 3.04-3.23 (m, 2H) 3.44-3.58 (m, 2H) 3.59-3.71 (m, 2H) 6.73 (d, J = 8 Hz, 1H) 7.86-7.97 (m, 1H) 8.42 (d, J = 2 Hz, 1H) 9.01 (s, 2H) 9.06 (s, 1H); MS (DCI/NH$_3$) m/z 282 (M + H)$^+$; Anal. C$_6$H$_{19}$N$_5$•2.6CF$_3$CO$_2$H: C, H, N. |
| 134 | 4-pyrazole boronic acid | 1) MW 2) S3 | 2-Methyl-5-[5-(1H-pyrazol-4-yl)-pyridin-2-yl]-octahydro-pyrrolo[3,4-c]pyrrole<br>$^1$H NMR (300 MHz, CD$_3$OD) δ ppm 2.34 (s, 3H) 2.46 (dd, J = 10, 4 Hz, 2H) 2.79-2.93 (m, 2H) 2.98-3.11 (m, 2H) 3.44 (d, J = 22 Hz, 2H) 3.51-3.60 (m, 2H) 6.63 (d, J = 8 Hz, 1H) 7.74 (dd, J = 9, 2 Hz, 1H) 7.86 (s, 2H) 8.25 (dd, J = 2, 1 Hz, 1H); MS (DCI/NH$_3$) m/z 270 (M + H)$^+$; Anal. C$_{15}$H$_{19}$N$_5$•3.6HCl: C, H, N. |
| 135 | 3-cyanophenyl boronic acid | 1) MW 2) S3 | 3-[6-(5-Methyl-hexahydro-pyrrolo[3,4-c]pyrrol-2-yl)-pyridin-3-yl]-benzonitrile<br>$^1$H NMR (300 MHz, CD$_3$OD) δ ppm 2.34 (s, 3H) 2.49 (dd, J = 10, 4 Hz, 2H) 2.78-2.92 (m, 2H) 3.01-3.14 (m, 2H) 3.44-3.52 (m, 2H) 3.57-3.71 (m, 2H) 6.68 (d, J = 9 Hz, 1H) 7.52-7.68 (m, 2H) 7.83-7.90 (m, 2H) 7.91-7.94 (m, J = 8 Hz, 1H) 8.35 (d, J = 3 Hz, 1H); MS (DCI/NH$_3$) m/z 305 (M + H)$^+$; Anal; C$_{19}$H$_{20}$ON$_4$•3.3HCl•0.21H$_2$O |
| 136 | 2-methoxypyrimid-5-yl boronic acid | 1) MW 2) S3 | 2-[5-(2-Methoxy-pyrimidin-5-yl)-pyridin-2-yl]-5-methyl-octahydro-pyrrolo[3,4-c]pyrrole<br>$^1$H NMR (300 MHz, CD$_3$OD) δ ppm 2.34 (s, 3H) 2.49 (dd, J = 10, 4 Hz, 2H) 2.78-2.90 (m, 2H) 2.98-3.12 (m, 2H) 3.43-3.51 (m, 2H) 3.57-3.67 (m, 2H) 4.04 (s, 3H) 6.69 (d, J = 8 Hz, 1H) 7.81 (dd, J = 9, 3 Hz, 1H) 8.29 (d, J = 3 Hz, 1H) 8.75 (s, 2H); MS (DCI/NH$_3$) m/z 312 (M + H)$^+$; Anal; C$_{17}$H$_{21}$N$_5$O•2.48HCl•0.08H$_2$O |
| 137 | 3,5-dimethylpyrazol-4-yl boronic acid | 1) MW 2) S3 | 2-[5-(3,5-Dimethyl-1H-pyrazol-4-yl)-pyridin-2-yl]-5-methyl-octahydro-pyrrolo[3,4-c]pyrrole<br>$^1$H NMR (300 MHz, CD$_3$OD) δ ppm 2.20 (s, 6H) 2.35 (s, 3H) 2.46 (dd, J = 10, 4 Hz, 2H) 2.81-2.94 (m, 2H) 2.98-3.13 (m, 2H) 3.41-3.50 (m, 2H) 3.51-3.62 (m, 2H) 6.66 (d, J = 9 Hz, 1H) 7.48 (dd, J = 9, 2 Hz, 1H) 7.93 (s, 1H); MS (DCI/NH$_3$) m/z 298 (M + H)$^+$; Anal; C$_{17}$H$_{23}$N$_5$•1.6HCl•2.3H$_2$O |
| 138 | 1-methylpyrazol-4-yl boronic acid | 1) MW 2) S3 | 2-Methyl-5-[5-(1-methyl-1H-pyrazol-4-yl)-pyridin-2-yl]-octahydro-pyrrolo[3,4-c]pyrrole<br>$^1$H NMR (300 MHz, CD$_3$OD) δ ppm 2.34 (s, 3H) 2.46 (dd, J = 10, 4 Hz, 2H) 2.81-2.93 (m, 2H) 2.96-3.11 (m, 2H) 3.39-3.48 (m, 2H) 3.50-3.60 (m, 2H) 3.91 (s, 3H) 6.62 (d, J = 9 Hz, 1H) 7.62-7.76 (m, 2H) 7.85 (s, 1H) 8.22 (s, 1H); ); MS (DCI/NH$_3$) m/z 284 (M + H)$^+$; Anal; C$_{16}$H$_{21}$N$_5$•2.76HCl•0.16H$_2$O |
| 139 | 3,5-dimethylisoxazol-4-yl boronic acid | 1) MW 2) S3 | 2-[5-(3,5-Dimethyl-isoxazol-4-yl)-pyridin-2-yl]-5-methyl-octahydro-pyrrolo[3,4-c]pyrrole<br>$^1$H NMR (300 MHz, CD$_3$OD) δ ppm 2.26 (s, 3H) 2.43 (s, 3H) 2.97 (s, 3H) 3.11-3.23 (m, 1H) 3.38-3.53 (m, 2H) 3.54-3.67 (m, 1H) 3.70-4.11 (m, 6H) 7.26 (t, J = 9 Hz, 1H) 7.96 (d, J = 18 Hz, 1H) 8.00-8.11 (m, 1H); MS (DCI/NH$_3$) m/z 299 (M + H)$^+$; Anal; C$_{17}$H$_{22}$N$_4$O•2.76HCl•0.16H$_2$O |
| 140 | 3-pyridyl boronic acid | 1) MW 2) S3 | 6-(5-Methyl-hexahydro-pyrrolo[3,4-c]pyrrol-2-yl)-[3,3']bipyridinyl dihydrochloride<br>$^1$H NMR (300 MHz, CD$_3$OD) δ ppm 2.35 (s, 3H) 2.50 (dd, J = 10, 4 Hz, 2H) 2.79-2.92 (m, 2H) 3.00-3.14 (m, 2H) 3.44-3.53 (m, 2H) 3.56-3.71 (m, 2H) 6.71 (d, J = 9 Hz, 1H) 7.42-7.54 (m, 1H) 7.87 (dd, J = 9, 3 Hz, 1H) 8.03 (d, J = 10 Hz, 1H) 8.35 (d, J = 2 Hz, 1H) 8.45 (d, J = 6 Hz, 1H) 8.74 (s, 1H); MS (DCI/NH$_3$) m/z 281 (M + H)$^+$; Anal; C$_{17}$H$_{20}$N$_4$•2.35HCl•3.27H$_2$O |
| 141 | 4-pyridyl boronic acid | 1) MW 2) S3 | 6-(5-Methyl-hexahydro-pyrrolo[3,4-c]pyrrol-2-yl)-[3,4']bipyridinyl trihydroclhloride<br>$^1$H NMR (300 MHz, CD$_3$OD) δ ppm 2.35 (s, 3H) 2.51 (dd, J = 10, 4 Hz, 2H) 2.78-2.91 (m, 2H) 3.00-3.15 (m, 2H) 3.44-3.56 (m, 2H) 3.61-3.74 (m, 2H) 6.70 (d, J = 9 Hz, 1H) 7.58-7.75 (m, 2H) 7.96 (dd, J = 9, 3 Hz, 1H) 8.40-8.61 (m, 3H); MS (DCI/NH$_3$) m/z 281 (M + H)$^+$; Anal; C$_{17}$H$_{20}$N$_4$•3HCl•2.5H$_2$O |

-continued

| Example | Reactants | Conditions | Resulting Compound |
|---|---|---|---|
| 142 | 4-cyanophenyl boronic acid | 1) MW<br>2) S3 | 4-[6-(5-Methyl-hexahydro-pyrrolo[3,4-c]pyrrol-2-yl)-pyridin-3-yl]-benzonitrile<br>$^1$H NMR (300 MHz, CD$_3$OD) δ ppm 2.97 (s, 3H) 3.34-3.61 (m, 4H) 3.61-3.98 (m, 6H) 7.05 (d, J = 9 Hz, 1H) 7.82 (s, 4H) 8.09-8.28 (m, 1H) 8.30-8.50 (m, 1H); MS (DCI/NH$_3$) m/z 305 (M + H)$^+$. |
| 143 | m-2-aminopyridine boronic acid | 1) MW<br>2) S3 | 6'-(5-Methyl-hexahydro-pyrrolo[3,4-c]pyrrol-2-yl)-[3,3']bipyridinyl-6-ylamine trihydrochloride<br>$^1$H NMR (300 MHz, CD$_3$OD) δ ppm 2.34 (s, 3H) 2.47 (dd, J = 10, 4 Hz, 2H) 2.81-2.92 (m, 2H) 2.98-3.11 (m, 2H) 3.39-3.50 (m, 2H) 3.52-3.65 (m, 2H) 6.65 (d, J = 9 Hz, 2H) 7.59-7.80 (m, 2H) 8.06 (s, 1H) 8.19 (s, 1H); MS (DCI/NH$_3$) m/z 296 (M + H)$^+$; Anal; C$_{17}$H$_{21}$N$_5$•3.0HCl•2.1H$_2$O |
| 144 | 3-pyrrolyl boronic acid | 1) MW<br>2) DeSi<br>3) S4 | 2-Methyl-5-[5-(1H-pyrrol-3-yl)-pyridin-2-yl]-octahydro-pyrrolo[3,4-c]pyrrole trifluoroacetate<br>$^1$H NMR (300 MHz, CD$_3$OD) δ ppm 2.96 (s, 3H) 3.34-3.60 (m, 4H) 3.63-3.93 (m, 6H) 6.44 (s, 1H) 6.83 (s, 1H) 7.12 (d, J = 9 Hz, 1H) 7.20 (s, 1H) 8.01 (s, 1H) 8.25 (dd, J = 9, 2 Hz, 1H); MS (DCI/NH$_3$) m/z 269 (M + H)$^+$; Anal; C$_{16}$H$_{20}$N$_4$•2.9C$_2$HF$_3$O$_2$•0.64H$_2$O |
| 145 | 2-pyrrolyl boronic acid | 1) MW<br>2) FB<br>3) S3 | 2-Methyl-5-[5-(1H-pyrrol-2-yl)-pyridin-2-yl]-octahydro-pyrrolo[3,4-c]pyrrole<br>$^1$H NMR (300 MHz, CD$_3$OD) δ ppm 2.33 (s, 3H) 2.45 (dd, J = 10, 4 Hz, 2H) 2.81-2.92 (m, 2H) 2.96-3.11 (m, 2H) 3.39-3.47 (m, 2H) 3.49-3.60 (m, 2H) 6.07-6.15 (m, 1H) 6.26-6.36 (m, 1H) 6.61 (d, J = 8 Hz, 1H) 6.71-6.80 (m, 1H) 7.73 (dd, J = 9, 3 Hz, 1H) 8.26 (d, J = 3 Hz, 1H); MS (DCI/NH$_3$) m/z 269 (M + H)$^+$; |
| 146 | 2-cyanopyridyl-3-boronic acid | 1) MW<br>2) S3 | 6'-(5-Methyl-hexahydro-pyrrolo[3,4-c]pyrrol-2-yl)-[3,3']bipyridinyl-2-carbonitrile dihydrochloride<br>$^1$H NMR (300 MHz, CD$_3$OD) δ ppm 2.35 (s, 3H) 2.52 (dd, J = 10, 4 Hz, 2H) 2.78-2.90 (m, 2H) 3.02-3.14 (m, 2H) 3.46-3.57 (m, 2H) 3.62-3.73 (m, 2H) 6.73 (d, J = 9 Hz, 1H) 7.70 (dd, J = 8, 5 Hz, 1H) 7.82 (dd, J = 9, 2 Hz, 1H) 8.02 (d, J = 8 Hz, 1H) 8.31 (d, J = 3 Hz, 1H) 8.63 (d, J = 6 Hz, 1H); MS (DCI/NH$_3$) m/z 306 (M + H)$^+$; Anal; C$_{18}$H$_{19}$N$_5$•2.22HCl•0.26H$_2$O |
| 147 | 3-furyl boronic acid | 1) MW<br>2) S3 | 2-(5-Furan-3-yl-pyridin-2-yl)-5-methyl-octahydro-pyrrolo[3,4-c]pyrrole dihydrochloride<br>$^1$H NMR (300 MHz, CD$_3$OD) δ ppm 2.34 (s, 3H) 2.46 (dd, J = 10, 4 Hz, 2H) 2.80-2.92 (m, 2H) 2.98-3.10 (m, 2H) 3.38-3.49 (m, 2H) 3.50-3.63 (m, 2H) 6.62 (d, J = 8 Hz, 1H) 6.68-6.76 (m, 1H) 7.51-7.55 (m, 1H) 7.71 (dd, J = 9, 2 Hz, 1H) 7.79 (s, 1H) 8.22 (d, J = 2 Hz, 1H); MS (DCI/NH$_3$) m/z 270 (M + H)$^+$; Anal; C$_{16}$H$_{19}$N$_3$O•2.23HCl•1.78H$_2$O |
| 148 | 2-thienylboronic acid | 1) MW<br>2) S3 | 2-Methyl-5-(5-thiophen-2-yl-pyridin-2-yl)-octahydro-pyrrolo[3,4-c]pyrrole hydrochloride<br>$^1$H NMR (300 MHz, CD$_3$OD) δ ppm 2.34 (s, 3H) 2.48 (dd, J = 10, 4 Hz, 2H) 2.79-2.91 (m, 2H) 2.98-3.11 (m, 2H) 3.41-3.50 (m, 2H) 3.53-3.66 (m, 2H) 6.62 (d, J = 9 Hz, 1H) 7.01-7.09 (m, 1H) 7.19-7.25 (m, 1H) 7.29 (d, J = 6 Hz, 1H) 7.73-7.82 (m, 1H) 8.30 (d, J = 3 Hz, 1H);); MS (DCI/NH$_3$) m/z 286 (M + H)$^+$; Anal; C$_{16}$H$_{19}$N$_3$S•1.61HCl•2.3H$_2$O |
| 149 | 3-thienylboronic acid | 1) MW<br>2) S3 | 2-Methyl-5-(5-thiophen-3-yl-pyridin-2-yl)-octahydro-pyrrolo[3,4-c]pyrrole dihydrochloride<br>$^1$H NMR (300 MHz, CD$_3$OD) δ ppm 2.34 (s, 3H) 2.47 (dd, J = 10, 4 Hz, 2H) 2.80-2.92 (m, 2H) 2.98-3.12 (m, 2H) 3.39-3.50 (m, 2H) 3.52-3.66 (m, 2H) 6.64 (d, J = 9 Hz, 1H) 7.34-7.40 (m, 1H) 7.43-7.51 (m, 2H) 7.83 (dd, J = 9, 2 Hz, 1H) 8.29-8.38 (m, 1H); ); MS (DCI/NH$_3$) m/z 286 (M + H)$^+$; Anal; C$_{16}$H$_{19}$N$_3$O•2.05HCl•2.27H$_2$O |
| 150 | 5-benzofuran boronic acid | 1) MW<br>2) S3 | 2-(5-Benzofuran-5-yl-pyridin-2-yl)-5-methyl-octahydro-pyrrolo[3,4-c]pyrrole dihydrochloride<br>$^1$H NMR (300 MHz, CD$_3$OD) δ ppm 2.36 (s, 3H) 2.50 (dd, J = 10, 4 Hz, 2H) 2.82-2.95 (m, 2H) 2.99-3.13 (m, 2H) 3.43-3.52 (m, 2H) 3.53-3.66 (m, 2H) 6.69 (d, J = 9 Hz, 1H) 6.83-6.90 (m, 1H) 7.42-7.49 (m, 1H) 7.51-7.58 (m, 1H) 7.70-7.79 (m, 2H) 7.85 (dd, J = 9, 2 Hz, 1H) 8.27-8.35 (m, 1H); MS (DCI/NH$_3$) m/z 320 (M + H)$^+$; Anal; C$_{20}$H$_{21}$N$_3$O•2.23HCl•2.02H$_2$O |
| 151 | 2-furyl boronic acid | 1) MW<br>2) S3 | 2-(5-Furan-2-yl-pyridin-2-yl)-5-methyl-octahydro-pyrrolo[3,4-c]pyrrole dihydrochloride<br>1H NMR (300 MHz, CD$_3$OD) δ ppm 2.34 (s, 3H) 2.47 (dd, J = 10,4 Hz, 2H) 2.80-2.91 (m, 2H) 2.98-3.12 (m, 2H) 3.40-3.51 (m, 2H) 3.54-3.66 (m, 2H) 6.44-6.49 (m, 1H) 6.55-6.58 (m, 1H) 6.63 (d, J = 8 Hz, 1H) 7.46-7.52 (m, 1H) 7.81 (dd, J = 9, 2 Hz, 1H) 8.37 (d, J = 2 Hz, 1H); MS (DCI/NH$_3$) m/z 270 (M + H)$^+$; Anal; C$_{16}$H$_{19}$N$_3$O•2.27HCl•1.27H$_2$O |

-continued

| Example | Reactants | Conditions | Resulting Compound |
|---|---|---|---|
| 152 | 3-carbazole boronic acid | 1) MW<br>2) S3 | 3-[6-(5-Methyl-hexahydyro-pyrrolo[3,4-c]pyrrol-2-yl)-pyridin-3-yl]-9H-carbazole trihydrochloride<br>$^1$H NMR (300 MHz, CD$_3$Cl) δ ppm 2.45 (s, 3H) 2.49-2.62 (m, 2H) 2.93-3.05 (m, 2H) 3.05-3.18 (m, 2H) 3.48-3.57 (m, 2H) 3.58-3.70 (m, 2H) 6.55 (d, J = 8 Hz, 1H) 7.39-7.52 (m, 3H) 7.54-7.61 (m, 1H) 7.81 (dd, J = 9, 3 Hz, 1H) 8.08-8.11 (m, 1H) 8.11-8.14 (m, 1H) 8.19 (s, 1H) 8.52 (d, J = 2 Hz, 1H); MS (DCI/NH$_3$) m/z 369 (M + H)$^+$; Anal; C$_{24}$H$_{24}$N$_4$•3.09HCl•1.96CH$_3$OH |
| 153 | 5-indolyl boronic acid | 1) I<br>2) S2 | 5-[6-(5-Methyl-hexahydro-pyrrolo[3,4-c]pyrrol-2-yl)-pyridin-3-yl]-1H-indole Fumarate<br>$^1$H NMR (CH$_3$OH-d$_4$, 300 MHz) δ ppm 2.93 (s, 3H), 3.19-3.39 (m, 4H), 3.50 (dd, J = 10.5, 6.8 Hz, 2H), 3.57-3.75 (m, 4H), 6.48 (d, J = 3.1 Hz, 1H), 6.71 (s, 3H), 6.78 (d, J = 8.5 Hz, 1H), 7.25 (d, J = 3.4 Hz, 1H), 7.29 (dd, J = 8.5, 2.0 Hz, 1H), 7.44 (d, J = 8.5 Hz, 1H), 7.70 (d, J = 1.4 Hz, 1H), 7.90 (dd, J = 8.8, 2.4 Hz, 1H), 8.36 (d, J = 2.4 Hz, 1H); MS (DCI/NH$_3$) m/z 319 (M + H)$^+$; Anal. C$_{20}$H$_{22}$N$_4$•1.7C$_4$H$_4$O$_4$•0.4H$_2$O: C, H, N. |
| 154 | 4-indolyl boronic acid | 1. I<br>2. S4 | 4-[6-(5-Methyl-hexahydro-pyrrolo[3,4-c]pyrrol-2-yl)-pyridin-3-yl]-1H-indole Trifluoroacetate<br>$^1$H NMR (CH$_3$OH-d$_4$, 300 MHz) δ ppm 2.99 (s, 3H), 3.33-4.05 (m, 10H), 6.55 (d, J = 3.1 Hz, 1H), 7.10 (d, J = 7.4 Hz, 1H), 7.18 (d, J = 9.2 Hz, 1H), 7.22 (t, J = 7.8 Hz, 1H), 7.36 (d, J = 3.4 Hz, 1H), 7.47 (d, J = 8.0 Hz, 1H), 8.22 (s, 1H), 8.32 (dd, J = 9.2, 2.1 Hz, 1H); MS (DCI/NH$_3$) m/z 319 (M + H)$^+$; Anal. C$_{20}$H$_{22}$N$_4$•2.1C$_2$F$_3$HO$_2$: C, H, N. |

Example 155

2-[6-(5-Methyl-hexahydro-pyrrolo[3,4-c]pyrrol-2-yl)-pyridin-3-yl]-2H-pyridazin-3-one To the product from Example 128C (0.1992 g, 0.70 mmol) was added pyridazinone (Strem, 0.108 g, 1.13 mmol), CuI (Aldrich, 0.048 g, 0.76 mmol), and K$_2$CO$_3$ (Aldrich, 0.354 g, 2.56 mmol) in 25 mL pyridine. The reaction mixture was heated to reflux for 2 days. An additional amount of pyridazinone (0.018 g, 0.187 mmol) and CuI (0.026 g, 0.40 mmol) was added. The reaction was allowed to reflux an additional 3 days. The reaction mixture was cooled to room temperature and concentrated under vacuum. The residue was partitioned between CH$_2$Cl$_2$ (50 mL) and NH$_4$OH aq (25 mL). The organic layer was dried over MgSO$_4$, concentrated and purified via HPLC (Xterra C$_{18}$, 30×100 mm, gradient 20% to 70% CH$_3$CN/NH$_4$HCO$_3$, flow rate 40 ml/min) to give 0.145 g, (0.49 mmol, 69% yield). $^1$H NMR (300 MHz, CD$_3$OD) □ ppm 2.34 (s, 3H) 2.49 (dd, J=10, 4 Hz, 2H) 2.80-2.90 (m, 2H) 3.00-3.13 (m, 2H) 3.44-3.53 (m, 2H) 3.57-3.68 (m, 2H) 6.65 (d, J=9 Hz, 1H) 7.06 (d, J=9 Hz, 1H) 7.46 (dd, J=9, 4 Hz, 1H) 7.74 (dd, J=9, 3 Hz, 1H) 8.03 (d, J=5 Hz, 1H) 8.26 (d, J=3 Hz, 1H). MS (DCl/NH$_3$) m/z 298 (M+H)$^+$.

Example 156A

5-(6-Chloro-pyridin-3-yl)-hexahydro-pyrrolo[3,4-c]pyrrole-2-carboxylic acid tert-butyl ester The product of Example 6C (5 g, 23.6 mmol), 5-bromo-2-chloropyridine (Aldrich, 5.02 g, 28.3 mmol), tris(dibenzylideneacetone)dipalladium (0) (Pd$_2$(dba)$_3$, Strem, 0.43 g, 0.47 mmol), 2,2'-bis(diphenylphosphino)-1,1'-binaphthyl (BINAP, Strem, 0.59 g, 0.94 mmol) and tert-BuONa (3.63 g, 37.8 mmol) in 50 mL toluene was warmed to 85° C. and allowed to stir for 20 h. The mixture was cooled to ambient temperature, filtered and concentrated under reduced pressure. The crude material was purified by column chromatography (SiO$_2$, 50% hexanes-EtOAc) to give 3.86 g of the title compound (12 mmol, 42% yield) as the major product. MS (DCl/NH$_3$) m/z 324 (M+H)$^+$.

Examples 156-187

The product of Example 156A was coupled with the indicated boronic acid, and processed according to the methods listed in the table below.

| Example | Boronic Acid | Conditions | Resulting Compound |
|---|---|---|---|
| 156 | Phenyl boronic acid | 1) H<br>2) FB<br>3) S4 | 2-(6-Phenyl-pyridin-3-yl)-octahydro-pyrrolo[3,4-c]pyrrole bis-trifluoroacetate $^1$H NMR (300 MHz, CD$_3$OD) δ ppm 3.32 (m, 4H), 3.62 (m, 6H), 7.57 (m, 3H), 7.68 (dd, J = 9.2, 2.7 Hz, 1H), 7.81 (m, 2H), 8.01 (m, 2H) MS (DCI/NH$_3$) m/z 266 (M + H)$^+$; Anal. calculated for C$_{17}$H$_{19}$N$_3$•2CF$_3$CO$_2$H: C, 51.12; H, 4.29; N, 8.52. Found: C, 51.12; H, 4.12; N, 8.37. |

-continued

| Example | Boronic Acid | Conditions | Resulting Compound |
|---|---|---|---|
| 157 | 3-Biphenyl boronic acid | 1) G<br>2) FB<br>3) S4 | 2-(6-Biphenyl-3-yl-pyridin-3-yl)-octahydro-pyrrolo[3,4-c]pyrrole trifluoroacetate<br>$^1$H NMR (CH$_3$OH-d$_4$, 300 MHz) δ 3.33 (m, 4H), 3.63 (m, 6H), 7.39 (m, 1H), 7.48 (m, 2H), 7.67 (m, 4H), 7.79 (m, 2H), 8.07 (m, 3H); MS (DCI/NH$_3$) m/z 342 (M + H)$^+$; Anal. calculated for C$_{23}$H$_{23}$N$_3$•2CF$_3$CO$_2$H: C, 56.94; H, 4.42; N, 7.38. Found: C, 56.64; H, 4.39; N, 7.09. |
| 158 | o-tolyl boronic acid | 1) H<br>2) FB<br>3) S4 | 2-(6-o-Tolyl-pyridin-3-yl)-octahydro-pyrrolo[3,4-c]pyrrole bis-trifluoroacetate $^1$H NMR (300 MHz, CD$_3$OD) δ ppm 2.30 (s, 3H), 3.30 (m, 3H), 3.35 (m, 1H), 3.62 (m, 6H), 7.41 (m, 4H), 7.70 (m, 2H), 8.05 (m, J = 2.7 Hz, 1H); MS (DCI/NH$_3$) m/z 280 (M + H)$^+$; Anal. calculated for C$_{18}$H$_{21}$N$_3$•2.1CF$_3$CO$_2$H: C, 51.39; H, 4.49; N, 8.10. Found: C, 51.56; H, 4.43; N, 8.11. |
| 159 | m-tolyl boronic acid | 1) I<br>2) FB<br>3) S4 | 2-(6-m-Tolyl-pyridin-3-yl)-octahydro-pyrrolo[3,4-c]pyrrole bis-trifluoroacetate $^1$H NMR (300 MHz, CD$_3$OD) δ ppm 2.45 (s, 3H), 3.26 (m, 2H), 3.36 (m, 2H), 3.63 (m, 6H), 7.36 (m, 1H), 7.45 (t, J = 7.5 Hz, 1H), 7.61 (m, 2H), 7.67 (dd, J = 9.2, 3.1 Hz, 1H), 7.99 (dd, J = 5.9, 2.9 Hz, 2H); MS (DCI/NH$_3$) m/z 280 (M + H)$^+$; Anal. calculated for C$_{18}$H$_{21}$N$_3$•2CF$_3$CO$_2$H: C, 52.09; H, 4.59; N, 8.28. Found: C, 52.10; H, 4.44; N, 8.23. |
| 160 | m-(trifluoro-methyl)phenyl boronic acid | 1) I<br>2) FB<br>3) S4 | 2-[6-(3-Trifluoromethyl-phenyl)-pyridin-3-yl]-octahydro-pyrrolo[3,4-c]pyrrole trifluoroacetate<br>$^1$H NMR (CH$_3$OH-d$_4$, 300 MHz) δ 3.28 (m, 4H), 3.56 (m, 6H), 7.37 (dd, J = 8.8, 3.1 Hz, 1H), 7.67 (m, 2H), 7.87 (d, J = 8.8 Hz, 1H), 8.10 (m, 2H), 8.18 (m, 1H); MS (DCI/NH$_3$) m/z 334 (M + H)$^+$; Anal. C$_{18}$H$_{18}$F$_3$N$_3$•1.6CF$_3$CO$_2$H: C, H, N. |
| 161 | m-tolyl boronic acid | 1) G<br>2) FB<br>3) S4 | 2-[6-(3-Methoxy-phenyl)-pyridin-3-yl]-octahydro-pyrrolo[3,4-c]pyrrole bis-trifluoroacetate $^1$H NMR (300 MHz, CD$_3$OD) δ ppm 3.28 (m, 2H), 3.35 (m, 2H), 3.62 (m, 6H), 3.89 (s, 3H), 7.10 (m, 1H), 7.37 (m, 2H), 7.47 (t, J = 8.1 Hz, 1H), 7.66 (dd, J = 9.2, 2.7 Hz, 1H), 8.00 (dd, J = 6.1, 2.7 Hz, 2H); MS (DCI/NH$_3$) m/z 296 (M + H)$^+$; Anal. calculated for C$_{18}$H$_{21}$N$_3$O•2 CF$_3$CO$_2$H: C, 50.48; H, 4.43; N, 8.03. Found: C, 50.68; H, 4.51; N, 8.09. |
| 162 | 3-trifluoromethoxy-phenyl boronic acid | 1) G<br>2) FB<br>3) S4 | 2-[6-(3-Trifluoromethoxy-phenyl)-pyridin-3-yl]-octahydro-pyrrolo[3,4-c]pyrrole trifluoroacetate $^1$H NMR (300 MHz, CD$_3$OD) δ ppm 3.26 (m, 2H), 3.34 (m, 2H), 3.56 (m, 6H), 7.31 (m, 1H), 7.38 (dd, J = 8.8, 3.1 Hz, 1H), 7.57 (t, J = 8.1 Hz, 1H), 7.79 (s, 1H), 7.84 (m, 1H), 7.85 (d, J = 8.8 Hz, 1H), 8.10 (d, J = 3.1 Hz, 1H); MS (DCI/NH$_3$) m/z 350 (M + H)$^+$; Anal. calculated for C$_{18}$H$_{18}$N$_3$F$_3$O•1.5 CF$_3$CO$_2$H: C, 47.74; H, 3.72; N, 7.95. Found: C, 47.83; H, 3.60; N, 7.80. |
| 163 | Thiophen-3-yl boronic acid | 1) G<br>2) FB<br>3) S4 | 2-(6-Thiophen-3-yl-pyridin-3-yl)-octahydro-pyrrolo[3,4-c]pyrrole bis-trifluoroacetate $^1$H NMR (300 MHz, CD$_3$OD) δ ppm 3.26 (m, 2H), 3.36 (m, 2H), 3.55 (m, 4H), 3.65 (m, 2H), 7.58 (dd, J = 8.8, 3.1 Hz, 1H), 7.62 (m, 2H), 7.94 (m, 1H), 7.96 (s, 1H), 7.99 (dd, J = 2.4, 1.7 Hz, 1H) MS (DCI/NH$_3$) m/z 272 (M + H)$^+$; Anal. calculated for C$_{15}$H$_{17}$N$_3$S•2CF$_3$CO$_2$H: C, 45.69; H, 3.83; N, 8.41. Found: C, 46.00; H, 3.74; N, 8.51. |
| 165 | 8-quinoline boronic acid | 1) G<br>2) FB<br>3) S4 | 8-[5-(Hexahydro-pyrrolo[3,4-c]pyrrol-2-yl)-pyridin-2-yl]-quinoline tris-trifluoroacetate $^1$H NMR (300 MHz, CD$_3$OD) δ ppm 3.30 (m, 2H), 3.39 (m, 2H), 3.69 (m, 6H), 7.82 (m, 1H), 7.89 (t, J = 7.8 Hz, 1H), 8.23 (d, J = 8.5 Hz, 1H), 8.28 (d, J = 3.1 Hz, 1H), 8.55 (d, J = 9.5 Hz, 1H), 8.59 (dd, J = 7.5, 1.0 Hz, 1H), 8.73 (dd, J = 8.5, 1.7 Hz, 1H), 9.15 (dd, J = 4.7, 1.7 Hz, 1H); MS (DCI/NH$_3$) m/z 317 (M + H)$^+$; Anal. calculated for C$_{20}$H$_{20}$N$_4$•3CF$_3$CO$_2$H: C, 47.43; H, 3.52; N, 8.51. Found: C, 47.67; H, 3.55; N, 8.53. |
| 166 | 3-aminophenyl boronic acid | 1) G<br>2) FB<br>3) S4 | 3-[5-(Hexahydro-pyrrolo[3,4-c]pyrrol-2-yl)-pyridin-2-yl]-phenylamine trifluoroacetate<br>$^1$H NMR (CH$_3$OH-d$_4$, 300 MHz) δ 3.27 (m, 1H), 3.34 (m, 3H) 3.57 (m, 4H), 3.64 (m, 2H), 7.07 (ddd, J = 7.8, 2.4, 1.7 Hz, 1H), 7.37 (m, 2H), 7.42 (m, 1H), 7.62 (dd, J = 9.1, 3.1 Hz, 1H), 7.95 (d, J = 8.8 Hz, 1H), 8.00 (d, J = 2.7 Hz, 1H); MS (DCI/NH$_3$) m/z 281 (M + H)$^+$; Anal. calculated for C$_{17}$H$_{20}$N$_4$•2.7CF$_3$CO$_2$H: C, 45.74; H, 3.89; N, 9.52. Found: C, 45.86; H, 3.90; N, 9.69. |
| 167 | 2-naphthalene boronic acid | 1) G<br>2) FB<br>3) S4 | 2-(6-Naphthalen-2-yl-pyridin-3-yl)-octahydro-pyrrolo[3,4-c]pyrrole bis-trifluoroacetate $^1$H NMR (300 MHz, CD$_3$OD) δ ppm 3.30 (m, 2H), 3.37 (m, 2H), 3.64 (m, 6H), 7.59 (m, 2H), 7.70 (dd, J = 9.0, 2.9 Hz, 1H), 7.92 (m, 1H), 7.98 (m, 2H), 8.05 (d, J = 5.1 Hz, 1H), 8.07 (s, 1H), 8.15 (d, J = 9.2 Hz, 1H), 8.35 (m, 1H); MS (DCI/NH$_3$) m/z 316 (M + H)$^+$; Anal. calculated for C$_{21}$H$_{21}$N$_3$•2CF$_3$CO$_2$H: C, 55.25; H, 4.27; N, 7.73. Found: C, 55.16; H, 4.23; N, 7.63. |
| 168 | 2-benzofuran boronic acid | 1) G<br>2) FB<br>3) S4 | 2-(6-Benzofuran-2-yl-pyridin-3-yl)-octahydro-pyrrolo[3,4-c]pyrrole bis-trifluoroacetate $^1$H NMR (300 MHz, CD$_3$OD) δ ppm 3.31 (m, 4H), 3.58 (m, 6H), 7.30 (m, 4H), 7.54 (d, J = 8.8 Hz, 1H), 7.63 (m, 1H), 7.94 (d, J = 8.8 Hz, 1H), 8.06 (d, J = 2.7 Hz, 1H); MS (DCI/NH$_3$) m/z 306 (M + H)$^+$; Anal. calculated for C$_{19}$H$_{19}$N$_3$O•2CF$_3$CO$_2$H: C, 51.79; H, 3.97; N, 7.88. Found: C, 51.52; H, 3.71; N, 7.69. |

-continued

| Example | Boronic Acid | Conditions | Resulting Compound |
|---|---|---|---|
| 169 | Benzo[b]thiophen-2-yl boronic acid | 1) I<br>2) FB<br>3) S4 | 2-(6-Benzo[b]thiophen-2-yl-pyridin-3-yl)-octahydro-pyrrolo[3,4-c]pyrrole trifluoroacetate<br>$^1$H NMR (CH$_3$OH-d$_4$, 300 MHz) δ 3.26 (m, 4H), 3.45 (m, 2H), 3.55 (m, 2H), 3.63 (m, 2H), 7.21 (dd, J = 8.8, 3.1 Hz, 1H), 7.32 (m, 2H), 7.73 (br s, 1H), 7.78 (m, 1H), 7.83 (m, 2H), 8.03 (br d, J = 2.7 Hz, 1H); MS (DCI/NH$_3$) m/z 322 (M + H)$^+$; Anal. calculated for C$_{19}$H$_{19}$N$_3$S•1.1CF$_3$CO$_2$H: C, 56.98; H, 4.53; N, 9.40. Found: C, 57.11; H, 4.44; N, 9.21. |
| 170 | 3-furanyl boronic acid | 1) G<br>2) FB<br>3) S4 | 5-(6-Furan-3-yl-pyridin-3-yl)-hexahydro-pyrrolo[3,4-c]pyrrole trifluoroacetate<br>$^1$H NMR (CH$_3$OH-d$_4$, 300 MHz) δ 3.25 (m, 2H), 3.33 (m, 2H), 3.55 (m, 4H), 3.64 (m, 2H), 6.97 (dd, J = 2.0, 1.0 Hz, 1H), 7.60 (dd, J = 9.2, 3.1 Hz, 1H), 7.70 (dd, J = 1.7, 1.7 Hz, 1H), 7.87 (d, J = 9.2 Hz, 1H), 7.91 (d, J = 2.7 Hz, 1H), 8.19 (dd, J = 1.4, 1.0 Hz, 1H). MS (DCI/NH$_3$) m/z 256 (M + H)$^+$; Anal. calculated for C$_{15}$H$_{17}$N$_3$O•2CF$_3$CO$_2$H: C, 47.21; H, 3.96; N, 8.69. Found: C, 47.17; H, 4.01; N, 8.65 |
| 171 | 3-Biphenyl boronic acid | 1) G<br>2) FB<br>3) RA<br>4) S1 | 2-(6-Biphenyl-3-yl-pyridin-3-yl)-5-methyl-octahydro-pyrrolo[3,4-c]pyrrole p-toluenesulfonate<br>$^1$H NMR (CH$_3$OH-d$_4$, 300 MHz) δ 2.34 (s, 3H), 2.96 (s, 3H), 3.35 (m, 6H), 3.62 (m, 4H), 7.21 (m, 2H), 7.36 (m, 2H), 7.46 (m, 2H), 7.53 (m, 1H), 7.63 (ddd, J = 7.8, 1.7, 1.0 Hz, 1H), 7.69 (m, 4H), 7.81 (ddd, J = 7.8, 1.7, 1.0 Hz, 1H) 7.82 (m, 1H), 8.10 (dd, J = 2.0, 1.4 Hz, 1H), 8.15 (br d, J = 2.7 Hz, 1H); MS (DCI/NH$_3$) m/z 356 (M + H)$^+$; Anal. calculated for C$_{24}$H$_{25}$N$_3$•C$_7$H$_8$O$_3$S•0.5H$_2$O: C, 69.38; H, 6.39; N, 7.83. Found: C, 69.24; H, 6.27; N, 7.78. |
| 172 | o-tolyl boronic acid | 1) H<br>2) FB<br>3) S5 | 2-Methyl-5-(6-o-tolyl-pyridin-3-yl)-octahydro-pyrrolo[3,4-c]pyrrole bis-L-tartrate<br>$^1$H NMR (300 MHz, CD$_3$OD) δ ppm 2.26 (s, 3H), 2.93 (s, 3H), 3.30 (m, 6H), 3.66 (m, 4H), 4.45 (m, 4H), 7.26 (m, 4H), 7.34 (m, 2H), 8.11 (m, 1H); MS (DCI/NH$_3$) m/z 294 (M + H)$^+$; Anal. calculated for C$_{19}$H$_{23}$N$_3$•2. C$_4$H$_6$O$_6$: C, 54.08; H, 5.90; N, 6.90. Found: C, 53.91; H, 5.72; N, 6.51. |
| 173 | m-tolyl boroic acid | 1) H<br>2) FB<br>3) RA<br>4) S5 | 2-Methyl-5-(6-m-tolyl-pyridin-3-yl)-octahydro-pyrrolo[3,4-c]pyrrole bis-L-tartrate<br>$^1$H NMR (300 MHz, CD$_3$OD) δ ppm 1.24 (m, 2H), 2.41 (s, 3H), 2.93 (s, 3H), 3.31 (m, 4H), 3.62 (d, J = 8.8 Hz, 2H), 3.69 (m, 2H), 4.45 (s, 4H), 7.18 (d, J = 7.5 Hz, 1H), 7.31 (m, 2H), 7.61 (d, J = 7.8 Hz, 1H), 7.66 (s, 1H), 7.70 (d, J = 8.8 Hz, 1H), 8.11 (d, J = 2.7 Hz, 1H); MS (DCI/NH$_3$) m/z 294 (M + H)$^+$; Anal. calculated for C$_{19}$H$_{23}$N$_3$•2.3C$_4$H$_6$O$_6$: C, 53.04; H, 5.81; N, 6.58. Found: C, 52.65; H, 6.16; N, 6.28. |
| 174 | m-(trifluoro-methyl)phenyl | 1) I<br>2) FB<br>3) RA<br>4) S5 | 2-Methyl-5-[6-(3-trifluoromethyl-phenyl)-pyridin-3-yl]-octahydro-pyrrolo[3,4-c]pyrrole L-tartrate<br>$^1$H NMR (CH$_3$OH-d$_4$, 300 MHz) δ 2.93 (s, 3H), 3.34 (m, 6H) 3.65 (m, 4H), 4.44 (s, 4H), 7.30 (dd, J = 8.8, 3.1 Hz, 1H), 7.63 (m, 2H), 7.81 (d, J = 8.8 Hz, 1H), 8.12 (m, 1H), 8.17 (br d, J = 3.1 Hz, 1H) 8.19 (m, 1H); MS (DCI/NH$_3$) m/z 348 (M + H)$^+$; Anal. C$_{19}$H$_{20}$F$_3$N$_3$•2.1C$_4$H$_6$O$_6$: C, H, N. |
| 175 | Phenyl boronic acid | 1) G<br>2) FB<br>3) RA<br>4) S5 | 2-Methyl-5-(6-phenyl-pyridin-3-yl)-octahydro-pyrrolo[3,4-c]pyrrole L-tartrate<br>$^1$H NMR (300 MHz, CD$_3$OD) δ ppm 2.87 (s, 3H), 3.30 (m, 6H), 3.60 (m, 4H), 4.40 (s, 2H), 7.29 (dd, J = 8.8, 2.7 Hz, 1H), 7.35 (m, 1H), 7.44 (m, 2H), 7.71 (d, J = 8.5 Hz, 1H), 7.83 (m, 2H), 8.12 (d, J = 3.1 Hz, 1H); MS (DCI/NH$_3$) m/z 280 (M + H)$^+$; Anal. calculated for C$_{18}$H$_{18}$N$_3$F$_3$O•1.05 C$_4$H$_6$O$_6$: C, 61.02; H, 6.30; N, 9.62. Found: C, 61.00; H, 5.99; N, 9.46. |
| 176 | 3-methoxyphenyl boronic acid | 1) G<br>2) FB<br>3) RA<br>4) S5 | 2-[6-(3-Methoxy-phenyl)-pyridin-3-yl]-5-methyl-octahydro-pyrrolo[3,4-c]pyrrole bis-L-tartrate<br>$^1$H NMR (300 MHz, CD$_3$OD) δ ppm 2.93 (s, 3H), 3.30 (m, 6H), 3.61 (m, 2H), 3.70 (m, 2H), 3.85 (m, 3H), 4.44 (m, 4H), 6.92 (m, 1H), 7.32 (m, 4H), 7.71 (d, J = 8.8 Hz, 1H), 8.12 (d, J = 3.1 Hz, 1H); MS (DCI/NH$_3$) m/z 310 (M + H)$^+$; Anal. calculated for C$_{19}$H$_{23}$N$_3$O•2.25 C$_4$H$_6$O$_6$•H$_2$O: C, 50.56; H, 5.83; N, 6.32. Found: C, 50.47; H, 5.92; N, 6.45. |
| 177 | 3-trifluoromethoxy-phenyl boronic acid | 1) G<br>2) FB<br>3) RA<br>4) S5 | 2-Methyl-5-[6-(3-trifluoromethoxy-phenyl)-pyridin-3-yl]-octahydro-pyrrolo[3,4-c]pyrrole bis-L-tartrate<br>$^1$H NMR (300 MHz, CD$_3$OD) δ ppm 2.93 (s, 3H), 3.33 (m, 6H), 3.63 (d, J = 8.5 Hz, 2H), 3.70 (m, 2H), 4.45 (s, 4H), 7.25 (m, 1H), 7.28 (dd, J = 8.8, 3.1 Hz, 1H), 7.52 (t, J = 8.1 Hz, 1H), 7.77 (d, J = 8.5 Hz, 1H), 7.80 (m, 1H), 7.86 (d, J = 8.1 Hz, 1H), 8.16 (d, J = 3.1 Hz, 1H); MS (DCI/NH$_3$) m/z 364 (M + H)$^+$; Anal. calculated for C$_{19}$H$_{23}$N$_3$O•2 C$_4$H$_6$O$_6$: C, 48.87; H, 4.86; N, 6.33. Found: C, 48.54; H, 4.89; N, 6.22. |
| 178 | 3-nitrophenyl boronic acid | 1) G<br>2) FB<br>3) RA<br>4) S1 | 2-Methyl-5-[6-(3-nitro-phenyl)-pyridin-3-yl]-octahydro-pyrrolo[3,4-c]pyrrole p-toluenesulfonate<br>$^1$H NMR (300 MHz, CD$_3$OD) δ ppm 2.35 (s, 3H), 2.94 (s, 3H), 3.26 (m, 3H), 3.43 (m, 3H), 3.68 (m, 3H), 3.99 (m, 1H), 7.22 (m, 2H), 7.33 (m, 1H), 7.69 (m, 3H), 7.88 (d, J = 8.8 Hz, 1H), 8.21 (m, 2H), 8.28 (m, 1H), 8.77 (dd, J = 1.9, 1.9 Hz, 1H); MS (DCI/NH$_3$) m/z 325 (M + H)$^+$; Anal. calculated for C$_{18}$H$_{20}$N$_4$O$_2$•C$_7$H$_8$O$_3$S•H$_2$O: C, 58.35; H, 5.88; N, 10.89. Found: C, 58.19; H, 5.64; N, 10.64. |

| Example | Boronic Acid | Conditions | Resulting Compound |
|---|---|---|---|
| 179 | Thiophen-3-yl boronic acid | 1) G<br>2) FB<br>3) RA<br>4) S1 | 2-Methyl-5-(6-thiophen-3-yl-pyridin-3-yl)-octahydro-pyrrolo[3,4-c]pyrrole p-toluenesulfonate<br>$^1$H NMR (300 MHz, CD$_3$OD) δ ppm 2.36 (s, 3H), 2.93 (s, 3H), 3.30 (m, 6H), 3.59 (m, 4H), 7.22 (d, J = 7.8 Hz, 2H), 7.27 (dd, J = 8.8, 3.1 Hz, 1H), 7.47 (dd, J = 5.1, 3.1 Hz, 1H), 7.58 (dd, J = 5.1, 1.4 Hz, 1H), 7.68 (m, 3H), 7.77 (dd, J = 2.9, 1.2 Hz, 1H), 8.05 (d, J = 2.7 Hz, 1H); MS (DCI/NH$_3$) m/z 286 (M + H)$^+$; Anal. calculated for C$_{16}$H$_{19}$N$_3$S•C$_7$H$_8$O$_3$S: C, 60.37; H, 5.95; N, 9.18. Found: C, 60.12; H, 5.92; N, 9.03. |
| 181 | 8-quinoline boronic acid | 1) G<br>2) FB<br>3) RA<br>4) S1 | 8-[5-(5-Methyl-hexahydro-pyrrolo[3,4-c]pyrrol-2-yl)-pyridin-2-yl]-quinoline p-toluenesulfonate<br>$^1$H NMR (300 MHz, CD$_3$OD) δ ppm 2.35 (s, 3H), 2.93 (s, 3H), 3.33 (m, 6H), 3.61 (m, 4H), 7.22 (d, J = 7.8 Hz, 2H), 7.37 (dd, J = 8.6, 2.9 Hz, 1H), 7.57 (dd, J = 8.3, 4.2 Hz, 1H), 7.71 (m, 3H), 7.86 (d, J = 8.8 Hz, 1H), 7.98 (ddd, J = 14.1, 7.6, 1.4 Hz, 2H), 8.19 (d, J = 2.7 Hz, 1H), 8.42 (dd, J = 8.5, 1.7 Hz, 1H), 8.87 (dd, J = 4.2, 1.9 Hz, 1H); MS (DCI/NH$_3$) m/z 331 (M + H)$^+$; Anal. calculated for C$_{21}$H$_{22}$N$_4$•C$_7$H$_8$O$_3$S: C, 66.91; H, 6.02; N, 11.15. Found: C, 66.80; H, 5.91; N, 11.14. |
| 182 | 2-naphthalene boronic acid | 1) G<br>2) FB<br>3) RA<br>4) S1 | 2-Methyl-5-(6-naphthalen-2-yl-pyridin-3-yl)-octahydro-pyrrolo[3,4-c]pyrrole p-toluenesulfonate<br>$^1$H NMR (300 MHz, CD$_3$OD) δ ppm 2.35 (s, 3H), 2.95 (s, 3H), 3.34 (m, 6H), 3.64 (m, 4H), 7.22 (m, 2H), 7.34 (dd, J = 8.8, 2.7 Hz, 1H), 7.50 (m, 2H), 7.70 (m, 2H), 7.90 (m, 4H), 8.02 (dd, J = 8.5, 1.7 Hz, 1H), 8.18 (d, J = 2.7 Hz, 1H), 8.32 (m, 1H); MS (DCI/NH$_3$) m/z 330 (M + H)$^+$; Anal. calculated for C$_{22}$H$_{23}$N$_3$•C$_7$H$_8$O$_3$S: C, 69.43; H, 6.23; N, 8.38. Found: C, 69.06; H, 5.86; N, 8.05. |
| 183 | Benzo[b]thiophen-2-yl boronic acid | 1) I<br>2) FB<br>3) RA<br>4) S4 | 2-(6-Benzo[b]thiophen-2-yl-pyridin-3-yl)-5-methyl-octahydro-pyrrolo[3,4-c]pyrrole p-toluenesulfonate<br>$^1$H NMR (CH$_3$OH-d$_4$, 300 MHz) δ 2.36 (s, 3H), 2.93 and 2.98 (rotamer s, 3H), 3.27 (m, 2H), 3.29 (m, 2H), 3.42 (m, 2H), 3.65 (m, 3H), 3.98 (m, 1H), 7.22 (m, 2H), 7.32 (m, 3H), 7.70 (m, 2H), 7.75 (br s, 1H), 7.78 (m, 1H), 7.84 (dd, J = 7.1, 2.0 Hz, 1H), 7.85 (dd, J = 8.5 Hz, 1H), 8.07 (br d, J = 2.4 Hz, 1H); MS (DCI/NH$_3$) m/z 322 (M + H)$^+$; Anal. calculated for C$_{20}$H$_{21}$N$_3$S•1.2C$_7$H$_8$O$_3$S•H$_2$O: C, 60.90; H, 5.87; N, 7.50. Found: C, 60.93; H, 5.74; N, 7.31. |
| 184 | 3-furanyl boronic acid | 1) G<br>2) FB<br>3) RA<br>4) S1 | 2-(6-Furan-3-yl-pyridin-3-yl)-5-methyl-octahydro-pyrrolo[3,4-c]pyrrole p-toluenesulfonate<br>$^1$H NMR (CH$_3$OH-d$_4$, 300 MHz) δ 2.35 (s, 4H) 2.95 (m, 4H), 3.29 (m, 3H), 3.42 (m, 3H), 3.64 (m, 3H), 6.93 (dd, J = 2.0, 1.0 Hz, 1H), 7.21 (m, 3H), 7.47 (m, 1H), 7.64 (dd, J = 1.7, 1.7 Hz, 1H), 7.68 (m, 3H), 7.72 (m, 1H), 7.97 (m, 1H), 8.11 (dd, J = 1.4, 1.0 Hz, 1H). MS (DCI/NH$_3$) m/z 270 (M + H)$^+$; Anal. calculated for C$_{15}$H$_{17}$N$_3$O•1.5C$_7$H$_8$O$_2$S: C, 60.32; H, 5.92; N, 7.96. Found: C, 60.34; H, 6.00; N, 8.11. |

Examples 185-187

The product of Example 156 was processed according to the method EC to afford 2-(6-chloropyridin-3-yl)-5-methyl-octahydro-pyrrolo[3,4-c]pyrrole, which was coupled with the specified boronic acid and converted to the title salts according to the methods listed in the table.

| Example | Boronic Acid | Conditions | Resulting Compound |
|---|---|---|---|
| 185 | 5-indolyl boronic acid | 1) I<br>2) S2 | 5-[5-(5-Methyl-hexahydro-pyrrolo[3,4-c]pyrrol-2-yl)-pyridin-2-yl]-1H-indole Trifluoroacetate<br>$^1$H NMR (CH$_3$OH-d$_4$, 300 MHz) δ ppm 2.97 (s, 3H), 3.33-3.83 (m, 10H), 6.62 (d, J = 3.1 Hz, 1H), 7.40 (d, J = 3.1 Hz, 1H), 7.54 (dd, J = 8.7, 1.6 Hz, 1H), 7.61 (d, J = 8.7 Hz, 1H), 7.86 (dd, J = 9.0, 2.2 Hz, 1H), 7.93 (s, 1H), 8.05 (s, 1H), 8.12 (d, J = 9.4 Hz, 1H); MS (DCI/NH$_3$) m/z 319 (M + H)$^+$; Anal. C$_{20}$H$_{22}$N$_4$•2.1C$_2$F$_3$HO$_2$: C, H, N. |
| 186 | 4-indolyl boronic acid | 1) I<br>2) S2 | 4-[5-(5-Methyl-hexahydro-pyrrolo[3,4-c]pyrrol-2-yl)-pyridin-2-yl]-1H-indole Trifluoroacetate<br>$^1$H NMR (CH$_3$OH-d$_4$, 300 MHz) δ ppm 2.98 (s, 3H), 3.13-4.11 (m, 10H), 6.65 (dd, J = 3.2, 0.8 Hz, 1H), 7.27-7.37 (m, J = 3.7, 3.7 Hz, 2H), 7.44-7.50 (m, 1H), 7.58-7.67 (m, 1H), 7.82-7.93 (m, 1H), 8.06 (s, 1H), 8.14 (d, J = 9.2 Hz, 1H); MS (DCI/NH$_3$) m/z 319 (M + H)$^+$; Anal. C$_{20}$H$_{22}$N$_4$•2C$_2$F$_3$HO$_2$: C, H, N. |
| 187 | 5-quinoline boronic acid | 1) I<br>2) S3 | 5-[5-(5-Methyl-hexahydro-pyrrolo[3,4-c]pyrrol-2-yl)-pyridin-2-yl]-quinoline Hydrochloride<br>$^1$H NMR (CH$_3$OH-d$_4$, 300 MHz) δ ppm 3.00 (d, J = 12.2 Hz, 3H), 3.03-3.41 (m, 2H), 3.41-3.82 (m, 8H), 4.03 (dd, J = 12.0, 7.3 Hz, 1H), 7.68-7.77 (m, 1H), 7.93 (dd, J = 8.8, 1.7 Hz, 1H), 7.97-8.09 (m, 2H), 8.17-8.25 (m, 1H), 8.26-8.37 (m, 2H), 9.10 (d, J = 8.8 Hz, 1H), |

-continued

| Example | Boronic Acid | Conditions | Resulting Compound |
|---------|--------------|------------|--------------------|
|         |              |            | 9.21 (d, J = 5.1 Hz, 1H); MS (DCI/NH$_3$) m/z 331 (M + H)$^+$; Anal. $C_{21}H_{22}N_4\cdot3.5HCl\cdot C_2H_6O$: C, H, N. |

Example 188

6a-Methyl-5-(6-m-tolyl-pyridin-3-yl)-octahydro-pyrrolo[3,4-b]pyrrole fumarate The diamine from Example 20G was coupled to 5-bromo-2-chloropyridine according to the procedure of Example 156A. The product was in turn coupled with m-tolyl boronic acid according to the procedure of method G, and further processed according to methods PD and S2 to provide the title compound: $^1$H NMR (MeOH-d$_4$, 300 MHz) δ 1.66 (s, 3H), 2.06-2.13 (m, 1H), 2.40 (s, 3H), 2.44-2.54 (m, 1H), 2.84-2.93 (m, 1H), 3.35-3.62 (m, 4H), 4.00 (d, J=11.2 Hz, 1H), 6.69 (s, 2.2H), 7.19-7.34 (m, 3H), 7.59-7.72 (m, 3H), 8.09 (d, J=2.4 Hz, 1H); MS (DCI/NH$_3$) m/z 294 (M+H)$^+$; Anal. $C_{19}H_{23}N_3\cdot1.1C_4H_4O_4$: C, H, N.

Examples 191-197

The product of Example 10 was reacted with 3,6-dichloropyridazine according to the procedure of Example 90, and the material was in turn coupled to the boronic acid and processed further according to the conditions listed in the table below:

| Example | Boronic Acid | Conditions | Resulting Compound |
|---------|--------------|------------|--------------------|
| 191 | p-tolyl boronic acid | 1) H<br>2) FB<br>3) S1 | (1R,5R)-3-(6-p-Tolyl-pyridazin-3-yl)-3,6-diaza-bicyclo[3.2.0]heptane bis(p-toluenesulfonate)<br>$^1$H NMR (MeOH-D$_4$, 300 MHz) δ 2.32 (s, 6H), 2.45 (s, 3H), 3.38-3.99 (m, 4H), 4.28-4.40 (m, 2H), 4.56 (d, J = 13.6 Hz, 1H), 5.03-5.34 (m, 1H), 7.19 (d, J = 7.8 Hz, 4H), 7.44 (m, 2H) 7.66 (d, J = 8.1 Hz, 4H) 7.76-8.00 (m, 3H) 8.37 (d, J = 9.8 Hz, 1H); MS (DCI/NH$_3$) m/z 267 (M + H)$^+$; Anal. Calculated for $C_{16}H_{18}N_4\cdot2.00C7H8SO3$: C, 59.00; H, 5.61; N, 9.17. Found: C, 58.92; H, 5.54; N, 9.08. |
| 192 | o-tolyl boronic acid | 1) H<br>2) FB<br>3) S1 | (1R,5R)-3-(6-o-Tolyl-pyridazin-3-yl)-3,6-diaza-bicyclo[3.2.0]heptane bis(p-toluenesulfonate)<br>$^1$H NMR (MeOH-D$_4$, 300 MHz) δ 2.35 (s, 6H), 2.39 (s, 3H), 3.54-3.80 (m, 3H), 3.84 (dd, J = 11.0, 5.3 Hz, 1H), 4.17-4.43 (m, 2H), 4.56 (d, J = 13.9 Hz, 1H), 5.19 (t, J = 6.1 Hz, 1H), 7.22 (d, J = 8.1 Hz, 4H) 7.33-7.59 (m, 2H) 7.68 (d, J = 8.1 Hz, 4H), 7.92 (d, J = 9.5 Hz, 1H), 8.11 (d, J = 9.5 Hz, 1H); MS (DCI/NH$_3$) m/z 267 (M + H)$^+$; Anal. Calculated for $C_{16}H_{18}N_4\cdot2.00C_7H_8SO_3\cdot1.00H_2O$: C, 57.31; H, 5.77; N, 8.91. Found: C, 57.90; H, 5.60; N, 8.79. |
| 193 | m-tolyl boronic acid | 1) H<br>2) FB<br>3) S1 | (1R,5R)-3-(6-m-Tolyl-pyridazin-3-yl)-3,6-diaza-bicyclo[3.2.0]heptane bis(p-toluenesulfonate)<br>$^1$H NMR (MeOH-D$_4$, 300 MHz) δ 2.32 (s, 6H), 2.48 (s, 3H), 3.58-3.99 (m, 4H), 4.20-4.40 (m, 2H), 4.58 (d, J = 13.6 Hz, 1H), 5.22 (t, J = 6.3 Hz, 1H), 7.19 (d, J = 8.1 Hz, 4H), 7.39-7.58 (m, 2H) 7.66 (d, J = 8.1 Hz, 4H), 7.70-7.86 (m, 2H) 7.94 (d, J = 9.8 Hz, 1H), 8.40 (d, J = 9.5 Hz, 1H); MS (DCI/NH$_3$) m/z 267 (M + H)$^+$; Anal. Calculated for $C_{16}H_{18}N_4\cdot2.10C_7H_8SO_3\cdot1.40H_2O$: C, 56.35; H, 5.79; N, 8.47. Found: C, 56.60; H, 5.78; N, 8.13. |
| 194 | 3,4-methylenedioxy-benzeneboronic acid | 1) H<br>2) FB<br>3) S1 | (1R,5R)-3-(6-Benzo[1,3]dioxol-5-yl-pyridazin-3-yl)-3,6-diazabicyclo[3.2.0]heptane bis(p-toluenesulfonate)<br>$^1$H NMR (MeOH-D$_4$, 300 MHz) δ 2.33 (s, 6H), 3.55-3.70 (m, 2H), 3.78 (dd, J = 12.1, 5.8 Hz, 1H), 3.88 (dd, J = 11.9, 5.1 Hz, 1H), 4.20-4.36 (m, 2H), 4.56 (d, J = 12.9 Hz, 1H), 5.21 (t, J = 5.8 Hz, 1H), 6.11 (s, 2H), 7.04 (d, J = 8.2 Hz, 1H), 7.20 (d, J = 8.1 Hz, 4H), 7.46-7.52 (m, 2H), 7.65 (d, J = 8.4 Hz, 4H), 7.88 (d, J = 9.9 Hz, 1H), 8.33 (d, J = 9.8 Hz, 1H); MS (DCI/NH$_3$) m/z 297 (M + H)$^+$; Anal. Calculated for $C_{16}H_{16}N_4O_2\cdot2.00C_7H_8SO_3$: C, 56.24; H, 5.03; N, 8.74. Found: C, 56.01; H, 4.94; N, 8.51. |
| 195 | p-tolyl boronic acid | 1) H<br>2) FB<br>3) RA<br>4) S1 | (1R,5R)-6-Methyl-3-(6-p-tolyl-pyridazin-3-yl)-3,6-diaza-bicyclo[3.2.0]heptane fumarate<br>$^1$H NMR (MeOH-D$_4$, 300 MHz) δ 2.40 (s, 3H), 2.89 (s, 3H), 3.31-3.66 (m, 3H), 3.91 (dd, J = 10.7, 4.6 Hz, 1H), 4.10-4.18 (m, 2H), 4.50 (d, J = 13.6 Hz, 1H), 4.68-4.97 (m, 1H), 6.68 (s, 2H), 7.18-7.44 (m, 3H), 7.84 (d, J = 8.5 Hz, 2H), 7.95 (d, J = 9.5 Hz, 1H); MS (DCI/NH$_3$) m/z 281 (M + H)$^+$; Anal. Calculated for $C_{17}H_{20}N_4\cdot1.10C_4H_4O_4\cdot0.50H_2O$: C, 61.90; H, 6.12; N, 13.49. Found: C, 61.97; H, 5.77; N, 13.72. |
| 196 | o-tolyl boronic acid | 1) H<br>2) FB<br>3) RA<br>4) S1 | (1R,5R)-6-Methyl-3-(6-o-tolyl-pyridazin-3-yl)-3,6-diaza-bicyclo[3.2.0]heptane bis(p-toluenesulfonate)<br>$^1$H NMR (MeOH-D$_4$, 300 MHz) δ 2.35 (s, 6H), 2.38 (s, 3H), 3.05 (s, 3H), 3.58-3.85 (m, 3H) 4.20 (d, J = 6.4 Hz, 2H), 4.30 (d, J = 10.5 Hz, 1H), 4.64 (d, J = 14.6 Hz, 1H) 4.98-5.18 (m, 1H), 7.21 (d, J = 7.8 Hz, 4H), 7.35-7.59 (m, 4H), 7.68 (d, J = 8.1 Hz, 4H) |

| Example | Boronic Acid | Conditions | Resulting Compound |
|---|---|---|---|
| 197 | 3,4-methylenedioxy benzeneboronic acid | 1) H<br>2) FB<br>3) RA<br>4) S1 | 7.95 (d, J = 9.8 Hz, 1H) 8.15 (d, J = 9.8 Hz, 1H); MS (DCI/NH$_3$) m/z 281 (M + H)$^+$; Anal. Calculated for C$_{17}$H$_{20}$N$_4$•2.10C$_7$H$_8$SO$_3$•1.00H$_2$O: C, 57.69; H, 5.93; N, 8.49. Found: C, 57.50; H, 5.60; N, 8.79.<br>(1R,5R)-3-(6-Benzo[1,3]dioxol-5-yl-pyridazin-3-yl)-6-methyl-3,6-diaza-bicyclo[3.2.0]heptane bis(p-toluenesulfonate)<br>$^1$H NMR (MeOH-D$_4$, 300 MHz) δ 2.31 (s, 6H), 3.04 (s, 3H), 3.52-3.79 (m, 3H), 4.05-4.38 (m, 3H), 4.61 (d, J = 13.9 Hz, 2H), 5.07 (t, J = 6.3 Hz, 1H), 6.10 (s, 2H), 7.03 (d, J = 7.8 Hz, 1H), 7.18 (d, J = 7.8 Hz, 4H), 7.35-7.56 (m, 2H), 7.64 (d, J = 8.1 Hz, 4H), 7.75 (d, J = 9.5 Hz, 1H), 8.22 (d, J = 9.8 Hz, 1H); MS (DCI/NH$_3$) m/z 311 (M + H)$^+$; Anal. Calculated for C$_{17}$H$_{18}$N$_4$O$_2$•2.10C$_7$H$_8$SO$_3$•1.00H$_2$O: C, 56.87; H, 5.23; N, 8.56. Found: C, 56.85; H, 5.37; N, 8.74. |

Examples 204-208

The product of Example 8B was reacted with 3,6-dichloropyridazine according to the procedure of Example 90, and the material was in turn coupled to the boronic acid and processed further according to the conditions listed in the table below:

Example 209-211

The product of Example 7J was reacted with 3,6-dichloropyridazine according to the procedure of Example 90, and subjected to N-methylation according to method EC. The material was in turn coupled to the boronic acid and processed further according to the conditions listed in the table below:

| Example | Boronic Acid | Conditions | Resulting Compound |
|---|---|---|---|
| 204 | 5-indolyl boronic acid | 1) MW<br>2) FB<br>3) S2 | (1S,5S)-5-[6-(3,6-Diaza-bicyclo[3.2.0]hept-3-yl)-pyridazin-3-yl]-1H-indole Fumarate<br>$^1$H NMR (CH$_3$OH-d$_4$, 300 MHz) δ ppm 3.29-3.38 (m, 1H), 3.45 (dd, J = 13.6, 5.1 Hz, 1H), 3.51-3.65 (m, 1H), 3.78 (dd, J = 11.4, 5.3 Hz, 1H), 4.17 (d, J = 11.2 Hz, 1H), 4.30 (dd, J = 11.0, 8.6 Hz, 1H), 4.48 (d, J = 13.6 Hz, 1H), 5.10 (dd, J = 7.1, 5.1 Hz, 1H), 6.55 (d, J = 2.4 Hz, 1H), 6.71 (s, 2H), 7.30 (d, J = 3.4 Hz, 1H), 7.34 (d, J = 9.5 Hz, 1H), 7.50 (d, J = 8.5 Hz, 1H), 7.75 (dd, J = 8.5, 1.7 Hz, 1H), 8.02 (d, J = 9.5 Hz, 1H), 8.13 (s, 1H); MS (APCI/NH$_3$) m/z 292 (M + H)$^+$; Anal. C$_{17}$H$_{17}$N$_5$•1.5C$_4$H$_4$O$_4$•0.5H$_2$O: C, H, N. |
| 205 | 5-indolyl boronic acid | 1) MW<br>2) RA<br>3) S4 | (1S,5S)-5-[6-(6-Methyl-3,6-diaza-bicyclo[3.2.0]hept-3-yl)-pyridazin-3-yl]-1H-indole Bis(trifluoroacetate)<br>$^1$H NMR (CH$_3$OH-d$_4$, 300 MHz) δ ppm 3.02 (s, 3H), 3.43-3.72 (m, 4H), 4.07-4.29 (m, 2H), 4.53-4.66 (m, 1H), 5.03 (s, 1H), 6.64 (d, J = 4.1 Hz, 1H), 7.39 (d, J = 3.4 Hz, 1H), 7.57-7.64 (m, 1H), 7.67-7.73 (m, 1H), 7.78 (d, J = 9.8 Hz, 1H), 8.20 (d, J = 1.4 Hz, 1H), 8.39 (d, J = 9.8 Hz, 1H); MS (DCI/NH$_3$) m/z 306 (M + H)$^+$; Anal. C$_{18}$H$_{19}$N$_5$•2C$_2$F$_3$HO$_2$: C, H, N. |
| 206 | 4-indolyl boronic acid | 1) MW<br>2) S4 | (1S,5S)-4-[6-(6-Methyl-3,6-diaza-bicyclo[3.2.0]hept-3-yl)-pyridazin-3-yl]-1H-indole Bis(trifluoroacetate)<br>$^1$H NMR (CH$_3$OH-d$_4$, 300 MHz) δ ppm 3.03 (s, 3H), 3.45-3.73 (m, 4H), 4.09-4.30 (m, 2H), 4.63 (d, J = 12.9 Hz, 1H), 5.04 (s, 1H), 6.81 (dd, J = 3.4, 1.0 Hz, 1H), 7.32 (t, J = 7.8 Hz, 1H), 7.43-7.49 (m, 2H), 7.63 (d, J = 7.8 Hz, 1H), 7.75 (d, J = 9.5 Hz, 1H), 8.33 (d, J = 9.5 Hz, 1H); MS (DCI/NH$_3$) m/z 306 (M + H)$^+$; Anal. C$_{18}$H$_{19}$N$_5$•2.5C$_2$F$_3$HO$_2$: C, H, N. |
| 207 | 5-(4,4,5,5-tetramethyl-1,3,2-dioxaborolan-2-yl)-1-benzofuran | 1) MW<br>2) S4 | (1S,5S)-3-(6-Benzofuran-5-yl-pyridazin-3-yl)-6-methyl-3,6-diaza-bicyclo[3.2.0]heptane Bis(trifluoroacetate)<br>$^1$H NMR (CH$_3$OH-d$_4$, 300 MHz) δ ppm 3.03 (s, 3H), 3.46-3.72 (m, 4H), 4.09-4.29 (m, J = 16.3 Hz, 2H), 4.56-4.68 (m, 1H), 5.04 (s, 1H), 6.99 (dd, J = 2.4, 1.0 Hz, 2H), 7.68 (d, J = 5.4 Hz, 1H), 7.71 (d, J = 4.4 Hz, 1H), 7.88 (d, J = 2.4 Hz, 1H), 7.93 (dd, J = 8.8, 2.0 Hz, 1H), 8.24 (d, J = 1.7 Hz, 1H), 8.30 (d, J = 9.5 Hz, 1H); MS (DCI/NH$_3$) m/z 307 (M + H)$^+$; Anal. C$_{18}$H$_{18}$N$_4$O•2.5C$_2$F$_3$HO$_2$: C, H, N. |
| 208 | p-aminobenzene boronic acid | 1) I<br>2) FB<br>3) S1 | (1S,5S)-4-[6-(3,6-Diaza-bicyclo[3.2.0]hept-3-yl)-pyridazin-3-yl]-phenylamine tri(p-toluenesulfonate)<br>$^1$H NMR (MeOH-D$_4$, 300 MHz) δ 2.33 (s, 9H), 3.76-4.05 (m, 4H), 4.20-4.40 (m, 2H), 4.58 (d, J = 1 3.9 Hz, 1H) 5.22 (t, J = 5.9 Hz, 1H) 7.20 (d, J = 8.5 Hz, 6H) 7.36 (d, J = 8.5 Hz, 2H) 7.67 (d, J = 8.1 Hz, 6H) 7.91 (d, J = 9.8 Hz, 1H) 8.01 (d, J = 8.8 Hz, 2H) 8.37 (d, J = 9.8 Hz, 1H); MS (DCI/NH$_3$) m/z 268 (M + H)$^+$; Anal. Calculated for C$_{15}$H$_{17}$N$_5$•3.23C$_7$H$_8$SO$_3$•0.50H$_2$O: C, 54.26; H, 5.31; N, 8.41. Found: C, 53.93; H, 4.82; N, 8.02. |

| Example | Boronic Acid | Conditions | Resulting Compound |
|---|---|---|---|
| 209 | 3-thienyl boronic acid | 1) MW<br>2) S4 | (1R,5S)-3-[6-(3-Methyl-3,6-diaza-bicyclo[3.2.0]hept-6-yl)-pyridazin-3-yl]-thiophene trifluroacetate<br>$^1$H NMR (CH$_3$OH-d$_4$, 300 MHz) δ ppm 3.08 (s, 3H), 3.19-3.38 (m, 2H), 3.51-3.61 (m, 1H), 3.91 (dd, J = 8.6, 3.2 Hz, 1H), 4.02 (dd, J = 25.1, 12.2 Hz, 2H), 4.30 (t, J = 8.3 Hz, 1H), 5.23 (dd, J = 6.6, 3.6 Hz, 1H), 7.01 (d, J = 9.2 Hz, 1H), 7.54 (dd, J = 5.1, 2.7 Hz, 1H), 7.71 (dd, J = 5.1, 1.4 Hz, 1H), 7.92 (d, J = 9.5 Hz, 1H), 7.96 (dd, J = 3.1, 1.4 Hz, 1H); MS (DCI/NH$_3$) m/z 273 (M + H)$^+$; Anal. C$_{14}$H$_{16}$N$_4$S•1.3C$_2$F$_3$HO$_2$•0.8H$_2$O: C, H, N. |
| 210 | 5-indolyl boronic acid | 1) I<br>2) FB<br>3) S1 | (1R,5S)-5-[6-(3-Methyl-3,6-diaza-bicyclo[3.2.0]hept-6-yl)-pyridazin-3-yl]-1H-indole bis(trifluroacetate)<br>$^1$H NMR (MeOH-D$_4$, 300 MHz) δ 3.05 (s, 3H), 3.50-3.61 (m, 1H), 3.88-4.08 (m, 4H) 4.13 (d, J = 12.9 Hz, 1H), 4.40 (t, J = 8.5 Hz, 1H), 5.30 (dd, J = 6.8, 3.7 Hz, 1H), 6.59 (d, J = 2.4 Hz, 1H), 7.24-7.43 (m, 2H) 7.55-(d, J = 8.8 Hz, 1H), 7.70 (dd, J = 8.5, 1.7 Hz, 1H), 8.14 (d, J = 1.7 Hz, 1H), 8.23 (d, J = 9.5 Hz, 1H); MS (DCI/NH$_3$) m/z 306 (M + H)$^+$; Anal. Calculated for C$_{18}$H$_{19}$N$_5$•2.00CF$_8$CO$_2$H•0.50H$_2$O: C, 50.09; H, 4.47; N, 12.43. Found: C, 49.97; H, 4.04; N, 12.07. |
| 211 | 4-indolyl boronic acid | 1) MW<br>2) S4 | (1R,5S)-4-[6-(3-Methyl-3,6-diaza-bicyclo[3.2.0]hept-6-yl)-pyridazin-3-yl]-1H-indole bis(trifluroacetate)<br>$^1$H NMR (CH$_3$OH-d$_4$, 300 MHz) δ ppm 3.10 (s, 3H), 3.30-3.41 (m, 2H), 3.60-3.72 (m, 1H), 3.99-4.09 (m, 2H), 4.18 (d, J = 12.9 Hz, 1H), 4.45 (t, J = 8.6 Hz, 1H), 5.36 (dd, J = 6.8, 4.1 Hz, 1H), 6.83 (dd, J = 3.2, 0.8 Hz, 1H), 7.25-7.32 (m, 1H), 7.39-7.46 (m, 3H), 7.60 (d, J = 8.1 Hz, 1H), 8.26 (d, J = 9.5 Hz, 1H); MS (DCI/NH$_3$) m/z 306 (M + H)$^+$; Anal. C$_{18}$H$_{19}$N$_5$•2.4C$_2$F$_3$HO$_2$•0.8H$_2$O: C, H, N. |

Example 212

3-Methyl-5-[6-(5-methyl-hexahydro-pyrrolo[3,4-c]pyrrol-2-yl)-pyridazin-3-yl]-1H-indazole bis(trifluoroacetate)

Example 212A

3-Methyl-5-trimethylstannanyl-indazole-1-carboxylic acid tert-butyl ester

Hexamethylditin (4.73 g, 14.4 mmol) was added to a mixture of 3-methyl-5-bromo-indazole-1-carboxylic acid tert-butyl ester (3.0 g, 9.6 mmol) and Pd(PPh$_3$)$_4$ (1.1 g, 0.96 mmol) in toluene (50 mL). The solution was purged with nitrogen, and heated to 115° C. under nitrogen for 2 h. The black reaction mixture was cooled to room temperature, loaded onto a column of silica gel and eluted with EtOAc-Hexane (5-30%) to provide the title compound (3.06 g, 80% yield): MS (DCI/NH$_3$) m/z 396 (M+H)$^+$.

Example 212B

3-Methyl-5-[6-(5-methyl-hexahydro-pyrrolo[3,4-c]pyrrol-2-yl)-pyridazin-3-yl]-1H-indazole bis(trifluoroacetate)

The product of Example 114 (120 mg, 0.5 mmol) was combined with the product of Example 212A (278 mg, 0.7 mmol). Dioxane (10 mL), tris(dibenzylidene)-dipalladium (Pd$_2$(dba)$_3$, 24 mg, 0.025 mmol), Pd (Pbu$^t{}_3$, 26 mg, 0.05 mmol) and CsF (152 mg, 1 mmol) were added, and the mixture was stirred at 100° C. under nitrogen for 16 h. The reaction was cooled to room temperature, diluted with ethyl acetate (30 mL) and washed with water. The organic phase was concentrated under vacuum, and the residue was purified by column chromatography (10% MeOH—CH$_2$Cl$_2$) to provide the free base (120 mg, 55% yield) which was converted to the title compound by method S4: $^1$H NMR (300 MHz, CH$_3$OH-d$_4$) δ 2.63 (s, 3H), 2.99 (s, 3H), 3.23-4.07 (m, 10H), 7.58-7.70 (m, J=8.6, 8.6 Hz, 2H), 8.03 (dd, J=8.8, 1.4 Hz, 1H), 8.36 (s, 1H), 8.42 ppm (d, J=9.8 Hz, 1H); MS (DCI/NH$_3$) m/z 335 (M+H)$^+$; Anal. calculated for C$_{19}$H$_{22}$N$_6$.2.28C$_2$F$_3$HO$_2$: C, 47.61; H, 4.12; N, 14.14. Found: C, 47.26; H, 3.92; N, 14.44.

Example 213

(1S,5S)-5-[6-(3,6-Diaza-bicyclo[3.2.0]hept-3-yl)-pyridin-3-yl]-3-methyl-1H-indazole tri(p-toluenesulfonate)

The product of Example 9 was reacted with 2,5-dibromopyridine according to the procedure of Example 128A, then coupled with the product of Example 212A according to the procedure of Example 212B. The resulting product was deprotected according to procedure FB and converted to the salt by method S4 to provide the title compound: $^1$H NMR (MeOH-D$_4$, 300 MHz) δ 2.32 (s, 9H), 2.65 (s, 3H) 3.67-3.73 (m, 2H), 3.82 (dd, J=13.2, 5.8 Hz, 1H), 3.90 (dd, J=11.2, 4.1 Hz, 1H), 4.25-4.37 (m, 2H), 4.58 (d, J=13.2 Hz, 1H), 5.24 (t, J=6.1 Hz, 1H), 7.20 (d, J=7.8 Hz, 6H), 7.41 (d, J=9.2 Hz, 1H), 7.64-7.70 (d, J=7.8 Hz, 6H), 7.72-7.75 (dd, J=8.8, 1.2 Hz, 1H), 7.80 (dd, J=8.8, 1.6 Hz, 1H), 8.16 (m, 1H), 8.26 (d, J=1.7 Hz, 1H), 8.46 (dd, J=9.5, 2.4 Hz, 1H); MS (DCI/NH$_3$) m/z 306 (M+H)$^+$; Anal. Calculated for C$_{18}$H$_{19}$N$_5$.3.30C$_7$H$_8$SO$_3$.1.50H$_2$O: C, 54.81; H, 5.42; N, 7.78. Found: C, 54.98; H, 5.30; N, 7.40.

Example 224

(1R,5S)-3-Phenyl-6-(6-phenyl-pyridazin-3-yl)-3,6-diaza-bicyclo[3.2.0]heptane bis(p-toluenesulfonate)

The diamine from Example 9 was coupled with 3-chloro-6-phenylpyridazine according to the procedure of Method A. The product was deprotected by the procedure of Method PD, then coupled with bromobenzene according to the general procedure of Example 156A. The product was then converted to the salt with p-toluenesulfonic acid according to Method S1 to provide the title compound: $^1$H NMR (CD$_3$OD, 300 MHz) δ 2.40 (s, 6H), 2.99-3.22 (m, 2H), 3.57-3.76 (m, 1H), 3.99 (d, J=10.5 Hz, 1H), 4.13-4.27 (m, 2H), 4.48-4.64 (m, 1H), 5.30-5.47 (m, 1H), 6.89 (t, J=7.3 Hz, 1H), 7.00 (d, J=8.1 Hz, 2H), 7.12-7.36 (m, 7H), 7.46-7.62 (m, 3H), 7.69 (d, J=8.5 Hz, 4H), 7.88-8.06 (m, 2H), 8.33 (d, J=9.8 Hz, 1H); MS (DCI/NH$_3$) m/z 329 (M+H)$^+$; Anal. Calculated for C$_{21}$H$_{20}$N$_4$·2.00C$_7$H$_8$SO$_3$·1.50H$_2$O: C, 60.07; H, 5.62; N, 8.01. Found: C, 59.97; H, 5.55; N, 7.92.

Examples 225-239

The product of Example 10 was reacted with 5-bromo-2-chloropyridine according to the procedure of Example 156A, then coupled with the listed boronic acid and processed according to the procedures indicated in the table below.

| Example | Boronic Acid | Conditions | Resulting Compound |
| --- | --- | --- | --- |
| 225 | 4-acetylphenyl boronic acid | 1. G<br>2. FB<br>3. S1 | (1R,5R)-1-{4-[5-(3,6-Diaza-bicyclo[3.2.0]hept-3-yl)-pyridin-2-yl]-phenyl}-ethanone p-toluenesulfonate<br>$^1$H NMR (CH$_3$OH-d$_4$, 300 MHz) δ 2.35 (s, 6H), 2.67 (s, 3H), 3.43 (dd, J$_1$ = 12.9 Hz, J$_2$ = 5.4 Hz, 1H), 3.55-3.67 (m, 1H), 4.09 (d, J = 11.2 Hz, 1H), 4.26-4.37 (m, 2H), 5.14 (t, J = 6.5 Hz, 1H), 7.21 (d, J = 7.8 Hz, 4H), 7.68 (d, J = 8.1 Hz, 4H), 7.95-8.01 (m, 3H), 8.17-8.22 (m, 3H), 8.28 (d, J = 3.1 Hz, 1H); MS (DCI/NH$_3$) m/z 294 (M + H)$^+$; Anal. C$_{18}$H$_{19}$N$_3$O·2C$_7$H$_8$O$_3$S: C, H, N. |
| 226 | 4-N,N-dimethylaminophenyl boronic acid | 1. G<br>2. FB<br>3. S1 | (1R,5R)-{4-[5-(3,6-Diaza-bicyclo[3.2.0]hept-3-yl)-pyridin-2-yl]-phenyl}-dimethyl-amine p-toluenesulfonate<br>$^1$H NMR (CH$_3$OH-d$_4$, 300 MHz) δ ppm 2.34 (s, 6H), 3.10 (s, 6H), 3.23 (dd, J = 10.5, 6.4 Hz, 1H), 3.31-3.39 (m, 1H), 3.51-3.64 (m, 1H), 3.79 (dd, J = 11.0, 5.3 Hz, 1H), 4.01 (d, J = 10.9 Hz, 1H), 4.21-4.35 (m, 2H), 5.12 (dd, J = 6.8, 5.4 Hz, 1H), 6.94 (d, J = 9.2 Hz, 2H), 7.21 (d, J = 8.1 Hz, 4H), 7.69 (d, J = 8.5 Hz, 4H), 7.73 (d, J = 9.2 Hz, 2H), 7.97-8.13 (m, 3H); MS (DCI/NH$_3$) m/z 295 (M + H)$^+$; Anal. C$_{18}$H$_{22}$N$_4$·2.4C$_7$H$_8$O$_3$S·0.3H$_2$O: C, H, N. |
| 227 | m-tolyl boronic acid | 1. G<br>2. FB<br>3. RA<br>4. S1 | (1R,5R)-6-Methyl-3-(6-m-tolyl-pyridin-3-yl)-3,6-diaza-bicyclo[3.2.0]heptane p-toluenesulfonate<br>$^1$H NMR (CH$_3$OH-d$_4$, 300 MHz) δ ppm 2.33 (s, 6H), 2.48 (s, 3H), 3.04 (s, 3H), 3.32-3.38 (m, 1H), 3.42 (dd, J = 12.9, 4.7 Hz, 1H), 3.57-3.69 (m, 1H), 4.08 (d, J = 10.8 Hz, 1H), 4.13-4.21 (m, 2H), 4.39 (d, J = 12.9 Hz, 1H), 5.01 (dd, J = 7.3, 4.6 Hz, 1H), 7.20 (d, J = 7.8 Hz, 4H), 7.42-7.56 (m, 2H), 7.58-7.71 (m, 6H), 7.99-8.06 (m, 1H), 8.10-8.21 (m, 2H); MS (DCI/NH$_3$) m/z 280 (M + H)$^+$; Anal. C$_{18}$H$_{21}$N$_3$·2C$_7$H$_8$O$_3$S: C, H, N. |
| 228 | p-tolyl boronic acid | 1. G<br>2. FB<br>3. RA<br>4. S1 | (1R,5R)-6-Methyl-3-(6-p-tolyl-pyridin-3-yl)-3,6-diaza-bicyclo[3.2.0]heptane p-toluenesulfonate<br>$^1$H NMR (CH$_3$OH-d$_4$, 300 MHz) δ ppm 2.34 (s, 6H), 2.46 (s, 3H), 3.04 (s, 3H), 3.31-3.36 (m, 1H), 3.40 (dd, J = 13.2, 4.7 Hz, 1H), 3.56-3.68 (m, 1H), 4.07 (d, J = 10.8 Hz, 1H), 4.11-4.21 (m, 2H), 4.37 (d, J = 12.9 Hz, 1H), 5.01 (dd, J = 7.3, 4.6 Hz, 1H), 7.20 (d, J = 7.8 Hz, 4H), 7.46 (d, J = 7.8 Hz, 2H), 7.67 (d, J = 8.1 Hz, 4H), 7.70-7.76 (m, 2H), 7.99-8.05 (m, 1H), 8.09-8.18 (m, 2H); MS (DCI/NH$_3$) m/z 280 (M + H)$^+$; Anal. C$_{18}$H$_{21}$N$_3$·2.25C$_7$H$_8$O$_3$S: C, H, N. |
| 229 | m-Cyanophenyl boronic acid | 1. G<br>2. FB<br>3. RA<br>4. S1 | (1R,5R)-3-[5-(6-Methyl-3,6-diaza-bicyclo[3.2.0]hept-3-yl)-pyridin-2-yl]-benzonitrile p-toluenesulfonate<br>$^1$H NMR (CH$_3$OH-d$_4$, 300 MHz) δ ppm 2.35 (s, 6H), 3.03 (s, 3H), 3.31-3.37 (m, 1H), 3.42 (dd, J = 13.1, 4.9 Hz, 1H), 3.56-3.68 (m, 1H), 4.09 (d, J = 10.9 Hz, 1H), 4.13-4.21 (m, 2H), 4.39 (d, J = 12.9 Hz, 1H), 5.01 (dd, J = 7.1, 4.7 Hz, 1H), 7.21 (d, J = 8.1 Hz, 4H), 7.68 (d, J = 8.1 Hz, 4H), 7.78 (t, J = 8.0 Hz, 1H), 7.90-7.97 (m, 2H), 8.10-8.18 (m, J = 9.2 Hz, 2H), 8.22-8.27 (m, 1H), 8.30 (d, J = 3.1 Hz, 1H); MS (DCI/NH$_3$) m/z 291 (M + H)$^+$; Anal. C$_{18}$H$_{18}$N$_4$·2.5C$_7$H$_8$O$_3$S: C, H, N. |
| 230 | 4-ethylphenyl boronic acid | 1. G<br>2. FB<br>3. RA<br>4. S1 | (1R,5R)-3-[6-(4-Ethyl-phenyl)-pyridin-3-yl]-6-methyl-3,6-diaza-bicyclo[3.2.0]heptane p-toluenesulfonate<br>$^1$H NMR (CH$_3$OH-d$_4$, 300 MHz) δ ppm 1.29 (t, J = 7.6 Hz, 3H), 2.34 (s, 6H), 2.77 (q, J = 7.1 Hz, 2H), 3.04 (s, 3H), 3.31-3.36 (m, 1H), 3.40 (dd, J = 13.2, 5.1 Hz, 1H), 3.57-3.68 (m, 1H), 4.07 (d, J = 10.8 Hz, 1H), 4.11-4.20 (m, 2H), 4.36 (d, J = 12.9 Hz, 1H), 5.01 (dd, J = 7.6, 4.9 Hz, 1H), 7.21 (d, J = 7.8 Hz, 4H), 7.48 (d, J = 8.8 Hz, 1H), 7.67 (d, J = 8.1 Hz, 4H), 7.75 (d, J = 8.5 Hz, 2H), 7.99-8.05 (m, 1H), 8.11-8.18 (m, 2H); MS (DCI/NH$_3$) m/z 294 (M + H)$^+$; Anal. C$_{19}$H$_{23}$N$_3$·2C$_7$H$_8$O$_3$S·0.7H$_2$O: C, H, N. |
| 231 | 4-acetylphenyl boronic acid | 1. G<br>2. FB<br>3. RA<br>4. S1 | (1R,5R)-1-{4-[5-(6-Methyl-3,6-diaza-bicyclo[3.2.0]hept-3-yl)-pyridin-2-yl]-phenyl}-ethanone p-toluenesulfonate<br>$^1$H NMR (CH$_3$OH-d$_4$, 300 MHz) δ 2.33 (s, 6H), 2.67 (s, 3H), |

-continued

| Example | Boronic Acid | Conditions | Resulting Compound |
|---|---|---|---|
| | | | 3.04 (s, 3H), 3.33-3.50 (m, 2H), 3.57-3.70 (m, 1H), 4.05-4.22 (m, 3H), 4.41 (d, J = 12.9 Hz, 1H), 5.02 (t, J = 4.7 Hz, 1H), 7.21 (d, J = 8.1 Hz, 4H), 7.67 (d, J = 8.1 Hz, 4H), 7.92-8.05 (m, 3H), 8.15-8.30 (m, 4H); MS (DCI/NH$_3$) m/z 308 (M + H)$^+$; Anal. C$_{19}$H$_{21}$N$_3$O·2C$_7$H$_8$O$_3$S: C, H, N. |
| 232 | 4-N,N-dimethylaminophenyl boronic acid | 1. G<br>2. FB<br>3. RA<br>4. S1 | (1R,5R)-Dimethyl-{4-[5-(6-methyl-3,6-diaza-bicyclo[3.2.0]hept-3-yl)-pyridin-2-yl]-phenyl}-amine p-toluenesulfonate<br>$^1$H NMR (CH$_3$OH-d$_4$, 300 MHz) δ ppm 2.34 (s, 6H), 3.03 (s, 3H), 3.10 (s, 6H), 3.21-3.39 (m, 2H), 3.53-3.67 (m, 1H), 4.02 (d, J = 10.8 Hz, 1H), 4.11-4.20 (m, 2H), 4.32 (d, J = 12.9 Hz, 1H), 4.99 (dd, J = 7.0, 4.6 Hz, 1H), 6.94 (d, J = 8.8 Hz, 2H), 7.21 (d, J = 7.8 Hz, 4H), 7.63-7.77 (m, 6H), 7.94-8.13 (m, 3H); MS (DCI/NH$_3$) m/z 309 (M + H)$^+$; Anal. C$_{19}$H$_{24}$N$_4$·2.3C$_7$H$_8$O$_3$S: C, H, N. |
| 233 | m-methoxylphenyl boronic acid | 1. G<br>2. FB<br>3. RA<br>4. S2 | (1R,5R)-3-[6-(3-Methoxy-phenyl)-pyridin-3-yl]-6-methyl-3,6-diaza-bicyclo[3.2.0]heptane fumarate<br>$^1$H NMR (CH$_3$OH-d$_4$, 300 MHz) δ ppm 2.96 (s, 3H), 3.08 (dd, J = 10.2, 6.4 Hz, 1H), 3.16 (dd, J = 12.9, 4.4 Hz, 1H), 3.47-3.59 (m, 1H), 3.86 (s, 3H), 3.97 (d, J = 10.5 Hz, 1H), 3.97-4.04 (m, 1H), 4.16-4.27 (m, 1H), 4.26 (d, J = 12.9 Hz, 1H), 4.94 (dd, J = 7.0, 4.9 Hz, 1H), 6.72 (s, 4H), 6.92-6.97 (m, 1H), 7.32-7.39 (m, 1H), 7.41-7.47 (m, 3H), 7.78 (dd, J = 8.8, 0.7 Hz, 1H), 8.27 (d, J = 2.4 Hz, 1H); MS (DCI/NH$_3$) m/z 296 (M + H)$^+$; Anal. Calculated for C$_{19}$H$_{23}$N$_3$·2.3C$_4$H$_4$O$_4$: C, H, N. |
| 234 | 3,4-methylenedioxybenzene boronic acid | 1. G<br>2. FB<br>3. RA<br>4. S2 | (1R,5R)-3-(6-Benzo[1,3]dioxol-5-yl-pyridin-3-yl)-6-methyl-3,6-diaza-bicyclo[3.2.0]heptane fumarate<br>$^1$H NMR (CH$_3$OH-d$_4$, 300 MHz) δ ppm 2.90 (s, 3H), 3.03-3.16 (m, 2H), 3.45-3.55 (m, 1H), 3.87-3.97 (m, 2H), 4.08-4.18 (m, 1H), 4.19 (d, J = 12.9 Hz, 1H), 5.99 (s, 2H), 6.68 (s, 2H), 6.90 (d, J = 8.8 Hz, 1H), 7.34-7.44 (m, 3H), 7.69 (d, J = 8.8 Hz, 1H), 8.21 (d, J = 3.1 Hz, 1H); MS (DCI/NH$_3$) m/z 310 (M + H)$^+$; Anal. Calculated for C$_{18}$H$_{19}$N$_3$O$_2$·1.1C$_4$H$_4$O$_4$: C, H, N. |
| 235 | 4-methoxybenzene boronic acid | 1. G<br>2. FB<br>3. RA<br>4. S2 | (1R,5R)-3-[6-(4-Methoxy-phenyl)-pyridin-3-yl]-6-methyl-3,6-diaza-bicyclo[3.2.0]heptane Fumarate<br>$^1$H NMR (CH$_3$OH-d$_4$, 300 MHz) δ ppm 2.91 (s, 3H), 3.03-3.16 (m, 2H), 3.45-3.56 (m, J = 13.6 Hz, 1H), 3.84 (s, 3H), 3.89-3.97 (m, 2H), 4.09-4.24 (m, J = 12.0, 12.0 Hz, 2H), 6.68 (s, 2H), 7.00 (d, J = 9.2 Hz, 2H), 7.42 (dd, J = 8.6, 2.9 Hz, 1H), 7.71 (dd, J = 8.8, 0.7 Hz, 1H), 7.80 (d, J = 9.2 Hz, 2H), 8.22 (d, J = 2.4 Hz, 1H); MS (DCI/NH$_3$) m/z 296 (M + H)$^+$; Anal. Calculated for C$_{18}$H$_{21}$N$_3$O·1.1C$_4$H$_4$O$_4$: C, H, N. |
| 236 | 3,4-dimethoxybenzen boronic acid | 1. G<br>2. FB<br>3. RA<br>4. S2 | (1R,5R)-3-[6-(3,4-Dimethoxy-phenyl)-pyridin-3-yl]-6-methyl-3,6-diaza-bicyclo[3.2.0]heptane Fumarate<br>$^1$H NMR (CH$_3$OH-d$_4$, 300 MHz) δ ppm 2.99 (s, 2H), 3.09 (s, 1H), 3.19 dd, J = 13.1, 4.9 Hz, 1H), 3.54-3.64 (m, 1H), 3.91 (s, 3H), 3.95 (s, 3H), 3.95-4.01 (m, 1H), 4.25-4.35 (m, 1H), 4.93-5.06 (m, 1H), 6.73 (s, 4H), 7.10 (d, J = 8.5 Hz, 1H), 7.45 (dd, J = 8.5, 2.0 Hz, 1H), 7.48-7.56 (m, 2H), 7.79 (d, J = 9.2 Hz, 1H), 8.25 (d, J = 2.7 Hz, 1H); MS (DCI/NH$_3$) m/z 326 (M + H)$^+$; Anal. Calculated for C$_{19}$H$_{23}$N$_3$O$_2$·1.8C$_4$H$_4$O$_4$: C, H, N. |
| 237 | Phenyl boronic acid | 1. G<br>2. FB<br>3. RA<br>4. S2 | (1R,5R)-6-Methyl-3-(6-phenyl-pyridin-3-yl)-3,6-diaza-bicyclo[3.2.0]heptane Fumarate<br>$^1$H NMR (CH$_3$OH-d$_4$, 300 MHz) δ ppm 2.91 (s, 3H), 3.05-3.19 (m, 2H), 3.45-3.56 (m, 1H), 3.89-3.98 (m, 2H), 4.15 (dd, J = 10.9, 8.8 Hz, 1H), 4.23 (d, J = 12.9 Hz, 1H), 4.85-4.90 (m, 1H), 6.68 (s, 2H), 7.32-7.50 (m, 5H), 7.77 (d, J = 8.8 Hz, 1H), 7.83-7.90 (m, 2H), 8.27 (d, J = 2.7 Hz, 1H); MS (DCI/NH$_3$) m/z 266 (M + H)$^+$; Anal. Calculated for C$_{17}$H$_{19}$N$_3$·1.4C$_4$H$_4$O$_4$: C, H, N. |
| 238 | Pyridine-3-boronic acid | 1. G<br>2. FB<br>3. RA<br>4. S2 | (1R,5R)-5-(6-Methyl-3,6-diaza-bicyclo[3.2.0]hept-3-yl)-[2,3']bipyridinyl Fumarate<br>$^1$H NMR (CH$_3$OH-d$_4$, 300 MHz) δ ppm 2.91 (s, 3H), 3.09-3.23 (m, 2H), 3.46-3.57 (m, 1H), 3.89-4.01 (m, 2H), 4.09-4.19 (m, 1H), 4.24 (d, J = 12.9 Hz, 1H), 4.85-4.90 (m, 1H), 6.69 (s, 2H), 7.45 (dd, J = 8.6, 2.9 Hz, 1H), 7.52 (dd, J = 8.1, 4.8, 0.7 Hz, 1H), 7.87 (d, J = 8.5 Hz, 1H), 8.32-8.39 (m, 2H), 8.52 (dd, J = 4.9, 1.5 Hz, 1H), 9.09 (dd, J = 2.4, 0.7 Hz, 1H); MS (DCI/NH$_3$) m/z 267 (M + H)$^+$; Anal. Calculated for C$_{16}$H$_{18}$N$_4$·1.2C$_4$H$_4$O$_4$: C, H, N. |
| 239 | 5-indolyl boronic acid | 1) I<br>2) FB<br>3) S1 | (1R,5R)-5-[5-(6-Methyl-3,6-diaza-bicyclo[3.2.0]hept-3-yl)-pyridin-2-yl]-1H-indole p-toluenesulfonate<br>$^1$H NMR (MeOH-D$_4$, 300 MHz) δ 2.34 (s, 3H), 2.97 (s, 3H), 3.07 (dd, J = 10.3, 6.3 Hz, 1H), 3.15 (dd, J = 12.7, 4.6 Hz, 1H), |

-continued

| Example | Boronic Acid | Conditions | Resulting Compound |
|---|---|---|---|
| | | | 3.41-3.69 (m, 1H), 3.96 (d, J = 10.5 Hz, 1H), 4.26 (d, J = 12.5 Hz, 1H), 4.90-5.02 (m, 1H), 6.53 (d, J = 2.4 Hz, 1H), 7.21 (d, J = 8.1 Hz, 2H), 7.29 (d, J = 3.4 Hz, 1H), 7.48 (d, J = 8.5 Hz, 1H), 7.53 (dd, J = 8.8, 2.7 Hz, 1H), 7.63 (dd, J = 8.5, 1.7 Hz, 1H), 7.69 (d, J = 8.1 Hz, 2H), 7.82 (d, J = 8.8 Hz, 1H), 8.05 (d, J = 1.4 Hz, 1H), 8.22 (d, J = 2.7 Hz, 1H); MS (DCI/NH$_3$) m/z 305 (M + H)$^+$; Anal. Calculated for C$_{19}$H$_{20}$N$_4$•1.07C$_7$H$_8$SO$_3$•0.50H$_2$O: C, 62.92; H, 5.89; N, 11.08. Found: C, 63.13; H, 5.87; N, 10.70. |

Example 240

The product of Example 10 was reacted with 5-bromo-2-chloropyridine according to the procedure of Example 156A, then coupled with the listed boronic acid and processed according to the procedures indicated in the table below.

| Example | Boronic Acid | Conditions | Resulting Compound |
|---|---|---|---|
| 240 | 5-indolyl boronic acid | 1) I<br>2) FB<br>3) S1 | (1S,5S)-5-[5-(6-Methyl-3,6-diaza-bicyclo[3.2.0]hept-3-yl)-pyridin-2-yl]-1H-indole p-toluenesulfonate<br>$^1$H NMR (MeOH-D$_4$, 300 MHz) δ 2.34 (s, 3H), 2.97 (s, 3H), 3.07 (dd, J = 10.3, 6.3 Hz, 1H), 3.15 (dd, J = 12.7, 4.6 Hz, 1H), 3.41-3.69 (m, 1H), 3.96 (d, J = 10.5 Hz, 1H), 4.26 (d, J = 12.5 Hz, 1H), 4.90-5.02 (m, 1H), 6.53 (d, J = 2.4 Hz, 1H), 7.21 (d, J = 8.1 Hz, 2H), 7.29 (d, J = 3.4 Hz, 1H), 7.48 (d, J = 8.5 Hz, 1H), 7.53 (dd, J = 8.8, 2.7 Hz, 1H), 7.63 (dd, J = 8.5, 1.7 Hz, 1H), 7.69 (d, J = 8.1 Hz, 2H), 7.82 (d, J = 8.8 Hz, 1H), 8.05 (d, J = 1.4 Hz, 1H), 8.22 (d, J = 2.7 Hz, 1H); MS (DCI/NH$_3$) m/z 305 (M + H)$^+$; Anal. Calculated for C$_{19}$H$_{20}$N$_4$•1.12C$_7$H$_8$SO$_3$•1.00H$_2$O: C, 62.56; H, 6.06; N, 10.87. Found: C, 62.75; H, 5.75; N, 10.48. |

Examples 243-246

The product of Example 8B was reacted with 5-bromo-2-chloropyridine according to the procedure of Example 156A, then coupled with the listed boronic acid and processed according to the procedures indicated in the table below.

| Example | Boronic Acid | Conditions | Resulting Compound |
|---|---|---|---|
| 243 | Phenylboronic acid | 1) H<br>2) Pd<br>3) S2 | (1R,5S)-6-(6-Phenyl-pyridin-3-yl)-3,6-diaza-bicyclo[3.2.0]heptane fumarate<br>$^1$H NMR (MeOH-D$_4$, 300 MHz) δ 3.20 (dd, J = 12.5, 3.4 Hz, 1H), 3.32-3.39 (m, 1H), 3.39-3.54 (m, 1H) 3.67-3.80 (m, 2H), 3.82 (dd, J = 7.8, 2.7 Hz, 1H), 4.07 (t, J = 7.8 Hz, 1H), 4.89-5.03 (m, 1H), 6.68 (s, 2H) 7.10 (dd, J = 8.6, 2.9 Hz, 1H) 7.34 (t, J = 7.3 Hz, 1H) 7.39-7.48 (m, 2H), 7.70 (d, J = 8.5 Hz, 1H), 7.78-7.86 (m, 2H), 7.92 (d, J = 2.7 Hz, 1H); MS (DCI/NH$_3$) m/z 252 (M + H)$^+$; Anal. Calculated for C$_{19}$H$_{20}$N$_4$•1.00C$_4$H$_4$O$_4$•0.10H$_2$O: C, 65.06; H, 5.79; N, 11.38. Found: C, 64.79; H, 5.42; N, 11.24. |
| 244 | m-tolyl boronic acid | 1) H<br>2) Pd<br>3) S2 | (1R,5S)-6-(6-m-Tolyl-pyridin-3-yl)-3,6-diaza-bicyclo[3.2.0]heptane fumarate<br>$^1$H NMR (MeOH-D$_4$, 300 MHz) δ 2.40 (s, 3H), 3.18 (dd, J = 12.5, 3.4 Hz, 1H), 3.35 (d, J = 7.5 Hz, 1H), 3.38-3.52 (m, 1H), 3.73 (dd, J = 12.2, 9.8 Hz, 2H), 3.81 (dd, J = 8.0, 2.9 Hz, 1H), 4.02-4.12 (m, 1H), 4.94 (dd, J = 6.4, 3.4 Hz, 1H), 6.68 (s, 2H), 7.09 (dd, J = 8.6, 2.9 Hz, 1H), 7.17 (d, J = 7.5 Hz, 1H), 7.31 (t, J = 7.6 Hz, 1H), 7.55-7.66 (m, 2H), 7.68 (d, J = 8.1 Hz, 1H), 7.91 (d, J = 2.4 Hz, 1H); MS (DCI/NH$_3$) m/z 266 (M + H)$^+$; Anal. Calculated for C$_{17}$H$_{19}$N$_3$•1.00C$_4$H$_4$O$_4$•0.10H$_2$O: C, 65.06; H, 5.79; N, 11.38. Found: C, 64.79; H, 5.42; N, 11.24. |

-continued

| Example | Boronic Acid | Conditions | Resulting Compound |
|---|---|---|---|
| 245 | Phenylboronic acid | 1) H<br>2) FB<br>3) RA<br>4) S2 | (1R,5S)-3-Methyl-6-(6-phenyl-pyridin-3-yl)-3,6-diaza-bicyclo[3.2.0]heptane fumarate<br>$^1$H NMR (MeOH-D$_4$, 300 MHz) δ 2.99 (s, 3H), 3.06 (dd, J = 11.9, 3.4 Hz, 1H), 3.16 (dd, J = 12.0, 7.3 Hz, 1H), 3.40-3.56 (m, 1H), 3.80-3.88 (m, 2H), 3.91 (d, J = 11.9 Hz, 1H), 4.07 (t, J = 8.0 Hz, 1H), 4.93 (dd, J = 6.4, 3.4 Hz, 1H), 6.69 (s, 2H) 7.09 (dd, J = 8.6, 2.9 Hz, 2H) 7.29-7.38 (m, 1H) 7.38-7.50 (m, 2H) 7.70 (d, J = 8.1 Hz, 2H) 7.77-7.86 (m, 2H) 7.92 (d, J = 2.7 Hz, 1H); MS (DCI/NH$_3$) m/z 266 (M + H)$^+$; Anal. Calculated for C$_{17}$H$_{19}$N$_3$•1.00C$_4$H$_4$O$_4$•0.60H$_2$O: C, 64.31; H, 6.22; N, 10.71. Found: C, 64.11; H, 5.86; N, 10.81. |
| 246 | 5-indolyl boronic acid | 1) I<br>2) FB<br>3) RA<br>4) S1 | (1R,5S)-5-[5-(3-Methyl-3,6-diaza-bicyclo[3.2.0]hept-6-yl)-pyridin-2-yl]-1H-indole fumarate<br>$^1$H NMR (MeOH-D$_4$, 300 MHz) δ 2.99 (s, 3H) 3.05 (dd, J = 12.0, 3.2 Hz, 1H), 3.15 (dd, J = 12.0, 7.6 Hz, 1H), 3.39-3.58 (m, 1H), 3.77-3.97 (m, 3H) 4.06 (t, J = 8.3 Hz, 1H), 4.91 (dd, J = 7.0, 2.9 Hz, 1H), 6.50 (d, J = 3.1 Hz, 1H), 6.69 (s, 2.6H), 7.10 (dd, J = 8.6, 2.9 Hz, 1H), 7.26 (d, J = 3.4 Hz, 1H), 7.42 (d, J = 8.5 Hz, 1H), 7.58 (dd, J = 8.5, 1.7 Hz, 1H), 7.70 (d, J = 8.5 Hz, 1H), 7.88 (d, J = 2.7 Hz, 1H), 7.99 (s, 1H); MS (DCI/NH$_3$) m/z 305 (M + H)$^+$; Anal. Calculated for C$_{19}$H$_{20}$N$_4$•1.30C$_4$H$_4$O$_4$•1.00H$_2$O•1.00C$_3$H$_8$O: C, 61.25; H, 6.65; N, 10.50. Found: C, 61.26; H, 6.25; N, 10.86. |

Examples 247-250

The product of Example 9 was reacted with 2,5-dibromopyridine according to the procedure of Example 128A, then coupled with the listed boronic acid and processed according to the procedures indicated in the table below.

| Example | Boronic Acid | Conditions | Resulting Compound |
|---|---|---|---|
| 247 | 5-indolyl boronic acid | 1) I<br>2) FB<br>3) S1 | (1S,5S)-5-[6-(3,6-Diaza-bicyclo[3.2.0]hept-3-yl)-pyridin-3-yl]-1H-indole bis(p-toluenesulfonate)<br>$^1$H NMR (MeOH-D$_4$, 300 MHz) δ 2.29 (s, 1H), 3.59-3.88 (m, 4H), 4.23 (d, J = 9.9 Hz, 1H), 4.33 (dd, J = 11.2, 8.8 Hz, 1H), 4.50 (d, J = 13.2 Hz, 1H), 5.22 (t, J = 6.1 Hz, 1H), 6.55 (d, J = 3.1 Hz, 1H), 7.20 (t, J = 8.1 Hz, 4H), 7.29-7.43 (m, 3H), 7.53 (d, J = 8.5 Hz, 1H), 7.66 (d, J = 8.1 Hz, 4H), 7.83 (d, J = 1.7 Hz, 1H), 8.14 (d, J = 2.4 Hz, 1H), 8.30-8.52 (m, 1H); MS (DCI/NH$_3$) m/z 291 (M + H)$^+$; Anal. Calculated for C$_{18}$H$_{18}$N$_4$•2.00C$_7$H$_8$SO$_3$•1.50H$_2$O: C, 58.76; H, 6.44; N, 7.61. Found: C, 58.58; H, 6.12; N, 7.50. |
| 248 | Phenylboronic acid | 1) H<br>2) FB<br>3) S1 | (1S,5S)-3-(5-Phenyl-pyridin-2-yl)-3,6-diaza-bicyclo[3.2.0]heptane bis(p-toluenesulfonate)<br>$^1$H NMR (MeOH-D$_4$, 300 MHz) δ 2.38 (s, 6H), 3.61-3.75 (m, 2H), 3.79 (dd, J = 13.6, 5.8 Hz, 1H), 3.88 (dd, J = 11.5, 4.7 Hz, 1H), 4.24 (d, J = 10.2 Hz, 1H), 4.27-4.39 (m, 1H), 4.51 (d, J = 13.2 Hz, 1H), 5.22 (t, J = 6.1 Hz, 1H), 7.20 (d, J = 7.8 Hz, 4H), 7.37 (d, J = 9.5 Hz, 1H), 7.42-7.58 (m, 2H), 7.59-7.78 (m, 7H), 8.16 (d, J = 1.7 Hz, 1H), 8.37 (dd, J = 9.5, 2.4 Hz, 1H); MS (DCI/NH$_3$) m/z 252 (M + H)$^+$; Anal. Calculated for C$_{16}$H$_{17}$N$_3$•2.10C$_7$H$_8$SO$_3$•0.50H$_2$O: C, 59.29; H, 5.64; N, 6.76. Found: C, 58.94; H, 5.87; N, 6.51. |
| 249 | Phenylboronic acid | 1) H<br>2) FB<br>3) RA<br>4) S1 | (1S,5S)-6-Methyl-3-(5-phenyl-pyridin-2-yl)-3,6-diaza-bicyclo[3.2.0]heptane fumarate<br>$^1$H NMR (MeOH-D$_4$, 300 MHz) δ 2.93 (s, 3H), 3.16-3.40 (m, 2H), 3.40-3.54 (m, 1H) 3.85-3.95 (m, 1H) 4.01-4.06 (m, 1H) 4.20 (d, J = 20.3 Hz, 1H) 4.43 (d, J = 13.2 Hz, 1H), 4.87-5.00 (m, 1H), 6.70 (s, 2H), 6.93 (d, J = 8.8 Hz, 1H), 7.32 (t, J = 7.1 Hz, 1H), 7.39-7.50 (m, 2H), 7.52-7.66 (m, 2H), 7.93 (dd, J = 8.5, 2.4 Hz, 1H), 8.44 (d, J = 2.7 Hz, 1H); MS (DCI/NH$_3$) m/z 266 (M + H)$^+$; Anal. Calculated for C$_{17}$H$_{19}$N$_3$•1.00C$_4$H$_4$O$_4$•0.50H$_2$O: C, 64.60; H, 6.20; N, 10.76. Found: C, 64.96; H, 6.30; N, 10.46. |
| 250 | 5-indolyl boronic acid | 1. MW<br>2. EC<br>3. S4 | (1S,5S)-5-[6-(6-Methyl-3,6-diaza-bicyclo[3.2.0]hept-3-yl)-pyridin-3-yl]-1H-indole Bis(trifluoroacetate) |

| Example | Boronic Acid | Conditions | Resulting Compound |
|---|---|---|---|
| | | | $^1$H NMR (CH$_3$OH-d$_4$, 300 MHz) δ ppm 3.03 (s, 3H), 3.40-3.71 (m, 4H), 4.06-4.26 (m, 2H), 4.50 (d, J = 14.6 Hz, 1H), 5.02 (s, 1H), 6.52 (dd, J = 3.2, 0.8 Hz, 1H), 7.20 (d, J = 9.2 Hz, 1H), 7.30 (d, J = 3.1 Hz, 1H), 7.35 (dd, J = 8.5, 2.0 Hz, 1H), 7.50 (d, J = 8.5 Hz, 1H), 7.80 (d, J = 1.0 Hz, 1H), 8.26 (dd, J = 9.0, 2.2 Hz, 1H), 8.34 (d, J = 1.7 Hz, 1H); MS (DCl/NH$_3$) m/z 305 (M + H)$^+$; Anal. C$_{19}$H$_{20}$N$_4$•2C$_2$F$_3$HO$_2$•1.25H$_2$O: C, H, N. |

Example 251

2-Methyl-5-(3-phenyl-isoxazol-5-yl)-octahydro-pyrrolo[3,4-c]pyrrole

Example 251A

2-Methyl-5-(3-phenyl-isoxazol-5-yl)-octahydro-pyrrolo[3,4-c]pyrrole fumarate The product of Example 6C (1 g, 7.9 mmol), and 5-chloro-3-phenyl-isoxazole (1.4 g, 7.9 mmol) (prepared according to literature procedure: Dannhardt, G.; Obergrusberger, I. Chemiker-Zeitung 1989, 113, 109-113) in DBU (1.3 g, 8.6 mmol) were warmed to 140-145° C. for 40 min. The reaction mixture was cooled to ambient temperature, CH$_2$Cl$_2$ was added, and the crude material was purified by flash column chromatography (SiO$_2$, 10% CH$_3$OH—CH$_2$Cl$_2$ with 1% NH$_4$OH) to provide 0.54 g of the coupled product (2.0 mmol, 25% yield). This was converted to the fumarate salt by method S4 to give 0.65 g of the title compound (1.69 mmol, 87% yield). $^1$H NMR (CH$_3$OH-d$_4$, 300 MHz) δ 2.84 (s, 3H), 3.15-3.32 (m, 3H), 3.42-3.62 (m, 7H), 5.62 (s, 1H), 7.42 (m, 3H), 7.65 (m, 2H), 8.11; MS (DCl/NH$_3$) m/z 270 (M+H)$^+$; Anal. calculated for C$_{16}$H$_{19}$N$_3$O.C$_4$H$_4$O$_4$: C, 62.33; H, 6.01; N, 10.90. Found: C, 62.23; H, 5.93; N, 10.82.

Example 252

2-(3-Phenyl-[1,2,4]thiadiazol-5-yl)-octahydro-pyrrolo[3,4-c]pyrrole

Example 252A

5-(3-Phenyl-[1,2,4]thiadiazol-5-yl)-hexahydro-pyrrolo[3,4-c]pyrrole-2-carboxylic acid tert-butyl ester 5-Chloro-3-phenyl-[1,2,4]thiadiazole (0.75 g, 3.81 mmol) was prepared according to literature procedure (Goerdeler, J. et al Chem. Ber. 1957, 90, 182) and was combined with the product of Example 6C (0.85 g, 4.0 mmol), tris(dibenzylideneacetone)dipalladium (0) Pd$_2$(dba)$_3$, Strem, 0.105 g, 0.11 mmol), 1,3-bis(2,6-di-1-propylphenyl)imidazolium chloride (Strem, 97 mg, 0.23 mmol) and tert-BuONa (Aldrich, 0.73 g, 7.6 mmol) in 40 mL PhCH$_3$. This mixture was degassed three times with N$_2$ backflush. The reaction was warmed to 85° C. for 18 h then was cooled to ambient temperature, concentrated under reduced pressure and purified via column chromatography (SiO$_2$, 50% hexanes-EtOAc) to give 1.02 g of the title compound (2.74 mmol, 72% yield). MS (DCl/NH$_3$) m/z 373 (M+H)$^+$.

Example 252B

2-(3-Phenyl-[1,2,4]thiadiazol-5-yl)-octahydro-pyrrolo[3,4-c]pyrrole p-toluenesulfonate The product of Example 252A was processed according to methods FB and S1 to provide the title salt: $^1$H NMR (CH$_3$OH-d$_4$, 300 MHz) δ 2.36 (s, 3H), 2.38 (m, 1H), 3.36 (m, 3H), 3.63 (m, 4H), 3.84 (m, 2H), 7.22 (m, 2H), 7.43 (m, 3H), 7.70 (m, 2H), 8.14 (m, 2H); MS (DCl/NH$_3$) m/z 273 (M+H)$^+$; Anal. calculated for C$_{14}$H$_{16}$N$_4$S.1.2C$_7$H$_8$O$_3$S: C, 56.17; H, 5.39; N, 11.70. Found: C, 56.28; H, 5.46; N, 11.63.

Example 253

2-Methyl-5-(3-phenyl-[1,2,4]thiadiazol-5-yl)-octahydro-pyrrolo[3,4-c]pyrrole fumarate The product of Example 252A was processed according to method FB, RA, and S4 to provide the title salt: $^1$H NMR (CH$_3$OH-d$_4$, 300 MHz) δ 2.81 (s, 3H), 3.17 (dd, J=11.2, 4.8 Hz, 2H), 3.36 (m, 2H), 3.48 (m, 2H), 3.63 (dd, J=11.2, 2.7 Hz, 2H), 3.78 (m, 2H), 6.69 (s, 2H), 7.44 (m, 3H), 8.13 (m, 2H); MS (DCl/NH$_3$) m/z 287 (M+H)$^+$; Anal. calculated for C$_{15}$H$_{18}$N$_4$S.C$_4$H$_4$O$_4$: C, 56.70; H, 5.51; N, 13.92. Found: C, 56.42; H, 5.51; N, 13.71.

Example 254

2-(4-Phenyl-thiophen-2-yl)-octahydro-pyrrolo[3,4-c]pyrrole p-toluenesulfonate

Example 254A

5-(4-Phenyl-thiophen-2-yl)-hexahydro-pyrrolo[3,4-c]pyrrole-2-carboxylic acid tert-butyl ester The product of Example 6C (0.75 g, 3.5 mmol) was combined with 2-bromo-4-phenyl-thiophene (0.8 g, 3.35 mmol, prepared according to literature procedure (Gronowitz, S.; Gjös, N.; Kellogg, R. M.; Wynberg, H. J. Org. Chem. 1967, 32, 463-464)), tris(dibenzylideneacetone)dipalladium (0) (Pd$_2$(dba)$_3$, Strem, 92 mg, 0.10 mmol), racemic-2,2'-bis (diphenylphosphino)-1,1'-binaphthyl (BiNAP, Strem, 0.10 g, 0.17 mmol), and NaOt-Bu (0.64 g, 6.7 mmol) in toluene (40 mL). This mixture was placed under vacuum, then purged with N$_2$ and stirred under nitrogen at 85° C. for 18 h. The reaction mixture was cooled to ambient temperature, filtered through diatomaceous earth and concentrated under reduced pressure. The residue was purified by column chromatography (SiO$_2$, 50% hexanes in EtOAc) to provide the title compound (0.39 g, 1.1 mmol, 33% yield). MS (DCI/NH$_3$) m/z 371 (M+H)$^+$.

Example 254B 2-(4-Phenyl-thiophen-2-yl)-octahydro-pyrrolo[3,4-c]pyrrole p-toluenesulfonate The product of Example 254A was processed according to methods FB and S1 to provide the title compound: $^1$H NMR (300 MHz, CD$_3$OD) δ ppm 2.36 (s, 3H), 3.24 (m, 6H), 3.41 (m, 2H), 3.57 (m, 2H), 6.41 (d, J=1.7 Hz, 1H), 6.84 (d, J=1.7 Hz, 1H), 7.24 (m, 3H), 7.34 (m, 2H), 7.57 (m, 2H), 7.70 (m, 2H); MS (DCI/NH$_3$) m/z 271 (M+H)$^+$; Anal. calculated for C$_{16}$H$_{18}$N$_2$S.1.1C$_7$H$_8$O$_3$S: C, 61.91; H, 5.87; N, 6.09. Found: C, 61.78; H, 6.14; N, 6.15.

Example 255

2-(5-Phenyl-[1,3,4]thiadiazol-2-yl)-octahydro-pyrrolo[3,4-c]pyrrole

Example 255A

2-Bromo-5-phenyl-[1,3,4]thiadiazole

A mixture of 2-amino-5-phenyl-1,3,4-thiadiazole sulfate (Aldrich, 2.5 g, 9.08 mmol) and 48% aqueous HBr (10 mL) was cooled to 5° C. and a solution of NaNO$_2$ (0.69 g, 9.99 mmol) H$_2$O (10 mL) was added dropwise at a rate so the internal temperature is maintained at approximately 5° C. The mixture was stirred for 15 min after the addition, then CuBr (0.69 g, 4.8 mmol) was added portion-wise so as to maintain the temperature at approximately 5° C. After the addition was complete, the mixture was allowed to warm to ambient temperature and stirred for 16 h. The mixture was diluted with 20 mL CH$_2$Cl$_2$ and 10 mL H$_2$O. The organic layer was separated and concentrated under reduced pressure to provide the title compound (1.63 g, 6.76 mmol, 74% yield). MS (DCI/NH$_3$) m/z 241, 243 (M+H)$^+$.

Example 255B 5-(5-Phenyl-[1,3,4]thiadiazol-2-yl)-hexahydro-pyrrolo[3,4-c]pyrrole-2-carboxylic acid tert-butyl ester The products of Examples 6C (0.70 g, 3.32 mmol) and 255A (0.88 g, 3.65 mmol) were reacted under the conditions of Example 254A to provide the title compound (0.53 g, 1.42 mmol, 43% yield). MS (DCI/NH$_3$) m/z 373 (M+H)$^+$.

Example 255C 2-(5-Phenyl-[1,3,4]thiadiazol-2-yl)-octahydro-pyrrolo[3,4-c]pyrrole fumarate The product of Example 255B was processed according to method FB and S4 to provide the title salt: $^1$H NMR (CH$_3$OH-d$_4$, 300 MHz) δ 3.27 (m, 1H), 3.33 (m, 3H), 3.60 (m, 4H), 3.79 (m, 2H), 6.68 (s, 2H), 7.46 (m, 3H), 7.80 (m, 2H); MS (DCI/NH$_3$) m/z 305 (M+H)$^+$; Anal. calculated for C$_{14}$H$_{16}$N$_4$S.C$_4$H$_4$O$_4$.0.3H$_2$O: C, 54.89; H, 5.27; N, 14.23. Found: C, 54.66; H, 6.10; N, 14.19.

Example 256

2-Methyl-5-(5-phenyl-[1,3,4]thiadiazol-2-yl)-octahydro-pyrrolo[3,4-c]pyrrole bis-p-toluenesulfonate The product of Example 255B was processed according to methods FB, RA, and S1 to provide the title salt: $^1$H NMR (300 MHz, CD$_3$OD) δ ppm 2.35 (s, 6H), 2.97 (s, 3H), 3.09 (m, 2H), 3.48 (m, 2H), 3.70 (m, 4H), 3.91 (m, 2H), 7.21 (m, 4H), 7.51 (m, 3H), 7.69 (m, 4H), 7.82 (m, 2H); MS (DCI/NH$_3$) m/z 287 (M+H)$^+$; Anal. calculated for C$_{15}$H$_{18}$N$_4$S.2.1C$_7$H$_8$O$_3$S.0.3H$_2$O: C, 54.59; H, 5.46; N, 8.57. Found: C, 54.24; H, 5.06; N, 8.54.

Example 257

2-(1-Phenyl-1H-pyrazol-4-yl)-octahydro-pyrrolo[3,4-c]pyrrole

Example 257A

4-Bromo-1-phenyl-1H-pyrazole

A solution of bromine (1.1 g, 6.94 mmol) in acetic acid (10 mL) was added to a mixture of 1-phenylpyrazole (Aldrich, 1 g, 6.94 mmol) in acetic acid (10 mL). This mixture was warmed to 100° C. in a pressure tube for 8 h. The material was cooled to ambient temperature, poured into ice and H$_2$O neutralized with excess saturated, aqueous NaHCO$_3$. Ethyl acetate (50 mL) was added and the layers were separated. The aqueous layer was extracted with EtOAc (2×15 mL) and the combined organic extract was dried over Na$_2$SO$_4$ and concentrated under reduced pressure to give a crude solid. Purification by column chromatography (SiO$_2$, 50% hexanes-EtOAc) provided the title compound (1.5 g, 6.72 mmol, 97% yield). MS (DCI/NH$_3$) m/z 223, 225 (M+H)$^+$.

Example 257B 5-(1-Phenyl-1H-pyrazol-4-yl)-hexahydro-pyrrolo[3,4-c]pyrrole-2-carboxylic acid tert-butyl ester To the product of Example 6C (0.5 g, 2.4 mmol) in 15 mL toluene in a pressure tube was added the product of Example 257A (0.68 g, 3.06 mmol), tris(dibenzylideneacetone)dipalladium (0) (Pd$_2$(dba)$_3$, Strem, 43 mg, 0.047 mmol), racemic-2,2'-bis(diphenylphosphino)-1,1'-binaphthyl (BINAP, Strem, 59 mg, 0.094 mmol), and tert-BuONa (0.362 g, 3.8 mmol). This mixture was warmed to 85° C. and stirred for 18 h. At this point, the reaction was incomplete, so additional Pd$_2$(dba)$_3$ (43 mg, 0.047 mmol) and BINAP (59 mg, 0.094 mmol) were added and the mixture stirred for an additional 24 h. The reaction was cooled to ambient temperature, filtered through Celite® diatomaceous earth, concentrated under reduced pressure and purified via flash column chromatography (SiO$_2$, 50% hexanes-EtOAc) to give the title compound (40 mg, 0.113 mmol, 5% yield). MS (DCI/NH$_3$) m/z 355 (M+H)$^+$.

Example 257C 2-(1-Phenyl-1H-pyrazol-4-yl)-octahydro-pyrrolo[3,4-c]pyrrole p-toluenesulfonate The product of Example 257B was processed according to methods FB and S1 to provide the title salt: $^1$H NMR (CH$_3$OH-d$_4$, 300 MHz) δ 2.35 (s, 3H), 2.98 (m, 2H), 3.18 (m, 2H), 3.23 (m, 2H), 3.35 (br d, J=9.5 Hz, 2H), 3.57 (m, 2H), 7.21 (m, 2H), 7.27 (tt, J=7.1, 1.4 Hz, 1H), 7.45 (m, 3H), 7.68 (m, 4H), 7.80 (d, J=0.7 Hz, 1H); MS (DCI/NH$_3$) m/z 255 (M+H)$^+$; Anal. calculated for C$_{15}$H$_{18}$N$_4$.1.1C$_7$H$_8$O$_3$S: C, 61.44; H, 6.09; N, 12.63. Found: C, 61.04; H, 6.09; N, 12.45.

Example 258

2-(5-Phenyl-isoxazol-3-yl)-octahydro-pyrrolo[3,4-c]pyrrole p-toluenesulfonate

Example 258A 5-(1-Methylsulfanyl-3-oxo-3-phenyl-propenyl)-hexahydro-pyrrolo[3,4-c]pyrrole-2-carboxylic acid tert-butyl ester 3,3-Bis-methylsulfanyl-1-phenyl-propenone (0.675 g, 3.0 mmol), was prepared according to literature procedure (Galli, F. et al WO 01/92251 A1) and was combined with the product of Example 6C (0.213 g, 1.0 mmol) in 10 mL MeOH. This mixture was warmed to 70° C. for 4 h then was cooled to ambient temperature, concentrated under reduced pressure and purified via column chromatography (SiO$_2$, 90/10/1 dichloromethane-methanol-NH$_4$OH) to give 0.169 g of the title compound (0.43 mmol, 43% yield). MS (DCl/NH$_3$) m/z 389 (M+H)$^+$.

Example 258B 5-(5-Phenyl-isoxazol-3-yl)-hexahydro-pyrrolo[3,4-c]pyrrole-2-carboxylic acid tert-butyl ester The product of example 258B (0.163 g, 0.42 mmol), hydroxylamine hydrochloride (0.126 g, 1.7 mmol), sodium acetate (0.13 g, 1.3 mmol) were combined in toluene (4 mL), acetic acid (2 mL), water (0.5 mL), and ethanol. The mixture was heated to reflux for 8 h. The mixture was poured into saturated aqueous sodium carbonate and extracted with EtOAc. The organics were dried over MgSO$_4$ and concentrated under reduced pressure. The residue was purified by column chromatography (SiO$_2$, 50% hexanes in EtOAc) to provide the title compound (0.109 g, 0.3 mmol, 71% yield). MS (DCl/NH$_3$) m/z 356 (M+H)$^+$.

Example 258C 2-(5-Phenyl-isoxazol-3-yl)-octahydro-pyrrolo[3,4-c]pyrrole p-toluenesulfonate The product of Example 258B was processed according to method FB, and S1 to provide the title salt: $^1$H NMR (300 MHz, CDCl$_3$) δ 2.24 (s, 3H) 2.92 (s, 2H) 3.18 (s, 2H) 3.31 (s, 2H) 3.49 (s, 1H) 3.52 (s, 1H) 3.61-3.75 (m, 2H) 6.08 (s, 1H) 7.09 (d, J=8 Hz, 3H) 7.38-7.55 (m, 3H) 7.67 (t, J=7 Hz, 3H) 9.27 ppm (s, 1H); MS (DCl/NH$_3$) m/z 256 (M+H)$^+$; Anal. calculated for C$_{15}$H$_{17}$N$_3$.1.2C$_7$H$_8$O$_3$S.0.9H$_2$O: C, 58.78; H, 5.99; N, 8.79. Found: C, 59.03; H, 5.73; N, 8.53.

Example 259

2-Methyl-5-(5-phenyl-isoxazol-3-yl)-octahydro-pyrrolo[3,4-c]pyrrole p-toluenesulfonate The product of Example 258C was processed according to method RA, and S1 to provide the title salt: 1H NMR (300 MHz) δ 2.23-2.49 (m, 3H) 2.87-2.94 (m, 3H) 2.95-3.01 (m, 2H) 3.10-3.72 (m, 8H) 6.48-6.61 (m, 1H) 7.13-7.29 (m, 2H) 7.42-7.55 (m, 3H) 7.65-7.74 (m, 2H) 7.72-7.85 ppm (m, 2H); MS (DCl/NH$_3$) m/z 270 (M+H)$^+$; Anal. Calculated for C$_{16}$H$_{19}$N$_5$3O.1.3C$_7$H$_8$SO$_3$C, 61.12; H, 6.01, 8.52. Found: C, 60.92; H, 5.74; N, 8.64

Example 260

2-(5-Phenyl-thiazol-2-yl)-octahydro-pyrrolo[3,4-c]pyrrole p-toluenesulfonate

Example 260A 5-(5-Bromo-thiazol-2-yl)-hexahydro-pyrrolo[3,4-c]pyrrole-2-carboxylic acid tert-butyl ester A solution of Example 6C (1.0 g, 4.2 mmol) in N,N-diisopropylethylamine (1.5 mL, 8.4 mmol) was treated with 2,5-dibromothiazole (0.89 g, 4.2 mmol, Aldrich). This mixture was warmed to 110° C. and stirred for 2 hours. The reaction mixture was cooled to ambient temperature, concentrated under reduced pressure, and purified by column chromatography (SiO$_2$, 20-40% ethyl acetate/hexanes gradient) to afford 1.1 g of the title compound (2.9 mmol, 69% yield). $^1$H NMR (CDCl$_3$, 300 MHz) δ 1.46 (s, 9H), 2.97-3.09 (m, 2H), 3.21-3.41 (m, 4H), 3.60-3.71 (m, 4H), 7.09 (s, 1H); MS (DCl/NH$_3$) m/z 376 (M+H$^+$).

Example 260B 5-(5-Phenyl-thiazol-2-yl)-hexahydro-pyrrolo[3,4-c]pyrrole-2-carboxylic acid tert-butyl ester The product of Example 260A was coupled with phenyl-boronic acid according to the procedure of method I to provide the title compound: $^1$H NMR (CDCl$_3$, 300 MHz) δ1.46 (s, 9H), 3.00-3.17 (m, 2H), 3.24-3.54 (m, 4H), 3.61-3.72 (m, 2H), 3.74-3.86 (m, 2H), 7.22 (m, 1H), 7.34 (t, 2H, J=7.6 Hz), 7.42 (d, 3H, J=8.5 Hz); MS (DCl/NH$_3$) m/z 372 (M+H$^+$).

Example 260C 2-(5-Phenyl-thiazol-2-yl)-octahydro-pyrrolo[3,4-c]pyrrole p-toluenesulfonate The product of Example 260B was processed according to methods FB and S1 to provide the title compound: $^1$H NMR (MeOH-d$_4$, 300 MHz) δ3.57-3.67 (m, 3H), 3.74-3.84 (m, 2H), 7.22 (d, 2H, J=7.8 Hz), 7.29 (m, 1H), 7.35-7.42 (m, 2H), 7.47-7.52 (m, 2H), 7.56 (s, 1H), 7.70 (m, 2H); MS (DCl/NH$_3$) m/z 272 (M+H$^+$).

Example 261

2-Methyl-5-(5-phenyl-thiazol-2-yl)-octahydro-pyrrolo[3,4-c]pyrrole p-toluenesulfonate The product of Example 260B was processed according to methods FB, RA and S1 to provide the title compound: $^1$H NMR (MeOH-d$_4$, 300 MHz) δ2.36 (s, 3H), 2.95 (s, 3H), 3.33-3.43 (m, 2H), 3.57-3.65 (m, 4H), 7.24 (t, 3H, J=8.0 Hz), 7.35 (t, 2H, J=7.6 Hz), 7.45-7.50 (m, 3H), 7.7 (d, 2H, J=8.1 Hz); MS (DCl/NH$_3$) m/z 286 (M+H$^+$). Anal. calculated for C$_{16}$H$_{19}$N$_3$S.C$_7$H$_8$O$_3$S: C, 60.37; H, 5.95; N, 9.18. Found: C, 60.04; H, 6.04; N, 9.15.

Example 262

2-(2-Phenyl-thiazol-5-yl)-octahydro-pyrrolo[3,4-c]pyrrole trifluoroacetate

Example 262A

2-Phenylthiazole

A solution of 2-bromothiazole (1.0 g, 6.1 mmol, Aldrich) in dioxane (25 mL) was treated with phenylboronic acid (0.82 g, 6.4 mmol), Pd(P$^t$Bu$_3$)$_2$ (0.16 g, 0.3 mmol, Strem) and Cs$_2$CO$_3$ (3.97 g, 12.2 mmol). The mixture was stirred at 80° C. for 12 hours. The reaction mixture was cooled to ambient temperature, concentrated under reduced pressure, and purified by column chromatography (SiO$_2$, 1:1 hexanes/ethyl acetate) to give provide the title compound (0.69 g, 4.3 mmol, 70%). $^1$H NMR (CDCl$_3$, 300 MHz) δ7.33 (m, 1H), 7.41-7.48 (m, 3H), 7.87 (d, 1H, J=3.4 Hz), 7.95-8.00 (m, 2H); MS (DCl/NH$_3$) m/z 162 (M+H$^+$).

Example 262B

5-Bromo-2-phenylthiazole

N-Bromosuccinimide (0.33 g, 1.86 mmol) was added to a solution of the product of Example 262A (0.15 g, 0.93 mmol) in N,N-dimethylformamide (5 mL). The reaction mixture was stirred at 50° C. for 12 hours. The mixture was then diluted with ethyl acetate (50 mL) and washed with brine (2×20 mL). The organic layer was dried over magnesium sulfate, concentrated under reduced pressure, and purified by column chromatography (SiO$_2$, 20-40% ethyl acetate/hexanes gradient) to provide the title compound (0.20 g, 0.81 mmol, 87%). $^1$H NMR (CDCl$_3$, 300 MHz) .δ7.43-7.46 (m, 3H), 7.74 (s, 1H), 7.85-7.88 (m, 2H); MS (DCl/NH$_3$) m/z 242 (M+H$^+$).

Example 262C

5-(2-Phenyl-thiazol-5-yl)-hexahydro-pyrrolo[3,4-c]pyrrole-2-carboxylic acid tert-butyl ester The product of Example 262B (0.63 g, 2.6 mmol) was combined with the product of Example 6C (0.55 g, 2.6 mmol), Pd$_2$dba$_3$ (0.07 g, 0.08 mmol), BINAP (0.81 g, 1.3 mmol) and sodium tert-butoxide (0.50 g, 5.2 mmol) in toluene (15 mL) The mixture was stirred at 80° C. for 12 hours. The reaction mixture was cooled to ambient temperature, diluted with ethyl acetate, filtered through a pad of Celite and concentrated under reduced pressure. Purification by column chromatography (SiO$_2$, 0-10% methanol/methylene chloride gradient) afforded the title compound (0.73 g, 1.96 mmol, 75% yield). $^1$H NMR (CDCl$_3$, 300 MHz) δ1.46 (s, 9H), 3.02-3.09 (m, 2H), 3.23 (m, 2H), 3.29-3.43 (s, 2H), 3.55 (dd, 2H, J=9.66 Hz, 7.29 Hz), 3.63-3.70 (m, 2H), 6.73 (s, 1H), 7.30-7.41 (m, 3H), 7.79 (d, 2H, J=7.1 Hz); MS (DCl/NH$_3$) m/z 372 (M+H$^+$).

Example 262D

2-(2-Phenyl-thiazol-5-yl)-octahydro-pyrrolo[3,4-c]pyrrole trifluoroacetate

The product of Example 262C was processed according to methods FB and S2 to provide the title compound: $^1$H NMR (MeOH-d$_4$, 300 MHz) δ 3.19-3.29 (m, 4H), 3.33-3.47 (m, 4H), 3.54-3.67 (m, 2H), 6.92 (s, 1H), 7.33-7.45 (m, 3H), 7.74-7.77 (m, 2H); MS (DCl/NH$_3$) m/z 272 (M+H$^+$). Anal. calculated for C$_{15}$H$_{17}$N$_3$S.C$_2$HF$_3$O$_2$: C, 52.98; H, 4.71; N, 10.90. Found: C, 52.71; H, 4.63; N, 10.68.

Example 263

2-Methyl-5-(2-phenyl-thiazol-5-yl)-octahydro-pyrrolo[3,4-c]pyrrole hydriodide The product of Example 262C (0.12 g, 0.44 mmol) was converted to the free amine by method FB. The amine was dissolved in methylene chloride (4 mL) and treated with methyl iodide (3.0 µL, 0.44 mmol). The reaction mixture was stirred at ambient temperature for 12 hours and then concentrated under reduced pressure. Purification by column chromatography (SiO$_2$, 0-20% methanol/methylene chloride gradient) afforded 0.11 g (0.24 mmol, 54% yield). $^1$H NMR (MeOH-d$_4$, 300 MHz) δ 3.15-3.27 (m, 5H), 3.35-3.52 (m, 6H), 3.97 (m, 1H), 6.96 (m, 1H), 7.34-7.45 (m, 3H), 7.74-7.78 (m, 2H); MS (DCl/NH$_3$) m/z 286 (M+H$^+$). Anal. calculated for C$_{16}$H$_{19}$N$_3$S.HI: C, 46.49; H, 4.88; N, 10.17. Found: C, 47.36; H, 5.17; N, 9.16.

Example 264

Example 264A

5-(4-Bromo-thiazol-2-yl)-hexahydro-pyrrolo[3,4-c]pyrrole-2-carboxylic acid tert-butyl ester The product of Example 6C (0.1 g, 0.47 mmol) and 2,4-dibromothiazole (0.11 g, 0.94 mmol) was combined with N,N-diisopropylethylamine (0.02 mL, 0.94 mmol) and the mixture was stirred at 110° C. for 1.5 hours. The reaction mixture was cooled to ambient temperature, concentrated under reduced pressure, and purified by column chromatography (SiO$_2$, 20-40% ethyl acetate/hexanes gradient) to provide the title compound (0.13 g, 0.34 mmol, 72% yield). $^1$H NMR (CDCl$_3$, 300 MHz) δ 1.46 (s, 9H) 2.96-3.09 (m, 2H) 3.18-3.47 (m, 4H) 3.58-3.77 (m, 4H) 6.37 (s, 1H); MS (DCl/NH$_3$) m/z 376 (M+H$^+$).

Example 264B

5-(4-Phenyl-thiazol-2-yl)-hexahydro-pyrrolo[3,4-c]pyrrole-2-carboxylic acid tert-butyl ester The product of Example 264A (0.11 g, 0.29 mmol) was combined with tributylphenyl tin (0.11 g, 0.29 mmol, Aldrich) and Pd(P$^t$Bu$_3$)$_2$ (0.020 g, 0.030 mmol) in toluene (2 mL). The mixture was stirred at 100° C. for 16 hours. Cesium fluoride (0.97 g, 0.64 mmol) was added to the reaction mixture after 20.5 hours. After an additional 5 hours time, the reaction mixture was cooled to ambient temperature, diluted with ethyl acetate, filtered through diatomaceous earth and purified by column chromatography (SiO$_2$, 20-40% ethyl acetate/hexanes gradient) to provide the title compound (0.01 g, 0.026 mmol, 9% yield).

Example 264C

2-(4-Phenyl-thiazol-2-yl)-octahydro-pyrrolo[3,4-c]pyrrole tosylate

The product of Example 264B was processed according to methods FB and S1 to provide the title compound: $^1$H NMR (MeOH-d$_4$, 300 MHz) δ 2.36 (s, 3H) 3.20-3.28 (m, 3H) 3.55-3.73 (m, 6H) 6.98 (s, 1H) 7.19-7.40 (m, 5H) 7.70 (d, J=8.5 Hz, 2H) 7.81 (d, J=8.5 Hz, 2H); MS (DCI/NH$_3$) m/z 272 (M+H$^+$). Anal. calculated for C$_{15}$H$_{17}$N$_3$S.1.15C$_7$H$_8$O$_3$S: C, 58.98; H, 5.63; N, 8.95. Found: C, 58.67; H, 5.64; N, 8.96.

Examples 265-275

N-alkylation of 2-(6-phenylpyridazin-3-yl)-octahydropyrrolo[3,4-c]pyrrole

The free base of the title compound (prepared as in Example 51) was converted to the indicated N-alkyl derivatives by reaction with the listed N-alkylating agent according to the procedures described below.

Method K: The N-alkylating agent (0.39 mmol) and 1M Na$_2$CO$_3$ (aq, 0.5 mL) were added to a solution of 2-(6-phenylpyridazin-3-yl)-octahydropyrrolo[3,4-c]pyrrole (98 mg, 0.37 mmol) in THF (0.5 mL). The mixture was stirred for 2 h, then diluted with dichloromethane (5 mL) and washed with water (2 mL). The organic phase was concentrated and the residue was purified by column chromatography to provide the N-alkylated product, which was converted to a salt by the listed procedure.

Method L: A solution of the N-alkylating agent (a carboxylic acid, 0.41 mmol) and carbonyldiimidazole (63 mg, 0.39 mmol) in DMF (0.4 mL) was stirred for 1 h, then treated with a solution of 2-(6-phenylpyridazin-3-yl)-octahydropyrrolo[3,4-c]pyrrole (89 mg, 0.33 mmol) in DMF (1 mL). The mixture was heated to 50° C. for 12 h, then diluted with CH$_2$Cl$_2$, washed with 0.2 M NaOH, dried over K$_2$CO$_3$ and concentrated. The residue was purified by column chromatography to provide the N-acyl intermediate. This was taken in THF (2 mL) and added dropwise to an ice-cooled mixture of LiAlH$_4$ (26 mg, 0.68 mmol) in THF 1 mL). The mixture was warmed to room temperature, heated to 50° C. for 15 min, then stirred at room temperature for 1 h. The reaction was quenched with excess Na$_2$SO$_4$.10H$_2$O, and filtered with an ethyl acetate rinse. The filtrate was concentrated and the residue purified by column chromatography to provide the N-alkyl derivative, which was converted to a salt by the listed method.

Method M: To a solution of 2-(6-phenylpyridazin-3-yl)-octahydropyrrolo[3,4-c]pyrrole (0.11 g, 0.41 mmol) in the N-alkylating agent (a ketone or aldehyde, 7 mL) was added NaBH(OAc)$_3$ (0.11 g, 0.53 mmol). The mixture was stirred at room temperature for 18 h, then concentrated under reduced pressure. The crude material was partitioned with CH$_2$Cl$_2$ (5 mL) and saturated, aqueous NaHCO$_3$ (3 mL), and the aqueous layer was further extracted with CH$_2$Cl$_2$ (3×5 mL). The combined extract was washed with brine, dried over anhydrous Na$_2$SO$_4$ and concentrated under reduced pressure. The residue was purified via column chromatography to provide the alkylated amine, which was converted to a salt by the listed procedure.

| Example | N-alkylating Agent | Conditions | Resulting Compound |
|---|---|---|---|
| 265 | Benzyl bromide | 1) K<br>2) S3 | 2-Benzyl-5-(6-phenylpyridazin-3-yl)-octahydropyrrolo[3,4-c]pyrrole hydrochloride<br>$^1$H NMR (MeOH-d$_4$, 300 MHz) δ 3.11-3.32 (m, 4H), 3.56-3.87 (m, 6H), 4.36 (s, 2H), 7.17 (d, J = 9 Hz, 1H), 7.38-7.58 (m, 8H), 7.86-7.99 (m, 3H); MS (DCI/NH$_3$) m/z 357 (M + H)$^+$; Anal. C$_{23}$H$_{24}$N$_4$•1.05HCl: C, H, N. |
| 266 | 4-chloromethyl pyridine | 1) K<br>2) S4 | 2-(6-Phenylpyridazin-3-yl)-5-(pyridin-4-ylmethyl)-octahydropyrrolo[3,4-c]pyrrole bis(trifluoroacetate)<br>$^1$H NMR (MeOH-d$_4$, 300 MHz) δ 3.13-3.52 (m, 6H), 3.73-3.91 (m, 4H), 4.30 (s, 2H), 7.46-7.59 (m, 4H), 7.66 (d, J = 6 Hz, 2H), 7.92-8.02 (m, 2H), 8.18 (d, J = 10 Hz, 1H), 8.67 (d, J = 5 Hz, 2H); MS (DCI/NH$_3$) m/z 358 (M + H)$^+$; Anal. C$_{22}$H$_{23}$N$_5$•2C$_2$HF$_3$O$_2$: C, H, N. |
| 267 | 2-chloromethyl pyridine | 1) K<br>2) S4 | 2-(6-Phenylpyridazin-3-yl)-5-(pyridin-2-ylmethyl)-octahydropyrrolo[3,4-c]pyrrole bis(trifluoroacetate)<br>$^1$H NMR (MeOH-d$_4$, 300 MHz) δ 3.36-3.51 (m, 4H), 3.75-3.96 (m, 6H), 4.61 (s, 2H), 7.41-7.58 (m, 6H), 7.90 (td, J = 8, 2 Hz, 1H), 7.93-7.99 (m, 2H), 8.15 (d, J = 10 Hz, 1H), 8.67 (d, J = 4 Hz, 1H); MS (DCI/NH$_3$) m/z 358 (M + H)$^+$; Anal. C$_{22}$H$_{23}$N$_5$•2C$_2$HF$_3$O$_2$: C, H, N. |
| 268 | 2-chloro-5-chloromethyl pyridine | 1) K<br>2) S3 | 2-(6-Chloropyridin-3-ylmethyl)-5-(6-phenylpyridazin-3-yl)-octahydropyrrolo[3,4-c]pyrrole hydrochloride<br>$^1$H NMR (MeOH-d$_4$, 300 MHz) δ 3.04-3.22 (m, 2H), 3.23-3.61 (m, 4H), 3.65-3.83 (m, 4H), 4.26 (s, 2H), 7.26 (d, J = 9 Hz, 1H), 7.41-7.59 (m, 4H), 7.89-8.03 (m, 4H), 8.47 (d, J = 2 Hz, 1H); MS (DCI/NH$_3$) m/z 392, 394 (M + H)$^+$; Anal. C$_{22}$H$_{22}$ClN$_5$•HCl: C, H, N. |
| 269 | 3-Pyridylacetic acid | 1) L<br>2) S4 | 2-(6-Phenylpyridazin-3-yl)-5-(2-pyridin-3-ylethyl)-octahydropyrrolo[3,4-c]pyrrole bis(trifluoroacetate)<br>$^1$H NMR (CD$_3$OD, 300 MHz) δ 3.17 (m, 2H), 3.38-3.61 (m, 4H), 3.76-3.95 (m, J = 2 Hz, 4H), 7.47-7.61 (m, 5H), 7.93-8.02 (m, 3H), 8.20 (d, J = 10 Hz, 1H), 8.54 (dd, J = 5, 1 Hz, 1H), 8.58 (d, J = 1 Hz, 1H); MS (DCI/NH$_3$) m/z 372 (M + H)$^+$; Anal. C$_{23}$H$_{25}$N$_5$•2.05C$_2$HF$_3$O$_4$: C, H, N. |
| 270 | 3-bromomethyl pyridine hydrobromide | 1) K<br>2) S4 | 2-(6-Phenylpyridazin-3-yl)-5-(pyridin-3-ylmethyl)-octahydropyrrolo[3,4-c]pyrrole bis(trifluoroacetate)<br>$^1$H NMR (MeOH-d$_4$, 300 MHz) δ 3.40-3.54 (m, 4H), 3.63-3.76 (m, 2H), 3.82-3.95 (m, 4H), 4.49 (s, 2H), 7.54-7.58 (m, 3H), 7.60 (ddd, J = 8, 5, 1 Hz, |

-continued

| Example | N-alkylating Agent | Conditions | Resulting Compound |
|---|---|---|---|
| 271 | Allyl iodide | 1) K<br>2) S1 | 1H), 7.66 (d, J = 10 Hz, 1H), 7.93-8.01 (m, 2H), 8.09 (ddd, J = 8, 2 Hz, 1H), 8.32 (d, J = 10 Hz, 1H), 8.68 (dd, J = 5, 1 Hz, 1H), 8.73 (d, J = 2 Hz, 1H); MS (DCI/NH$_3$) m/z 358 (M + H)$^+$; Anal. C$_{22}$H$_{23}$N$_5$•2.5C$_2$HF$_3$O$_2$: C, H, N.<br>2-Allyl-5-(6-phenyl-pyridazin-3-yl)-octahydro-pyrrolo[3,4-c]pyrrole bis-p-toluenesulfonate)<br>$^1$H NMR (300 MHz, CD$_3$OD) δ ppm 2.28 (s, 6H), 3.24 (m, 1H), 3.50 (m, 3H), 3.89 (m, 8H), 5.58 (m, 2H), 6.03 (m, 1H), 7.17 (d, J = 8.1 Hz, 4H), 7.58 (m, 3H), 7.64 (d, J = 8.1 Hz, 4H), 7.73 (dd, J = 27.5, 9.5 Hz, 1H), 7.96 (m, 2H), 8.30 (dd, J = 23.9, 9.7 Hz, 1H); MS (DCI/NH$_3$) m/z 307 (M + H)$^+$; Anal. calculated for C$_{19}$H$_{22}$N$_4$•2C$_7$H$_8$O$_3$S•0.5H$_2$O: C, 60.07; H, 5.96; N, 8.49. Found: C, 60.37; H, 5.68; N, 8.52. |
| 272 | Crotonaldehyde | 1) M<br>2) S1 | 2-But-2-enyl-5-(6-phenyl-pyridazin-3-yl)-octahydro-pyrrolo[3,4-c]pyrrole bis-p-toluenesulfonate<br>$^1$H NMR (300 MHz, CD$_3$OD) δ ppm 1.78 (d, J = 5.8 Hz, 3H), 2.31 (s, 6H), 3.14 (m, 2H), 3.48 (m, 2H), 3.87 (m, 8H), 5.83 (m, 2H), 7.18 (d, J = 7.8 Hz, 4H), 7.58 (m, 3H), 7.66 (m, 4H), 7.73 (dd, J = 25.1, 10.2 Hz, 1H), 7.97 (m, 2H), 8.31 (dd, J = 22.4, 9.8 Hz, 1H); MS (DCI/NH$_3$) m/z 321 (M + H)$^+$; Anal. calculated for C$_{20}$H$_{24}$N$_4$•2C$_7$H$_8$O$_3$S: C, 61.42; H, 6.06; N, 8.43. Found: C, 61.15; H, 5.83; N, 8.40. |
| 273 | Acetaldehyde | 1) M<br>2) S1 | 2-Ethyl-5-(6-phenyl-pyridazin-3-yl)-octahydro-pyrrolo[3,4-c]pyrrole bis-p-toluenesulfonate<br>$^1$H NMR (300 MHz, CD$_3$OD) δ ppm 1.37 (q, J = 7.7 Hz, 3H), 2.30 (s, 6H), 3.41 (m, 6H), 3.94 (m, 6H), 7.18 (d, J = 7.8 Hz, 4H), 7.58 (m, 3H), 7.65 (d, J = 8.1 Hz, 4H), 7.74 (dd, J = 28.1, 10.2 Hz, 1H), 7.96 (d, J = 3.7 Hz, 2H), 8.32 (dd, J = 27.0, 10.0 Hz, 1H); MS (DCI/NH$_3$) m/z 295 (M + H)$^+$; Anal. calculated for C$_{18}$H$_{22}$N$_4$•2C$_7$H$_8$O$_3$S: C, 60.17; H, 6.00; N, 8.77. Found: C, 59.74; H, 5.98; N, 8.68. |
| 274 | Propionaldehyde | 1) M<br>2) S1 | 2-(6-Phenyl-pyridazin-3-yl)-5-propyl-octahydro-pyrrolo[3,4-c]pyrrole tris-p-toluenesulfonate)<br>$^1$H NMR (300 MHz, CD$_3$OD) δ ppm 1.01 (q, J = 7.5 Hz, 3H), 1.76 (m, 1H), 2.31 (s, 9H), 3.33 (m, 6H), 3.94 (m, 7H), 7.19 (d, J = 8.1 Hz, 6H), 7.58 (m, 3H), 7.66 (m, 6H), 7.75 (m, J = 30.8 Hz, 1H), 7.97 (m, 2H), 8.31 (dd, J = 28.6, 9.7 Hz, 1H); MS (DCI/NH$_3$) m/z 309 (M + H)$^+$; Anal. calculated for C$_{19}$H$_{24}$N$_4$•3C$_7$H$_8$O$_3$S•0.8NH$_3$: C, 57.29; H, 6.06; N, 8.02. Found: C, 57.67; H, 5.58; N, 8.41. |
| 275 | Acetone | 1) M<br>2) S1 | 2-Isopropyl-5-(6-phenyl-pyridazin-3-yl)-octahydro-pyrrolo[3,4-c]pyrrole bis-p-toluenesulfonate<br>$^1$H NMR (300 MHz, CD$_3$OD) δ ppm 1.40 (d, J = 6.8 Hz, 3H), 1.44 (d, J = 6.8 Hz, 3H), 2.30 (s, 6H), 3.24 (m, 1H), 3.51 (m, 4H), 3.94 (m, 6H), 7.18 (d, J = 8.1 Hz, 4H), 7.58 (m, 3H), 7.65 (d, J = 8.1 Hz, 4H), 7.70 (m, 1H), 7.97 (m, 2H), 8.30 (dd, J = 31.9, 9.8 Hz, 1H); MS (DCI/NH$_3$) m/z 309 (M + H)$^+$; Anal. calculated for C$_{19}$H$_{24}$N$_4$•2C$_7$H$_8$O$_3$S: C, 60.71; H, 6.18; N, 8.58. Found: C, 60.45; H, 5.99; N, 8.47. |

Examples 276-281

5-aryl-2-benzenesulfanyl-1,3,4-oxadiazole derivatives were prepared from the commercially available 5-aryl-1,3,4-oxadiazolyl-2-thiols according to the following procedure:

Example 276A

2-Benzylsulfanyl-5-phenyl-[1,3,4]oxadiazole

5-Phenyl-[1,3,4]oxadiazole-2-thiol (Aldrich, 3.1 g, 17.4 mmol) was added to EtOH (30 mL) and cooled to 0° C. while stirring. Diisopropylethylamine (3.1 mL, 17.4 mmol) was then added and the mixture became a clear solution. Benzyl bromide (2.08 mL, 17.4 mmol) was added and the resulting mixture was allowed to warm to room temperature while stirring. After 45 min, a thick white precipitate formed. The mixture was stirred an additional 1 hr followed by the addition of 1M NaOH (3 mL). The mixture was filtered, washed with 1M NaOH (2×20 mL), 3% citric acid (2×20 mL), H$_2$O (2×20 mL) and the precipitate was dried under vacuum to afford 4.31 g (92%) 2-benzylsulfanyl-5-phenyl-[1,3,4]oxadiazole as a white solid. $^1$H NMR (CDCl$_3$, 300 MHz) δ 4.57 (s, 2H), 7.37 (m, 3H), 7.48 (m, 5H), 7.99 (m, 2H); MS (DCI/NH$_3$) m/z 269 (M+H)$^+$.

Example 276B (3aR,6aR)-5-(5-Phenyl-[1,3,4]oxadiazol-2-yl)-hexahydro-pyrrolo[3,4-b]pyrrole-1-carboxylic acid tert-butyl ester To provide the title compound, the product of Example 14H, 0.20 g, 0.95 mmol) and diisopropylethylamine (0.17 mL, 0.95 mmol) were dissolved in 1,2-dichlorobenzene (3 mL). The 2-benzylsulfanyl-5-aryl-[1,3,4]oxadiazole (0.23 g, 0.86 mmol, prepared according to the procedure of Example 276A) was added and the mixture heated to 220° C. under microwave irradiation for 15 min. After cooling, the reaction mixture was diluted with CH$_2$Cl$_2$ (25 mL), washed successively with sat. NaHCO$_3$ (10 mL), H$_2$O (10 mL), and brine (10 mL), dried (Na$_2$SO$_4$) and concentrated under vacuum.

The residue was purified by column chromatography (100% CH$_2$Cl$_2$ to 95/5/0.5 CH$_2$Cl$_2$:MeOH:NH$_4$OH) to provide the title compound (56 mg, 18%) as a yellow solid: $^1$H NMR (CD$_3$OD, 300 MHz) δ 1.48 (s, 9H), 1.78-1.93 (m, 1H), 2.04-2.21 (m, 1H), 3.16 (m, 1H), 3.42-3.57 (m, 3H), 3.68-3.90 (m, 3H), 4.42 (m, 1H), 7.51 (m, 3H), 7.89 (m, 2H); MS (DCI/NH$_3$) m/z 357 (M+H)$^+$. The product was carried through deprotection and/or salt formation steps as listed in the table below.

Examples 276-281

General Coupling Procedure (OD): The diamine (1 mmol) and diisopropylethylamine (1-2 mmol) were dissolved in 1,2-dichlorobenzene (3 mL). A 5-aryl-substituted 2-benzylsulfanyl-[1,3,4]oxadiazole (1-2 mmol) was added and the mixture heated to 220° C. under microwave irradiation for 15 min. After cooling, the reaction mixture was diluted with CH$_2$Cl$_2$ (25 mL), washed successively with sat. NaHCO$_3$ (10 mL), H$_2$O (10 mL), and brine (10 mL), dried (Na$_2$SO$_4$) and concentrated under vacuum. The residue was purified by column chromatography. Examples 276-281 were prepared by reacting the 2-benzylsulfanyl-[1,3,4]oxadiazole derivative substituted at the 5-position with the listed aryl group and the corresponding diamine according to the conditions listed in the table below.

| Example | Aryl | Diamine | Conditions | Resulting Compound |
|---|---|---|---|---|
| 276 | Phenyl | Example 14H | 1) OD<br>2) FB | (3aR,6aR)-5-(5-Phenyl-[1,3,4]oxadiazol-2-yl)-octahydro-pyrrolo[3,4-b]pyrrole<br>$^1$H NMR (CD$_3$OD, 300 MHz) δ 1.72-1.83 (m, 1H), 2.02-2.18 (m, 1H), 2.88-3.06 (m, 3H), 3.40-3.46 (m, 1H), 3.57-3.63 (m, 1H), 3.71-3.81 (m, 2H), 3.94-4.00 (m, 1H), 7.52 (m, 3H), 7.90 (m, 2H); MS (DCI/NH$_3$) m/z 257 (M + H)$^+$; Anal. C$_{14}$H$_{16}$N$_4$O•0.67H$_2$O: C, H, N |
| 277 | Phenyl | Example 6C | 1) B<br>2) FB<br>3) S3 | 2-(5-Phenyl-[1,3,4]oxadiazol-2-yl)-octahydro-pyrrolo[3,4-c]pyrrole bis hydrochloride<br>$^1$H NMR (DMSO-d$_6$, 300 MHz) δ 3.06-3.25 (m, 4H) 3.38-3.47 (m, 2H) 3.52-3.63 (m, 2H) 3.65-3.76 (m, 2H) 7.51-7.58 (m, 3H) 7.82-7.90 (m, 2H) 9.17 (s, 2H); MS (DCI/NH$_3$) m/z 257 (M + H)$^+$; Anal. C$_{14}$H$_{16}$N$_4$O•1.8HCl: C, H, N. |
| 278 | p-methoxy phenyl | Example 6C | 1) B<br>2) FB<br>3) S4 | 2-[5-(4-Methoxy-phenyl)-[1,3,4]oxadiazol-2-yl]-octahydro-pyrrolo[3,4-c]pyrrole trifluoroacetate<br>$^1$H NMR (DMSO-d$_6$, 300 MHz) δ 3.08-3.21 (m, 4H) 3.37-3.49 (m, 2H) 3.49-3.57 (m, 2H) 3.61-3.71 (m, 2H) 3.83 (s, 3H) 7.06-7.14 (m, 2H) 7.75-7.83 (m, 2H) 8.88 (s, 2H); MS (DCI/NH$_3$) m/z 287 (M + H)$^+$; Anal. C$_{15}$H$_{18}$N$_4$O$_2$•C$_2$HF$_3$O$_2$: C, H, N. |
| 279 | p-methoxy pheny | Example 6C | 1) B<br>2) FB<br>3) RA<br>4) S3 | 2-[5-(4-Methoxy-phenyl)-[1,3,4]oxadiazol-2-yl]-5-methyl-octahydro-pyrrolo[3,4-c]pyrrole hydrochloride<br>$^1$H NMR (DMSO-d$_6$, 300 MHz) δ 2.81 (dd, J = 6.6, 4.9 Hz, 3H) 2.86-2.96 (m, 1H) 3.04-3.20 (m, 1H) 3.23-3.36 (m, 2H) 3.47-3.58 (m, 2H) 3.59-3.66 (m, 2H) 3.66-3.82 (m, 2H) 3.83 (s, 3H) 7.05-7.16 (m, 2H) 7.75-7.86 (m, 2H); MS (DCI/NH$_3$) m/z 301 (M + H)$^+$; Anal. C$_{16}$H$_{20}$N$_4$O$_2$•1.3HCl: C, H, N. |
| 280 | p-chloro phenyl | Example 6C | 1) B<br>2) FB<br>3) S4 | 2-[5-(4-Chloro-phenyl)-[1,3,4]oxadiazol-2-yl]-octahydro-pyrrolo[3,4-c]pyrrole trifluoroacetate<br>$^1$H NMR (DMSO-d$_6$, 300 MHz) δ 3.11-3.22 (m, 4H) 3.38-3.49 (m, 2H) 3.51-3.59 (m, 2H) 3.64-3.74 (m, 2H) 7.44-7.75 (m, 2H) 7.79-8.00 (m, 2H) 8.97 (s, 2H); MS (DCI/NH$_3$) m/z 291 (M + H)$^+$; Anal. C14H15ClN4O•3.7C2HF3O2: C, H, N. |
| 281 | Phenyl | Example 5D | 1) B<br>2) S4 | 6-Methyl-3-(5-phenyl-[1,3,4]oxadiazol-2-yl)-3,6-diaza-bicyclo[3.2.1]octane bis trifluoroacetate<br>$^1$H NMR (MeOD-d$_4$, 300 MHz) δ 2.07-2.28 (m, 1H) 2.41-2.56 (m, 1H) 2.88-2.97 (m, 1H) 2.99 (s, 3H) 3.24 (dd, J = 12.4, 5.6 Hz, 1H) 3.35-3.59 (m, 2H) 3.74-4.00 (m, 2H) 4.01-4.31 (m, 2H) 7.40-7.68 (m, 3H) 7.84-8.07 (m, 2H); MS (DCI/NH$_3$) m/z 271 (M + H)$^+$; Anal. C15H18N4O•2.2C2HF3O2: C, H, N. |

Example 282

2-(2-Methoxy-biphenyl-4-yl)-octahydro-pyrrolo[3,4-c]pyrrole

Example 282A

5-(3-Methoxy-phenyl)-hexahydro-pyrrolo[3,4-c]pyrrole-2-carboxylic acid tert-butyl ester The product of Example 6C (1.0 g, 4.71 mmol), 3-bromoanisole (1.15 g, 6.12 mmol), tris(dibenzylideneacetone)dipalladium (0) ($Pd_2(dba)_3$, Strem, 86 mg, 0.094 mmol), racemic-2,2'-bis(diphenylphosphino)-1,1'-binaphthyl (BINAP, Strem, 0.117 g, 0.188 mmol), and tert-BuONa (0.724 g, 7.54 mmol) were combined in 20 mL toluene. This mixture was warmed to 85° C. and stirred for 18 h then was cooled to ambient temperature, filtered and concentrated under reduced pressure. The crude residue was purified via flash column chromatography ($SiO_2$, 50% hexanes-EtOAc) to give 1.45 g of the title compound (4.6 mmol, 97% yield). MS ($DCl/NH_3$) m/z 319 $(M+H)^+$.

Example 282B

5-(4-Iodo-3-methoxy-phenyl)-hexahydro-pyrrolo[3,4-c]pyrrole-2-carboxylic acid tert-butyl ester To the product of Example 282A (0.7 g, 2.2 mmol) in 30 mL $CH_2Cl_2$ at ambient temperature was added 1.16 g of $TlOAc$ (Aldrich, 4.4 mmol) as described in Pirrung, M., et al, JACS, 2001, 123, 3638-3643. This mixture was stirred for 5 min then $I_2$ (0.67 g, 2.64 mmol) in $CH_2Cl_2$ (70 mL) was added dropwise. Thallium (I) iodide formed a precipitate in the course of this reaction. This mixture stirred at ambient temperature for 2 h then was filtered. The filtrate was washed with 10% aqueous $Na_2S_2O_3$ (15 mL), $NaHCO_3$ (10 mL), and saturated, aqueous NaCl (10 mL). The organic material was concentrated under reduced pressure and purified via flash column chromatography ($SiO_2$, 50% hexanes-EtOAc) to provide the title compound (0.68 g, 70% yield). MS ($DCl/NH_3$) m/z 445 $(M+H)^+$.

Example 282C

5-(2-Methoxy-biphenyl-4-yl)-hexahydro-pyrrolo[3,4-c]pyrrole-2-carboxylic acid tert-butyl ester The product of Example 282B (0.68 g, 1.53 mmol), phenylboronic acid (Aldrich, 0.59 g, 3.07 mmol), tris(dibenzylideneacetone)dipalladium (0) ($Pd_2(dba)_3$, Strem, 56 mg, 0.061 mmol), 1,3-bis(2,6-di-i-propylphenyl)imidazolium chloride (Strem, 65 mg, 0.15 mmol), and 2M $Na_2CO_3$ (aq, 4 mL) were combined in toluene (20 mL). The mixture was warmed to 85° C. and stirred for 18 h; however, the mixture contained mostly starting material, so additional $Pd_2(dba)_3$ (56 mg, 0.061 mmol) and 1,3-bis(2,6-di-l-propylphenyl)imidazolium chloride (65 mg, 0.15 mmol) were added and the mixture stirred for another 18 h at 85° C. The reaction was cooled to ambient temperature, filtered, concentrated under reduced pressure and purified by column chromatography ($SiO_2$, 50% hexanes-EtOAc) to give the title compound (0.17 g, 28% yield). MS ($DCl/NH_3$) m/z 395 $(M+H)^+$.

Example 282D

2-(2-Methoxy-biphenyl-4-yl)-octahydro-pyrrolo[3,4-c]pyrrole trifluoroacetate To the product of Example 282C (0.17 g, 0.43 mmol) in 6 mL $CH_2Cl_2$ was added 3 mL trifluoroacetic acid (TFA) according to the general procedure to give 0.122 g of the title compound (0.30 mmol, 69% yield). $^1H$ NMR ($CH_3OH$-$d_4$, 300 MHz) δ 3.25 (m, 4H), 3.35 (m, 2H), 3.52 (m, 2H), 3.62 (m, 2H), 3.78 (s, 3H), 6.41 (dd, J=6.8, 2.4 Hz, 1H), 6.42 (s, 1H), 7.18 (m, 2H), 7.31 (m, 2H), 7.42 (m, 2H); MS ($DCl/NH_3$) m/z 295 $(M+H)^+$; Anal. calculated for $C_{19}H_{22}N_2O \cdot CF_3CO_2H$: C, 61.76; H, 5.68; N, 6.86. Found: C, 62.03; H, 5.91; N, 7.02.

Example 283

2-(2-Methoxy-biphenyl-4-yl)-5-methyl-octahydro-pyrrolo[3,4-c]pyrrole

Example 283A

2-(2-Methoxy-biphenyl-4-yl)-5-methyl-octahydro-pyrrolo[3,4-c]pyrrole

To the product of Example 282D (0.102 g, 0.25 mmol) in 3 mL 37% aqueous HCHO was added 54 mg $NaBH(OAc)_3$ (0.25 mmol). This material stirred at ambient temperature for 4 h then was quenched with 5 mL saturated, aqueous $NaHCO_3$. $CH_2Cl_2$ (5 mL) was added, the layers separated and the aqueous layer was extracted 3×5 mL $CH_2Cl_2$. The combined organics were dried over $Na_2SO_4$, concentrated under reduced pressure and purified via flash column chromatography ($SiO_2$, 1% $NH_4OH$:9% $CH_3OH$:90% $CH_2Cl_2$) to give 69 mg of the title compound (2.24 mmol, 90% yield) which was carried on to the next reaction without further purification.

Example 283B

2-(2-Methoxy-biphenyl-4-yl)-5-methyl-octahydro-pyrrolo[3,4-c]pyrrole p-toluenesulfonate To the product of Example 283A (69 mg, 0.224 mmol) in 3 mL 10% EtOH in EtOAc was added p-toluenesulfonic acid (p-TsOH.$H_2O$, 45 mg, 0.24 mmol) in 2 mL 10% EtOH in EtOAc. Diethyl ether (1 mL) was added and the mixture stirred at ambient temperature until a precipitate formed. Filtration yielded 28 mg of the title compound (0.043 mmol, 19% yield). $^1H$ NMR ($CH_3OH$-$d_4$, 300 MHz) δ 2.35 (s, 6H), 2.92 and 2.98 (rotamer s, 3H), 3.19 (m, 3H) 3.38 (m, 3H), 3.63 (m, 3H), 3.77 (s, 3H), 3.98 (m, 1H), 6.50 (m, 1H), 6.52 (s, 1H), 7.16 (m, 1H), 7.22 (m, 5H), 7.32 (m, 2H), 7.42 (m, 2H), 7.70 (m, 4H); MS ($DCl/NH_3$) m/z 309 $(M+H)^+$; Anal. calculated for $C_{20}H_{24}N_2O \cdot 2C_7H_8O_3S$: C, 62.55; H, 6.18; N, 4.29. Found: C, 62.17; H, 5.95; N, 4.18.

Example 284

4-(Hexahydro-pyrrolo[3,4-c]pyrrol-2-yl)-biphenyl-2-ol di-bromide

Demethylation Procedure (deMe): A solution of the product of Example 282C (0.28 g, 0.71 mmol) in $CH_2Cl_2$ (15 mL)

was cooled to −78° C. and BBr₃ (2.8 mL of a 1 M solution in heptane, 2.8 mmol) was added dropwise via syringe. The mixture was stirred at −78° C. for 30 min then was allowed to warm to room temperature and stirred for an additional 3 h. The mixture was cooled to −78° C. and ~3 mL CH₃OH was added dropwise and the mixture was allowed to warm to ambient temperature. After concentration under reduced pressure, 5 mL of 10% CH₃OH in EtOAc was added. The resulting solids were isolated via filtration to give 0.25 g of the title compound (0.56 mmol, 80% yield). $^1$H NMR (300 MHz, CD₃OD) δ ppm 3.32 (m, 6H), 3.50 (dd, J=9.8, 1.7 Hz, 2H), 3.61 (m, 2H), 7.16 (t, J=4.4 Hz, 1H), 7.21 (m, 1H), 7.33 (m, 3H), 7.50 (m, 3H); MS (DCl/NH₃) m/z 281 (M+H)$^+$; Anal. calculated for $C_{18}H_{20}N_2O \cdot 2HBr$: C, 48.89; H, 5.01; N, 6.34. Found: C, 48.53; H, 5.04; N, 6.14.

Example 285

4-(5-Methyl-hexahydro-pyrrolo[3,4-c]pyrrol-2-yl)-biphenyl-2-ol bis-p-toluenesulfonate The product of Example 284 was processed according to the methods RA and S1 to provide the title compound 7% yield). $^1$H NMR (300 MHz, CD₃OD) δ 2.36 (s, 6H), 2.91 (s, 3H), 3.18 (m, 6H), 3.52 (m, 4H), 7.13 (m, 1H), 7.22 (m, 5H), 7.40 (m, 5H), 7.69 ppm (m, 5H); MS (DCl/NH₃) m/z 295 (M+H)$^+$; Anal. calculated for $C_{19}H_{22}N_2O \cdot 1.7C_7H_8O_3S$: C, 63.21; H, 6.11; N, 4.77. Found: C, 62.93; H, 5.68; N, 5.10.

Example 286

Example 286A

5-[6-(3-Methoxy-phenyl)-pyridazin-3-yl]-hexahydro-pyrrolo[3,4-c]pyrrole-2-carboxylic acid tert-butyl ester The product of Example 90 (0.50 g, 1.5 mmol), m-methoxy-phenylboronic acid (0.47 g, 3.1 mmol), aqueous Na₂CO₃ (2M, 2.5 mL), tris(dibenzylideneacetone)dipalladium (0) (Pd₂(dba)₃, Strem, 56 mg, 0.062 mmol) and 1,3-bis(2,6-di-i-propylphenyl)imidazolium chloride (Strem, 65 mg, 0.15 mmol) were combined in toluene (20 mL) were combined in toluene (20 mL). The mixture was deoxygenated by three vacuum/N₂ purge cycles. The mixture was stirred under nitrogen at 85° C. for 18 h then cooled to room temperature, filtered, concentrated under reduced pressure and purified by column chromatography (SiO₂, 50% hexanes in ethyl acetate) to provide the title compound (0.51 g, 84% yield). MS (DCl/NH₃) m/z 397 (M+H)$^+$.

Example 286B

3-[6-(Hexahydro-pyrrolo[3,4-c]pyrrol-2-yl)-pyridazin-3-yl]-phenol dihydrobromide The product of Example 286A (0.63 g, 1.6 mmol) was processed according to the procedure 'deMe' as described in Example 284 to provide the title compound (0.77 g) as a crude solid, suitable for the next reaction: MS (DCl/NH₃) m/z 283 (M+H)$^+$.

Example 286C

5-[6-(3-Hydroxy-phenyl)-pyridazin-3-yl]-hexahydro-pyrrolo[3,4-c]pyrrole-2-carboxylic acid tert-butyl ester The product of Example 286B (~1.6 mmol) was dissolved in THF (15 mL). Aqueous NaHCO₃ (2M, 4 mL) was added, followed by di-tert-butyl dicarbonate (0.49 g, 2.2 mmol). This mixture was stirred at ambient temperature for 1 h then extracted CH₂Cl₂ (2×5 mL). The combined extract was washed with brine (3 mL), dried over anhydrous Na₂SO₄, concentrated under reduced pressure and purified by column chromatography (SiO₂, 1% NH₄OH:9% CH₃OH:90% CH₂Cl₂) to provide the title compound (0.34 g, 56% from Example 286A). MS (DCl/NH₃) m/z 383 (M+H)$^+$.

Example 286D

3-[6-(Hexahydro-pyrrolo[3,4-c]pyrrol-2-yl)-pyridazin-3-yl]-phenol tri-hydrochloride The product of Example 286C was processed according to the methods FB and S3 to provide the title compound in 29% yield: $^1$H NMR (300 MHz, CD₃OD) δ ppm 3.31 (m, 4H), 3.70 (m, 6H), 6.86 (ddd, J=8.0, 2.4, 1.2 Hz, 1H), 7.12 (d, J=9.5 Hz, 1H), 7.29 (t, J=7.8 Hz, 1H), 7.37 (m, 2H), 7.85 (d, J=9.5 Hz, 1H); MS (DCl/NH₃) m/z 283 (M+H)$^+$; Anal. calculated for $C_{16}H_{18}N_4O \cdot 3.8HCl \cdot 1.3NH_4OH$: C, 41.20; H, 6.12; N, 15.91. Found: C, 40.90; H, 6.27; N, 16.26.

Example 287

4-[6-(Hexahydro-pyrrolo[3,4-c]pyrrol-2-yl)-pyridazin-3-yl]-phenol bis-trifluoroacetate Example 287A 4-[6-(Hexahydro-pyrrolo[3,4-c]pyrrol-2-yl)-pyridazin-3-yl]-phenol dihydrobromide The product of Example 95 was processed according to the procedure deME as described in Example 284 to provide the title compound as a crude salt in 89% yield: MS (DCl/NH₃) m/z 283 (M+H)$^+$.

Example 287B

5-[6-(4-Hydroxy-phenyl)-pyridazin-3-yl]-hexahydro-pyrrolo[3,4-c]pyrrole-2-carboxylic acid tert-butyl ester The product of Example 287A was treated with di-tert-butyl dicarbonate according to the procedure Boc as described in Example 286C to provide the crude title compound: MS (DCl/NH₃) m/z 383 (M+H)$^+$.

Example 287C

4-[6-(Hexahydro-pyrrolo[3,4-c]Pyrrol-2-yl)-pyridazin-3-yl]-phenol bis-trifluoroacetate The product of Example 287B was processed according to the methods FB and S4 to provide the title compound in 87% yield: $^1$H NMR (300 MHz, CD₃OD) δ ppm 3.37 (m, 4H), 3.66 (dd, J=11.5, 7.1 Hz, 2H), 3.74 (dd, J=11.7, 3.2 Hz, 2H), 3.93 (m, 2H), 6.96 (m, 2H), 7.65 (d, J=9.8 Hz, 1H), 7.83 (m, 2H), 8.29 (d, J=9.8 Hz, 1H); MS (DCl/NH₃) m/z 282 (M+H)$^+$; Anal. calculated for $C_{16}H_{18}N_4O \cdot 2.4CF_3CO_2H$: C, 44.93; H, 3.70; N, 10.08. Found: C, 45.16; H, 3.61; N, 10.22.

Example 288

Diethyl-(2-{3-[6-(hexahydro-pyrrolo[3,4-c]pyrrol-2-yl)-pyridazin-3-yl]-phenoxy}-ethyl)-amine bis-p-toluenesulfonate

Example 288A

5-{6-[3-(2-Diethylamino-ethoxy)-phenyl]-pyridazin-3-yl}-hexahydro-pyrrolo[3,4-c]pyrrole-2-carboxylic acid tert-butyl ester Polymer-bound triphenylphosphine (Aldrich, 0.61 g, 1.8 mmol) was added to an ice-cooled solution of the product of Example 286C (0.28 g, 0.73 mmol) and N,N-diethylethanolamine (0.24 mL, 1.8 mmol) in $CH_2Cl_2$. Di-iso-propyl-azodicarboxylate (Aldrich, 0.36 mL, 1.8 mmol) was added dropwise via syringe. This mixture was stirred at 0° C. for 1 h then kept at room temperature for 72 h. The reaction mixture was filtered through diatomaceous earth, concentrated under reduced pressure and purified by column chromatography ($SiO_2$, 1% $NH_4OH$:9% $CH_3OH$:90% $CH_2Cl_2$) to provide the title compound (0.19 g, 54% yield). MS ($DCI/NH_3$) m/z 482 $(M+H)^+$.

Example 288B

Diethyl-(2-{3-[6-(hexahydro-pyrrolo[3,4-c]pyrrol-2-yl)-pyridazin-3-yl]-phenoxy}-ethyl)-amine bis-p-toluenesulfonate The product of Example 288A (0.18 g, 0.37 mmol) was processed according to the methods FB and S1 to provide the title compound in 43% yield: $^1H$ NMR (300 MHz, $CD_3OD$) δ ppm 1.39 (t, J=7.3 Hz, 6H), 1.38 (s, 6H), 3.32 (m, 8H), 3.71 (m, 8H), 4.44 (dd, J=4.8 Hz, 2H), 7.11 (dd, J=7.6, 2.2 Hz, 1H), 7.21 (m, 5H), 7.46 (t, J=8.0 Hz, 1H), 7.57 (m, 1H), 7.67 (m, 5H), 7.97 (d, J=9.5 Hz, 1H); MS ($DCI/NH_3$) m/z 382 $(M+H)^+$; Anal. calculated for $C_{22}H_{31}N_5O.2C_7H_8O_3S.1.1H_2O$: C, 57.98; H, 6.65; N, 9.39. Found: C, 57.67; H, 6.64; N, 9.11.

Example 289

Diethyl-(2-{4-[6-(hexahydro-pyrrolo[3,4-c]pyrrol-2-yl)-pyridazin-3-yl]-phenoxy}-ethyl)-amine tris-trifluoroacetate The product of Example 287B was processed successively according to the procedures of Example 288A, FB, and S4 to provide the title compound: $^1H$ NMR (300 MHz, $CD_3OD$) δ ppm 1.39 (t, J=7.3 Hz, 6H), 3.37 (m, 8H), 3.65 (m, 4H), 3.76 (dd, J=11.2, 2.7 Hz, 2H), 3.91 (m, 2H), 4.45 (m, 2H), 7.19 (m, 2H), 7.53 (d, J=9.8 Hz, 1H), 7.98 (m, 2H), 8.21 (d, J=9.8 Hz, 1H); MS ($DCI/NH_3$) m/z 382 $(M+H)^+$; Anal. calculated for $C_{22}H_{31}N_5O.3CF_3CO_2H$: C, 46.48; H, 4.74; N, 9.68. Found: C, 46.56; H, 4.72; N, 9.55.

Example 290

(2-{4-[6-(Hexahydro-pyrrolo[3,4-c]pyrrol-2-yl)-pyridazin-3-yl]-phenoxy}-ethyl)-dimethyl-amine tris-trifluoroacetate The product of Example 287B was coupled to N,N-dimethylethanolamine according to the procedure of Example 288A. The product was further processed according to the methods FB and S4 to provide the title compound: $^1H$ NMR (300 MHz, $CD_3OD$) δ ppm 3.01 (s, 6H), 3.39 (m, 4H), 3.65 (m, 4H), 3.76 (m, 2H), 3.91 (m, 2H), 4.44 (m, 2H), 7.19 (m, 2H), 7.53 (d, J=9.5 Hz, 1H), 7.98 (m, 2H), 8.20 (d, J=9.8 Hz, 1H); MS ($DCI/NH_3$) m/z 354 $(M+H)^+$; Anal. calculated for $C_{20}H_{27}N_5O.3CF_3CO_2H$: C, 44.90; H, 4.35; N, 10.07. Found: C, 44.85; H, 4.16; N, 9.92.

Examples 291-294

The N-methyl derivatives of Examples 286-290 were prepared according to the methods indicated in the table below:

| Example | Starting Material | Conditions | Resulting Compound |
|---|---|---|---|
| 291 | Example 286 | 1) RA<br>2) S3 | 3-[6-(5-Methyl-hexahydro-pyrrolo[3,4-c]pyrrol-2-yl)-pyridazin-3-yl]-phenol tri-hydrochloride $^1H$ NMR (300 MHz, $CD_3OD$) δ ppm 2.96 (s, 3H), 3.31 (m, 4H), 3.61 (m, 6H), 6.86 (ddd, J = 7.9, 2.5, 1.2 Hz, 1H), 7.16 (d, J = 9.5 Hz, 1H), 7.29 (t, J = 7.8 Hz, 1H), 7.37 (m, 2H), 7.86 (d, J = 9.5 Hz, 1H); MS ($DCI/NH_3$) m/z 297 $(M + H)^+$; Anal. calculated for $C_{17}H_{20}N_4O$•2.5HCl•0.75$H_2O$: C, 50.91; H, 6.03; N, 13.97. Found: C, 51.03; H, 6.36; N, 13.98. |
| 292 | Example 287 | 1) RA<br>2) S1 | 4-[6-(5-Methyl-hexahydro-pyrrolo[3,4-c]pyrrol-2-yl)-pyridazin-3-yl]-phenol bis-p-toluenesulfonate<br>$^1H$ NMR (300 MHz, $CD_3OD$) δ ppm 2.31 (m, 6H), 3.00 (s, 3H), 3.20 (m, 1H), 3.47 (m, 3H), 3.89 (m, 6H), 6.97 (m, 2H), 7.19 (m, 4H), 7.65 (m, 5H), 7.81 (d, J = 8.5 Hz, 2H), 8.24 (dd, J = 24.8, 10.9 Hz, 1H); MS ($DCI/NH_3$) m/z 297 $(M + H)^+$; Anal. calculated for $C_{17}H_{20}N_4O$•2$C_7H_8O_3S$: C, 58.11; H, 5.66; N, 8.74. Found: C, 57.96; H, 5.56; N, 8.69. |
| 293 | Example 288 | 1) RA<br>2) S2 | Diethyl-(2-{3-[6-(5-methyl-hexahydro-pyrrolo[3,4-c]pyrrol-2-yl)-pyridazin-3-yl]-phenoxy}-ethyl)-amine bis-fumarate $^1H$ NMR (300 MHz, $CD_3OD$) δ ppm 1.38 (t, J = 7.3 Hz, 6H), 2.88 (s, 3H), 3.28 (m, 4H), 3.35 (q, J = 7.1 Hz, 4H), 3.62 (m, 6H), 3.78 (m, 2H), 4.44 (dd, J = 4.8 Hz, 2H), 6.70 (s, 4H), 7.09 (ddd, J = 8.1, 2.5, 0.8 Hz, 1H), 7.15 (d, J = 9.5 Hz, 1H), 7.45 (t, J = 8.0 Hz, 1H), 7.54 (m, 1H), 7.65 (m, 1H), 7.91 (d, J = 9.5 Hz, 1H); MS ($DCI/NH_3$) m/z 396 $(M + H)^+$; Anal. |

| Example | Starting Material | Conditions | Resulting Compound |
|---|---|---|---|
| 294 | Example 289 | 1) RA<br>2) S1 | calculated for $C_{23}H_{33}N_5O \cdot 2C_4H_4O_4 \cdot NH_4OH$: C, 56.18; H, 7.00; N, 12.68. Found: C, 56.40; H, 6.50; N, 12.94. Diethyl-(2-{4-[6-(5-methyl-hexahydro-pyrrolo[3,4-c]pyrrol-2-yl)-pyridazin-3-yl]-phenoxy}-ethyl)-amine bis-p-toluenesulfonate<br>$^1$H NMR (300 MHz, CD$_3$OD) δ ppm 1.38 (t, J = 7.3 Hz, 6H), 2.35 (s, 6H), 2.94 (s, 3H), 3.32 (m, 8H), 3.64 (m, 6H), 3.77 (m, 2H), 4.41 (m, 2H), 7.14 (m, 3H), 7.22 (m, 4H), 7.69 (m, 4H), 7.87 (d, J = 9.5 Hz, 1H), 7.93 (m, 2H); MS (DCI/NH$_3$) m/z 396 (M + H)$^+$; Anal. calculated for $C_{23}H_{33}N_5O \cdot 2C_7H_8O_3S \cdot 0.25H_2O$: C, 59.70; H, 6.70; N, 9.41. Found: C, 59.41; H, 6.71; N, 9.36. |

Example 295A

5-[6-(4-Amino-phenyl)-pyridazin-3-yl]-hexahydro-pyrrolo[3,4-c]pyrrole-2-carboxylic acid tert-butyl ester The product of Example 90 (0.97 g, 3.0 mmol) and 4-aminophenylboronic acid, pinacol ester (TCI, 1.92 g, 7.5 mmol) were coupled according to the procedure of method (G, H, I) to provide the title compound (0.91 g, 2.39 mmol, 80% yield). MS (DCI/NH$_3$) m/z 181 (M+H)$^+$.

Examples 295-300

The product of Example 295A (164 mg, 0.43 mmol) and an acylating agent (0.86 mmol) were combined in CH$_2$Cl$_2$ (2.0 mL) containing anhydrous pyridine (0.10 mL, 1.2 mmol) and stirred at rt to 40° C. for 2-18 h. The mixture was cooled to room temperature, partitioned with CH$_2$Cl$_2$ (10 mL) and 1 N aq. NaOH (5 mL) and the layers were separated. The organic layer was washed with satd. aq. NH$_4$Cl (2×5 mL) and brine (5 mL), dried (Na$_2$SO$_4$) and concentrated under reduced pressure to give the acylated product in 51%-84% yield. The crude materials were further processed as indicated below to provide the title compounds.

| Example | Acylating AgentI | Conditions | Resulting Compound |
|---|---|---|---|
| 295 | Methanesulfonyl chloride | 1) EC<br>2) S2 | N-{4-[6-(5-Methyl-hexahydro-pyrrolo[3,4-c]pyrrol-2-yl)-pyridazin-3-yl]-phenyl}-methanesulfonamide fumarate<br>$^1$H NMR (D$_2$O, 300 MHz) δ 2.89 (s, 3H) 3.07 (s, 3H) 3.22-3.56 (m, 4H) 3.58-3.78 (m, 4H) 3.82-4.05 (m, 2H) 6.48 (s, 2H) 7.18 (d, J = 9.5 Hz, 1H), 7.20-7.34 (m, 2H) 7.66-7.80 (m, 2H) 7.86 (d, J = 9.5 Hz, 1H); MS (DCI/NH$_3$) m/z 374 (M + H)$^+$; Anal. $C_{18}H_{23}N_5O_2S \cdot 1.0\ C_4H_4O_4 \cdot 2.6\ H_2O$: C, H, N. |
| 296 | Benzoyl chloride | 1) FB<br>2) S2 | N-{4-[6-(Hexahydro-pyrrolo[3,4-c]pyrrol-2-yl)-pyridazin-3-yl]-phenyl}-benzamide fumarate<br>$^1$H NMR (MeOD-d$_4$, 300 MHz) δ 3.12-3.21 (m, 2H) 3.25-3.30 (m, 2H) 3.48-3.59 (m, 2H) 3.62-3.71 (m, 2H) 3.75-3.83 (m, 2H) 6.72 (s, 1H) 7.07 (d, J = 8.9 Hz, 1H) 7.48-7.55 (m, 2H) 7.55-7.60 (d, J = 8.9 Hz, 1H) 7.70-7.75 (m, 2H) 7.83-7.90 (m, 2H) 7.93-8.00 (m, 3H); MS (DCI/NH$_3$) m/z 386 (M + H)$^+$; Anal. $C_{23}H_{23}N_5O \cdot 0.7\ C_4H_4O_4$: C, H, N. |
| 297 | Methanesulfonyl chloride | 1) FB<br>2) S2 | N-{4-[6-(Hexahydro-pyrrolo[3,4-c]pyrrol-2-yl)-pyridazin-3-yl]-phenyl}-methanesulfonamide fumarate<br>$^1$H NMR (D$_2$O, 300 MHz) δ 3.04 (s, 3H) 3.18-3.30 (m, 4H) 3.47-3.55 (m, 2H) 3.54-3.69 (m, 4H) 6.41 (s, 1H) 6.95 (d, J = 9.5 Hz, 1H) 7.19-7.25 (m, 2H) 7.63 (d, J = 9.8 Hz, 1H) 7.65-7.70 (m, 2H);<br>MS (DCI/NH$_3$) m/z 360 (M + H)$^+$; Anal. $C_{17}H_{21}N_5O_2S \cdot 0.8\ C_4H_4O_4$: C, H, N. |
| 298 | Dimethyl sulfamoyl chloride | 1) FB<br>2) S2 | N-{4-[6-(Hexahydro-pyrrolo[3,4-c]pyrrol-2-yl)-pyridazin-3-yl]-phenyl}-dimethylaminosulfonamide fumarate<br>$^1$H NMR (D$_2$O, 300 MHz) δ 2.73 (s, 6H) 3.20-3.31 (m, 2H) 3.30-3.39 (m, 2H) 3.56-3.67 (m, 4H) 3.76-3.87 (m, 2H) 6.49 (s, 4H) 7.17-7.25 (m, 2H) 7.29 (d, J = 9.8 Hz, 1H) 7.66-7.74 (m, 2H) 7.89 (d, J = 9.8 Hz, 1H); MS (DCI/NH$_3$) m/z 389 (M + H)$^+$ |

-continued

| Example | Acylating AgentI | Conditions | Resulting Compound |
|---|---|---|---|
| 299 | Acetic anhydride | 1) FB<br>2) S4 | N-{4-[6-(Hexahydro-pyrrolo[3,4-c]pyrrol-2-yl)-pyridazin-3-yl]-phenyl}-acetamide trifluoroacetate<br>$^1$H NMR (MeOD-$d_4$, 300 MHz) δ 2.15 (s, 3H) 3.26-3.40 (m, 4H) 3.58-3.67 (m, 2H) 3.67-3.74 (m, 2H) 3.76-3.86 (m, 2H) 7.25 (d, J = 9.6 Hz, 1H) 7.66-7.75 (m, 2H) 7.86-7.95 (m, 2H) 8.00 (d, J = 9.5 Hz, 1H); MS (DCI/NH$_3$) m/z 324 (M + H)$^+$; Anal. $C_{18}H_{21}N_5O \cdot 1.3C_2HF_3O_2$: C, H, N. |
| 300 | Acetic anhydride | 1) FB<br>2) RA<br>3) S4 | N-{4-[6-(5-Methyl-hexahydro-pyrrolo[3,4-c]pyrrol-2-yl)-pyridazin-3-yl]-phenyl}-acetamide trifluoroacetate<br>$^1$H NMR (MeOD-$d_4$, 300 MHz) δ 2.15 (s, 3H) 2.96 (s, 3H) 3.33-3.43 (m, 4H) 3.57-3.74 (m, 4H) 3.75-3.84 (m, 2H) 7.16 (d, J = 9.5 Hz, 1H) 7.65-7.72 (m, 2H) 7.85-7.92 (m, 2H) 7.90 (d, J = 9.4 Hz, 1H); MS (DCI/NH$_3$) m/z 338 (M + H)$^+$; Anal. $C_{19}H_{23}N_5O \cdot C_2HF_3O_2$: C, H, N. |

Example 301

2-(2-Phenyl-pyrimidin-5-yl)-octahydro-pyrrolo[3,4-c]pyrrole

Example 301A

5-Pyrimidin-5-yl-hexahydro-pyrrolo[3,4-c]pyrrole-2-carboxylic acid tert-butyl ester A mixture of the product of Example 6C (2.045 g, 9.63 mmol), 5-bromopyrimidine (1.84 g, 11.6 mmol), tris(dibenzylideneacetone)dipalladium (0) Pd$_2$(dba)$_3$, Strem, 0.265 g, 0.29 mmol), racemic-2,2'-bis(diphenylphosphino)-1,1'-binaphthyl (BINAP, Strem, 0.30 g, 0.48 mmol) and tert-BuONa (sodium tert-butoxide, 1.85 g, 19.3 mmol) in 75 mL PhCH$_3$ was degassed three times with a N$_2$ back-flush. The mixture was warmed to 85° C., stirred for 48 h then was cooled, filtered and concentrated under reduced pressure. Purification by column chromatography (SiO$_2$, 50% hexanes-EtOAc) gave 2.68 g of the title compound (9.23 mmol, 95% yield). MS (DCI/NH$_3$) m/z 291 (M+H)$^+$.

Example 301B

5-(2-Bromo-pyrimidin-5-yl)-hexahydro-pyrrolo[3,4-c]pyrrole-2-carboxylic acid tert-butyl ester To a solution of the product of Example 301A (2.68 g, 9.23 mmol) in 75 mL of CH$_3$CN at 0° C. was added N-bromosuccinimide (NBS, 1.64 g, 9.23 mmol) in 50 mL CH$_3$CN portionwise via cannula. The mixture was allowed to warm to ambient temperature and stir for 16 h. The reaction mixture was quenched by the addition of 25 mL H$_2$O then 50 mL CH$_2$Cl$_2$ was added. The layers were separated and the aqueous layer was extracted 3×20 mL CH$_2$Cl$_2$. The combined organic layers were washed with 10 mL saturated, aqueous NaCl (brine), then were dried over Na$_2$SO$_4$, and concentrated under reduced pressure. Purification via column chromatography (SiO$_2$, 75% hexanes-EtOAc) gave 1.2 g of the title compound (3.25 mmol, 35% yield). MS (DCI/NH$_3$) m/z 369, 371 (M+H)$^+$.

Examples 301-304

The product of Example 301B was coupled with an aryl boronic acid and further processed by methods listed in the table below to provide the title compounds:

| Example | Boronic Acid | Conditions | Resulting Compound |
|---|---|---|---|
| 301 | Phenyl boronic acid | 1) H<br>2) FB<br>3) S1 | 2-(2-Phenyl-pyrimidin-5-yl)-octahydro-pyrrolo[3,4-c]pyrrole p-toluenesulfonate<br>$^1$H NMR (CH$_3$OH-$d_4$, 300 MHz) δ 2.35 (s, 3H), 3.27 (m, 4H), 3.45 (m, 2H), 3.59 (m, 4H), 7.20 (m, 2H), 7.42 (m, 3H), 7.69 (m, 2H), 8.22 (m, 2H), 8.30 (s, 2H); MS (DCI/NH$_3$) m/z 267 (M + H)$^+$; Anal. calculated for $C_{16}H_{18}N_4 \cdot 1.25C_7H_8O_3S$: C, 61.73; H, 5.86; N, 11.63; Found: C, 61.47; H, 5.85; N, 11.71. |
| 302 | Phenyl boronic acid | 1) H<br>2) FB<br>3) RA<br>4) S1 | 2-Methyl-5-(2-phenyl-pyrimidin-5-yl)-octahydro-pyrrolo[3,4-c]pyrrole p-toluenesulfonate<br>$^1$H NMR (CH$_3$OH-$d_4$, 300 MHz) δ 2.35 (s, 3H), 2.95 (s, 3H), 3.30 (m, 2H), 3.35 (m, 4H), 3.65 (m, 4H), 7.21 (m, 2H), 7.43 (m, 3H), 7.69 (m, 2H), 8.23 (m, 2H), 8.36 (s, 2H); MS (DCI/NH$_3$) m/z 281 (M + H)$^+$; Anal. calculated for $C_{17}H_{20}N_4 \cdot C_7H_8O_3S$: C, 63.69; H, 6.24; N, 12.38; Found: C, 63.32; H, 6.12; N, 12.07. |

| Example | Boronic Acid | Conditions | Resulting Compound |
|---|---|---|---|
| 303 | o-methoxyphenyl boronic acid | 1) H<br>2) DeMe<br>3) FB<br>4) S1 | 2-[5-(Hexahydro-pyrrolo[3,4-c]pyrrol-2-yl)-pyrimidin-2-yl]-phenol p-toluenesulfonate<br>$^1$H NMR (300 MHz, CD$_3$OD) δ ppm 0.93 (m, 1H), 1.35 (m, 1H), 2.35 (s, 3H), 3.30 (m, 2H), 3.56 (m, 6H), 6.91 (m, 2H), 7.22 (m, 2H), 7.28 (ddd, J = 8.1, 7.1, 1.7 Hz, 1H), 7.69 (m, 2H), 8.30 (dd, J = 8.1, 1.7 Hz, 1H), 8.37 (s, 2H); MS (DCI/NH$_3$) m/z 283 (M + H)$^+$; Anal. calculated for C$_{16}$H$_{18}$N$_4$O•1.5C$_7$H$_8$O$_3$S•H$_2$O: C, 56.97; H, 5.77; N, 10.03. Found: C, 57.04; H, 5.44; N, 10.30. |
| 304 | o-methoxyphenyl boronic acid | 1) H<br>2) DeMe<br>3) FB<br>4) RA<br>5) S1 | 2-[5-(5-Methyl-hexahydro-pyrrolo[3,4-c]pyrrol-2-yl)-pyrimidin-2-yl]-phenol p-toluenesulfonate $^1$H NMR (300 MHz, CD$_3$OD) □ ppm 2.35 (s, 3H), 2.95 (s, 3H), 3.28 (m, 4H), 3.37 (m, 3H), 3.67 (m, 3H), 6.89 (m, 2H), 7.22 (m, 2H), 7.27 (dd, J = 7.5, 1.7 Hz, 1H), 7.69 (m, 2H), 8.30 (dd, J = 8.3, 1.9 Hz, 1H), 8.40 (s, 2H); MS (DCI/NH$_3$) m/z 297 (M + H)$^+$; Anal. calculated for C$_{16}$H$_{18}$N$_4$O•C$_7$H$_8$O$_3$S•0.25H$_2$O: C, 60.93; H, 6.07; N, 11.84. Found: C, 60.84; H, 5.98; N, 11.58. |

Example 305

5-(4-Bromo-phenyl)-hexahydro-pyrrolo[3,4-c]pyrrole-2-carboxylic acid tert-butyl ester The product of Example 6C (0.75 g, 3.53 mmol), 1,4-dibromobenzene (0.83 g, 3.53 mmol), tris(dibenzylideneacetone)dipalladium (0) (Pd$_2$(dba)$_3$, Strem, 65 mg, 0.071 mmol), racemic-2,2'-bis(diphenylphosphino)-1,1'-binaphthyl (BiNAP, Strem, 88 mg, 0.14 mmol), and NaOt-Bu (0.54 g, 5.6 mmol) were combined in toluene (15 mL). This mixture was stirred at 100° C. for 24 h. The reaction mixture was cooled to ambient temperature, filtered, concentrated under reduced pressure and purified by column chromatography (SiO$_2$, 70% hexanes in EtOAc) to give the title compound (0.65 g, 1.8 mmol, 50% yield). MS (DCI/NH$_3$) m/z 367 (M+H)$^+$.

Examples 306-309

The intermediate Example 305 was coupled with an aryl boronic acid and further processed by methods listed to provide the title compounds:

| Example | Boronic Acid | Conditions | Resulting Compound |
|---|---|---|---|
| 306 | 3-pyridinyl boronic acid | 1) G<br>2) FB<br>3) S4 | 2-(4-Pyridin-3-yl-phenyl)-octahydro-pyrrolo[3,4-c]pyrrole bis-trifluoroacetate $^1$H NMR (300 MHz, CD$_3$OD) δ ppm 3.25 (m, 4H), 3.45 (m, 2H), 3.53 (m, 2H), 3.63 (m, 2H), 6.89 (m, 2H), 7.67 (m, 2H), 7.86 (dd, J = 8.1, 5.4 Hz, 1H), 8.56 (m, 2H), 8.95 (s, 1H); MS (DCI/NH$_3$) m/z 266 (M + H)$^+$; Anal. calculated for C$_{17}$H$_{19}$N$_3$•2CF$_3$CO$_2$H•0.5H$_2$O: C, 50.20; H, 4.41; N, 8.38. Found: C, 50.51; H, 4.29; N, 8.12. |
| 307 | 3-pyridinyl boronic acid | 1) G<br>2) FB<br>3) RA<br>4) S1 | 2-Methyl-5-(4-pyridin-3-yl-phenyl)-octahydro-pyrrolo[3,4-c]pyrrole p-toluenesulfonate $^1$H NMR (300 MHz, CD$_3$OD) δ ppm 2.36 (s, 3H), 2.93 (s, 3H), 3.23 (m, 4H), 3.38 (m, 2H), 3.59 (m, 3H), 3.99 (m, J = 7.5 Hz, 1H), 6.94 (d, J = 8.8 Hz, 2H), 7.22 (m, 2H), 7.69 (m, 4H), 7.89 (m, 1H), 8.59 (d, J = 5.8 Hz, 2H), 8.97 (s, 1H); MS (DCI/NH$_3$) m/z 280 (M + H)$^+$; Anal. calculated for C$_{18}$H$_{21}$N$_3$•1.8C$_7$H$_8$O$_3$S: C, 62.36; H, 6.05; N, 7.13. Found: C, 62.32; H, 6.01; N, 7.13. |
| 308 | Phenyl boronic acid | 1) H<br>2) FB<br>3) S4 | 2-Biphenyl-4-yl-octahydro-pyrrolo[3,4-c]pyrrole trifluoroacetate<br>$^1$H NMR (300 MHz, CD$_3$OD) δ ppm 3.29 (m, 6H), 3.52 (d, J = 8.8 Hz, 2H), 3.61 (m, 2H), 6.83 (m, 2H), 7.23 (m, 1H), 7.37 (m, 2H), 7.52 (m, 4H); MS (DCI/NH$_3$) m/z 265 (M + H)$^+$; Anal. calculated for C$_{18}$H$_{20}$N$_2$•CF$_3$CO$_2$H•0.2H$_2$O: C, 62.89; H, 5.65; N, 7.33. Found: C, 62.84; H, 5.41; N, 7.11. |
| 309 | Phenyl boronic acid | 1) H<br>2) FB<br>3) RA<br>4) S3 | 2-Biphenyl-4-yl-5-methyl-octahydro-pyrrolo[3,4-c]pyrrole hydrochloride $^1$H NMR (300 MHz, CD$_3$OD) δ ppm 2.92 (s, 3H), 3.21 (m, 2H), 3.40 (m, 4H), 3.64 (m, 3H), 3.98 (m, 1H), 6.96 (m, 2H), 7.25 (t, J = 7.8 Hz, 1H), 7.38 (t, J = 7.6 Hz, 2H), 7.54 (m, 4H); MS (DCI/NH$_3$) m/z 279 (M + H)$^+$; Anal. calculated for C$_{19}$H$_{22}$N$_2$•HCl: C, 64.96; H, 6.89; N, 7.97. Found: C, 64.68; H, 7.08; N, 7.76. |

Example 310

1-Methyl-5-[6-(5-methyl-hexahydro-pyrrolo[3,4-c]pyrrol-2-yl)-pyridazin-3-yl]-1H-indole Fumarate The product of Example 115 was converted to the free base by method FB. This material was subjected to indole N-methylation according to the procedure of Method RA, followed by salt formation according to method S2 to provide the title compound: $^1$H NMR (CH$_3$OH-d$_4$, 300 MHz) δ 2.87 (s, 3H), 3.19-3.39 (m, 4H), 3.52-3.68 (m, 4H), 3.73-3.81 (m, 2H), 3.84 (s, 3H), 6.53 (d, J=3.1 Hz, 1H), 6.68 (s, 2H), 7.16 (d, J=9.5 Hz, 1H), 7.22 (d, J=3.1 Hz, 1H), 7.48 (d, J=8.5 Hz, 1H), 7.79 (dd, J=8.8, 1.7 Hz, 1H), 7.94 (d, J=9.5 Hz, 1H), 8.10 ppm (d, J=1.4 Hz, 1H); MS (DCl/NH$_3$) m/z 334 (M+H)$^+$; Anal. C$_{20}$H$_{23}$N$_5$·1.14C$_4$H$_4$O$_4$: C, H, N.

Example 311

Dimethyl-{5-[6-(5-methyl-hexahydro-pyrrolo[3,4-c]pyrrol-2-yl)-pyridazin-3-yl]-1H-indol-3-ylmethyl}-amine fumarate The product of Example 115 was converted to the free base by method FB. The free base (90 mg, 0.28 mmol), 37% formaldehyde solution (34 mg, 0.42 mmol) and 2M dimethylamine solution in THF (0.21 ml, 0.42 mmol) were combined in dioxane (1 mL) and HOAc (1 mL), and the mixture was stirred at room temperature for 4 h. The mixture was concentrated, and the residue was purified by preparative HPLC (Xterra® column, NH$_4$HCO$_3$—CH$_3$CN). The product was converted to the title compound according to method S2 (81 mg, 50% yield): $^1$H NMR (CH$_3$OH-d$_4$, 300 MHz) δ ppm 2.78-2.85 (m, 9H), 3.32-3.41 (m, 4H), 3.42-3.49 (m, 2H), 3.61 (dd, J=10.8, 6.9 Hz, 2H), 3.84 (d, J=11.9 Hz, 2H), 4.50 (s, 2H), 6.52 (s, 3H), 7.08 (d, J=9.5 Hz, 1H), 7.49-7.57 (m, 2H), 7.78 (dd, J=8.7, 1.4 Hz, 1H), 7.85 (d, J=9.5 Hz, 1H), 8.22 (s, 1H); MS (DCl/NH$_3$) m/z 377 (M+H)$^+$; Anal. C$_{22}$H$_{28}$N$_6$·1.6C$_4$H$_4$O$_4$·H$_2$O: C, H, N.

Example 312

(1S,5S)-6-[6-(6-Methyl-3,6-diaza-bicyclo[3.2.0]hept-3-yl)-pyridazin-3-yl]-2,3,4,9-tetrahydro-1H-carbazole Bis(trifluoroacetate)

Example 312A

N-{4-[6-(6-Methyl-3,6-diaza-bicyclo[3.2.0]hept-3-yl)-pyridazin-3-yl]-phenyl}-hydrazinecarboxylic acid tert-butyl ester The free base of the product of Example 85 (790 mg, 2 mmol), tert-butyl carbazate (317 mg, 2.4 mmol), cesium carbonate (910 mg, 2.8 mmol) and CuI (29 mg, 0.15 mmol) were combined in DMF (8 mL). The mixture was stirred at 80° C. under N$_2$ for 16 hours. The reaction mixture was purified via column chromatography (SiO$_2$, 10% CH$_2$Cl$_2$-MeOH) to give 0.6 g of the title compound (1.5 mol, 75% yield). $^1$H NMR (300 MHz, CD$_3$OD) δ 1.52 (s, 9H), 2.41 (s, 3H), 3.18-3.41 (m, 4H), 3.59 (dd, J=11.4, 8.3 Hz, 1H), 3.94-4.03 (m, 2H), 4.06 (dd, J=6.8, 4.4 Hz, 1H), 7.15 (d, J=9.5 Hz, 1H), 7.58 (d, J=8.8 Hz, 2H), 7.85-7.94 ppm (m, J=9.2, 7.1 Hz, 3H); MS (DCl/NH$_3$) m/z 397 (M+H)$^+$.

Example 312B

6-[6-(6-Methyl-3,6-diaza-bicyclo[3.2.0]hept-3-yl)-pyridazin-3-yl]-2,3,4,9-tetrahydro-1H-carbazole bis (trifluoroacetate)

The product of Example 312A (200 mg, 0.5 mmol), cyclohexanone (98 mg, 1 mmol) and p-toluenesulfonic acid (30 mg, 0.15 mmol) were combined in EtOH (3 mL), and the mixture was heated in the microwave reactor to 150° C. for 10 minutes. The crude reaction mixture was purified by preparative HPLC (Xterra® column, 0.1% TFA-CH$_3$CN), to provide the title compound (19.9 mg, 6% yield). 1H NMR (300 MHz, CD$_3$OD) δ 1.85-2.01 (m, 4H), 2.72-2.82 (m, 5H), 2.96-3.09 (m, 2H), 3.43-3.70 (m, 4H), 4.06-4.28 (m, 2H), 4.52-4.64 (m, 1H), 4.95-5.09 (m, 1H), 7.46 (d, J=8.5 Hz, 1H), 7.60 (dd, J=8.5, 2.0 Hz, 1H), 7.80 (d, J=9.8 Hz, 1H), 8.00 (d, J=1.7 Hz, 1H), 8.42 ppm (d, J=9.8 Hz, 1H); MS (DCl/NH$_3$) m/z 360 (M+H)$^+$; Anal. calculated for C$_{22}$H$_{25}$N$_5$·2.5C$_2$F$_3$HO$_2$·0.3H$_2$O: C, 49.90; H, 4.36; N, 10.78. Found: C, 49.85; H, 4.51; N, 10.89.

Example 314

2-(5-Phenyl-1H-pyrazol-3-yl)-2,5-diaza-bicyclo[2.2.1]heptane bis-p-toluenesulfonate

Example 314A 5-(1-Methylsulfanyl-3-oxo-3-phenyl-propenyl)-2,5-diaza-bicyclo[2.2.1]heptane-2-carboxylic acid tert-butyl ester 3,3-Bis-methylsulfanyl-1-phenyl-propenone (0.675 g, 3.0 mmol), was prepared according to literature procedure (Galli, f. et al WO 01/92251 A1) and was combined with the product of Example 24 (0.200 g, 1.0 mmol) in 10 mL MeOH. This mixture was warmed to 70° C. for 4 h then was cooled to ambient temperature, concentrated under reduced pressure and purified via column chromatography (SiO$_2$, 10% CH$_3$OH—CH$_2$Cl$_2$ with 1% NH$_4$OH) to give 0.159 g of the title compound (0.38 mmol, 38% yield). MS (DCl/NH$_3$) m/z 375 (M+H)$^+$.

Example 314B 5-(5-Phenyl-1H-pyrazol-3-yl)-2,5-diaza-bicyclo[2.2.1]heptane-2-carboxylic acid tert-butyl ester The product of example 314B (0.143 g, 0.42 mmol), hydrazine 1.0M solution in THF (1.7 mL, 1.7 mmol), sodium acetate (0.13 g, 1.3 mmol) were combined in toluene (4 mL), acetic acid (2 mL), water (0.5 mL), and ethanol. The mixture was heated to reflux for 8 h. The mixture was poured into saturated Aq sodium carbonate and extracted with EtOAc the organics were dried over MgSO$_4$ and concentrated under reduced pressure. The residue was purified by column chromatography (SiO$_2$, 10% CH$_3$OH—CH$_2$Cl$_2$ with 1%

NH₄OH) to provide the title compound (0.088 g, 0.24 mmol, 57% yield). MS (DCl/NH₃) m/z 356 (M+H)⁺.

Example 314C 2-(5-Phenyl-1H-pyrazol-3-yl)-2,5-diaza-bicyclo[2.2.1]heptane bis-p-toluenesulfonate The product of Example 314B was processed according to method FB, and S1 to provide the title salt. 1H NMR (CH₃OH-d₄, (300 MHz) δ 2.04-2.20 (m, 2H) 2.26-2.42 (m, 6H) 3.35-3.44 (m, 1H) 3.45-3.66 (m, 2H) 3.66-3.86 (m, 1H) 4.49-4.72 (m, 2H) 6.28-6.47 (m, 1H) 7.14-7.30 (m, 5H) 7.45-7.59 (m, 1H) 7.62-7.83 ppm (m, 7H). MS (DCl/NH₃) m/z 241 (M+H)⁺. Anal. calculated for C₁₄H₁₆N₄.2.C₇H₈O₃S.0: C, 57.51; H, 5.52; N, 9.58. Found: C, 57.39; H, 5.19; N, 9.14

Example 315

Example 315A

Benzyl (1S,5S)-6-(5-cyano-3-pyridinyl)-3,6-diazabicyclo[3.2.0]heptane-3-carboxylate The product of Example 7J (830 mg, 3.58 mmol) in toluene (20 mL) was treated with Pd₂(dba)₃ (71.0 mg, 0.072 mmol), BINAP (134 mg, 0.214 mmol), Cs₂CO₃ (2.32 g, 7.16 mmol) and 3-bromo-5-cyanopyridine (0.98 g, 5.37 mmol). The mixture was heated at 100° C. under N₂ for 10 hours and then allowed to cool to room temperature and diluted with ethyl acetate (100 mL). The brown solution was washed with water (2×10 mL) and concentrated under reduced pressure. The residue was purified by chromatography (SiO₂, EtOAc:hexane, 50:50, R_f 0.3) to provide the title compound (770 mg, 64% yield). ¹H NMR (MeOH-d₄, 300 MHz) δ 3.2 (dd, J=12.9, 4.Hz, 1H), 3.30-3.4 (m, 2H), 3.6 (dd, J=8.2, 3.Hz, 1H), 3.96-4.10 (m, 3H), 4.74 (dd, J=6.1, 4.0 Hz, 1H), 5.10 (m, 2H), 7.15 (dd, J=2.7, 1.7 Hz, 1H), 7.25 (m, 3H), 7.35 (m, 2H), 7.96 (d, J=2.7 Hz, 1H), 8.15 (d, J=1.7 Hz, 1H); MS (DCl/NH₃) m/z 335 (M+H)⁺.

Example 315B

Benzyl (1S,5S)-6-(6-bromo-5-cyano-3-pyridinyl)-3,6-diazabicyclo[3.2.0]heptane-3-carboxylate The product of Example 315A was treated with N-bromosuccinimide in acetonitrile according to the method of Example 301B to provide the title compound: MS (DCl/NH₃) m/z 413/415 (M+H)⁺.

Example 315C

Benzyl (1S,5S)-6-(6-[2-thienyl]-5-cyano-3-pyridinyl)-3,6-diazabicyclo[3.2.0]heptane-3-carboxylate The product of Example 315B was coupled with 2-thienyl boronic acid according to the procedure of method I to provide the title compound: MS (DCl/NH₃) m/z 417 (M+H)⁺.

Example 315D (1R,5S)-5-(3,6-Diaza-bicyclo[3.2.0]hept-6-yl)-2-thiophen-2-yl-nicotinonitrile trifluoroacetate The product of Example 315C was stirred in trifluoroacetic acid at 65° C. for 2 h, then cooled to room temperature and concentrated under vacuum. The residue was triturated with 10% methanol in ether to provide the title compound:
¹H NMR (MeOH-D₄, 300 MHz) δ 3.20 (dd, J=12.9, 3.8 Hz, 1H), 3.33-3.42 (m, 1H), 3.41-3.61 (m, 1H), 3.66-3.89 (m, 3H), 4.13 (t, J=8.1 Hz, 1H), 5.01 (dd, J=6.6, 3.6 Hz, 1H), 7.14 (dd, J=5.1, 3.7 Hz, 1H), 7.36 (d, J=2.7 Hz, 1H), 7.53 (d, J=5.1 Hz, 1H), 7.95 (d, J=3.7 Hz, 1H), 8.10 (d, J=3.1 Hz, 1H); MS (DCl/NH₃) m/z 283 (M+H)⁺; Anal. Calculated for C₁₅H₁₄N₄S.1.12CF₃CO₂H.1.90H₂O: C, 54.08; H, 5.64; N, 9.83. Found: C, 54.33; H, 5.30; N, 9.46.

Example 316

(1R,5S)-5-(3-Methyl-3,6-diaza-bicyclo[3.2.0]hept-6-yl)-2-thiophen-2-yl-nicotinonitrile fumarate The product of Example 315D was processed according to method RA, then converted to the salt according to method S2: ¹H NMR (MeOH-D₄, 300 MHz) δ 2.82-2.93 (m, 4H), 3.00 (dd, J=11.7, 7.0 Hz, 1H), 3.39-3.58 (m, 1H), 3.73 (d, J=11.9 Hz, 1H), 3.77-3.91 (m, 2H), 4.10 (t, J=8.1 Hz, 1H), 4.96 (dd, J=6.8, 3.4 Hz, 1H), 6.69 (s, 2H), 7.13 (dd, J=5.1, 3.7 Hz, 1H), 7.30 (d, J=2.7 Hz, 1H), 7.52 (d, J=5.1 Hz, 1H), 7.93 (d, J=3.7 Hz, 1H), 8.07 (d, J=3.1 Hz, 1H); MS (DCl/NH₃) m/z 297 (M+H)⁺; Anal. Calculated for C₁₆H₁₆N₄S.1.10 C₄H₄O₄.1.10H₂O: C, 62.26; H, 6.25; N, 10.18. Found: C, 62.34; H, 6.31; N, 10.43.

Example 318

(1S,5S)-3-(4-Pyridin-3-yl-phenyl)-3,6-diaza-bicyclo[3.2.0]heptane bis(p-toluenesulfonate)

Example 318A (1S,5R)-3-(4-bromophenyl)-3,6-diaza-bicyclo[3.2.0]heptane-6-carboxylate t-butyl ester The product of Example 8B was coupled with p-dibromobenzene according to the procedure of Example 128A to provide the title compound.

Example 318B (1S,5S)-3-(4-Pyridin-3-yl-phenyl)-3,6-diaza-bicyclo[3.2.0]heptane bis(p-toluenesulfonate)

The product of Example 318A was coupled with pyridine-3-boronic acid according to the procedure of Method I. The product was further processed according to method FB and method S1 to provide the title compound: ¹H NMR (MeOH-D₄, 300 MHz) δ 2.37 (s, 6H) 3.02 (dd, J=10.5, 6.1 Hz, 1H), 3.10 (dd, J=12.5, 4.7 Hz, 1H), 3.39-3.60 (m, 1H), 3.75 (dd, J=11.0, 5.3 Hz, 1H), 3.93 (d, J=10.9 Hz, 1H), 4.14 (d, J=12.5 Hz, 1H), 4.25 (dd, J=10.8, 8.5 Hz, 1H), 5.02 (dd, J=7.0, 4.9 Hz, 1H), 6.93-7.16 (m, 2H) 7.23 (d, J=8.1 Hz, 4H) 7.47 (dd, J=8.0, 4.9 Hz, 1H) 7.56-7.66 (m, 3H) 7.64-7.80 (m, 4H) 7.95-8.15 (m, 1H) 8.44 (dd, J=4.9, 1.5 Hz, 1H) 8.75 (d, J=1.7 Hz, 1H); MS (DCl/NH₃) m/z 252 (M+H)⁺; Anal. Calculated for C₁₆H₁₇N₃.2.20 C₇H₈SO₃.0.50H₂O: C, 59.00; H, 5.61; N, 6.57. Found: C, 58.75; H, 5.72; N, 6.75.

Example 319

(1S,5S)-6-Methyl-3-(4-pyridin-3-yl-phenyl)-3,6-diaza-bicyclo[3.2.0]heptane bis(p-toluenesulfonate)

The product of Example 318A was coupled with pyridine-3-boronic acid according to method I, and further processed according to methods FB, RA, and S1 to provide the title compound: $^1$H NMR (MeOH-D$_4$, 300 MHz) δ 2.39 (S, 6H), 2.89-2.90 (m, 4H), 3.11 (dd, J=13.2, 4.7 Hz, 1H), 3.38-3.62 (m, 1H), 3.94 (d, J=9.8 Hz, 1H), 4.01-4.16 (m, 2H), 4.16-4.34 (m, 1H), 4.72-5.05 (m, 1H), 7.08 (d, J=8.5 Hz, 2H), 7.22 (d, J=8.1 Hz, 4H), 7.51-7.91 (m, 6H) 8.35 (d, J=8.1 Hz, 1H), 8.55 (d, J=3.7 Hz, 1H), 8.89 (s (br.), 1H); MS (DCI/NH$_3$) m/z 266 (M+H)$^+$; Anal. Calculated for $C_{17}H_{19}N_3 \cdot 2.00$ $C_7H_8SO_3 \cdot 0.60 H_2O$: C, 60.00; H, 5.88; N, 6.77. Found: C, 59.92; H, 5.72; N, 6.74.

Example 320

(1S,5S)-5-[4-(3,6-Diaza-bicyclo[3.2.0]hept-3-yl)-phenyl]-3-methyl-1H-indazole bis(p-toluene-sulfonate)

The product of Example 318A was coupled with the product of Example 212A according to the procedure of Example 212B. The product was further processed according to methods FB and S1 to provide the title compound: $^1$H NMR (MeOH-D$_4$, 300 MHz) δ 2.28 (s, 6H), 2.53 (s, 3H), 2.59 (d, J=9.8 Hz, 1H), 2.91 (dd, J=10.3, 5.9 Hz, 1H), 3.02 (dd, J=11.7, 4.9 Hz, 1H), 3.33-3.44 (m, 1H), 3.89 (d, J=10.5 Hz, 1H), 4.04-4.21 (m, 2H), 4.87-5.05 (m, J=4.7 Hz, 1H), 6.96 (d, J=8.5 Hz, 2H), 7.10 (d, J=7.8 Hz, 4H), 7.41-7.54 (m, 5H), 7.56-7.69 (m, 3H), 7.90 (s, 1H); MS (DCI/NH$_3$) m/z 305 (M+H)$^+$; Anal. Calculated for $C_{19}H_{20}N_4 \cdot 2.00$ $C_7H_8SO_3 \cdot 0.60 H_2O$: C, 59.84; H, 5.60; N, 8.46. Found: C, 60.04; H, 5.72; N, 8.70.

Example 321

Determination of Biological Activity

To determine the effectiveness of representative compounds of this invention as α7 nAChRs, the compounds of the invention were evaluated according to the [3H]-methyllycaconitine (MLA) binding assay and considering the [3H]-cytisine binding assay, which were performed as described below.

[3H]-Cytisine Binding

Binding conditions were modified from the procedures described in Pabreza L A, Dhawan, S, Kellar K J, [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 µg of protein and 0.75 nM [3H]-cytisine (30 C$_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 µL) was added to each well and radioactivity determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/1+[Ligand]/K$_D$].

[3H]-Methylycaconitine (MLA) Binding

Binding conditions were similar to those for [3H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM CaCl$_2$, 2 mM MgCl$_2$, and 50 mM Tris-Cl, pH 7.4, 22° C.). Samples containing 100-200 µg of protein, 5 nM [3H]-MLA (25 C$_i$/mmol; Perkin Elmer/NEN Life Science Products, Boston, Mass.) and 0.1% bovine serum albumin (BSA, Millipore, Bedford, Mass.) were incubated in a final volume of 500 µL for 60 minutes at 22° C. Seven log-dilution concentrations of each compound were tested in duplicate. Non-specific binding was determined in the presence of 10 µM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 µL) was added to each well and radioactivity was determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/1+[Ligand]/K$_D$].

Compounds of the invention had K$_i$ values of from about 1 nanomolar to about 10 micromolar when tested by the MLA assay, many having a K$_i$ of less than 1 micromolar. [3H]-Cytisine binding values of compounds of the invention ranged from about 50 nanomolar to at least 100 micromolar. The determination of preferred compounds typically considered the K$_i$ value as measured by MLA assay in view of the K$_i$ value as measured by [3H]-cytisine binding, such that in the formula D=K$_{i\,MLA}$/K$_{i\,3H\text{-}cytisine}$, D is about 50. Preferred compounds typically exhibited greater potency at α7 receptors compared to α4β2 receptors.

Compounds of the invention are α7 nAChRs ligands that modulate function of α7 nAChRs by altering the activity of the receptor. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula (I):

Z—Ar$_1$-Ar$_2$  (I)

wherein:

Z is a diazabicyclic amine of formula:

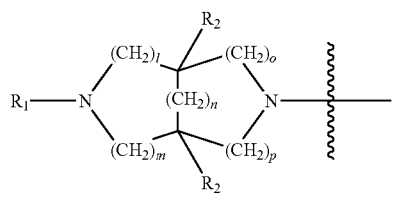

(II)

Ar$_1$ is a pyridine ring of formula:

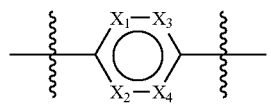

(a)

wherein, only one of X$_1$, X$_2$, X$_3$, and X$_4$ is N and the remaining are —CR$_3$;

Ar$_2$ is selected from the group consisting of 5- or 6-membered heteroaryl, bicyclic heteroaryl, 3,4-(methylenedioxy) phenyl, carbazolyl, tetrahydrocarbazolyl, naphthyl, and phenyl, substituted with 0, 1, 2, or 3 substituents selected from the group consisting of alkenyl, alkoxy, alkoxyalkoxy, alkoxyalkyl, alkoxycarbonyl, alkoxysulfonyl, alkyl, alkylcarbonyl, arylcarbonyl, alkylcarbonyloxy, alkylsulfonyl, alkylthio, alkynyl, carboxy, cyano, formyl, haloalkoxy, haloalkyl, halogen, hydroxy, hydroxyalkyl, mercapto, nitro, —NR$_A$R$_B$, (NR$_A$R$_B$)alkyl, (NR$_A$R$_B$)carbonyl, (NR$_A$R$_B$)sulfonyl, and phenyl;

l, m, o, and p are each independently 0, 1, or 2, and n is 0, provided that the sum total of l, m, n, o, and p is 3, 4, or 5, and further provided that the sum of l and o is at least 1 and the sum of m and p is at least 1;

R$_1$ is selected from the group consisting of hydrogen, alkenyl, alkyl alkoxycarbonyl, arylalkyl, and heteroarylalkyl;

R$_2$ at each occurrence is independently selected from the group consisting of hydrogen, alkoxycarbonyl, and alkyl;

R$_3$ at each occurrence is independently selected from the group consisting of hydrogen, alkoxy, alkyl, cyano, and hydroxy;

R$_A$ and R$_B$ are each independently selected from the group consisting of hydrogen, alkyl, alkylcarbonyl, alkylsulfonyl, arylcarbonyl, formyl and (NR$_C$R$_D$)sulfonyl; and R$_C$ and R$_D$ are each independently selected from the group consisting of hydrogen and alkyl;

or a pharmaceutically acceptable salt thereof.

2. The compound as in claim 1, wherein Z is the diazabicyclic amine selected from the group consisting of:

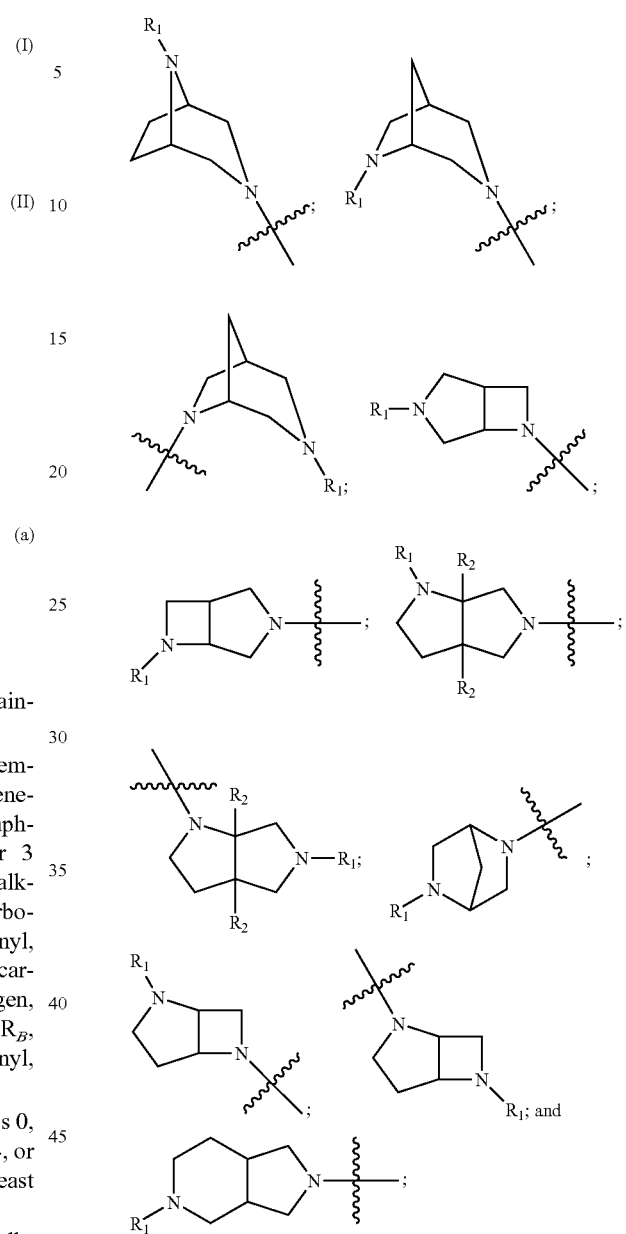

or a pharmaceutically acceptable salt, thereof.

3. The compound of claim 1, wherein Ar$_2$ is selected from the group consisting of benzofuranyl; benzothienyl; carbazolyl; tetrahydrocarbazolyl; furyl; imidazolyl; 3-indolyl; 4-indolyl; 5-indolyl; isoxazolyl; naphthyl; pyrazolyl; pyridazinyl; pyridyl; pyrimidinyl; 2-pyrrolyl; 3-pyrrolyl; quinolinyl; thienyl; 3,4-(methylenedioxy)phenyl; and phenyl; wherein the phenyl is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$) alkyl, (NR$_A$R$_B$) alkoxy, and phenyl; or a pharmaceutically acceptable salt thereof.

4. The compound of claim 1, wherein Ar$_2$ is selected from the group consisting of:

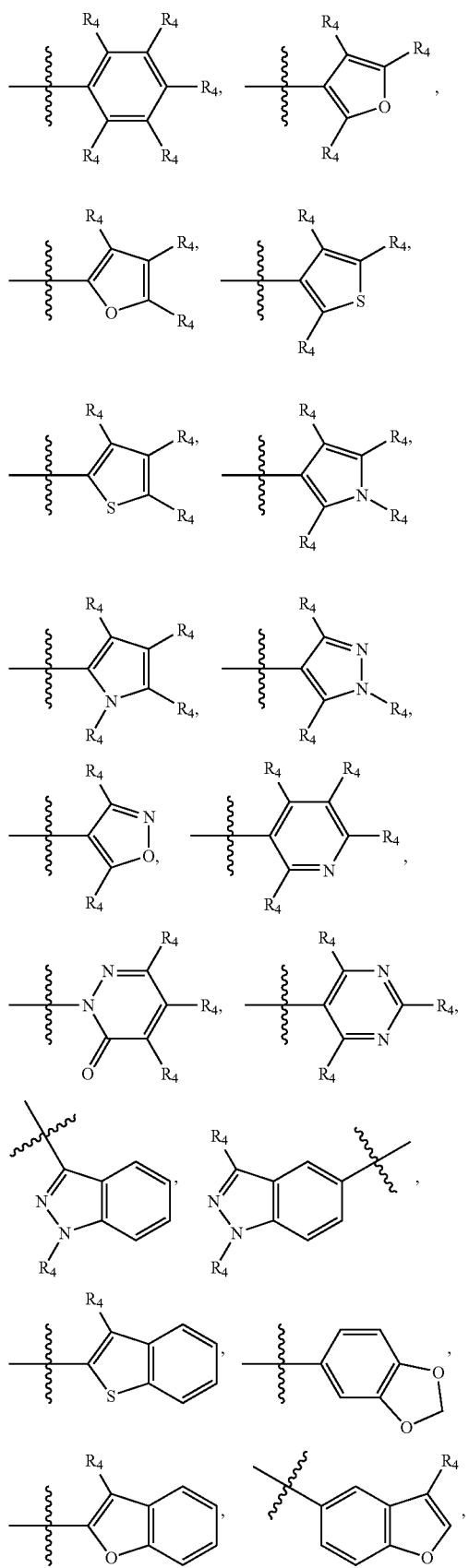

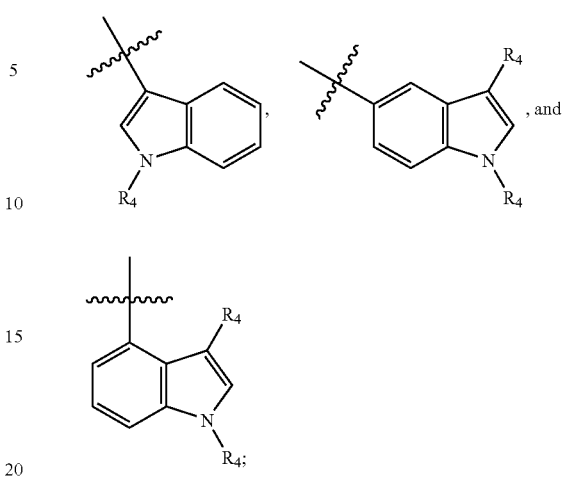

wherein R₄ at each occurrence is independently selected from the group consisting of hydrogen, alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl; or a pharmaceutically acceptable salt thereof.

5. The compound of claim 1, wherein Ar₂ is selected from the group consisting of phenyl, para-acetylaminophenyl, meta-aminophenyl, para-aminophenyl, para(2-(diethylamino)ethoxy)phenyl, meta(2-(diethylamino)ethoxy)phenyl, para-(dimethylamino)phenyl, para-bromophenyl, meta-cyanophenyl, para-cyanophenyl, meta-hydroxyphenyl, para-hydroxyphenyl, para-iodophenyl, meta-methylphenyl, para-methylphenyl, 3,5-dimethylphenyl, meta-methoxyphenyl, para-methoxyphenyl, meta-trifluoromethoxyphenyl, meta-nitrophenyl, para-nitrophenyl, and meta-trifluoromethylphenyl; or a pharmaceutically acceptable salt thereof.

6. The compound of claim 1, wherein Z is

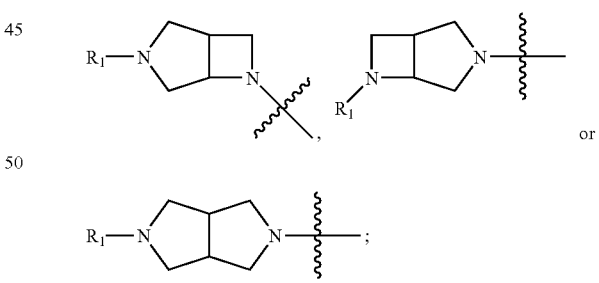

or a pharmaceutically acceptable salt thereof.

7. The compound of claim 6, wherein Ar₂ is selected from the group consisting of 3-indolyl, 5-indolyl; 1-methyl-3-indolyl, 1-methyl-5-indolyl, 3-methyl-5-indolyl, 3,4-(methylenedioxy)phenyl, and phenyl, wherein Ar₂ is substituted with 0, 1, or 2 substituents selected from the group consisting of alkoxy, alkoxycarbonyl, alkyl, alkylcarbonyl, carboxy, cyano, halogen, haloalkoxy, haloalkyl, hydroxy, nitro, —NR$_A$R$_B$, (NR$_A$R$_B$)alkyl, (NR$_A$R$_B$)alkoxy, and phenyl; or a pharmaceutically acceptable salt thereof.

8. The compound of claim 6, wherein Z is

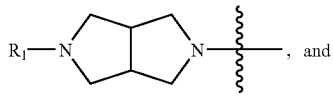, and

Ar$_2$ is selected from the group consisting of heteroaryl and bicyclic heteroaryl, provided that Ar$_2$ is not 1-pyrrolyl or 1-indolyl; or a pharmaceutically acceptable salt, thereof.

9. The compound of claim 1, selected from the group consisting of:

2-(6-Phenyl-pyridin-3-yl)-octahydro-pyrrolo[3,4-c]pyrrole;
2-(6-o-Tolyl-pyridin-3-yl)-octahydro-pyrrolo[3,4-c]pyrrole;
2-(6-m-Tolyl-pyridin-3-yl)-octahydro-pyrrolo[3,4-c]pyrrole;
2-(6-biphenyl-3-yl-pyridin-3-yl)-octahydro-pyrrolo[3,4-c]pyrrole;
2-(6-biphenyl-3-yl-pyridin-3-yl)-5-methyl-octahydro-pyrrolo[3,4-c]pyrrole;
2-[6-(3-trifluoromethyl-phenyl)-pyridin-3-yl]-octahydro-pyrrolo[3,4-c]pyrrole;
2-methyl-5-[6-(3-trifluoromethyl-phenyl)-pyridin-3-yl]-octahydro-pyrrolo[3,4-c]pyrrole;
3-[5-(hexahydro-pyrrolo[3,4-c]pyrrol-2-yl)-pyridin-2-yl]-phenylamine;
5-(6-furan-3-yl-pyridin-3-yl)-hexahydro-pyrrolo[3,4-c]pyrrole;
2-(6-furan-3-yl-pyridin-3-yl)-5-methyl-octahydro-pyrrolo[3,4-c]pyrrole;
2-(6-benzo[b]thiophen-2-yl-pyridin-3-yl)-octahydro-pyrrolo[3,4-c]pyrrole;
2-(6-benzo[b]thiophen-2-yl-pyridin-3-yl)-5-methyl-octahydro-pyrrolo[3,4-c]pyrrole;
2-(5-phenyl-pyridin-2-yl)-octahydro-pyrrolo[3,4-c]pyrrole;
2-methyl-5-(5-phenyl-pyridin-2-yl)-octahydro-pyrrolo[3,4-c]pyrrole;
(1R,5R)-1-{4-[5-(3,6-diaza-bicyclo[3.2.0]hept-3-yl)-pyridin-2-yl]-phenyl}-ethanone;
(1R,5R)-1-{4-[5-(6-methyl-3,6-diaza-bicyclo[3.2.0]hept-3-yl)-pyridin-2-yl]-phenyl}-ethanone;
6a-methyl-5-(6-m-tolyl-pyridin-3-yl)-octahydro-pyrrolo[3,4-b]pyrrole;
2-methyl-5-(5-pyrimidin-5-yl-pyridin-2-yl)-octahydro-pyrrolo[3,4-c]pyrrole;
2-methyl-5-[5-(1H-pyrazol-4-yl)-pyridin-2-yl]-octahydro-pyrrolo[3,4-c]pyrrole;
3-[6-(5-methyl-hexahydro-pyrrolo[3,4-c]pyrrol-2-yl)-pyridin-3-yl]-benzonitrile;
2-[5-(2-methoxy-pyrimidin-5-yl)-pyridin-2-yl]-5-methyl-octahydro-pyrrolo[3,4-c]pyrrole;
2-[5-(3,5-dimethyl-1H-pyrazol-4-yl)-pyridin-2-yl]-5-methyl-octahydro-pyrrolo[3,4-c]pyrrole;
2-methyl-5-[5-(1-methyl-1H-pyrazol-4-yl)-pyridin-2-yl]-octahydro-pyrrolo[3,4-c]pyrrole;
2-[5-(3,5-dimethyl-isoxazol-4-yl)-pyridin-2-yl]-5-methyl-octahydro-pyrrolo[3,4-c]pyrrole;
6-(5-methyl-hexahydro-pyrrolo[3,4-c]pyrrol-2-yl)-[3,3']bipyridinyl;
6-(5-methyl-hexahydro-pyrrolo[3,4-c]pyrrol-2-yl)-[3,4']bipyridinyl;
4-[6-(5-methyl-hexahydro-pyrrolo[3,4-c]pyrrol-2-yl)-pyridin-3-yl]-benzonitrile;
6'-(5-methyl-hexahydro-pyrrolo[3,4-c]pyrrol-2-yl)-[3,3']bipyridinyl-6-ylamine;
2-methyl-5-[5-(1H-pyrrol-3-yl)-pyridin-2-yl]-octahydro-pyrrolo[3,4-c]pyrrole;
2-methyl-5-[5-(1H-pyrrol-2-yl)-pyridin-2-yl]-octahydro-pyrrolo[3,4-c]pyrrole;
6'-(5-methyl-hexahydro-pyrrolo[3,4-c]pyrrol-2-yl)-[3,3']bipyridinyl-2-carbonitrile;
2-(5-furan-3-yl-pyridin-2-yl)-5-methyl-octahydro-pyrrolo[3,4-c]pyrrole;
2-methyl-5-(5-thiophen-2-yl-pyridin-2-yl)-octahydro-pyrrolo[3,4-c]pyrrole;
2-methyl-5-(5-thiophen-3-yl-pyridin-2-yl)-octahydro-pyrrolo[3,4-c]pyrrole;
2-(5-benzofuran-5-yl-pyridin-2-yl)-5-methyl-octahydro-pyrrolo[3,4-c]pyrrole;
2-(5-furan-2-yl-pyridin-2-yl)-5-methyl-octahydro-pyrrolo[3,4-c]pyrrole;
3-[6-(5-methyl-hexahydro-pyrrolo[3,4-c]pyrrol-2-yl)-pyridin-3-yl]-9H-carbazole;
5-[6-(5-methyl-hexahydro-pyrrolo[3,4-c]pyrrol-2-yl)-pyridin-3-yl]-1H-indole;
4-[6-(5-methyl-hexahydro-pyrrolo[3,4-c]pyrrol-2-yl)-pyridin-3-yl]-1H-indole;
2-[6-(5-methyl-hexahydro-pyrrolo[3,4-c]pyrrol-2-yl)-pyridin-3-yl]-2H-pyridazin-3-one;
2-[6-(3-methoxy-phenyl)-pyridin-3-yl]-octahydro-pyrrolo[3,4-c]pyrrole
2-[6-(3-trifluoromethoxy-phenyl)-pyridin-3-yl]-octahydro-pyrrolo[3,4-c]pyrrole;
2-(6-thiophen-3-yl-pyridin-3-yl)-octahydro-pyrrolo[3,4-c]pyrrole;
8-[5-(hexahydro-pyrrolo[3,4-c]pyrrol-2-yl)-pyridin-2-yl]-quinoline;
2-(6-naphthalen-2-yl-pyridin-3-yl)-octahydro-pyrrolo[3,4-c]pyrrole;
2-(6-benzofuran-2-yl-pyridin-3-yl)-octahydro-pyrrolo[3,4-c]pyrrole;
2-methyl-5-(6-o-tolyl-pyridin-3-yl)-octahydro-pyrrolo[3,4-c]pyrrole;
2-methyl-5-(6-m-tolyl-pyridin-3-yl)-octahydro-pyrrolo[3,4-c]pyrrole;
2-methyl-5-(6-phenyl-pyridin-3-yl)-octahydro-pyrrolo[3,4-c]pyrrole;
2-[6-(3-methoxy-phenyl)-pyridin-3-yl]-5-methyl-octahydro-pyrrolo[3,4-c]pyrrole;
2-methyl-5-[6-(3-trifluoromethoxy-phenyl)-pyridin-3-yl]-octahydro-pyrrolo[3,4-c]pyrrole;
2-methyl-5-[6-(3-nitro-phenyl)-pyridin-3-yl]-octahydro-pyrrolo[3,4-c]pyrrole;
2-methyl-5-(6-thiophen-3-yl-pyridin-3-yl)-octahydro-pyrrolo[3,4-c]pyrrole;
8-[5-(5-methyl-hexahydro-pyrrolo[3,4-c]pyrrol-2-yl)-pyridin-2-yl]-quinoline;
2-methyl-5-(6-naphthalen-2-yl-pyridin-3-yl)-octahydro-pyrrolo[3,4-c]pyrrole;
5-[5-(5-methyl-hexahydro-pyrrolo[3,4-c]pyrrol-2-yl)-pyridin-2-yl]-1H-indole;
4-[5-(5-methyl-hexahydro-pyrrolo[3,4-c]pyrrol-2-yl)-pyridin-2-yl]-1H-indole;
5-[5-(5-methyl-hexahydro-pyrrolo[3,4-c]pyrrol-2-yl)-pyridin-2-yl]-quinoline;
(1S,5S)-5-[6-(3,6-diaza-bicyclo[3.2.0]hept-3-yl)-pyridin-3-yl]-3-methyl-1H-indazole;

(1R,5R)-{4-[5-(3,6-diaza-bicyclo[3.2.0]hept-3-yl)-pyridin-2-yl]-phenyl}-dimethyl-amine;
(1R,5R)-6-methyl-3-(6-m-tolyl-pyridin-3-yl)-3,6-diaza-bicyclo[3.2.0]heptane;
(1R,5R)-6-methyl-3-(6-p-tolyl-pyridin-3-yl)-3,6-diaza-bicyclo[3.2.0]heptane;
(1R,5R)-3-[5-(6-methyl-3,6-diaza-bicyclo[3.2.0]hept-3-yl)-pyridin-2-yl]-benzonitrile;
(1R,5R)-3-[6-(4-ethyl-phenyl)-pyridin-3-yl]-6-methyl-3,6-diaza-bicyclo[3.2.0]heptane;
(1R,5R)-dimethyl-{4-[5-(6-methyl-3,6-diaza-bicyclo[3.2.0]hept-3-yl)-pyridin-2-yl]-phenyl}-amine;
(1R,5R)-3-[6-(3-methoxy-phenyl)-pyridin-3-yl]-6-methyl-3,6-diaza-bicyclo[3.2.0]heptane;
(1R,5R)-3-(6-benzo[1,3]dioxol-5-yl-pyridin-3-yl)-6-methyl-3,6-diaza-bicyclo[3.2.0]heptane;
(1R,5R)-3-[6-(4-methoxy-phenyl)-pyridin-3-yl]-6-methyl-3,6-diaza-bicyclo[3.2.0]heptane;
(1R,5R)-3-[6-(3,4-dimethoxy-phenyl)-pyridin-3-yl]-6-methyl-3,6-diaza-bicyclo[3.2.0]heptane;
(1R,5R)-6-methyl-3-(6-phenyl-pyridin-3-yl)-3,6-diaza-bicyclo[3.2.0]heptane;
(1R,5R)-5-(6-methyl-3,6-diaza-bicyclo[3.2.0]hept-3-yl)-[2,3']bipyridinyl;
(1R,5R)-5-[5-(6-methyl-3,6-diaza-bicyclo[3.2.0]hept-3-yl)-pyridin-2-yl]-1H-indole;
(1S,5S)-5-[5-(6-methyl-3,6-diaza-bicyclo[3.2.0]hept-3-yl)-pyridin-2-yl]-1H-indole;
(1R,5S)-6-(6-phenyl-pyridin-3-yl)-3,6-diaza-bicyclo[3.2.0]heptane;
(1R,5S)-6-(6-m-tolyl-pyridin-3-yl)-3,6-diaza-bicyclo[3.2.0]heptane;
(1R,5S)-3-methyl-6-(6-phenyl-pyridin-3-yl)-3,6-diaza-bicyclo[3.2.0]heptane;
(1R,5S)-5-[5-(3-methyl-3,6-diaza-bicyclo[3.2.0]hept-6-yl)-pyridin-2-yl]-1H-indole;
(1S,5S)-5-[6-(3,6-diaza-bicyclo[3.2.0]hept-3-yl)-pyridin-3-yl]-1H-indole;
(1S,5S)-3-(5-phenyl-pyridin-2-yl)-3,6-diaza-bicyclo[3.2.0]heptane;
(1S,5S)-6-methyl-3-(5-phenyl-pyridin-2-yl)-3,6-diaza-bicyclo[3.2.0]heptane;
(1S,5S)-5-[6-(6-methyl-3,6-diaza-bicyclo[3.2.0]hept-3-yl)-pyridin-3-yl]-1H-indole;
or a pharmaceutically acceptable salt thereof.

10. The compound of claim 1 that is (1R,5R)-5-[5-(6-methyl-3,6-diaza-bicyclo [3.2.0]hept-3-yl)-pyridin-2-yl]-1H-indole or a pharmaceutically acceptable salt thereof.

11. The compound of claim 1 that is (1S,5S)-5-[5-(6-methyl-3,6-diaza-bicyclo [3.2.0]hept-3-yl)-pyridin-2-yl]-1H-indole or a pharmaceutically acceptable salt thereof.

12. The compound of claim 1 that is 5-[5-(5-methyl-hexahydro-pyrrolo[3,4-c]pyrrol-2-yl)-pyridin-2-yl]-1H-indole or a pharmaceutically acceptable salt thereof.

13. The compound of claim 1 that is 2-(6-thiophen-3-yl-pyridin-3-yl)-octahydro-pyrrolo [3,4-c]pyrrole or a pharmaceutically acceptable salt thereof.

14. The compound of claim 1 that is 2-methyl-5-(6-thiophen-3-yl-pyridin-3-yl)-octahydro-pyrrolo [3,4-c]pyrrole or a pharmaceutically acceptable salt thereof.

15. The compound of claim 1 that is (1R,5R)-6-Methyl-3-(6-phenyl-pyridin-3-yl)-3,6-diaza-bicyclo[3.2.0]heptane or a pharmaceutically acceptable salt thereof.

16. The compound of claim 1 that is 2-(6-phenyl-pyridin-3-yl)-octahydro-pyrrolo[3,4-c]pyrrole or a pharmaceutically acceptable salt thereof.

17. The compound of claim 1 that is 2-methyl-5-(6-phenyl-pyridin-3-yl)-octahydro-pyrrolo[3,4-c]pyrrole or a pharmaceutically acceptable salt, ester, or amide thereof.

18. The compound of claim 1 that is (1S,5S)-5-[6-(6-methyl-3,6-diaza-bicyclo[3.2.0]hept-3-yl)-pyridin-3-yl]-1H-indole or a pharmaceutically acceptable salt, ester, or amide thereof.

19. The compound of claim 1 that is 2-(5-phenyl-pyridin-2-yl)-octahydro-pyrrolo [3,4-c]pyrrole or a pharmaceutically acceptable salt thereof.

20. A pharmaceutical composition comprising a therapeutically effective amount of the compound of claim 1 or a pharmaceutically acceptable salt thereof, in combination with a pharmaceutically acceptable carrier.

* * * * *